(12) United States Patent
Molina Espeja et al.

(10) Patent No.: US 10,876,098 B2
(45) Date of Patent: Dec. 29, 2020

(54) POLYNUCLEOTIDE, HOST CELL AND A METHOD TO RECOMBINANTLY PRODUCE THE PROTEIN ENCODED BY SAID POLYNUCLEOTIDE HAVING PEROXYGENATIVE ACTIVITY

(71) Applicant: CONSEJO SUPERIOR DE INVESTIGACIONES CIENTIFICAS (CSIC), Madrid (ES)

(72) Inventors: Patricia Molina Espeja, Madrid (ES); Francisco José Plou Gasca, Madrid (ES); Miguel Alcalde Galeote, Madrid (ES); Patricia Gómez De Santos, Madrid (ES)

(73) Assignee: CONSEJO SUPERIOR DE INVESTIGACIONES CIENTIFICAS (CSIC), Madrid (ES)

( * ) Notice: Subject to any disclaimer, the term of this patent is extended or adjusted under 35 U.S.C. 154(b) by 236 days.

(21) Appl. No.: 15/775,369

(22) PCT Filed: Nov. 14, 2016

(86) PCT No.: PCT/ES2016/070809
§ 371 (c)(1),
(2) Date: Sep. 11, 2018

(87) PCT Pub. No.: WO2017/081355
PCT Pub. Date: May 18, 2017

(65) Prior Publication Data
US 2019/0024058 A1    Jan. 24, 2019

(30) Foreign Application Priority Data
Nov. 13, 2015   (ES) ................... 201531641

(51) Int. Cl.
| | | |
|---|---|---|
| *C12N 9/08* | (2006.01) | |
| *C12N 15/80* | (2006.01) | |
| *C12R 1/69* | (2006.01) | |
| *C12R 1/685* | (2006.01) | |
| *C12P 7/02* | (2006.01) | |
| *C12P 7/22* | (2006.01) | |
| *C12P 7/26* | (2006.01) | |

(52) U.S. Cl.
CPC .......... *C12N 9/0065* (2013.01); *C12N 15/80* (2013.01); *C12P 7/02* (2013.01); *C12P 7/22* (2013.01); *C12P 7/26* (2013.01); *C12Y 111/02001* (2013.01); *C12R 1/685* (2013.01); *C12R 1/69* (2013.01)

(58) Field of Classification Search
CPC ......... C12N 9/0065; C12N 15/80; C12P 7/22; C12P 7/26; C12P 7/02; C12Y 111/02001; C12R 1/69; C12R 1/68
See application file for complete search history.

(56) References Cited

FOREIGN PATENT DOCUMENTS

| WO | WO 0172999 A1 | 10/2001 |
|---|---|---|
| WO | WO 2015079064 A2 | 6/2015 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Viña -Gonzalez et al., "Focused Directed Evolution of Aryl-Alcohol Oxidase in Saccharomyces cerevisiae by Using Chimeric Signal Peptides", Applied and Environmental Microbiology, Sep. 2015, vol. 81, No. 18, pp. 6461-6462.
Mate et al., "Modification of the peroxgenative:peroxidative activity ratio in the unspecific peroxgenase from Agrocybe aegerita by structure-guided evolution", Protein Engineering, Design and Selection, Mar. 2017, vol. 30, No. 3, pp. 191-198.
Database UniProt, Apr. 29, 2015, "SubName: Full =Unplaced genomic scaffold K443scaffold 20, whole genome shotgun sequence {ECO:0000313:EMBL:KIK06072.I};", retrieved from EB1 accession No. UNIPROT:A0A0C9Y789 Database accession No. A0A0C9Y789 *sequence*.
Extended European Search Report dated Apr. 8, 2019 for EP application No. 16863726.2.
C. R. Otey, et al., "High-Throughput Screen for Aromatic Hydroxylation", Methods in Molecular Biology, vol. 230, 2003, pp. 141-148.
Canada, et al., "Directed Evolution of Toluene ortho-Monooxygenase for Enhanced 1-Naphthol Synthesis and Chlorinated Ethene Degradation", Journal of Bacteriology, vol. 184, Jan. 2002, pp. 344-349.
Cirino, et al., "A Self-Sufficient Peroxide-Driven Hydroxylation Biocatalyst", Angewandte Chemie, vol. 42, Jul. 16, 2003, pp. 3299-3301.
Coelho et al., "Olefin Cyclopropanation via Carbene Transfer Catalyzed by Engineered Cytochrome P450 Enzymes", Science vol. 339, Dec 20, 2012, pp. 307-310.

(Continued)

*Primary Examiner* — Delia M Ramirez
(74) *Attorney, Agent, or Firm* — Womble Bond Dickinson (US) LLP

(57) ABSTRACT

The invention relates to an unspecific peroxygenase of the *Agrocybe aegerita* fungus, obtained by means of directed molecular evolution to facilitate the functional expression thereof in an active, soluble and stable form. The peroxygenase described in the invention shows a significant improvement in the functional expression thereof, improved monooxygenase activity and reduced peroxidase activity, in relation to the monooxygenase and peroxidase activities showed by the unspecific wild-type peroxygenase of *A. aegerita*. The peroxygenase of the invention is useful in chemical processes, including industrial transformations such as the selective oxyfunctionalisation of carbon-hydrogen bonds of various organic compounds.

10 Claims, 13 Drawing Sheets
Specification includes a Sequence Listing.

(56) References Cited

OTHER PUBLICATIONS

D. González-Perez, et al., "Mutagenic Organized Recombination Process by Homologous In Vivo Grouping (MORPHING) for Directed Enzyme Evolution" PLoS ONE, vol. 9, Mar. 10, 2014, e90919.
E. Garcia-Ruiz, et al., "Directed evolution of a temperature-, peroxide- and alkaline pH-tolerant versatile peroxidase", The Biochemical Journal, vol. 441, Jan. 1, 2012, pp. 487-498.
Garikipati, et al., "Whole-Cell Biocatalysis for 1-Naphthol Production in Liquid-Liquid Biphasic Systems", Applied and Environmental Microbiology, vol. 75, Aug. 21, 2009, pp. 6545-6552.
Gomez de Santos, et al., "Selective Synthesis of the Human Drug Metabolite 5"-Hydroxypropranolol by an Evolved Self-Sufficient Peroxygenase", ACS Catalysis, vol. 8, Apr. 19, 2018, pp. 4789-4799.
H. Zhao, et al., "Molecular evolution by staggered extension process (StEP) in vitro recombination", Nature Biotechnology, vol. 16, Jan. 23, 1998, pp: 258-261.
International Search Report dated Sep. 3, 2017, for PCT application No. ES2016/070809.
J. R. Shuster, "Gene Expression in yeast: protein secretion", Current Opinions in Biotechnology, vol. 2, Oct. 1991, pp. 685-690.
Joo, et al., "Laboratory evolution of peroxide-mediated cytochrome P450 hydroxylation", Nature, vol. 399, Jun. 17, 1999, pp. 670-673.
Kluge et al., "Spectrophotometric assay for detection of aromatic hydroxylation catalyzed by fungal haloperoxidase-peroxygenase", Applied Microbiology and Biotechnology, vol. 75, Apr. 5, 2007, pp. 1473-1478.
Kluge, et al., "Hydroxylation of naphthalene by aromatic peroxygenase from Agrocybe aegerita proceeds via oxygen transfer from H2O2 and intermediary epoxidation", Applied Microbiology and Technology, vol. 81, Sep. 25, 2008, pp. 1071-1076.
M. Alcalde, "Mutagenesis Protocols in *Saccharomyces cerevisiae* by In Vivo Overlap Extension", Methods in Molecular Biology, vol. 634, 2010, pp. 3-14.
M.A. Romanos, et al., "Foreign Gene Expression in Yeast: a Review", Yeast, vol. 8, Feb. 14, 1992, pp. 423-488.
Meinhold, et al., "Engineering Cytochrome P450 BM3 for Terminal Alkane Hydroxylation", Advanced Synthesis and Catalysis, vol. 348, Apr. 5, 2006, pp. 763-772.
Molina-Espeja, et al., "Directed Evolution of Unspecific Peroxygenase from Agrocybe aegerita", Applied and Environmental Microbiology, vol. 80, Mar. 28, 2014, pp. 3496-3507.
Molina-Espeja, et al., "Synthesis of 1-Naphthol by a Natural Peroxygenase Engineered by Directed Evolution", Chembiochem: a European Journal of Chemical Biology, vol. 17, Jan. 21, 2016, pp. 341-349.
Needleman, et al., "A General Method Applicable to the Search for Similarities in the Amino Acid Sequence of Two Proteins", Journal of Molecular Biology, vol. 48, Mar. 28,1970, pp. 443-453.
Pearson, et al., "Improved tools for biological sequence comparison", Proceedings of the National Academy of Sciences of the US, vol. 85, Apr. 1988, pp. 2444-2448.
Pecyna, et al. "Molecular characterization of aromatic peroxygenase from Agrocybe aegerita", Applied Microbiology and Technology, vol. 84, May 12, 2009, pp. 885-897.
Rakestraw, et al., "Directed Evolution of a Secretory Leader for the ImprovedExpression of Heterologous Proteins and Full-Length Antibodies in *S. cerevisiae*", Biotechnology and Bioengineering, Aug. 15, 2009, vol. 103, pp. 1192-1201.
Rui, et al., "Saturation Mutagenesis of Toluene ortho-Monooxygenase of *Burkholderia cepacia* G4 for Enhanced 1-Naphthol Synthesis and Chloroform Degradation", Applied and Environmental Microbiology, vol. 70, Jun. 2004, pp. 3246-3252.
S. Kille, et al., "Reducing Codon Redundancy and Screening Effort of Combinatorial Protein Libraries Created by Saturation Mutagenesis", ACS Synthetic Biology, vol. 2, Jun. 15, 2012, pp. 83-92.
Smith, et al., "Identification of Common Molecular Subsequences", Journal of Molecular Biology, vol. 147, Mar. 25, 1981, pp. 195-197.
Smith, et al., "Overlapping Genes and Information Theory", Journal of Theoretical Biology, vol. 91, Jul. 21, 1981, pp. 379-380.
Written Opinion of the International Searching Authority dated Sep. 3, 2017, for PCT application No. ES2016/070809.

\* cited by examiner

SEQUENCE LISTING

<160> NUMBER OF SEQ ID NOS: 66

<210> SEQ ID NO 1
<211> LENGTH: 987
<212> TYPE: DNA
<213> ORGANISM: Agrocybe aegerita
<220> FEATURE:
<221> NAME/KEY: CDS
<222> LOCATION: (1)..(987)

<400> SEQUENCE: 1

```
gag cca gga tta cct cct ggt cct ctc gag aat agc tct gca aag ttg     48
Glu Pro Gly Leu Pro Pro Gly Pro Leu Glu Asn Ser Ser Ala Lys Leu
1               5                   10                  15 gtg aac gac gag gct cac cca tgg aag ccg ctt cga cct ggc gat att     96
Val Asn Asp Glu Ala His Pro Trp Lys Pro Leu Arg Pro Gly Asp Ile
            20                  25                  30 cgt gga cct tgc cct ggt ctc aat act ctg gca tct cac ggg tac ctc    144
Arg Gly Pro Cys Pro Gly Leu Asn Thr Leu Ala Ser His Gly Tyr Leu
        35                  40                  45
```

```
ccg aga aat ggc gtt gca acc ccg gtg caa ata ata aac gcg gtt cag        192
Pro Arg Asn Gly Val Ala Thr Pro Val Gln Ile Ile Asn Ala Val Gln
 50                  55                  60 gaa gga ctc aat ttc gac aat caa gcc gca gtc ttc gcc aca tat gcg        240
Glu Gly Leu Asn Phe Asp Asn Gln Ala Ala Val Phe Ala Thr Tyr Ala
 65                  70                  75                  80 gcc cac ctt gtg gac ggc aat ctc att acg gac ttg ctg agc atc gga        288
Ala His Leu Val Asp Gly Asn Leu Ile Thr Asp Leu Leu Ser Ile Gly
                 85                  90                  95 cgc aag acg cgg ctc act ggg cct gat cca cca ccc ccc gct tcc gtt        336
Arg Lys Thr Arg Leu Thr Gly Pro Asp Pro Pro Pro Pro Ala Ser Val
            100                 105                 110 ggt gga ctc aat gag cat ggc acc ttc gaa ggc gac gcc agt atg acc        384
Gly Gly Leu Asn Glu His Gly Thr Phe Glu Gly Asp Ala Ser Met Thr
        115                 120                 125 cga ggt gac gca ttc ttt ggc aac aac cac gat ttc aat gag acg ctc        432
Arg Gly Asp Ala Phe Phe Gly Asn Asn His Asp Phe Asn Glu Thr Leu
130                 135                 140 ttc gaa cag ttg gtt gac tac agc aac cga ttt gga gga gga aaa tac        480
Phe Glu Gln Leu Val Asp Tyr Ser Asn Arg Phe Gly Gly Gly Lys Tyr
145                 150                 155                 160 aat ctt acc gtc gcg ggg gag ctc cgt ttc aag cgc att caa gac tcc        528
Asn Leu Thr Val Ala Gly Glu Leu Arg Phe Lys Arg Ile Gln Asp Ser
                165                 170                 175 att gcg acc aac ccc aat ttc tcc ttt gtt gac ttt agg ttc ttt act        576
Ile Ala Thr Asn Pro Asn Phe Ser Phe Val Asp Phe Arg Phe Phe Thr
            180                 185                 190 gct tac ggc gag acc acc ttc ccc gcg aat ctt ttt gtg gat ggg cgc        624
Ala Tyr Gly Glu Thr Thr Phe Pro Ala Asn Leu Phe Val Asp Gly Arg
        195                 200                 205 agg gac gac ggc cag cta gat atg gat gct gca cgg agt ttt ttc caa        672
Arg Asp Asp Gly Gln Leu Asp Met Asp Ala Ala Arg Ser Phe Phe Gln
210                 215                 220 ttc agc cgt atg cct gac gat ttc ttc cgc gca ccc agc ccg aga agt        720
Phe Ser Arg Met Pro Asp Asp Phe Phe Arg Ala Pro Ser Pro Arg Ser
225                 230                 235                 240 ggc aca gga gtc gag gta gtt ata cag gct cat cct atg cag ccc gga        768
Gly Thr Gly Val Glu Val Val Ile Gln Ala His Pro Met Gln Pro Gly
                245                 250                 255 aga aat gtc ggc aag atc aac agc tac acc gtc gac cca aca tcc tct        816
Arg Asn Val Gly Lys Ile Asn Ser Tyr Thr Val Asp Pro Thr Ser Ser
            260                 265                 270 gac ttt tcc acc ccc tgc ttg atg tac gag aaa ttc gtc aac ata acg        864
Asp Phe Ser Thr Pro Cys Leu Met Tyr Glu Lys Phe Val Asn Ile Thr
        275                 280                 285 gtc aag tca ctc tac ccg aat ccg acg gtg cag ctt cgc aaa gcc ctt        912
Val Lys Ser Leu Tyr Pro Asn Pro Thr Val Gln Leu Arg Lys Ala Leu
290                 295                 300 aat acg aat ctc gat ttc ttc ttc cag gga gtc gcc gct gga tgt acc        960
Asn Thr Asn Leu Asp Phe Phe Phe Gln Gly Val Ala Ala Gly Cys Thr
305                 310                 315                 320 cag gtc ttc cca tac ggg cga gat tga                                   987
Gln Val Phe Pro Tyr Gly Arg Asp
                325

<210> SEQ ID NO 2
<211> LENGTH: 328
<212> TYPE: PRT
<213> ORGANISM: Agrocybe aegerita
```

<400> SEQUENCE: 2

```
Glu Pro Gly Leu Pro Gly Pro Leu Glu Asn Ser Ser Ala Lys Leu
1               5                   10                  15

Val Asn Asp Glu Ala His Pro Trp Lys Pro Leu Arg Pro Gly Asp Ile
            20                  25                  30

Arg Gly Pro Cys Pro Gly Leu Asn Thr Leu Ala Ser His Gly Tyr Leu
                35                  40                  45

Pro Arg Asn Gly Val Ala Thr Pro Val Gln Ile Ile Asn Ala Val Gln
        50                  55                  60

Glu Gly Leu Asn Phe Asp Asn Gln Ala Ala Val Phe Ala Thr Tyr Ala
65                  70                  75                  80

Ala His Leu Val Asp Gly Asn Leu Ile Thr Asp Leu Leu Ser Ile Gly
                85                  90                  95

Arg Lys Thr Arg Leu Thr Gly Pro Asp Pro Pro Pro Ala Ser Val
            100                 105                 110

Gly Gly Leu Asn Glu His Gly Thr Phe Glu Gly Asp Ala Ser Met Thr
                115                 120                 125

Arg Gly Asp Ala Phe Phe Gly Asn Asn His Asp Phe Asn Glu Thr Leu
130                 135                 140

Phe Glu Gln Leu Val Asp Tyr Ser Asn Arg Phe Gly Gly Lys Tyr
145                 150                 155                 160

Asn Leu Thr Val Ala Gly Glu Leu Arg Phe Lys Arg Ile Gln Asp Ser
                165                 170                 175

Ile Ala Thr Asn Pro Asn Phe Ser Phe Val Asp Phe Arg Phe Phe Thr
                180                 185                 190

Ala Tyr Gly Glu Thr Thr Phe Pro Ala Asn Leu Phe Val Asp Gly Arg
                195                 200                 205

Arg Asp Asp Gly Gln Leu Asp Met Asp Ala Ala Arg Ser Phe Gln
210                 215                 220

Phe Ser Arg Met Pro Asp Asp Phe Phe Arg Ala Pro Ser Pro Arg Ser
225                 230                 235                 240

Gly Thr Gly Val Glu Val Val Ile Gln Ala His Pro Met Gln Pro Gly
                245                 250                 255

Arg Asn Val Gly Lys Ile Asn Ser Tyr Thr Val Asp Pro Thr Ser Ser
                260                 265                 270

Asp Phe Ser Thr Pro Cys Leu Met Tyr Glu Lys Phe Val Asn Ile Thr
                275                 280                 285

Val Lys Ser Leu Tyr Pro Asn Pro Thr Val Gln Leu Arg Lys Ala Leu
            290                 295                 300

Asn Thr Asn Leu Asp Phe Phe Phe Gln Gly Val Ala Ala Gly Cys Thr
305                 310                 315                 320

Gln Val Phe Pro Tyr Gly Arg Asp
                325
```

<210> SEQ ID NO 3
<211> LENGTH: 1116
<212> TYPE: DNA
<213> ORGANISM: Agrocybe aegerita
<220> FEATURE:
<221> NAME/KEY: CDS
<222> LOCATION: (1)..(1113)
<220> FEATURE:
<221> NAME/KEY: mat_peptide
<222> LOCATION: (130)..(1116)

<400> SEQUENCE: 3

```
atg aaa tat ttt ccc ctg ttc cca acc ttg gtc tac gca gtg ggg gtc     48
Met Lys Tyr Phe Pro Leu Phe Pro Thr Leu Val Tyr Ala Val Gly Val
        -40             -35             -30 gtt gct ttt cct gac tac gcc tca ttg gcc ggc ctc agc cag cag gaa     96
Val Ala Phe Pro Asp Tyr Ala Ser Leu Ala Gly Leu Ser Gln Gln Glu
    -25             -20             -15 ttg gac gct ata atc cca aca ctc gag gcc cga gag cca gga tta cct    144
Leu Asp Ala Ile Ile Pro Thr Leu Glu Ala Arg Glu Pro Gly Leu Pro
-10              -5              -1   1               5 cct ggt cct ctc gag aat agc tct gca aag ttg gtg aac gac gag gct    192
Pro Gly Pro Leu Glu Asn Ser Ser Ala Lys Leu Val Asn Asp Glu Ala
                10              15              20 cac cca tgg aag ccg ctt cga cct ggc gat att cgt gga cct tgc cct    240
His Pro Trp Lys Pro Leu Arg Pro Gly Asp Ile Arg Gly Pro Cys Pro
            25              30              35 ggt ctc aat act ctg gca tct cac ggg tac ctc ccg aga aat ggc gtt    288
Gly Leu Asn Thr Leu Ala Ser His Gly Tyr Leu Pro Arg Asn Gly Val
        40              45              50 gca acc ccg gtg caa ata ata aac gcg gtt cag gaa gga ctc aat ttc    336
Ala Thr Pro Val Gln Ile Ile Asn Ala Val Gln Glu Gly Leu Asn Phe
    55              60              65 gac aat caa gcc gca gtc ttc gcc aca tat gcg gcc cac ctt gtg gac    384
Asp Asn Gln Ala Ala Val Phe Ala Thr Tyr Ala Ala His Leu Val Asp
70              75              80              85 ggc aat ctc att acg gac ttg ctg agc atc gga cgc aag acg cgg ctc    432
Gly Asn Leu Ile Thr Asp Leu Leu Ser Ile Gly Arg Lys Thr Arg Leu
                90              95              100 act ggg cct gat cca cca ccc ccc gct tcc gtt ggt gga ctc aat gag    480
Thr Gly Pro Asp Pro Pro Pro Pro Ala Ser Val Gly Gly Leu Asn Glu
            105             110             115 cat ggc acc ttc gaa ggc gac gcc agt atg acc cga ggt gac gca ttc    528
His Gly Thr Phe Glu Gly Asp Ala Ser Met Thr Arg Gly Asp Ala Phe
        120             125             130 ttt ggc aac aac cac gat ttc aat gag acg ctc ttc gaa cag ttg gtt    576
Phe Gly Asn Asn His Asp Phe Asn Glu Thr Leu Phe Glu Gln Leu Val
    135             140             145 gac tac agc aac cga ttt gga gga gga aaa tac aat ctt acc gtc gcg    624
Asp Tyr Ser Asn Arg Phe Gly Gly Gly Lys Tyr Asn Leu Thr Val Ala
150             155             160             165 ggg gag ctc cgt ttc aag cgc att caa gac tcc att gcg acc aac ccc    672
Gly Glu Leu Arg Phe Lys Arg Ile Gln Asp Ser Ile Ala Thr Asn Pro
                170             175             180 aat ttc tcc ttt gtt gac ttt agg ttc ttt act gct tac ggc gag acc    720
Asn Phe Ser Phe Val Asp Phe Arg Phe Phe Thr Ala Tyr Gly Glu Thr
            185             190             195 acc ttc ccc gcg aat ctt ttt gtg gat ggg cgc agg gac gac ggc cag    768
Thr Phe Pro Ala Asn Leu Phe Val Asp Gly Arg Arg Asp Asp Gly Gln
        200             205             210 cta gat atg gat gct gca cgg agt ttt ttc caa ttc agc cgt atg cct    816
Leu Asp Met Asp Ala Ala Arg Ser Phe Phe Gln Phe Ser Arg Met Pro
    215             220             225 gac gat ttc ttc cgc gca ccc agc ccg aga agt gga aca gga gtc gag    864
Asp Asp Phe Phe Arg Ala Pro Ser Pro Arg Ser Gly Thr Gly Val Glu
230             235             240             245 gta gtt ata cag gct cat cct atg cag ccc gga aga aat gtc ggc aag    912
Val Val Ile Gln Ala His Pro Met Gln Pro Gly Arg Asn Val Gly Lys
                250             255             260 atc aac agc tac acc gtc gac cca aca tcc tct gac ttt tcc acc ccc    960
Ile Asn Ser Tyr Thr Val Asp Pro Thr Ser Ser Asp Phe Ser Thr Pro
            265             270             275
```

```
tgc ttg atg tac gag aaa ttc gtc aac ata acg gtc aag tca ctc tac      1008
Cys Leu Met Tyr Glu Lys Phe Val Asn Ile Thr Val Lys Ser Leu Tyr
        280                 285                 290 ccg aat ccg acg gtg cag ctt cgc aaa gcc ctt aat acg aat ctc gat      1056
Pro Asn Pro Thr Val Gln Leu Arg Lys Ala Leu Asn Thr Asn Leu Asp
295                 300                 305 ttc ttc ttc cag gga gtc gcc gct gga tgt acc cag gtc ttc cca tac      1104
Phe Phe Phe Gln Gly Val Ala Ala Gly Cys Thr Gln Val Phe Pro Tyr
310                 315                 320                 325 ggg cga gat tga                                                       1116
Gly Arg Asp <210> SEQ ID NO 4
<211> LENGTH: 371
<212> TYPE: PRT
<213> ORGANISM: Agrocybe aegerita

<400> SEQUENCE: 4

Met Lys Tyr Phe Pro Leu Phe Pro Thr Leu Val Tyr Ala Val Gly Val
            -40                 -35                 -30

Val Ala Phe Pro Asp Tyr Ala Ser Leu Ala Gly Leu Ser Gln Gln Glu
        -25                 -20                 -15

Leu Asp Ala Ile Ile Pro Thr Leu Glu Ala Arg Glu Pro Gly Leu Pro
    -10                  -5              -1   1                   5

Pro Gly Pro Leu Glu Asn Ser Ser Ala Lys Leu Val Asn Asp Glu Ala
                    10                  15                  20

His Pro Trp Lys Pro Leu Arg Pro Gly Asp Ile Arg Gly Pro Cys Pro
                25                  30                  35

Gly Leu Asn Thr Leu Ala Ser His Gly Tyr Leu Pro Arg Asn Gly Val
            40                  45                  50

Ala Thr Pro Val Gln Ile Ile Asn Ala Val Gln Glu Gly Leu Asn Phe
        55                  60                  65

Asp Asn Gln Ala Ala Val Phe Ala Thr Tyr Ala Ala His Leu Val Asp
70                  75                  80                  85

Gly Asn Leu Ile Thr Asp Leu Leu Ser Ile Gly Arg Lys Thr Arg Leu
                90                  95                  100

Thr Gly Pro Asp Pro Pro Pro Ala Ser Val Gly Gly Leu Asn Glu
            105                 110                 115

His Gly Thr Phe Glu Gly Asp Ala Ser Met Thr Arg Gly Asp Ala Phe
            120                 125                 130

Phe Gly Asn Asn His Asp Phe Asn Glu Thr Leu Phe Glu Gln Leu Val
        135                 140                 145

Asp Tyr Ser Asn Arg Phe Gly Gly Lys Tyr Asn Leu Thr Val Ala
150                 155                 160                 165

Gly Glu Leu Arg Phe Lys Arg Ile Gln Asp Ser Ile Ala Thr Asn Pro
                170                 175                 180

Asn Phe Ser Phe Val Asp Phe Arg Phe Thr Ala Tyr Gly Glu Thr
            185                 190                 195

Thr Phe Pro Ala Asn Leu Phe Val Asp Gly Arg Arg Asp Asp Gly Gln
        200                 205                 210

Leu Asp Met Asp Ala Ala Arg Ser Phe Gln Phe Ser Arg Met Pro
    215                 220                 225

Asp Asp Phe Phe Arg Ala Pro Ser Pro Arg Ser Gly Thr Gly Val Glu
230                 235                 240                 245

Val Val Ile Gln Ala His Pro Met Gln Pro Gly Arg Asn Val Gly Lys
```

|  |  |  |  | 250 |  |  |  | 255 |  |  |  | 260 |  |  |  |
|---|---|---|---|---|---|---|---|---|---|---|---|---|---|---|---|
| Ile | Asn | Ser | Tyr | Thr | Val | Asp | Pro | Thr | Ser | Ser | Asp | Phe | Ser | Thr | Pro |
|  |  |  |  | 265 |  |  |  |  | 270 |  |  |  | 275 |  |  |
| Cys | Leu | Met | Tyr | Glu | Lys | Phe | Val | Asn | Ile | Thr | Val | Lys | Ser | Leu | Tyr |
|  |  |  | 280 |  |  |  |  | 285 |  |  |  |  | 290 |  |  |
| Pro | Asn | Pro | Thr | Val | Gln | Leu | Arg | Lys | Ala | Leu | Asn | Thr | Asn | Leu | Asp |
|  | 295 |  |  |  |  |  |  | 300 |  |  |  |  | 305 |  |  |
| Phe | Phe | Phe | Gln | Gly | Val | Ala | Ala | Gly | Cys | Thr | Gln | Val | Phe | Pro | Tyr |
| 310 |  |  |  |  | 315 |  |  |  |  | 320 |  |  |  |  | 325 |
| Gly | Arg | Asp |

<210> SEQ ID NO 5
<211> LENGTH: 1116
<212> TYPE: DNA
<213> ORGANISM: Agrocybe aegerita
<220> FEATURE:
<221> NAME/KEY: CDS
<222> LOCATION: (1)..(1113)
<220> FEATURE:
<221> NAME/KEY: mat_peptide
<222> LOCATION: (130)..(1116)

<400> SEQUENCE: 5

| atg | aaa | tat | ttt | ccc | ctg | ttc | cca | acc | ttg | gtc | tac | gca | gtg | ggg | gtc | 48 |
|---|---|---|---|---|---|---|---|---|---|---|---|---|---|---|---|---|
| Met | Lys | Tyr | Phe | Pro | Leu | Phe | Pro | Thr | Leu | Val | Tyr | Ala | Val | Gly | Val |  |
|  | -40 |  |  |  |  | -35 |  |  |  |  | -30 |  |  |  |  |  |

| gtt | gct | ttt | cct | gac | tac | gcc | tca | ttg | gcc | ggc | ctc | agc | cag | cag | gaa | 96 |
|---|---|---|---|---|---|---|---|---|---|---|---|---|---|---|---|---|
| Val | Ala | Phe | Pro | Asp | Tyr | Ala | Ser | Leu | Ala | Gly | Leu | Ser | Gln | Gln | Glu |  |
|  | -25 |  |  |  |  | -20 |  |  |  |  | -15 |  |  |  |  |  |

| ttg | gac | gct | ata | atc | cca | aca | ctc | gag | gcc | cga | gag | cca | gga | tta | cct | 144 |
|---|---|---|---|---|---|---|---|---|---|---|---|---|---|---|---|---|
| Leu | Asp | Ala | Ile | Ile | Pro | Thr | Leu | Glu | Ala | Arg | Glu | Pro | Gly | Leu | Pro |  |
|  | -10 |  |  |  |  | -5 |  |  |  |  | -1 | 1 |  |  | 5 |  |

| cct | ggt | cct | ctc | gag | aat | agc | tct | gca | aag | ttg | gtg | aac | gac | gag | gct | 192 |
|---|---|---|---|---|---|---|---|---|---|---|---|---|---|---|---|---|
| Pro | Gly | Pro | Leu | Glu | Asn | Ser | Ser | Ala | Lys | Leu | Val | Asn | Asp | Glu | Ala |  |
|  |  |  |  | 10 |  |  |  |  | 15 |  |  |  |  | 20 |  |  |

| cac | cca | tgg | aag | ccg | ctt | cga | cct | ggc | gat | att | cgt | gga | cct | tgc | cct | 240 |
|---|---|---|---|---|---|---|---|---|---|---|---|---|---|---|---|---|
| His | Pro | Trp | Lys | Pro | Leu | Arg | Pro | Gly | Asp | Ile | Arg | Gly | Pro | Cys | Pro |  |
|  |  |  |  | 25 |  |  |  |  | 30 |  |  |  |  | 35 |  |  |

| ggt | ctc | aat | act | ctg | gca | tct | cac | ggg | tac | ctc | ccg | aga | aat | ggc | gtt | 288 |
|---|---|---|---|---|---|---|---|---|---|---|---|---|---|---|---|---|
| Gly | Leu | Asn | Thr | Leu | Ala | Ser | His | Gly | Tyr | Leu | Pro | Arg | Asn | Gly | Val |  |
|  |  |  | 40 |  |  |  |  | 45 |  |  |  |  | 50 |  |  |  |

| gca | acc | ccg | gtg | caa | ata | ata | aac | gcg | gtt | cag | gaa | gga | ctc | aat | ttc | 336 |
|---|---|---|---|---|---|---|---|---|---|---|---|---|---|---|---|---|
| Ala | Thr | Pro | Val | Gln | Ile | Ile | Asn | Ala | Val | Gln | Glu | Gly | Leu | Asn | Phe |  |
|  | 55 |  |  |  |  | 60 |  |  |  |  | 65 |  |  |  |  |  |

| gac | aat | caa | gcc | gca | gtc | ttc | gcc | aca | tat | gcg | gcc | cac | ctt | gtg | gac | 384 |
|---|---|---|---|---|---|---|---|---|---|---|---|---|---|---|---|---|
| Asp | Asn | Gln | Ala | Ala | Val | Phe | Ala | Thr | Tyr | Ala | Ala | His | Leu | Val | Asp |  |
| 70 |  |  |  |  | 75 |  |  |  |  | 80 |  |  |  |  | 85 |  |

| ggc | aat | ctc | att | acg | gac | ttg | ctg | agc | atc | gga | cgc | aag | acg | cgg | ctc | 432 |
|---|---|---|---|---|---|---|---|---|---|---|---|---|---|---|---|---|
| Gly | Asn | Leu | Ile | Thr | Asp | Leu | Leu | Ser | Ile | Gly | Arg | Lys | Thr | Arg | Leu |  |
|  |  |  |  | 90 |  |  |  |  | 95 |  |  |  |  | 100 |  |  |

| act | ggg | cct | gat | cca | cca | ccc | ccc | gct | tcc | gtt | ggt | gga | ctc | aat | gag | 480 |
|---|---|---|---|---|---|---|---|---|---|---|---|---|---|---|---|---|
| Thr | Gly | Pro | Asp | Pro | Pro | Pro | Pro | Ala | Ser | Val | Gly | Gly | Leu | Asn | Glu |  |
|  |  |  | 105 |  |  |  |  | 110 |  |  |  |  | 115 |  |  |  |

| cat | ggc | acc | ttc | gaa | ggc | gac | gcc | agt | atg | acc | cga | ggt | gac | gca | ttc | 528 |
|---|---|---|---|---|---|---|---|---|---|---|---|---|---|---|---|---|
| His | Gly | Thr | Phe | Glu | Gly | Asp | Ala | Ser | Met | Thr | Arg | Gly | Asp | Ala | Phe |  |
|  |  |  | 120 |  |  |  |  | 125 |  |  |  |  | 130 |  |  |  |

| ttt | ggc | aac | aac | cac | gat | ttc | aat | gag | acg | ctc | ttc | gaa | cag | ttg | gtt | 576 |
|---|---|---|---|---|---|---|---|---|---|---|---|---|---|---|---|---|
| Phe | Gly | Asn | Asn | His | Asp | Phe | Asn | Glu | Thr | Leu | Phe | Glu | Gln | Leu | Val |  |
|  |  |  | 135 |  |  |  |  | 140 |  |  |  |  | 145 |  |  |  |

| gac | tac | agc | aac | cga | ttt | gga | gga | gga | aaa | tac | aat | ctt | acc | gtc | gcg | 624 |
|---|---|---|---|---|---|---|---|---|---|---|---|---|---|---|---|---|

```
Asp Tyr Ser Asn Arg Phe Gly Gly Gly Lys Tyr Asn Leu Thr Val Ala
150                 155                 160                 165 ggg gag ctc cgt ttc aag cgc att caa gac tcc att gcg acc aac ccc      672
Gly Glu Leu Arg Phe Lys Arg Ile Gln Asp Ser Ile Ala Thr Asn Pro
                170                 175                 180 aat ttc tcc ttt gtt gac ttt agg ttc ttt act gct tac ggc gag acc      720
Asn Phe Ser Phe Val Asp Phe Arg Phe Phe Thr Ala Tyr Gly Glu Thr
            185                 190                 195 acc ttc ccc gcg aat ctt ttt gtg gat ggg cgc agg gac gac ggc cag      768
Thr Phe Pro Ala Asn Leu Phe Val Asp Gly Arg Arg Asp Asp Gly Gln
        200                 205                 210 cta gat atg gat gct gca cgg agt ttt ttc caa ttc agc cgt atg cct      816
Leu Asp Met Asp Ala Ala Arg Ser Phe Phe Gln Phe Ser Arg Met Pro
    215                 220                 225 gac gat ttc ttc cgc gca ccc agc ccg aga agt ggc aca gga gtc gag      864
Asp Asp Phe Phe Arg Ala Pro Ser Pro Arg Ser Gly Thr Gly Val Glu
230                 235                 240                 245 gta gtt ata cag gct cat cct atg cag ccc gga aga aat gtc ggc aag      912
Val Val Ile Gln Ala His Pro Met Gln Pro Gly Arg Asn Val Gly Lys
                250                 255                 260 atc aac agc tac acc gtc gac cca aca tcc tct gac ttt tcc acc ccc      960
Ile Asn Ser Tyr Thr Val Asp Pro Thr Ser Ser Asp Phe Ser Thr Pro
            265                 270                 275 tgc ttg atg tac gag aaa ttc gtc aac ata acg gtc aag tca ctc tac     1008
Cys Leu Met Tyr Glu Lys Phe Val Asn Ile Thr Val Lys Ser Leu Tyr
        280                 285                 290 ccg aat ccg acg gtg cag ctt cgc aaa gcc ctt aat acg aat ctc gat     1056
Pro Asn Pro Thr Val Gln Leu Arg Lys Ala Leu Asn Thr Asn Leu Asp
    295                 300                 305 ttc ttc ttc cag gga gtc gcc gct gga tgt acc cag gtc ttc cca tac     1104
Phe Phe Phe Gln Gly Val Ala Ala Gly Cys Thr Gln Val Phe Pro Tyr
310                 315                 320                 325 ggg cga gat tga                                                     1116
Gly Arg Asp <210> SEQ ID NO 6
<211> LENGTH: 371
<212> TYPE: PRT
<213> ORGANISM: Agrocybe aegerita

<400> SEQUENCE: 6

Met Lys Tyr Phe Pro Leu Phe Pro Thr Leu Val Tyr Ala Val Gly Val
            -40                 -35                 -30

Val Ala Phe Pro Asp Tyr Ala Ser Leu Ala Gly Leu Ser Gln Gln Glu
        -25                 -20                 -15

Leu Asp Ala Ile Ile Pro Thr Leu Glu Ala Arg Glu Pro Gly Leu Pro
    -10                 -5                  -1  1               5

Pro Gly Pro Leu Glu Asn Ser Ser Ala Lys Leu Val Asn Asp Glu Ala
                10                  15                  20

His Pro Trp Lys Pro Leu Arg Pro Gly Asp Ile Arg Gly Pro Cys Pro
            25                  30                  35

Gly Leu Asn Thr Leu Ala Ser His Gly Tyr Leu Pro Arg Asn Gly Val
        40                  45                  50

Ala Thr Pro Val Gln Ile Ile Asn Ala Val Gln Glu Gly Leu Asn Phe
    55                  60                  65

Asp Asn Gln Ala Ala Val Phe Ala Thr Tyr Ala Ala His Leu Val Asp
70                  75                  80                  85

Gly Asn Leu Ile Thr Asp Leu Leu Ser Ile Gly Arg Lys Thr Arg Leu
```

|   |   |   | 90 |   |   |   | 95 |   |   |   | 100 |   |   |

Thr Gly Pro Asp Pro Pro Pro Ala Ser Val Gly Gly Leu Asn Glu
              105                 110                 115

His Gly Thr Phe Glu Gly Asp Ala Ser Met Thr Arg Gly Asp Ala Phe
        120                 125                 130

Phe Gly Asn Asn His Asp Phe Asn Glu Thr Leu Phe Glu Gln Leu Val
        135                 140                 145

Asp Tyr Ser Asn Arg Phe Gly Gly Lys Tyr Asn Leu Thr Val Ala
150                 155                 160                 165

Gly Glu Leu Arg Phe Lys Arg Ile Gln Asp Ser Ile Ala Thr Asn Pro
                170                 175                 180

Asn Phe Ser Phe Val Asp Phe Arg Phe Phe Thr Ala Tyr Gly Glu Thr
            185                 190                 195

Thr Phe Pro Ala Asn Leu Phe Val Asp Gly Arg Arg Asp Asp Gly Gln
            200                 205                 210

Leu Asp Met Asp Ala Ala Arg Ser Phe Phe Gln Phe Ser Arg Met Pro
        215                 220                 225

Asp Asp Phe Phe Arg Ala Pro Ser Pro Arg Ser Gly Thr Gly Val Glu
230                 235                 240                 245

Val Val Ile Gln Ala His Pro Met Gln Pro Gly Arg Asn Val Gly Lys
                250                 255                 260

Ile Asn Ser Tyr Thr Val Asp Pro Thr Ser Ser Asp Phe Ser Thr Pro
            265                 270                 275

Cys Leu Met Tyr Glu Lys Phe Val Asn Ile Thr Val Lys Ser Leu Tyr
        280                 285                 290

Pro Asn Pro Thr Val Gln Leu Arg Lys Ala Leu Asn Thr Asn Leu Asp
        295                 300                 305

Phe Phe Phe Gln Gly Val Ala Ala Gly Cys Thr Gln Val Phe Pro Tyr
310                 315                 320                 325

Gly Arg Asp

<210> SEQ ID NO 7
<211> LENGTH: 987
<212> TYPE: DNA
<213> ORGANISM: Artificial Sequence
<220> FEATURE:
<223> OTHER INFORMATION: wt-JaWa Variant
<220> FEATURE:
<221> NAME/KEY: CDS
<222> LOCATION: (1)..(987)

<400> SEQUENCE: 7 gag cca gga tta cct cct ggt cct ctc gag aat agc tct gca aag ttg    48
Glu Pro Gly Leu Pro Pro Gly Pro Leu Glu Asn Ser Ser Ala Lys Leu
1               5                   10                  15 gtg aac gac gag gct cac cca tgg aag ccg ctt cga cct ggc gat att    96
Val Asn Asp Glu Ala His Pro Trp Lys Pro Leu Arg Pro Gly Asp Ile
            20                  25                  30 cgt gga cct tgc cct ggt ctc aat act ctg gca tct cac ggg tac ctc    144
Arg Gly Pro Cys Pro Gly Leu Asn Thr Leu Ala Ser His Gly Tyr Leu
        35                  40                  45 ccg aga aat ggc gtt gca acc ccg gtg caa ata ata aac gcg gtt cag    192
Pro Arg Asn Gly Val Ala Thr Pro Val Gln Ile Ile Asn Ala Val Gln
    50                  55                  60 gaa gga ctc aat ttc gac aat caa gcc gca gtc ttc gcc aca tat gcg    240
Glu Gly Leu Asn Phe Asp Asn Gln Ala Ala Val Phe Ala Thr Tyr Ala
65                  70                  75                  80

| | | |
|---|---|---|
| gcc cac ctt gtg gac ggc aat ctc att acg gac ttg ctg agc atc gga<br>Ala His Leu Val Asp Gly Asn Leu Ile Thr Asp Leu Leu Ser Ile Gly<br>                                  85                    90                    95 | 288 |
| cgc aag acg cgg ctc act ggg cct gat cca cca ccc ccc gct tcc gtt<br>Arg Lys Thr Arg Leu Thr Gly Pro Asp Pro Pro Pro Pro Ala Ser Val<br>                              100                   105                  110 | 336 |
| ggt gga ctc aat gag cat ggc acc ttc gaa ggc gac gcc agt atg acc<br>Gly Gly Leu Asn Glu His Gly Thr Phe Glu Gly Asp Ala Ser Met Thr<br>                   115                   120                   125 | 384 |
| cga ggt gac gca ttc ttt ggc aac aac cac gat ttc aat gag acg ctc<br>Arg Gly Asp Ala Phe Phe Gly Asn Asn His Asp Phe Asn Glu Thr Leu<br>          130                   135                   140 | 432 |
| ttc gaa cag ttg gtt gac tac agc aac cga ttt gga gga gga aaa tac<br>Phe Glu Gln Leu Val Asp Tyr Ser Asn Arg Phe Gly Gly Gly Lys Tyr<br>145                   150                   155                   160 | 480 |
| aat ctt acc gtc gcg ggg gag ctc cgt ttc aag cgc att caa gac tcc<br>Asn Leu Thr Val Ala Gly Glu Leu Arg Phe Lys Arg Ile Gln Asp Ser<br>                   165                   170                   175 | 528 |
| att gcg acc aac ccc aat ttc tcc ttt gtt gac ttt agg ttc ttt act<br>Ile Ala Thr Asn Pro Asn Phe Ser Phe Val Asp Phe Arg Phe Phe Thr<br>          180                   185                   190 | 576 |
| gct tac ggc gag acc acc ttc ccc gcg aat ctt ttt gtg gat ggg cgc<br>Ala Tyr Gly Glu Thr Thr Phe Pro Ala Asn Leu Phe Val Asp Gly Arg<br>                   195                   200                   205 | 624 |
| agg gac gac ggc cag cta gat atg gat gct gca cgg agt ttt ttc caa<br>Arg Asp Asp Gly Gln Leu Asp Met Asp Ala Ala Arg Ser Phe Phe Gln<br>          210                   215                   220 | 672 |
| ttc agc cgt atg cct gac gat ttc ttc cgc gca ccc agc ccg aga agt<br>Phe Ser Arg Met Pro Asp Asp Phe Phe Arg Ala Pro Ser Pro Arg Ser<br>225                   230                   235                   240 | 720 |
| gac aca gga gtc gag gta gtt ata cag gct cat cct atg cag ccc gga<br>Asp Thr Gly Val Glu Val Val Ile Gln Ala His Pro Met Gln Pro Gly<br>                   245                   250                   255 | 768 |
| aaa aat gtc ggc aag atc aac agc tac acc gtc gac cca aca tcc tct<br>Lys Asn Val Gly Lys Ile Asn Ser Tyr Thr Val Asp Pro Thr Ser Ser<br>          260                   265                   270 | 816 |
| gac ttt tcc acc ccc tgc ttg atg tac gag aaa ttc gtc aac ata acg<br>Asp Phe Ser Thr Pro Cys Leu Met Tyr Glu Lys Phe Val Asn Ile Thr<br>                   275                   280                   285 | 864 |
| gtc aag tca ctc tac ccg aat ccg acg gtg cag ctt cgc aaa gcc ctt<br>Val Lys Ser Leu Tyr Pro Asn Pro Thr Val Gln Leu Arg Lys Ala Leu<br>          290                   295                   300 | 912 |
| aat acg aat ctc gat ttc ttc ttc cag gga gtc gcc gct gga tgt acc<br>Asn Thr Asn Leu Asp Phe Phe Phe Gln Gly Val Ala Ala Gly Cys Thr<br>305                   310                   315                   320 | 960 |
| cag gtc ttc cca tac ggg cga gat tga<br>Gln Val Phe Pro Tyr Gly Arg Asp<br>                   325 | 987 |

<210> SEQ ID NO 8
<211> LENGTH: 328
<212> TYPE: PRT
<213> ORGANISM: Artificial Sequence
<220> FEATURE:
<223> OTHER INFORMATION: Synthetic Construct

<400> SEQUENCE: 8

Glu Pro Gly Leu Pro Pro Gly Pro Leu Glu Asn Ser Ser Ala Lys Leu
1                   5                    10                   15

Val Asn Asp Glu Ala His Pro Trp Lys Pro Leu Arg Pro Gly Asp Ile
                 20                   25                   30

Arg Gly Pro Cys Pro Gly Leu Asn Thr Leu Ala Ser His Gly Tyr Leu
            35                  40                  45

Pro Arg Asn Gly Val Ala Thr Pro Val Gln Ile Ile Asn Ala Val Gln
 50                  55                  60

Glu Gly Leu Asn Phe Asp Asn Gln Ala Ala Val Phe Ala Thr Tyr Ala
 65                  70                  75                  80

Ala His Leu Val Asp Gly Asn Leu Ile Thr Asp Leu Leu Ser Ile Gly
                85                  90                  95

Arg Lys Thr Arg Leu Thr Gly Pro Asp Pro Pro Pro Ala Ser Val
            100                 105                 110

Gly Gly Leu Asn Glu His Gly Thr Phe Glu Gly Asp Ala Ser Met Thr
            115                 120                 125

Arg Gly Asp Ala Phe Phe Gly Asn Asn His Asp Phe Asn Glu Thr Leu
130                 135                 140

Phe Glu Gln Leu Val Asp Tyr Ser Asn Arg Phe Gly Gly Lys Tyr
145                 150                 155                 160

Asn Leu Thr Val Ala Gly Glu Leu Arg Phe Lys Arg Ile Gln Asp Ser
                165                 170                 175

Ile Ala Thr Asn Pro Asn Phe Ser Phe Val Asp Phe Arg Phe Phe Thr
                180                 185                 190

Ala Tyr Gly Glu Thr Thr Phe Pro Ala Asn Leu Phe Val Asp Gly Arg
            195                 200                 205

Arg Asp Asp Gly Gln Leu Asp Met Asp Ala Ala Arg Ser Phe Phe Gln
210                 215                 220

Phe Ser Arg Met Pro Asp Phe Phe Arg Ala Pro Ser Pro Arg Ser
225                 230                 235                 240

Asp Thr Gly Val Glu Val Val Ile Gln Ala His Pro Met Gln Pro Gly
                245                 250                 255

Lys Asn Val Gly Lys Ile Asn Ser Tyr Thr Val Asp Pro Thr Ser Ser
                260                 265                 270

Asp Phe Ser Thr Pro Cys Leu Met Tyr Glu Lys Phe Val Asn Ile Thr
            275                 280                 285

Val Lys Ser Leu Tyr Pro Asn Pro Thr Val Gln Leu Arg Lys Ala Leu
290                 295                 300

Asn Thr Asn Leu Asp Phe Phe Phe Gln Gly Val Ala Ala Gly Cys Thr
305                 310                 315                 320

Gln Val Phe Pro Tyr Gly Arg Asp
            325

<210> SEQ ID NO 9
<211> LENGTH: 1116
<212> TYPE: DNA
<213> ORGANISM: Artificial Sequence
<220> FEATURE:
<223> OTHER INFORMATION: Wt-JaWa variant with wild signal peptide
<220> FEATURE:
<221> NAME/KEY: CDS
<222> LOCATION: (1)..(1113)
<220> FEATURE:
<221> NAME/KEY: mat_peptide
<222> LOCATION: (130)..(1116)

<400> SEQUENCE: 9 atg aaa tat ttt ccc ctg ttc cca acc ttg gtc ttc gca gcg agg gtc      48
Met Lys Tyr Phe Pro Leu Phe Pro Thr Leu Val Phe Ala Ala Arg Val
            -40                 -35                 -30 gtt gct ttt cct gcc tac gcc tca ttg gcc ggc ctc agc cag cag gaa      96

```
Val Ala Phe Pro Ala Tyr Ala Ser Leu Ala Gly Leu Ser Gln Gln Glu
        -25             -20             -15 ttg gac gct ata atc cca aca ctc gag gcc cga gag cca gga tta cct    144
Leu Asp Ala Ile Ile Pro Thr Leu Glu Ala Arg Glu Pro Gly Leu Pro
    -10              -5              -1   1               5 cct ggt cct ctc gag aat agc tct gca aag ttg gtg aac gac gag gct    192
Pro Gly Pro Leu Glu Asn Ser Ser Ala Lys Leu Val Asn Asp Glu Ala
                10              15              20 cac cca tgg aag ccg ctt cga cct ggc gat att cgt gga cct tgc cct    240
His Pro Trp Lys Pro Leu Arg Pro Gly Asp Ile Arg Gly Pro Cys Pro
            25              30              35 ggt ctc aat act ctg gca tct cac ggg tac ctc ccg aga aat ggc gtt    288
Gly Leu Asn Thr Leu Ala Ser His Gly Tyr Leu Pro Arg Asn Gly Val
        40              45              50 gca acc ccg gtg caa ata ata aac gcg gtt cag gaa gga ctc aat ttc    336
Ala Thr Pro Val Gln Ile Ile Asn Ala Val Gln Glu Gly Leu Asn Phe
    55              60              65 gac aat caa gcc gca gtc ttc gcc aca tat gcg gcc cac ctt gtg gac    384
Asp Asn Gln Ala Ala Val Phe Ala Thr Tyr Ala Ala His Leu Val Asp
70              75              80              85 ggc aat ctc att acg gac ttg ctg agc atc gga cgc aag acg cgg ctc    432
Gly Asn Leu Ile Thr Asp Leu Leu Ser Ile Gly Arg Lys Thr Arg Leu
            90              95              100 act ggg cct gat cca cca ccc ccc gct tcc gtt ggt gga ctc aat gag    480
Thr Gly Pro Asp Pro Pro Pro Pro Ala Ser Val Gly Gly Leu Asn Glu
        105             110             115 cat ggc acc ttc gaa ggc gac gcc agt atg acc cga ggt gac gca ttc    528
His Gly Thr Phe Glu Gly Asp Ala Ser Met Thr Arg Gly Asp Ala Phe
    120             125             130 ttt ggc aac aac cac gat ttc aat gag acg ctc ttc gaa cag ttg gtt    576
Phe Gly Asn Asn His Asp Phe Asn Glu Thr Leu Phe Glu Gln Leu Val
135             140             145 gac tac agc aac cga ttt gga gga gga aaa tac aat ctt acc gtc gcg    624
Asp Tyr Ser Asn Arg Phe Gly Gly Gly Lys Tyr Asn Leu Thr Val Ala
150             155             160             165 ggg gag ctc cgt ttc aag cgc att caa gac tcc att gcg acc aac ccc    672
Gly Glu Leu Arg Phe Lys Arg Ile Gln Asp Ser Ile Ala Thr Asn Pro
            170             175             180 aat ttc tcc ttt gtt gac ttt agg ttc ttt act gct tac ggc gag acc    720
Asn Phe Ser Phe Val Asp Phe Arg Phe Phe Thr Ala Tyr Gly Glu Thr
        185             190             195 acc ttc ccc gcg aat ctt ttt gtg gat ggg cgc agg gac gac ggc cag    768
Thr Phe Pro Ala Asn Leu Phe Val Asp Gly Arg Arg Asp Asp Gly Gln
    200             205             210 cta gat atg gat gct gca cgg agt ttt ttc caa ttc agc cgt atg cct    816
Leu Asp Met Asp Ala Ala Arg Ser Phe Phe Gln Phe Ser Arg Met Pro
215             220             225 gac gat ttc ttc cgc gca ccc agc ccg aga agt gac aca gga gtc gag    864
Asp Asp Phe Phe Arg Ala Pro Ser Pro Arg Ser Asp Thr Gly Val Glu
230             235             240             245 gta gtt ata cag gct cat cct atg cag ccc gga aaa aat gtc ggc aag    912
Val Val Ile Gln Ala His Pro Met Gln Pro Gly Lys Asn Val Gly Lys
            250             255             260 atc aac agc tac acc gtc gac cca aca tcc tct gac ttt tcc acc ccc    960
Ile Asn Ser Tyr Thr Val Asp Pro Thr Ser Ser Asp Phe Ser Thr Pro
        265             270             275 tgc ttg atg tac gag aaa ttc gtc aac ata acg gtc aag tca ctc tac    1008
Cys Leu Met Tyr Glu Lys Phe Val Asn Ile Thr Val Lys Ser Leu Tyr
    280             285             290
```

```
ccg aat ccg acg gtg cag ctt cgc aaa gcc ctt aat acg aat ctc gat    1056
Pro Asn Pro Thr Val Gln Leu Arg Lys Ala Leu Asn Thr Asn Leu Asp
    295                 300                 305 ttc ttc ttc cag gga gtc gcc gct gga tgt acc cag gtc ttc cca tac    1104
Phe Phe Phe Gln Gly Val Ala Ala Gly Cys Thr Gln Val Phe Pro Tyr
310                 315                 320                 325 ggg cga gat tga                                                    1116
Gly Arg Asp
```

<210> SEQ ID NO 10
<211> LENGTH: 371
<212> TYPE: PRT
<213> ORGANISM: Artificial Sequence
<220> FEATURE:
<223> OTHER INFORMATION: Synthetic Construct

<400> SEQUENCE: 10

```
Met Lys Tyr Phe Pro Leu Phe Pro Thr Leu Val Phe Ala Ala Arg Val
            -40                 -35                 -30

Val Ala Phe Pro Ala Tyr Ala Ser Leu Ala Gly Leu Ser Gln Gln Glu
        -25                 -20                 -15

Leu Asp Ala Ile Ile Pro Thr Leu Glu Ala Arg Glu Pro Gly Leu Pro
    -10                  -5                  -1   1               5

Pro Gly Pro Leu Glu Asn Ser Ser Ala Lys Leu Val Asn Asp Glu Ala
                 10                  15                  20

His Pro Trp Lys Pro Leu Arg Pro Gly Asp Ile Arg Gly Pro Cys Pro
            25                  30                  35

Gly Leu Asn Thr Leu Ala Ser His Gly Tyr Leu Pro Arg Asn Gly Val
        40                  45                  50

Ala Thr Pro Val Gln Ile Ile Asn Ala Val Gln Glu Gly Leu Asn Phe
    55                  60                  65

Asp Asn Gln Ala Ala Val Phe Ala Thr Tyr Ala Ala His Leu Val Asp
70                  75                  80                  85

Gly Asn Leu Ile Thr Asp Leu Leu Ser Ile Gly Arg Lys Thr Arg Leu
                90                  95                 100

Thr Gly Pro Asp Pro Pro Pro Ala Ser Val Gly Gly Leu Asn Glu
            105                 110                 115

His Gly Thr Phe Glu Gly Asp Ala Ser Met Thr Arg Gly Asp Ala Phe
        120                 125                 130

Phe Gly Asn Asn His Asp Phe Asn Glu Thr Leu Phe Glu Gln Leu Val
135                 140                 145

Asp Tyr Ser Asn Arg Phe Gly Gly Lys Tyr Asn Leu Thr Val Ala
150                 155                 160                 165

Gly Glu Leu Arg Phe Lys Arg Ile Gln Asp Ser Ile Ala Thr Asn Pro
                170                 175                 180

Asn Phe Ser Phe Val Asp Phe Arg Phe Phe Thr Ala Tyr Gly Glu Thr
            185                 190                 195

Thr Phe Pro Ala Asn Leu Phe Val Asp Gly Arg Arg Asp Asp Gly Gln
        200                 205                 210

Leu Asp Met Asp Ala Ala Arg Ser Phe Phe Gln Phe Ser Arg Met Pro
    215                 220                 225

Asp Asp Phe Phe Arg Ala Pro Ser Pro Arg Ser Asp Thr Gly Val Glu
230                 235                 240                 245

Val Val Ile Gln Ala His Pro Met Gln Pro Gly Lys Asn Val Gly Lys
                250                 255                 260

Ile Asn Ser Tyr Thr Val Asp Pro Thr Ser Ser Asp Phe Ser Thr Pro
```

```
                    265                 270                 275
Cys Leu Met Tyr Glu Lys Phe Val Asn Ile Thr Val Lys Ser Leu Tyr
                280                 285                 290

Pro Asn Pro Thr Val Gln Leu Arg Lys Ala Leu Asn Thr Asn Leu Asp
            295                 300                 305

Phe Phe Phe Gln Gly Val Ala Ala Gly Cys Thr Gln Val Phe Pro Tyr
310                 315                 320                 325

Gly Arg Asp

<210> SEQ ID NO 11
<211> LENGTH: 1116
<212> TYPE: DNA
<213> ORGANISM: Artificial Sequence
<220> FEATURE:
<223> OTHER INFORMATION: Wt-JaWa variant with modified signal peptide
<220> FEATURE:
<221> NAME/KEY: CDS
<222> LOCATION: (1)..(1113)
<220> FEATURE:
<221> NAME/KEY: mat_peptide
<222> LOCATION: (130)..(1116)

<400> SEQUENCE: 11 atg aaa tat ttt ccc ctg ttc cca acc ttg gtc tac gca gtg ggg gtc      48
Met Lys Tyr Phe Pro Leu Phe Pro Thr Leu Val Tyr Ala Val Gly Val
            -40                 -35                 -30 gtt gct ttt cct gac tac gcc tca ttg gcc ggc ctc agc cag cag gaa      96
Val Ala Phe Pro Asp Tyr Ala Ser Leu Ala Gly Leu Ser Gln Gln Glu
        -25                 -20                 -15 ttg gac gct ata atc cca aca ctc gag gcc cga gag cca gga tta cct     144
Leu Asp Ala Ile Ile Pro Thr Leu Glu Ala Arg Glu Pro Gly Leu Pro
    -10                 -5                 -1   1               5 cct ggt cct ctc gag aat agc tct gca aag ttg gtg aac gac gag gct     192
Pro Gly Pro Leu Glu Asn Ser Ser Ala Lys Leu Val Asn Asp Glu Ala
                10                  15                  20 cac cca tgg aag ccg ctt cga cct ggc gat att cgt gga cct tgc cct     240
His Pro Trp Lys Pro Leu Arg Pro Gly Asp Ile Arg Gly Pro Cys Pro
            25                  30                  35 ggt ctc aat act ctg gca tct cac ggg tac ctc ccg aga aat ggc gtt     288
Gly Leu Asn Thr Leu Ala Ser His Gly Tyr Leu Pro Arg Asn Gly Val
        40                  45                  50 gca acc ccg gtg caa ata ata aac gcg gtt cag gaa gga ctc aat ttc     336
Ala Thr Pro Val Gln Ile Ile Asn Ala Val Gln Glu Gly Leu Asn Phe
    55                  60                  65 gac aat caa gcc gca gtc ttc gcc aca tat gcg gcc cac ctt gtg gac     384
Asp Asn Gln Ala Ala Val Phe Ala Thr Tyr Ala Ala His Leu Val Asp
70                  75                  80                  85 ggc aat ctc att acg gac ttg ctg agc atc gga cgc aag acg cgg ctc     432
Gly Asn Leu Ile Thr Asp Leu Leu Ser Ile Gly Arg Lys Thr Arg Leu
                90                  95                 100 act ggg cct gat cca cca ccc ccc gct tcc gtt ggt gga ctc aat gag     480
Thr Gly Pro Asp Pro Pro Pro Pro Ala Ser Val Gly Gly Leu Asn Glu
            105                 110                 115 cat ggc acc ttc gaa ggc gac gcc agt atg acc cga ggt gac gca ttc     528
His Gly Thr Phe Glu Gly Asp Ala Ser Met Thr Arg Gly Asp Ala Phe
        120                 125                 130 ttt ggc aac aac cac gat ttc aat gag acg ctc ttc gaa cag ttg gtt     576
Phe Gly Asn Asn His Asp Phe Asn Glu Thr Leu Phe Glu Gln Leu Val
    135                 140                 145 gac tac agc aac cga ttt gga gga gga aaa tac aat ctt acc gtc gcg     624
Asp Tyr Ser Asn Arg Phe Gly Gly Gly Lys Tyr Asn Leu Thr Val Ala
```

```
ggg gag ctc cgt ttc aag cgc att caa gac tcc att gcg acc aac ccc      672
Gly Glu Leu Arg Phe Lys Arg Ile Gln Asp Ser Ile Ala Thr Asn Pro
                170                 175                 180 aat ttc tcc ttt gtt gac ttt agg ttc ttt act gct tac ggc gag acc      720
Asn Phe Ser Phe Val Asp Phe Arg Phe Phe Thr Ala Tyr Gly Glu Thr
                185                 190                 195 acc ttc ccc gcg aat ctt ttt gtg gat ggg cgc agg gac gac ggc cag      768
Thr Phe Pro Ala Asn Leu Phe Val Asp Gly Arg Arg Asp Asp Gly Gln
                200                 205                 210 cta gat atg gat gct gca cgg agt ttt ttc caa ttc agc cgt atg cct      816
Leu Asp Met Asp Ala Ala Arg Ser Phe Phe Gln Phe Ser Arg Met Pro
                215                 220                 225 gac gat ttc ttc cgc gca ccc agc ccg aga agt gac aca gga gtc gag      864
Asp Asp Phe Phe Arg Ala Pro Ser Pro Arg Ser Asp Thr Gly Val Glu
230                 235                 240                 245 gta gtt ata cag gct cat cct atg cag ccc gga aaa aat gtc ggc aag      912
Val Val Ile Gln Ala His Pro Met Gln Pro Gly Lys Asn Val Gly Lys
                250                 255                 260 atc aac agc tac acc gtc gac cca aca tcc tct gac ttt tcc acc ccc      960
Ile Asn Ser Tyr Thr Val Asp Pro Thr Ser Ser Asp Phe Ser Thr Pro
                265                 270                 275 tgc ttg atg tac gag aaa ttc gtc aac ata acg gtc aag tca ctc tac     1008
Cys Leu Met Tyr Glu Lys Phe Val Asn Ile Thr Val Lys Ser Leu Tyr
                280                 285                 290 ccg aat ccg acg gtg cag ctt cgc aaa gcc ctt aat acg aat ctc gat     1056
Pro Asn Pro Thr Val Gln Leu Arg Lys Ala Leu Asn Thr Asn Leu Asp
                295                 300                 305 ttc ttc ttc cag gga gtc gcc gct gga tgt acc cag gtc ttc cca tac     1104
Phe Phe Phe Gln Gly Val Ala Ala Gly Cys Thr Gln Val Phe Pro Tyr
310                 315                 320                 325 ggg cga gat tga                                                     1116
Gly Arg Asp <210> SEQ ID NO 12
<211> LENGTH: 371
<212> TYPE: PRT
<213> ORGANISM: Artificial Sequence
<220> FEATURE:
<223> OTHER INFORMATION: Synthetic Construct

<400> SEQUENCE: 12

Met Lys Tyr Phe Pro Leu Phe Pro Thr Leu Val Tyr Ala Val Gly Val
            -40                 -35                 -30

Val Ala Phe Pro Asp Tyr Ala Ser Leu Ala Gly Leu Ser Gln Gln Glu
        -25                 -20                 -15

Leu Asp Ala Ile Ile Pro Thr Leu Glu Ala Arg Glu Pro Gly Leu Pro
    -10                  -5                  -1   1               5

Pro Gly Pro Leu Glu Asn Ser Ser Ala Lys Leu Val Asn Asp Glu Ala
                10                  15                  20

His Pro Trp Lys Pro Leu Arg Pro Gly Asp Ile Arg Gly Pro Cys Pro
                25                  30                  35

Gly Leu Asn Thr Leu Ala Ser His Gly Tyr Leu Pro Arg Asn Gly Val
                40                  45                  50

Ala Thr Pro Val Gln Ile Ile Asn Ala Val Gln Glu Gly Leu Asn Phe
                55                  60                  65

Asp Asn Gln Ala Ala Val Phe Ala Thr Tyr Ala Ala His Leu Val Asp
70                  75                  80                  85
```

```
Gly Asn Leu Ile Thr Asp Leu Leu Ser Ile Gly Arg Lys Thr Arg Leu
                 90                  95                 100

Thr Gly Pro Asp Pro Pro Pro Ala Ser Val Gly Gly Leu Asn Glu
            105                 110                 115

His Gly Thr Phe Glu Gly Asp Ala Ser Met Thr Arg Gly Asp Ala Phe
            120                 125                 130

Phe Gly Asn Asn His Asp Phe Asn Glu Thr Leu Phe Glu Gln Leu Val
            135                 140                 145

Asp Tyr Ser Asn Arg Phe Gly Gly Lys Tyr Asn Leu Thr Val Ala
150                 155                 160                 165

Gly Glu Leu Arg Phe Lys Arg Ile Gln Asp Ser Ile Ala Thr Asn Pro
                170                 175                 180

Asn Phe Ser Phe Val Asp Phe Arg Phe Phe Thr Ala Tyr Gly Glu Thr
                185                 190                 195

Thr Phe Pro Ala Asn Leu Phe Val Asp Gly Arg Arg Asp Asp Gly Gln
            200                 205                 210

Leu Asp Met Asp Ala Ala Arg Ser Phe Gln Phe Ser Arg Met Pro
215                 220                 225

Asp Asp Phe Phe Arg Ala Pro Ser Pro Arg Ser Asp Thr Gly Val Glu
230                 235                 240                 245

Val Val Ile Gln Ala His Pro Met Gln Pro Gly Lys Asn Val Gly Lys
                250                 255                 260

Ile Asn Ser Tyr Thr Val Asp Pro Thr Ser Ser Asp Phe Ser Thr Pro
                265                 270                 275

Cys Leu Met Tyr Glu Lys Phe Val Asn Ile Thr Val Lys Ser Leu Tyr
            280                 285                 290

Pro Asn Pro Thr Val Gln Leu Arg Lys Ala Leu Asn Thr Asn Leu Asp
            295                 300                 305

Phe Phe Phe Gln Gly Val Ala Ala Gly Cys Thr Gln Val Phe Pro Tyr
310                 315                 320                 325

Gly Arg Asp

<210> SEQ ID NO 13
<211> LENGTH: 984
<212> TYPE: DNA
<213> ORGANISM: Artificial Sequence
<220> FEATURE:
<223> OTHER INFORMATION: PaDa-I variant without signal peptide
<220> FEATURE:
<221> NAME/KEY: CDS
<222> LOCATION: (1)..(984)

<400> SEQUENCE: 13 gag cca gga tta cct cct ggt cct ctc gag aat agc tct gca aag ttg      48
Glu Pro Gly Leu Pro Pro Gly Pro Leu Glu Asn Ser Ser Ala Lys Leu
1               5                   10                  15 gtg aac gac gag gct cac cca tgg aag ccg ctt cga cct ggc gat att      96
Val Asn Asp Glu Ala His Pro Trp Lys Pro Leu Arg Pro Gly Asp Ile
                20                  25                  30 cgt gga cct tgc cct ggt ctc aat act ctg gca tct cac ggg tac ctc     144
Arg Gly Pro Cys Pro Gly Leu Asn Thr Leu Ala Ser His Gly Tyr Leu
            35                  40                  45 ccg aga aat ggc gtt gca acc ccg gcg caa ata ata aac gcg gtt cag     192
Pro Arg Asn Gly Val Ala Thr Pro Ala Gln Ile Ile Asn Ala Val Gln
        50                  55                  60 gaa gga ttc aat ttc gac aat caa gcc gca atc ttc gcc aca tat gcg     240
Glu Gly Phe Asn Phe Asp Asn Gln Ala Ala Ile Phe Ala Thr Tyr Ala
65                  70                  75                  80
```

```
gcc cac ctt gtg gac ggc aat ctc att acg gac ttg ctg agc atc gga        288
Ala His Leu Val Asp Gly Asn Leu Ile Thr Asp Leu Leu Ser Ile Gly
                85                  90                  95 cgc aag acg cgg ctc act ggg cct gat cca cca ccc ccc gct tcc gtt        336
Arg Lys Thr Arg Leu Thr Gly Pro Asp Pro Pro Pro Pro Ala Ser Val
            100                 105                 110 ggt gga ctc aat gag cat ggc acc ttc gaa ggc gac gcc agt atg acc        384
Gly Gly Leu Asn Glu His Gly Thr Phe Glu Gly Asp Ala Ser Met Thr
        115                 120                 125 cga ggt gac gca ttc ttt ggc aac aac cac gat ttc aat gag acg ctc        432
Arg Gly Asp Ala Phe Phe Gly Asn Asn His Asp Phe Asn Glu Thr Leu
    130                 135                 140 ttc gaa cag ttg gtt gac tac agc aac cga ttt gga gga aaa tac            480
Phe Glu Gln Leu Val Asp Tyr Ser Asn Arg Phe Gly Gly Lys Tyr
145                 150                 155                 160 aat ctt acc gtc gcg ggg gag ctc cgt ttc aag cgc att caa gac tcc        528
Asn Leu Thr Val Ala Gly Glu Leu Arg Phe Lys Arg Ile Gln Asp Ser
                165                 170                 175 att gcg acc aac ccc aat ttc tcc ttt gtt gac ttt agg ttc ttt act        576
Ile Ala Thr Asn Pro Asn Phe Ser Phe Val Asp Phe Arg Phe Phe Thr
            180                 185                 190 gct tac ggc gag acc acc ttc ccc gcg aat ctt ttt gtg gat ggg cgc        624
Ala Tyr Gly Glu Thr Thr Phe Pro Ala Asn Leu Phe Val Asp Gly Arg
        195                 200                 205 agg gac gac ggc cag cta gat atg gat gct gca cgg agt ttt tca caa        672
Arg Asp Asp Gly Gln Leu Asp Met Asp Ala Ala Arg Ser Phe Phe Gln
    210                 215                 220 ttc agc cgt atg cct gac gat ttc ttc cgc gca ccc agc ccg aga agt        720
Phe Ser Arg Met Pro Asp Asp Phe Phe Arg Ala Pro Ser Pro Arg Ser
225                 230                 235                 240 ggc aca gga gtc gag gta gtt gta cag gct cat cct atg cag ccc gga        768
Gly Thr Gly Val Glu Val Val Val Gln Ala His Pro Met Gln Pro Gly
                245                 250                 255 aga aat gtc ggc aag atc aac agc tac acc gtc gac cca aca tcc tct        816
Arg Asn Val Gly Lys Ile Asn Ser Tyr Thr Val Asp Pro Thr Ser Ser
            260                 265                 270 gac ttt tcc acc ccc tgc ttg atg tac gag aaa ttc gtc aac ata acg        864
Asp Phe Ser Thr Pro Cys Leu Met Tyr Glu Lys Phe Val Asn Ile Thr
        275                 280                 285 gtc aag tca ctc tac ccg aat ccg acg gtg cag ctt cgc aaa gcc ctt        912
Val Lys Ser Leu Tyr Pro Asn Pro Thr Val Gln Leu Arg Lys Ala Leu
    290                 295                 300 aat acg aat ctc gat ttc tta ttc cag gga gtc gcc gct gga tgt acc        960
Asn Thr Asn Leu Asp Phe Leu Phe Gln Gly Val Ala Ala Gly Cys Thr
305                 310                 315                 320 cag gtc ttc cca tac ggg cga gat                                        984
Gln Val Phe Pro Tyr Gly Arg Asp
                325

<210> SEQ ID NO 14
<211> LENGTH: 328
<212> TYPE: PRT
<213> ORGANISM: Artificial Sequence
<220> FEATURE:
<223> OTHER INFORMATION: Synthetic Construct

<400> SEQUENCE: 14

Glu Pro Gly Leu Pro Pro Gly Pro Leu Glu Asn Ser Ser Ala Lys Leu
1               5                   10                  15

Val Asn Asp Glu Ala His Pro Trp Lys Pro Leu Arg Pro Gly Asp Ile
```

```
                    20                  25                  30
Arg Gly Pro Cys Pro Gly Leu Asn Thr Leu Ala Ser His Gly Tyr Leu
                35                  40                  45
Pro Arg Asn Gly Val Ala Thr Pro Ala Gln Ile Ile Asn Ala Val Gln
 50                  55                  60
Glu Gly Phe Asn Phe Asp Asn Gln Ala Ala Ile Phe Ala Thr Tyr Ala
 65                  70                  75                  80
Ala His Leu Val Asp Gly Asn Leu Ile Thr Asp Leu Leu Ser Ile Gly
                85                  90                  95
Arg Lys Thr Arg Leu Thr Gly Pro Asp Pro Pro Pro Ala Ser Val
                100                 105                 110
Gly Gly Leu Asn Glu His Gly Thr Phe Glu Gly Asp Ala Ser Met Thr
                115                 120                 125
Arg Gly Asp Ala Phe Phe Gly Asn Asn His Asp Phe Asn Glu Thr Leu
                130                 135                 140
Phe Glu Gln Leu Val Asp Tyr Ser Asn Arg Phe Gly Gly Lys Tyr
145                 150                 155                 160
Asn Leu Thr Val Ala Gly Glu Leu Arg Phe Lys Arg Ile Gln Asp Ser
                165                 170                 175
Ile Ala Thr Asn Pro Asn Phe Ser Phe Val Asp Phe Arg Phe Thr
                180                 185                 190
Ala Tyr Gly Glu Thr Thr Phe Pro Ala Asn Leu Phe Val Asp Gly Arg
                195                 200                 205
Arg Asp Asp Gly Gln Leu Asp Met Asp Ala Ala Arg Ser Phe Phe Gln
                210                 215                 220
Phe Ser Arg Met Pro Asp Asp Phe Phe Arg Ala Pro Ser Pro Arg Ser
225                 230                 235                 240
Gly Thr Gly Val Glu Val Val Val Gln Ala His Pro Met Gln Pro Gly
                245                 250                 255
Arg Asn Val Gly Lys Ile Asn Ser Tyr Thr Val Asp Pro Thr Ser Ser
                260                 265                 270
Asp Phe Ser Thr Pro Cys Leu Met Tyr Glu Lys Phe Val Asn Ile Thr
                275                 280                 285
Val Lys Ser Leu Tyr Pro Asn Pro Thr Val Gln Leu Arg Lys Ala Leu
                290                 295                 300
Asn Thr Asn Leu Asp Phe Leu Phe Gln Gly Val Ala Ala Gly Cys Thr
305                 310                 315                 320
Gln Val Phe Pro Tyr Gly Arg Asp
                325

<210> SEQ ID NO 15
<211> LENGTH: 1113
<212> TYPE: DNA
<213> ORGANISM: Artificial Sequence
<220> FEATURE:
<223> OTHER INFORMATION: PaDa-I variant with wild signal peptide
<220> FEATURE:
<221> NAME/KEY: CDS
<222> LOCATION: (1)..(1113)
<220> FEATURE:
<221> NAME/KEY: mat_peptide
<222> LOCATION: (130)..(1113)

<400> SEQUENCE: 15 atg aaa tat ttt ccc ctg ttc cca acc ttg gtc ttc gca gcg agg gtc    48
Met Lys Tyr Phe Pro Leu Phe Pro Thr Leu Val Phe Ala Ala Arg Val
            -40                 -35                 -30
```

```
gtt gct ttt cct gcc tac gcc tca ttg gcc ggc ctc agc cag cag gaa      96
Val Ala Phe Pro Ala Tyr Ala Ser Leu Ala Gly Leu Ser Gln Gln Glu
        -25             -20             -15 ttg gac gct ata atc cca aca ctc gag gcc cga gag cca gga tta cct     144
Leu Asp Ala Ile Ile Pro Thr Leu Glu Ala Arg Glu Pro Gly Leu Pro
    -10              -5               -1   1               5 cct ggt cct ctc gag aat agc tct gca aag ttg gtg aac gac gag gct     192
Pro Gly Pro Leu Glu Asn Ser Ser Ala Lys Leu Val Asn Asp Glu Ala
                 10              15              20 cac cca tgg aag ccg ctt cga cct ggc gat att cgt gga cct tgc cct     240
His Pro Trp Lys Pro Leu Arg Pro Gly Asp Ile Arg Gly Pro Cys Pro
             25              30              35 ggt ctc aat act ctg gca tct cac ggg tac ctc ccg aga aat ggc gtt     288
Gly Leu Asn Thr Leu Ala Ser His Gly Tyr Leu Pro Arg Asn Gly Val
         40              45              50 gca acc ccg gcg caa ata ata aac gcg gtt cag gaa gga ttc aat ttc     336
Ala Thr Pro Ala Gln Ile Ile Asn Ala Val Gln Glu Gly Phe Asn Phe
     55              60              65 gac aat caa gcc gca atc ttc gcc aca tat gcg gcc cac ctt gtg gac     384
Asp Asn Gln Ala Ala Ile Phe Ala Thr Tyr Ala Ala His Leu Val Asp
 70              75              80              85 ggc aat ctc att acg gac ttg ctg agc atc gga cgc aag acg cgg ctc     432
Gly Asn Leu Ile Thr Asp Leu Leu Ser Ile Gly Arg Lys Thr Arg Leu
                 90              95             100 act ggg cct gat cca cca ccc ccc gct tcc gtt ggt gga ctc aat gag     480
Thr Gly Pro Asp Pro Pro Pro Pro Ala Ser Val Gly Gly Leu Asn Glu
            105             110             115 cat ggc acc ttc gaa ggc gac gcc agt atg acc cga ggt gac gca ttc     528
His Gly Thr Phe Glu Gly Asp Ala Ser Met Thr Arg Gly Asp Ala Phe
        120             125             130 ttt ggc aac aac cac gat ttc aat gag acg ctc ttc gaa cag ttg gtt     576
Phe Gly Asn Asn His Asp Phe Asn Glu Thr Leu Phe Glu Gln Leu Val
    135             140             145 gac tac agc aac cga ttt gga gga gga aaa tac aat ctt acc gtc gcg     624
Asp Tyr Ser Asn Arg Phe Gly Gly Gly Lys Tyr Asn Leu Thr Val Ala
150             155             160             165 ggg gag ctc cgt ttc aag cgc att caa gac tcc att gcg acc aac ccc     672
Gly Glu Leu Arg Phe Lys Arg Ile Gln Asp Ser Ile Ala Thr Asn Pro
            170             175             180 aat ttc tcc ttt gtt gac ttt agg ttt ttt act gct tac ggc gag acc     720
Asn Phe Ser Phe Val Asp Phe Arg Phe Phe Thr Ala Tyr Gly Glu Thr
        185             190             195 acc ttc ccc gcg aat ctt ttt gtg gat ggg cgc agg gac gac ggc cag     768
Thr Phe Pro Ala Asn Leu Phe Val Asp Gly Arg Arg Asp Asp Gly Gln
    200             205             210 cta gat atg gat gct gca cgg agt ttt ttc caa ttc agc cgt atg cct     816
Leu Asp Met Asp Ala Ala Arg Ser Phe Phe Gln Phe Ser Arg Met Pro
215             220             225 gac gat ttc ttc cgc gca ccc agc ccg aga agt ggc aca gga gtc gag     864
Asp Asp Phe Phe Arg Ala Pro Ser Pro Arg Ser Gly Thr Gly Val Glu
230             235             240             245 gta gtt gta cag gct cat cct atg cag ccc gga aga aat gtc ggc aag     912
Val Val Val Gln Ala His Pro Met Gln Pro Gly Arg Asn Val Gly Lys
            250             255             260 atc aac agc tac acc gtc gac cca aca tcc tct gac ttt tcc acc ccc     960
Ile Asn Ser Tyr Thr Val Asp Pro Thr Ser Ser Asp Phe Ser Thr Pro
        265             270             275 tgc ttg atg tac gag aaa ttc gtc aac ata acg gtc aag tca ctc tac    1008
Cys Leu Met Tyr Glu Lys Phe Val Asn Ile Thr Val Lys Ser Leu Tyr
    280             285             290
```

```
ccg aat ccg acg gtg cag ctt cgc aaa gcc ctt aat acg aat ctc gat    1056
Pro Asn Pro Thr Val Gln Leu Arg Lys Ala Leu Asn Thr Asn Leu Asp
295                 300                 305 ttc tta ttc cag gga gtc gcc gct gga tgt acc cag gtc ttc cca tac    1104
Phe Leu Phe Gln Gly Val Ala Ala Gly Cys Thr Gln Val Phe Pro Tyr
310                 315                 320                 325 ggg cga gat                                                        1113
Gly Arg Asp <210> SEQ ID NO 16
<211> LENGTH: 371
<212> TYPE: PRT
<213> ORGANISM: Artificial Sequence
<220> FEATURE:
<223> OTHER INFORMATION: Synthetic Construct

<400> SEQUENCE: 16

Met Lys Tyr Phe Pro Leu Phe Pro Thr Leu Val Phe Ala Ala Arg Val
            -40                 -35                 -30

Val Ala Phe Pro Ala Tyr Ala Ser Leu Ala Gly Leu Ser Gln Gln Glu
        -25                 -20                 -15

Leu Asp Ala Ile Ile Pro Thr Leu Glu Ala Arg Glu Pro Gly Leu Pro
    -10                  -5                 -1   1               5

Pro Gly Pro Leu Glu Asn Ser Ser Ala Lys Leu Val Asn Asp Glu Ala
                 10                  15                  20

His Pro Trp Lys Pro Leu Arg Pro Gly Asp Ile Arg Gly Pro Cys Pro
             25                  30                  35

Gly Leu Asn Thr Leu Ala Ser His Gly Tyr Leu Pro Arg Asn Gly Val
         40                  45                  50

Ala Thr Pro Ala Gln Ile Ile Asn Ala Val Gln Glu Gly Phe Asn Phe
     55                  60                  65

Asp Asn Gln Ala Ala Ile Phe Ala Thr Tyr Ala Ala His Leu Val Asp
 70                  75                  80                  85

Gly Asn Leu Ile Thr Asp Leu Leu Ser Ile Gly Arg Lys Thr Arg Leu
                 90                  95                 100

Thr Gly Pro Asp Pro Pro Pro Ala Ser Val Gly Gly Leu Asn Glu
            105                 110                 115

His Gly Thr Phe Glu Gly Asp Ala Ser Met Thr Arg Gly Asp Ala Phe
            120                 125                 130

Phe Gly Asn Asn His Asp Phe Asn Glu Thr Leu Phe Glu Gln Leu Val
        135                 140                 145

Asp Tyr Ser Asn Arg Phe Gly Gly Lys Tyr Asn Leu Thr Val Ala
150                 155                 160                 165

Gly Glu Leu Arg Phe Lys Arg Ile Gln Asp Ser Ile Ala Thr Asn Pro
                170                 175                 180

Asn Phe Ser Phe Val Asp Phe Arg Phe Phe Thr Ala Tyr Gly Glu Thr
            185                 190                 195

Thr Phe Pro Ala Asn Leu Phe Val Asp Gly Arg Arg Asp Gly Gln
        200                 205                 210

Leu Asp Met Asp Ala Ala Arg Ser Phe Phe Gln Phe Ser Arg Met Pro
    215                 220                 225

Asp Asp Phe Phe Arg Ala Pro Ser Pro Arg Ser Gly Thr Gly Val Glu
230                 235                 240                 245

Val Val Val Gln Ala His Pro Met Gln Pro Gly Arg Asn Val Gly Lys
            250                 255                 260
```

```
Ile Asn Ser Tyr Thr Val Asp Pro Thr Ser Ser Asp Phe Ser Thr Pro
            265                 270                 275

Cys Leu Met Tyr Glu Lys Phe Val Asn Ile Thr Val Lys Ser Leu Tyr
        280                 285                 290

Pro Asn Pro Thr Val Gln Leu Arg Lys Ala Leu Asn Thr Asn Leu Asp
    295                 300                 305

Phe Leu Phe Gln Gly Val Ala Ala Gly Cys Thr Gln Val Phe Pro Tyr
310                 315                 320                 325

Gly Arg Asp

<210> SEQ ID NO 17
<211> LENGTH: 1113
<212> TYPE: DNA
<213> ORGANISM: Artificial Sequence
<220> FEATURE:
<223> OTHER INFORMATION: PaDa-I variant with modified signal peptide
<220> FEATURE:
<221> NAME/KEY: CDS
<222> LOCATION: (1)..(1113)
<220> FEATURE:
<221> NAME/KEY: mat_peptide
<222> LOCATION: (130)..(1113)

<400> SEQUENCE: 17
```

| | | |
|---|---|---|
| atg aaa tat ttt ccc ctg ttc cca acc ttg gtc tac gca gtg ggg gtc<br>Met Lys Tyr Phe Pro Leu Phe Pro Thr Leu Val Tyr Ala Val Gly Val<br>           -40                 -35                -30 | | 48 |
| gtt gct ttt cct gac tac gcc tca ttg gcc ggc ctc agc cag cag gaa<br>Val Ala Phe Pro Asp Tyr Ala Ser Leu Ala Gly Leu Ser Gln Gln Glu<br>      -25                 -20                 -15 | | 96 |
| ttg gac gct ata atc cca aca ctc gag gcc cga gag cca gga tta cct<br>Leu Asp Ala Ile Ile Pro Thr Leu Glu Ala Arg Glu Pro Gly Leu Pro<br>-10                 -5                 -1  1             5 | | 144 |
| cct ggt cct ctc gag aat agc tct gca aag ttg gtg aac gac gag gct<br>Pro Gly Pro Leu Glu Asn Ser Ser Ala Lys Leu Val Asn Asp Glu Ala<br>              10                15                20 | | 192 |
| cac cca tgg aag ccg ctt cga cct ggc gat att cgt gga cct tgc cct<br>His Pro Trp Lys Pro Leu Arg Pro Gly Asp Ile Arg Gly Pro Cys Pro<br>        25                 30                 35 | | 240 |
| ggt ctc aat act ctg gca tct cac ggg tac ctc ccg aga aat ggc gtt<br>Gly Leu Asn Thr Leu Ala Ser His Gly Tyr Leu Pro Arg Asn Gly Val<br>    40                 45                50 | | 288 |
| gca acc ccg gcg caa ata ata aac gcg gtt cag gaa gga ttc aat ttc<br>Ala Thr Pro Ala Gln Ile Ile Asn Ala Val Gln Glu Gly Phe Asn Phe<br>55                 60                65 | | 336 |
| gac aat caa gcc gca atc ttc gcc aca tat gcg gcc cac ctt gtg gac<br>Asp Asn Gln Ala Ala Ile Phe Ala Thr Tyr Ala Ala His Leu Val Asp<br>70                 75                80                85 | | 384 |
| ggc aat ctc att acg gac ttg ctg agc atc gga cgc aag acg cgg ctc<br>Gly Asn Leu Ile Thr Asp Leu Leu Ser Ile Gly Arg Lys Thr Arg Leu<br>              90                95               100 | | 432 |
| act ggg cct gat cca cca ccc ccc gct tcc gtt ggt gga ctc aat gag<br>Thr Gly Pro Asp Pro Pro Pro Ala Ser Val Gly Gly Leu Asn Glu<br>        105                110               115 | | 480 |
| cat ggc acc ttc gaa ggc gac gcc agt atg acc cga ggt gac gca ttc<br>His Gly Thr Phe Glu Gly Asp Ala Ser Met Thr Arg Gly Asp Ala Phe<br>        120                125               130 | | 528 |
| ttt ggc aac aac cac gat ttc aat gag acg ctc ttc gaa cag ttg gtt<br>Phe Gly Asn Asn His Asp Phe Asn Glu Thr Leu Phe Glu Gln Leu Val<br>135                 140                145 | | 576 |
| gac tac agc aac cga ttt gga gga gga aaa tac aat ctt acc gtc gcg | | 624 |

| | | | | | | | | | | | | |
|---|---|---|---|---|---|---|---|---|---|---|---|---|
| Asp | Tyr | Ser | Asn | Arg | Phe | Gly | Gly | Lys | Tyr | Asn | Leu | Thr | Val | Ala |
| 150 | | | | | 155 | | | | | 160 | | | | 165 |

```
ggg gag ctc cgt ttc aag cgc att caa gac tcc att gcg acc aac ccc     672
Gly Glu Leu Arg Phe Lys Arg Ile Gln Asp Ser Ile Ala Thr Asn Pro
            170                 175                 180 aat ttc tcc ttt gtt gac ttt agg ttc ttt act gct tac ggc gag acc     720
Asn Phe Ser Phe Val Asp Phe Arg Phe Phe Thr Ala Tyr Gly Glu Thr
                185                 190                 195 acc ttc ccc gcg aat ctt ttt gtg gat ggg cgc agg gac gac ggc cag     768
Thr Phe Pro Ala Asn Leu Phe Val Asp Gly Arg Arg Asp Asp Gly Gln
            200                 205                 210 cta gat atg gat gct gca cgg agt ttt ttc caa ttc agc cgt atg cct     816
Leu Asp Met Asp Ala Ala Arg Ser Phe Phe Gln Phe Ser Arg Met Pro
        215                 220                 225 gac gat ttc ttc cgc gca ccc agc ccg aga agt ggc aca gga gtc gag     864
Asp Asp Phe Phe Arg Ala Pro Ser Pro Arg Ser Gly Thr Gly Val Glu
230                 235                 240                 245 gta gtt gta cag gct cat cct atg cag ccc gga aga aat gtc ggc aag     912
Val Val Val Gln Ala His Pro Met Gln Pro Gly Arg Asn Val Gly Lys
                250                 255                 260 atc aac agc tac acc gtc gac cca aca tcc tct gac ttt tcc acc ccc     960
Ile Asn Ser Tyr Thr Val Asp Pro Thr Ser Ser Asp Phe Ser Thr Pro
            265                 270                 275 tgc ttg atg tac gag aaa ttc gtc aac ata acg gtc aag tca ctc tac    1008
Cys Leu Met Tyr Glu Lys Phe Val Asn Ile Thr Val Lys Ser Leu Tyr
        280                 285                 290 ccg aat ccg acg gtg cag ctt cgc aaa gcc ctt aat acg aat ctc gat    1056
Pro Asn Pro Thr Val Gln Leu Arg Lys Ala Leu Asn Thr Asn Leu Asp
295                 300                 305 ttc tta ttc cag gga gtc gcc gct gga tgt acc cag gtc ttc cca tac    1104
Phe Leu Phe Gln Gly Val Ala Ala Gly Cys Thr Gln Val Phe Pro Tyr
310                 315                 320                 325 ggg cga gat                                                        1113
Gly Arg Asp <210> SEQ ID NO 18
<211> LENGTH: 371
<212> TYPE: PRT
<213> ORGANISM: Artificial Sequence
<220> FEATURE:
<223> OTHER INFORMATION: Synthetic Construct

<400> SEQUENCE: 18

Met Lys Tyr Phe Pro Leu Phe Pro Thr Leu Val Tyr Ala Val Gly Val
            -40                 -35                 -30

Val Ala Phe Pro Asp Tyr Ala Ser Leu Ala Gly Leu Ser Gln Gln Glu
        -25                 -20                 -15

Leu Asp Ala Ile Ile Pro Thr Leu Glu Ala Arg Glu Pro Gly Leu Pro
    -10                 -5                  -1   1               5

Pro Gly Pro Leu Glu Asn Ser Ser Ala Lys Leu Val Asn Asp Glu Ala
                10                  15                  20

His Pro Trp Lys Pro Leu Arg Pro Gly Asp Ile Arg Gly Pro Cys Pro
                25                  30                  35

Gly Leu Asn Thr Leu Ala Ser His Gly Tyr Leu Pro Arg Asn Gly Val
            40                  45                  50

Ala Thr Pro Ala Gln Ile Ile Asn Ala Val Gln Glu Gly Phe Asn Phe
        55                  60                  65

Asp Asn Gln Ala Ala Ile Phe Ala Thr Tyr Ala Ala His Leu Val Asp
70                  75                  80                  85
```

Gly Asn Leu Ile Thr Asp Leu Leu Ser Ile Gly Arg Lys Thr Arg Leu
                    90                  95                 100

Thr Gly Pro Asp Pro Pro Pro Ala Ser Val Gly Gly Leu Asn Glu
            105                 110                 115

His Gly Thr Phe Glu Gly Asp Ala Ser Met Thr Arg Gly Asp Ala Phe
            120                 125                 130

Phe Gly Asn Asn His Asp Phe Asn Glu Thr Leu Phe Glu Gln Leu Val
135                 140                 145

Asp Tyr Ser Asn Arg Phe Gly Gly Lys Tyr Asn Leu Thr Val Ala
150                 155                 160                 165

Gly Glu Leu Arg Phe Lys Arg Ile Gln Asp Ser Ile Ala Thr Asn Pro
                    170                 175                 180

Asn Phe Ser Phe Val Asp Phe Arg Phe Phe Thr Ala Tyr Gly Glu Thr
                185                 190                 195

Thr Phe Pro Ala Asn Leu Phe Val Asp Gly Arg Arg Asp Asp Gly Gln
            200                 205                 210

Leu Asp Met Asp Ala Ala Arg Ser Phe Phe Gln Phe Ser Arg Met Pro
            215                 220                 225

Asp Asp Phe Phe Arg Ala Pro Ser Pro Arg Ser Gly Thr Gly Val Glu
230                 235                 240                 245

Val Val Val Gln Ala His Pro Met Gln Pro Gly Arg Asn Val Gly Lys
                    250                 255                 260

Ile Asn Ser Tyr Thr Val Asp Pro Thr Ser Ser Asp Phe Ser Thr Pro
                265                 270                 275

Cys Leu Met Tyr Glu Lys Phe Val Asn Ile Thr Val Lys Ser Leu Tyr
            280                 285                 290

Pro Asn Pro Thr Val Gln Leu Arg Lys Ala Leu Asn Thr Asn Leu Asp
            295                 300                 305

Phe Leu Phe Gln Gly Val Ala Ala Gly Cys Thr Gln Val Phe Pro Tyr
310                 315                 320                 325

Gly Arg Asp

<210> SEQ ID NO 19
<211> LENGTH: 984
<212> TYPE: DNA
<213> ORGANISM: Artificial Sequence
<220> FEATURE:
<223> OTHER INFORMATION: JaWa variant without signal peptide
<220> FEATURE:
<221> NAME/KEY: CDS
<222> LOCATION: (1)..(984)

<400> SEQUENCE: 19

```
gag cca gga tta cct cct ggt cct ctc gag aat agc tct gca aag ttg      48
Glu Pro Gly Leu Pro Pro Gly Pro Leu Glu Asn Ser Ser Ala Lys Leu
1               5                   10                  15 gtg aac gac gag gct cac cca tgg aag ccg ctt cga cct ggc gat att      96
Val Asn Asp Glu Ala His Pro Trp Lys Pro Leu Arg Pro Gly Asp Ile
            20                  25                  30 cgt gga cct tgc cct ggt ctc aat act ctg gca tct cac ggg tac ctc     144
Arg Gly Pro Cys Pro Gly Leu Asn Thr Leu Ala Ser His Gly Tyr Leu
        35                  40                  45 ccg aga aat ggc gtt gca acc ccg gcg caa ata ata aac gcg gtt cag     192
Pro Arg Asn Gly Val Ala Thr Pro Ala Gln Ile Ile Asn Ala Val Gln
    50                  55                  60 gaa gga ttc aat ttc gac aat caa gcc gca atc ttc gcc aca tat gcg     240
Glu Gly Phe Asn Phe Asp Asn Gln Ala Ala Ile Phe Ala Thr Tyr Ala
```

```
                65                  70                  75                  80
gcc cac ctt gtg gac ggc aat ctc att acg gac ttg ctg agc atc gga           288
Ala His Leu Val Asp Gly Asn Leu Ile Thr Asp Leu Leu Ser Ile Gly
                85                  90                  95 cgc aag acg cgg ctc act ggg cct gat cca cca ccc ccc gct tcc gtt           336
Arg Lys Thr Arg Leu Thr Gly Pro Asp Pro Pro Pro Pro Ala Ser Val
                100                 105                 110 ggt gga ctc aat gag cat ggc acc ttc gaa ggc gac gcc agt atg acc           384
Gly Gly Leu Asn Glu His Gly Thr Phe Glu Gly Asp Ala Ser Met Thr
                115                 120                 125 cga ggt gac gca ttc ttt ggc aac aac cac gat ttc aat gag acg ctc           432
Arg Gly Asp Ala Phe Phe Gly Asn Asn His Asp Phe Asn Glu Thr Leu
        130                 135                 140 ttc gaa cag ttg gtt gac tac agc aac cga ttt gga gga gga aaa tac           480
Phe Glu Gln Leu Val Asp Tyr Ser Asn Arg Phe Gly Gly Gly Lys Tyr
145                 150                 155                 160 aat ctt acc gtc gcg ggg gag ctc cgt ttc aag cgc att caa gac tcc           528
Asn Leu Thr Val Ala Gly Glu Leu Arg Phe Lys Arg Ile Gln Asp Ser
                165                 170                 175 att gcg acc aac ccc aat ttc tcc ttt gtt gac ttt agg ttc ttt act           576
Ile Ala Thr Asn Pro Asn Phe Ser Phe Val Asp Phe Arg Phe Phe Thr
                180                 185                 190 gct tac ggc gag acc acc ttc ccc gcg aat ctt ttt gtg gat ggg cgc           624
Ala Tyr Gly Glu Thr Thr Phe Pro Ala Asn Leu Phe Val Asp Gly Arg
                195                 200                 205 agg gac gac ggc cag cta gat atg gat gct gca cgg agt ttt ttc caa           672
Arg Asp Asp Gly Gln Leu Asp Met Asp Ala Ala Arg Ser Phe Phe Gln
        210                 215                 220 ttc agc cgt atg cct gac gat ttc ttc cgc gca ccc agc ccg aga agt           720
Phe Ser Arg Met Pro Asp Asp Phe Phe Arg Ala Pro Ser Pro Arg Ser
225                 230                 235                 240 gac aca gga gtc gag gta gtt gta cag gct cat cct atg cag ccc gga           768
Asp Thr Gly Val Glu Val Val Val Gln Ala His Pro Met Gln Pro Gly
                245                 250                 255 aaa aat gtc ggc aag atc aac agc tac acc gtc gac cca aca tcc tct           816
Lys Asn Val Gly Lys Ile Asn Ser Tyr Thr Val Asp Pro Thr Ser Ser
                260                 265                 270 gac ttt tcc acc ccc tgc ttg atg tac gag aaa ttc gtc aac ata acg           864
Asp Phe Ser Thr Pro Cys Leu Met Tyr Glu Lys Phe Val Asn Ile Thr
                275                 280                 285 gtc aag tca ctc tac ccg aat ccg acg gtg cag ctt cgc aaa gcc ctt           912
Val Lys Ser Leu Tyr Pro Asn Pro Thr Val Gln Leu Arg Lys Ala Leu
                290                 295                 300 aat acg aat ctc gat ttc tta ttc cag gga gtc gcc gct gga tgt acc           960
Asn Thr Asn Leu Asp Phe Leu Phe Gln Gly Val Ala Ala Gly Cys Thr
305                 310                 315                 320 cag gtc ttc cca tac ggg cga gat                                           984
Gln Val Phe Pro Tyr Gly Arg Asp
                325
```

<210> SEQ ID NO 20
<211> LENGTH: 328
<212> TYPE: PRT
<213> ORGANISM: Artificial Sequence
<220> FEATURE:
<223> OTHER INFORMATION: Synthetic Construct

<400> SEQUENCE: 20

```
Glu Pro Gly Leu Pro Gly Pro Leu Glu Asn Ser Ser Ala Lys Leu
1               5                   10                  15
```

Val Asn Asp Glu Ala His Pro Trp Lys Pro Leu Arg Pro Gly Asp Ile
        20                  25                  30

Arg Gly Pro Cys Pro Gly Leu Asn Thr Leu Ala Ser His Gly Tyr Leu
    35                  40                  45

Pro Arg Asn Gly Val Ala Thr Pro Ala Gln Ile Ile Asn Ala Val Gln
50                  55                  60

Glu Gly Phe Asn Phe Asp Asn Gln Ala Ala Ile Phe Ala Thr Tyr Ala
65                  70                  75                  80

Ala His Leu Val Asp Gly Asn Leu Ile Thr Asp Leu Ser Ile Gly
                85                  90                  95

Arg Lys Thr Arg Leu Thr Gly Pro Asp Pro Pro Pro Ala Ser Val
            100                 105                 110

Gly Gly Leu Asn Glu His Gly Thr Phe Glu Gly Asp Ala Ser Met Thr
            115                 120                 125

Arg Gly Asp Ala Phe Phe Gly Asn Asn His Asp Phe Asn Glu Thr Leu
            130                 135                 140

Phe Glu Gln Leu Val Asp Tyr Ser Asn Arg Phe Gly Gly Gly Lys Tyr
145                 150                 155                 160

Asn Leu Thr Val Ala Gly Glu Leu Arg Phe Lys Arg Ile Gln Asp Ser
                165                 170                 175

Ile Ala Thr Asn Pro Asn Phe Ser Phe Val Asp Phe Arg Phe Phe Thr
            180                 185                 190

Ala Tyr Gly Glu Thr Thr Phe Pro Ala Asn Leu Phe Val Asp Gly Arg
            195                 200                 205

Arg Asp Asp Gly Gln Leu Asp Met Asp Ala Ala Arg Ser Phe Gln
210                 215                 220

Phe Ser Arg Met Pro Asp Asp Phe Phe Arg Ala Pro Ser Pro Arg Ser
225                 230                 235                 240

Asp Thr Gly Val Glu Val Val Gln Ala His Pro Met Gln Pro Gly
                245                 250                 255

Lys Asn Val Gly Lys Ile Asn Ser Tyr Thr Val Asp Pro Thr Ser Ser
            260                 265                 270

Asp Phe Ser Thr Pro Cys Leu Met Tyr Glu Lys Phe Val Asn Ile Thr
            275                 280                 285

Val Lys Ser Leu Tyr Pro Asn Pro Thr Val Gln Leu Arg Lys Ala Leu
290                 295                 300

Asn Thr Asn Leu Asp Phe Leu Phe Gln Gly Val Ala Ala Gly Cys Thr
305                 310                 315                 320

Gln Val Phe Pro Tyr Gly Arg Asp
                325

<210> SEQ ID NO 21
<211> LENGTH: 1113
<212> TYPE: DNA
<213> ORGANISM: Artificial Sequence
<220> FEATURE:
<223> OTHER INFORMATION: JaWa variant with wild signal peptide
<220> FEATURE:
<221> NAME/KEY: CDS
<222> LOCATION: (1)..(1113)
<220> FEATURE:
<221> NAME/KEY: mat_peptide
<222> LOCATION: (130)..(1113)

<400> SEQUENCE: 21 atg aaa tat ttt ccc ctg ttc cca acc ttg gtc ttc gca gcg agg gtc    48
Met Lys Tyr Phe Pro Leu Phe Pro Thr Leu Val Phe Ala Ala Arg Val
        -40                 -35                 -30

```
gtt gct ttt cct gcc tac gcc tca ttg gcc ggc ctc agc cag cag gaa      96
Val Ala Phe Pro Ala Tyr Ala Ser Leu Ala Gly Leu Ser Gln Gln Glu
        -25                 -20                 -15 ttg gac gct ata atc cca aca ctc gag gcc cga gag cca gga tta cct     144
Leu Asp Ala Ile Ile Pro Thr Leu Glu Ala Arg Glu Pro Gly Leu Pro
    -10                  -5                  -1   1              5 cct ggt cct ctc gag aat agc tct gca aag ttg gtg aac gac gag gct     192
Pro Gly Pro Leu Glu Asn Ser Ser Ala Lys Leu Val Asn Asp Glu Ala
                     10                  15                  20 cac cca tgg aag ccg ctt cga cct ggc gat att cgt gga cct tgc cct     240
His Pro Trp Lys Pro Leu Arg Pro Gly Asp Ile Arg Gly Pro Cys Pro
             25                  30                  35 ggt ctc aat act ctg gca tct cac ggg tac ctc ccg aga aat ggc gtt     288
Gly Leu Asn Thr Leu Ala Ser His Gly Tyr Leu Pro Arg Asn Gly Val
         40                  45                  50 gca acc ccg gcg caa ata ata aac gcg gtt cag gaa gga ttc aat ttc     336
Ala Thr Pro Ala Gln Ile Ile Asn Ala Val Gln Glu Gly Phe Asn Phe
     55                  60                  65 gac aat caa gcc gca atc ttc gcc aca tat gcg gcc cac ctt gtg gac     384
Asp Asn Gln Ala Ala Ile Phe Ala Thr Tyr Ala Ala His Leu Val Asp
70                  75                  80                  85 ggc aat ctc att acg gac ttg ctg agc atc gga cgc aag acg cgg ctc     432
Gly Asn Leu Ile Thr Asp Leu Leu Ser Ile Gly Arg Lys Thr Arg Leu
                 90                  95                 100 act ggg cct gat cca cca ccc ccc gct tcc gtt ggt gga ctc aat gag     480
Thr Gly Pro Asp Pro Pro Pro Pro Ala Ser Val Gly Gly Leu Asn Glu
             105                 110                 115 cat ggc acc ttc gaa ggc gac gcc agt atg acc cga ggt gac gca ttc     528
His Gly Thr Phe Glu Gly Asp Ala Ser Met Thr Arg Gly Asp Ala Phe
         120                 125                 130 ttt ggc aac aac cac gat ttc aat gag acg ctc ttc gaa cag ttg gtt     576
Phe Gly Asn Asn His Asp Phe Asn Glu Thr Leu Phe Glu Gln Leu Val
     135                 140                 145 gac tac agc aac cga ttt gga gga gga aaa tac aat ctt acc gtc gcg     624
Asp Tyr Ser Asn Arg Phe Gly Gly Gly Lys Tyr Asn Leu Thr Val Ala
150                 155                 160                 165 ggg gag ctc cgt ttc aag cgc att caa gac tcc att gcg acc aac ccc     672
Gly Glu Leu Arg Phe Lys Arg Ile Gln Asp Ser Ile Ala Thr Asn Pro
                 170                 175                 180 aat ttc tcc ttt gtt gac ttt agg ttc ttt act gct tac ggc gag acc     720
Asn Phe Ser Phe Val Asp Phe Arg Phe Phe Thr Ala Tyr Gly Glu Thr
             185                 190                 195 acc ttc ccc gcg aat ctt ttt gtg gat ggg cgc agg gac gac ggc cag     768
Thr Phe Pro Ala Asn Leu Phe Val Asp Gly Arg Arg Asp Asp Gly Gln
         200                 205                 210 cta gat atg gat gct gca cgg agt ttt ttc caa ttc agc cgt atg cct     816
Leu Asp Met Asp Ala Ala Arg Ser Phe Phe Gln Phe Ser Arg Met Pro
     215                 220                 225 gac gat ttc ttc cgc gca ccc agc ccg aga agt gac aca gga gtc gag     864
Asp Asp Phe Phe Arg Ala Pro Ser Pro Arg Ser Asp Thr Gly Val Glu
230                 235                 240                 245 gta gtt gta cag gct cat cct atg cag ccc gga aaa aat gtc ggc aag     912
Val Val Val Gln Ala His Pro Met Gln Pro Gly Lys Asn Val Gly Lys
                 250                 255                 260 atc aac agc tac acc gtc gac cca aca tcc tct gac ttt tcc acc ccc     960
Ile Asn Ser Tyr Thr Val Asp Pro Thr Ser Ser Asp Phe Ser Thr Pro
             265                 270                 275 tgc ttg atg tac gag aaa ttc gtc aac ata acg gtc aag tca ctc tac    1008
Cys Leu Met Tyr Glu Lys Phe Val Asn Ile Thr Val Lys Ser Leu Tyr
```

```
                    280                 285                 290
ccg aat ccg acg gtg cag ctt cgc aaa gcc ctt aat acg aat ctc gat      1056
Pro Asn Pro Thr Val Gln Leu Arg Lys Ala Leu Asn Thr Asn Leu Asp
295                 300                 305 ttc tta ttc cag gga gtc gcc gct gga tgt acc cag gtc ttc cca tac      1104
Phe Leu Phe Gln Gly Val Ala Ala Gly Cys Thr Gln Val Phe Pro Tyr
310             315                 320                 325 ggg cga gat                                                          1113
Gly Arg Asp <210> SEQ ID NO 22
<211> LENGTH: 371
<212> TYPE: PRT
<213> ORGANISM: Artificial Sequence
<220> FEATURE:
<223> OTHER INFORMATION: Synthetic Construct

<400> SEQUENCE: 22

Met Lys Tyr Phe Pro Leu Phe Pro Thr Leu Val Phe Ala Ala Arg Val
            -40                 -35                 -30

Val Ala Phe Pro Ala Tyr Ala Ser Leu Ala Gly Leu Ser Gln Gln Glu
        -25                 -20                 -15

Leu Asp Ala Ile Ile Pro Thr Leu Glu Ala Arg Glu Pro Gly Leu Pro
    -10                 -5              -1   1               5

Pro Gly Pro Leu Glu Asn Ser Ser Ala Lys Leu Val Asn Asp Glu Ala
                10                  15                  20

His Pro Trp Lys Pro Leu Arg Pro Gly Asp Ile Arg Gly Pro Cys Pro
            25                  30                  35

Gly Leu Asn Thr Leu Ala Ser His Gly Tyr Leu Pro Arg Asn Gly Val
        40                  45                  50

Ala Thr Pro Ala Gln Ile Ile Asn Ala Val Gln Glu Gly Phe Asn Phe
    55                  60                  65

Asp Asn Gln Ala Ala Ile Phe Ala Thr Tyr Ala Ala His Leu Val Asp
70                  75                  80                  85

Gly Asn Leu Ile Thr Asp Leu Leu Ser Ile Gly Arg Lys Thr Arg Leu
                90                  95                  100

Thr Gly Pro Asp Pro Pro Pro Ala Ser Val Gly Gly Leu Asn Glu
            105                 110                 115

His Gly Thr Phe Glu Gly Asp Ala Ser Met Thr Arg Gly Asp Ala Phe
        120                 125                 130

Phe Gly Asn Asn His Asp Phe Asn Glu Thr Leu Phe Glu Gln Leu Val
    135                 140                 145

Asp Tyr Ser Asn Arg Phe Gly Gly Lys Tyr Asn Leu Thr Val Ala
150                 155                 160                 165

Gly Glu Leu Arg Phe Lys Arg Ile Gln Asp Ser Ile Ala Thr Asn Pro
                170                 175                 180

Asn Phe Ser Phe Val Asp Phe Arg Phe Phe Thr Ala Tyr Gly Glu Thr
            185                 190                 195

Thr Phe Pro Ala Asn Leu Phe Val Asp Gly Arg Arg Asp Asp Gly Gln
        200                 205                 210

Leu Asp Met Asp Ala Ala Arg Ser Phe Gln Phe Ser Arg Met Pro
    215                 220                 225

Asp Asp Phe Phe Arg Ala Pro Ser Pro Arg Ser Asp Thr Gly Val Glu
230                 235                 240                 245

Val Val Val Gln Ala His Pro Met Gln Pro Gly Lys Asn Val Gly Lys
                250                 255                 260
```

```
Ile Asn Ser Tyr Thr Val Asp Pro Thr Ser Ser Asp Phe Ser Thr Pro
            265                 270                 275

Cys Leu Met Tyr Glu Lys Phe Val Asn Ile Thr Val Lys Ser Leu Tyr
        280                 285                 290

Pro Asn Pro Thr Val Gln Leu Arg Lys Ala Leu Asn Thr Asn Leu Asp
    295                 300                 305

Phe Leu Phe Gln Gly Val Ala Ala Gly Cys Thr Gln Val Phe Pro Tyr
310                 315                 320                 325

Gly Arg Asp

<210> SEQ ID NO 23
<211> LENGTH: 1113
<212> TYPE: DNA
<213> ORGANISM: Artificial Sequence
<220> FEATURE:
<223> OTHER INFORMATION: JaWa variant with wild modified signal peptide
<220> FEATURE:
<221> NAME/KEY: CDS
<222> LOCATION: (1)..(1113)
<220> FEATURE:
<221> NAME/KEY: mat_peptide
<222> LOCATION: (130)..(1113)

<400> SEQUENCE: 23 atg aaa tat ttt ccc ctg ttc cca acc ttg gtc tac gca gtg ggg gtc    48
Met Lys Tyr Phe Pro Leu Phe Pro Thr Leu Val Tyr Ala Val Gly Val
        -40                 -35                 -30 gtt gct ttt cct gac tac gcc tca ttg gcc ggc ctc agc cag cag gaa    96
Val Ala Phe Pro Asp Tyr Ala Ser Leu Ala Gly Leu Ser Gln Gln Glu
    -25                 -20                 -15 ttg gac gct ata atc cca aca ctc gag gcc cga gag cca gga tta cct   144
Leu Asp Ala Ile Ile Pro Thr Leu Glu Ala Arg Glu Pro Gly Leu Pro
-10                  -5                  -1   1               5 cct ggt cct ctc gag aat agc tct gca aag ttg gtg aac gac gag gct   192
Pro Gly Pro Leu Glu Asn Ser Ser Ala Lys Leu Val Asn Asp Glu Ala
                10                  15                  20 cac cca tgg aag ccg ctt cga cct ggc gat att cgt gga cct tgc cct   240
His Pro Trp Lys Pro Leu Arg Pro Gly Asp Ile Arg Gly Pro Cys Pro
            25                  30                  35 ggt ctc aat act ctg gca tct cac ggg tac ctc ccg aga aat ggc gtt   288
Gly Leu Asn Thr Leu Ala Ser His Gly Tyr Leu Pro Arg Asn Gly Val
        40                  45                  50 gca acc ccg gcg caa ata ata aac gcg gtt cag gaa gga ttc aat ttc   336
Ala Thr Pro Ala Gln Ile Ile Asn Ala Val Gln Glu Gly Phe Asn Phe
    55                  60                  65 gac aat caa gcc gca atc ttc gcc aca tat gcg gcc cac ctt gtg gac   384
Asp Asn Gln Ala Ala Ile Phe Ala Thr Tyr Ala Ala His Leu Val Asp
70                  75                  80                  85 ggc aat ctc att acg gac ttg ctg agc atc gga cgc aag acg cgg ctc   432
Gly Asn Leu Ile Thr Asp Leu Leu Ser Ile Gly Arg Lys Thr Arg Leu
                90                  95                 100 act ggg cct gat cca cca ccc ccc gct tcc gtt ggt gga ctc aat gag   480
Thr Gly Pro Asp Pro Pro Pro Pro Ala Ser Val Gly Gly Leu Asn Glu
            105                 110                 115 cat ggc acc ttc gaa ggc gac gcc agt atg acc cga ggt gac gca ttc   528
His Gly Thr Phe Glu Gly Asp Ala Ser Met Thr Arg Gly Asp Ala Phe
        120                 125                 130 ttt ggc aac aac cac gat ttc aat gag acg ctc ttc gaa cag ttg gtt   576
Phe Gly Asn Asn His Asp Phe Asn Glu Thr Leu Phe Glu Gln Leu Val
    135                 140                 145
```

| | | |
|---|---|---|
| gac tac agc aac cga ttt gga gga gga aaa tac aat ctt acc gtc gcg<br>Asp Tyr Ser Asn Arg Phe Gly Gly Gly Lys Tyr Asn Leu Thr Val Ala<br>150                   155                       160                   165 | 624 |
| ggg gag ctc cgt ttc aag cgc att caa gac tcc att gcg acc aac ccc<br>Gly Glu Leu Arg Phe Lys Arg Ile Gln Asp Ser Ile Ala Thr Asn Pro<br>          170                       175                       180 | 672 |
| aat ttc tcc ttt gtt gac ttt agg ttc ttt act gct tac ggc gag acc<br>Asn Phe Ser Phe Val Asp Phe Arg Phe Phe Thr Ala Tyr Gly Glu Thr<br>               185                       190                   195 | 720 |
| acc ttc ccc gcg aat ctt ttt gtg gat ggg cgc agg gac gac ggc cag<br>Thr Phe Pro Ala Asn Leu Phe Val Asp Gly Arg Arg Asp Asp Gly Gln<br>200                   205                     210 | 768 |
| cta gat atg gat gct gca cgg agt ttt ttc caa ttc agc cgt atg cct<br>Leu Asp Met Asp Ala Ala Arg Ser Phe Phe Gln Phe Ser Arg Met Pro<br>215                   220                     225 | 816 |
| gac gat ttc ttc cgc gca ccc agc ccg aga agt gac aca gga gtc gag<br>Asp Asp Phe Phe Arg Ala Pro Ser Pro Arg Ser Asp Thr Gly Val Glu<br>230                   235                     240                   245 | 864 |
| gta gtt gta cag gct cat cct atg cag ccc gga aaa aat gtc ggc aag<br>Val Val Val Gln Ala His Pro Met Gln Pro Gly Lys Asn Val Gly Lys<br>               250                       255                   260 | 912 |
| atc aac agc tac acc gtc gac cca aca tcc tct gac ttt tcc acc ccc<br>Ile Asn Ser Tyr Thr Val Asp Pro Thr Ser Ser Asp Phe Ser Thr Pro<br>                   265                     270                   275 | 960 |
| tgc ttg atg tac gag aaa ttc gtc aac ata acg gtc aag tca ctc tac<br>Cys Leu Met Tyr Glu Lys Phe Val Asn Ile Thr Val Lys Ser Leu Tyr<br>          280                       285                       290 | 1008 |
| ccg aat ccg acg gtg cag ctt cgc aaa gcc ctt aat acg aat ctc gat<br>Pro Asn Pro Thr Val Gln Leu Arg Lys Ala Leu Asn Thr Asn Leu Asp<br>295                   300                     305 | 1056 |
| ttc tta ttc cag gga gtc gcc gct gga tgt acc cag gtc ttc cca tac<br>Phe Leu Phe Gln Gly Val Ala Ala Gly Cys Thr Gln Val Phe Pro Tyr<br>310                   315                     320                   325 | 1104 |
| ggg cga gat<br>Gly Arg Asp | 1113 |

<210> SEQ ID NO 24
<211> LENGTH: 371
<212> TYPE: PRT
<213> ORGANISM: Artificial Sequence
<220> FEATURE:
<223> OTHER INFORMATION: Synthetic Construct

<400> SEQUENCE: 24

Met Lys Tyr Phe Pro Leu Phe Pro Thr Leu Val Tyr Ala Val Gly Val
               -40                    -35                    -30

Val Ala Phe Pro Asp Tyr Ala Ser Leu Ala Gly Leu Ser Gln Gln Glu
     -25                    -20                    -15

Leu Asp Ala Ile Ile Pro Thr Leu Glu Ala Arg Glu Pro Gly Leu Pro
-10                    -5                    -1  1                 5

Pro Gly Pro Leu Glu Asn Ser Ser Ala Lys Leu Val Asn Asp Glu Ala
               10                     15                     20

His Pro Trp Lys Pro Leu Arg Pro Gly Asp Ile Arg Gly Pro Cys Pro
          25                       30                     35

Gly Leu Asn Thr Leu Ala Ser His Gly Tyr Leu Pro Arg Asn Gly Val
         40                     45                     50

Ala Thr Pro Ala Gln Ile Ile Asn Ala Val Gln Glu Gly Phe Asn Phe
    55                     60                     65

Asp Asn Gln Ala Ala Ile Phe Ala Thr Tyr Ala Ala His Leu Val Asp

```
             70                  75                  80                  85
    Gly Asn Leu Ile Thr Asp Leu Leu Ser Ile Gly Arg Lys Thr Arg Leu
                    90                  95                 100

Thr Gly Pro Asp Pro Pro Pro Ala Ser Val Gly Gly Leu Asn Glu
                105                 110                 115

His Gly Thr Phe Glu Gly Asp Ala Ser Met Thr Arg Gly Asp Ala Phe
                120                 125                 130

Phe Gly Asn Asn His Asp Phe Asn Glu Thr Leu Phe Glu Gln Leu Val
                135                 140                 145

Asp Tyr Ser Asn Arg Phe Gly Gly Lys Tyr Asn Leu Thr Val Ala
    150                 155                 160                 165

Gly Glu Leu Arg Phe Lys Arg Ile Gln Asp Ser Ile Ala Thr Asn Pro
                    170                 175                 180

Asn Phe Ser Phe Val Asp Phe Arg Phe Thr Ala Tyr Gly Glu Thr
                185                 190                 195

Thr Phe Pro Ala Asn Leu Phe Val Asp Gly Arg Arg Asp Asp Gly Gln
                200                 205                 210

Leu Asp Met Asp Ala Ala Arg Ser Phe Phe Gln Phe Ser Arg Met Pro
                215                 220                 225

Asp Asp Phe Phe Arg Ala Pro Ser Pro Arg Ser Asp Thr Gly Val Glu
    230                 235                 240                 245

Val Val Val Gln Ala His Pro Met Gln Pro Gly Lys Asn Val Gly Lys
                    250                 255                 260

Ile Asn Ser Tyr Thr Val Asp Pro Thr Ser Ser Asp Phe Ser Thr Pro
                    265                 270                 275

Cys Leu Met Tyr Glu Lys Phe Val Asn Ile Thr Val Lys Ser Leu Tyr
                    280                 285                 290

Pro Asn Pro Thr Val Gln Leu Arg Lys Ala Leu Asn Thr Asn Leu Asp
                    295                 300                 305

Phe Leu Phe Gln Gly Val Ala Ala Gly Cys Thr Gln Val Phe Pro Tyr
    310                 315                 320                 325

Gly Arg Asp

<210> SEQ ID NO 25
<211> LENGTH: 129
<212> TYPE: DNA
<213> ORGANISM: Agrocybe aegerita
<220> FEATURE:
<221> NAME/KEY: CDS
<222> LOCATION: (1)..(129)

<400> SEQUENCE: 25 atg aaa tat ttt ccc ctg ttc cca acc ttg gtc ttc gca gcg agg gtc      48
Met Lys Tyr Phe Pro Leu Phe Pro Thr Leu Val Phe Ala Ala Arg Val
 1               5                  10                  15 gtt gct ttt cct gcc tac gcc tca ttg gcc ggc ctc agc cag cag gaa      96
Val Ala Phe Pro Ala Tyr Ala Ser Leu Ala Gly Leu Ser Gln Gln Glu
            20                  25                  30 ttg gac gct ata atc cca aca ctc gag gcc cga                         129
Leu Asp Ala Ile Ile Pro Thr Leu Glu Ala Arg
        35                  40

<210> SEQ ID NO 26
<211> LENGTH: 43
<212> TYPE: PRT
<213> ORGANISM: Agrocybe aegerita

<400> SEQUENCE: 26
```

```
Met Lys Tyr Phe Pro Leu Phe Pro Thr Leu Val Phe Ala Ala Arg Val
1               5                   10                  15

Val Ala Phe Pro Ala Tyr Ala Ser Leu Ala Gly Leu Ser Gln Gln Glu
            20                  25                  30

Leu Asp Ala Ile Ile Pro Thr Leu Glu Ala Arg
        35                  40
```

```
<210> SEQ ID NO 27
<211> LENGTH: 129
<212> TYPE: DNA
<213> ORGANISM: Artificial Sequence
<220> FEATURE:
<223> OTHER INFORMATION: Signal peptide modified with respect to the
      wild signal peptide from A. aegerita
<220> FEATURE:
<221> NAME/KEY: CDS
<222> LOCATION: (1)..(129)

<400> SEQUENCE: 27
```

```
atg aaa tat ttt ccc ctg ttc cca acc ttg gtc tac gca gtg ggg gtc      48
Met Lys Tyr Phe Pro Leu Phe Pro Thr Leu Val Tyr Ala Val Gly Val
1               5                   10                  15 gtt gct ttt cct gac tac gcc tca ttg gcc ggc ctc agc cag cag gaa      96
Val Ala Phe Pro Asp Tyr Ala Ser Leu Ala Gly Leu Ser Gln Gln Glu
            20                  25                  30 ttg gac gct ata atc cca aca ctc gag gcc cga                          129
Leu Asp Ala Ile Ile Pro Thr Leu Glu Ala Arg
        35                  40
```

```
<210> SEQ ID NO 28
<211> LENGTH: 43
<212> TYPE: PRT
<213> ORGANISM: Artificial Sequence
<220> FEATURE:
<223> OTHER INFORMATION: Synthetic Construct

<400> SEQUENCE: 28
```

```
Met Lys Tyr Phe Pro Leu Phe Pro Thr Leu Val Tyr Ala Val Gly Val
1               5                   10                  15

Val Ala Phe Pro Asp Tyr Ala Ser Leu Ala Gly Leu Ser Gln Gln Glu
            20                  25                  30

Leu Asp Ala Ile Ile Pro Thr Leu Glu Ala Arg
        35                  40
```

```
<210> SEQ ID NO 29
<211> LENGTH: 1113
<212> TYPE: DNA
<213> ORGANISM: Artificial Sequence
<220> FEATURE:
<223> OTHER INFORMATION: W24F variant obtained from the PaDa-I variant
<220> FEATURE:
<221> NAME/KEY: CDS
<222> LOCATION: (1)..(1113)
<220> FEATURE:
<221> NAME/KEY: mat_peptide
<222> LOCATION: (130)..(1113)

<400> SEQUENCE: 29
```

```
atg aaa tat ttt ccc ctg ttc cca acc ttg gtc tac gca gtg ggg gtc      48
Met Lys Tyr Phe Pro Leu Phe Pro Thr Leu Val Tyr Ala Val Gly Val
                -40                 -35                 -30 gtt gct ttt cct gac tac gcc tca ttg gcc ggc ctc agc cag cag gaa      96
Val Ala Phe Pro Asp Tyr Ala Ser Leu Ala Gly Leu Ser Gln Gln Glu
            -25                 -20                 -15
```

| | |
|---|---|
| ttg gac gct ata atc cca aca ctc gag gcc cga gag cca gga tta cct<br>Leu Asp Ala Ile Ile Pro Thr Leu Glu Ala Arg Glu Pro Gly Leu Pro<br>    -10                               -5                     -1 1                5 | 144 |
| cct ggt cct ctc gag aat agc tct gca aag ttg gtg aac gac gag gct<br>Pro Gly Pro Leu Glu Asn Ser Ser Ala Lys Leu Val Asn Asp Glu Ala<br>                 10                           15                           20 | 192 |
| cac cca ttt aag ccg ctt cga cct ggc gat att cgt gga cct tgc cct<br>His Pro Phe Lys Pro Leu Arg Pro Gly Asp Ile Arg Gly Pro Cys Pro<br>            25                       30                      35 | 240 |
| ggt ctc aat act ctg gca tct cac ggg tac ctc ccg aga aat ggc gtt<br>Gly Leu Asn Thr Leu Ala Ser His Gly Tyr Leu Pro Arg Asn Gly Val<br>        40                     45                      50 | 288 |
| gca acc ccg gcg caa ata ata aac gcg gtt cag gaa gga ttc aat ttc<br>Ala Thr Pro Ala Gln Ile Ile Asn Ala Val Gln Glu Gly Phe Asn Phe<br>      55                     60                      65 | 336 |
| gac aat caa gcc gca atc ttc gcc aca tat gcg gcc cac ctt gtg gac<br>Asp Asn Gln Ala Ala Ile Phe Ala Thr Tyr Ala Ala His Leu Val Asp<br>70                      75                     80                     85 | 384 |
| ggc aat ctc att acg gac ttg ctg agc atc gga cgc aag acg cgg ctc<br>Gly Asn Leu Ile Thr Asp Leu Leu Ser Ile Gly Arg Lys Thr Arg Leu<br>              90                     95                   100 | 432 |
| act ggg cct gat cca cca ccc ccc gct tcc gtt ggt gga ctc aat gag<br>Thr Gly Pro Asp Pro Pro Pro Pro Ala Ser Val Gly Gly Leu Asn Glu<br>            105                     110                 115 | 480 |
| cat ggc acc ttc gaa ggc gac gcc agt atg acc cga ggt gac gca ttc<br>His Gly Thr Phe Glu Gly Asp Ala Ser Met Thr Arg Gly Asp Ala Phe<br>              120                     125                 130 | 528 |
| ttt ggc aac aac cac gat ttc aat gag acg ctc ttc gaa cag ttg gtt<br>Phe Gly Asn Asn His Asp Phe Asn Glu Thr Leu Phe Glu Gln Leu Val<br>     135                     140                     145 | 576 |
| gac tac agc aac cga ttt gga gga gga aaa tac aat ctt acc gtc gcg<br>Asp Tyr Ser Asn Arg Phe Gly Gly Gly Lys Tyr Asn Leu Thr Val Ala<br>150                   155                     160                165 | 624 |
| ggg gag ctc cgt ttc aag cgc att caa gac tcc att gcg acc aac ccc<br>Gly Glu Leu Arg Phe Lys Arg Ile Gln Asp Ser Ile Ala Thr Asn Pro<br>              170                     175                 180 | 672 |
| aat ttc tcc ttt gtt gac ttt agg ttc ttt act gct tac ggc gag acc<br>Asn Phe Ser Phe Val Asp Phe Arg Phe Phe Thr Ala Tyr Gly Glu Thr<br>           185                     190                 195 | 720 |
| acc ttc ccc gcg aat ctt ttt gtg gat ggg cgc agg gac gac ggc cag<br>Thr Phe Pro Ala Asn Leu Phe Val Asp Gly Arg Arg Asp Asp Gly Gln<br>        200                     205                    210 | 768 |
| cta gat atg gat gct gca cgg agt ttt ttc caa ttc agc cgt atg cct<br>Leu Asp Met Asp Ala Ala Arg Ser Phe Phe Gln Phe Ser Arg Met Pro<br>      215                     220                     225 | 816 |
| gac gat ttc ttc cgc gca ccc agc ccg aga agt ggc aca gga gtc gag<br>Asp Asp Phe Phe Arg Ala Pro Ser Pro Arg Ser Gly Thr Gly Val Glu<br>230                   235                     240                245 | 864 |
| gta gtt gta cag gct cat cct atg cag ccc gga aga aat gtc ggc aag<br>Val Val Val Gln Ala His Pro Met Gln Pro Gly Arg Asn Val Gly Lys<br>              250                     255                 260 | 912 |
| atc aac agc tac acc gtc gac cca aca tcc tct gac ttt tcc acc ccc<br>Ile Asn Ser Tyr Thr Val Asp Pro Thr Ser Ser Asp Phe Ser Thr Pro<br>                265                     270                 275 | 960 |
| tgc ttg atg tac gag aaa ttc gtc aac ata acg gtc aag tca ctc tac<br>Cys Leu Met Tyr Glu Lys Phe Val Asn Ile Thr Val Lys Ser Leu Tyr<br>          280                     285                 290 | 1008 |
| ccg aat ccg acg gtg cag ctt cgc aaa gcc ctt aat acg aat ctc gat<br>Pro Asn Pro Thr Val Gln Leu Arg Lys Ala Leu Asn Thr Asn Leu Asp<br>     295                     300                     305 | 1056 |

```
ttc tta ttc cag gga gtc gcc gct gga tgt acc cag gtc ttc cca tac    1104
Phe Leu Phe Gln Gly Val Ala Ala Gly Cys Thr Gln Val Phe Pro Tyr
310             315                 320                 325 ggg cga gat                                                         1113
Gly Arg Asp <210> SEQ ID NO 30
<211> LENGTH: 371
<212> TYPE: PRT
<213> ORGANISM: Artificial Sequence
<220> FEATURE:
<223> OTHER INFORMATION: Synthetic Construct

<400> SEQUENCE: 30

Met Lys Tyr Phe Pro Leu Phe Pro Thr Leu Val Tyr Ala Val Gly Val
                -40                 -35                 -30

Val Ala Phe Pro Asp Tyr Ala Ser Leu Ala Gly Leu Ser Gln Gln Glu
        -25                 -20                 -15

Leu Asp Ala Ile Ile Pro Thr Leu Glu Ala Arg Glu Pro Gly Leu Pro
    -10                  -5                  -1   1               5

Pro Gly Pro Leu Glu Asn Ser Ser Ala Lys Leu Val Asn Asp Glu Ala
                 10                  15                  20

His Pro Phe Lys Pro Leu Arg Pro Gly Asp Ile Arg Gly Pro Cys Pro
             25                  30                  35

Gly Leu Asn Thr Leu Ala Ser His Gly Tyr Leu Pro Arg Asn Gly Val
             40                  45                  50

Ala Thr Pro Ala Gln Ile Ile Asn Ala Val Gln Glu Gly Phe Asn Phe
         55                  60                  65

Asp Asn Gln Ala Ala Ile Phe Ala Thr Tyr Ala Ala His Leu Val Asp
70                  75                  80                  85

Gly Asn Leu Ile Thr Asp Leu Leu Ser Ile Gly Arg Lys Thr Arg Leu
                 90                  95                 100

Thr Gly Pro Asp Pro Pro Pro Ala Ser Val Gly Gly Leu Asn Glu
                105                 110                 115

His Gly Thr Phe Glu Gly Asp Ala Ser Met Thr Arg Gly Asp Ala Phe
             120                 125                 130

Phe Gly Asn Asn His Asp Phe Asn Glu Thr Leu Phe Glu Gln Leu Val
    135                 140                 145

Asp Tyr Ser Asn Arg Phe Gly Gly Lys Tyr Asn Leu Thr Val Ala
150                 155                 160                 165

Gly Glu Leu Arg Phe Lys Arg Ile Gln Asp Ser Ile Ala Thr Asn Pro
                170                 175                 180

Asn Phe Ser Phe Val Asp Phe Arg Phe Phe Thr Ala Tyr Gly Glu Thr
            185                 190                 195

Thr Phe Pro Ala Asn Leu Phe Val Asp Gly Arg Arg Asp Asp Gly Gln
        200                 205                 210

Leu Asp Met Asp Ala Ala Arg Ser Phe Gln Phe Ser Arg Met Pro
    215                 220                 225

Asp Asp Phe Phe Arg Ala Pro Ser Pro Arg Ser Gly Thr Gly Val Glu
230                 235                 240                 245

Val Val Val Gln Ala His Pro Met Gln Pro Gly Arg Asn Val Gly Lys
                250                 255                 260

Ile Asn Ser Tyr Thr Val Asp Pro Thr Ser Ser Asp Phe Ser Thr Pro
            265                 270                 275

Cys Leu Met Tyr Glu Lys Phe Val Asn Ile Thr Val Lys Ser Leu Tyr
```

```
            280                 285                 290
Pro Asn Pro Thr Val Gln Leu Arg Lys Ala Leu Asn Thr Asn Leu Asp
        295                 300                 305

Phe Leu Phe Gln Gly Val Ala Ala Gly Cys Thr Gln Val Phe Pro Tyr
310                 315                 320                 325

Gly Arg Asp

<210> SEQ ID NO 31
<211> LENGTH: 1113
<212> TYPE: DNA
<213> ORGANISM: Artificial Sequence
<220> FEATURE:
<223> OTHER INFORMATION: W24F variant obtained from the Jawa variant
<220> FEATURE:
<221> NAME/KEY: CDS
<222> LOCATION: (1)..(1113)
<220> FEATURE:
<221> NAME/KEY: mat_peptide
<222> LOCATION: (130)..(1113)

<400> SEQUENCE: 31 atg aaa tat ttt ccc ctg ttc cca acc ttg gtc tac gca gtg ggg gtc      48
Met Lys Tyr Phe Pro Leu Phe Pro Thr Leu Val Tyr Ala Val Gly Val
            -40                 -35                 -30 gtt gct ttt cct gac tac gcc tca ttg gcc ggc ctc agc cag cag gaa      96
Val Ala Phe Pro Asp Tyr Ala Ser Leu Ala Gly Leu Ser Gln Gln Glu
        -25                 -20                 -15 ttg gac gct ata atc cca aca ctc gag gcc cga gag cca gga tta cct     144
Leu Asp Ala Ile Ile Pro Thr Leu Glu Ala Arg Glu Pro Gly Leu Pro
    -10                  -5                  -1   1               5 cct ggt cct ctc gag aat agc tct gca aag ttg gtg aac gac gag gct     192
Pro Gly Pro Leu Glu Asn Ser Ser Ala Lys Leu Val Asn Asp Glu Ala
                    10                  15                  20 cac cca ttt aag ccg ctt cga cct ggc gat att cgt gga cct tgc cct     240
His Pro Phe Lys Pro Leu Arg Pro Gly Asp Ile Arg Gly Pro Cys Pro
                25                  30                  35 ggt ctc aat act ctg gca tct cac ggg tac ctc ccg aga aat ggc gtt     288
Gly Leu Asn Thr Leu Ala Ser His Gly Tyr Leu Pro Arg Asn Gly Val
        40                  45                  50 gca acc ccg gcg caa ata ata aac gcg gtt cag gaa gga ttc aat ttc     336
Ala Thr Pro Ala Gln Ile Ile Asn Ala Val Gln Glu Gly Phe Asn Phe
55                  60                  65 gac aat caa gcc gca atc ttc gcc aca tat gcg gcc cac ctt gtg gac     384
Asp Asn Gln Ala Ala Ile Phe Ala Thr Tyr Ala Ala His Leu Val Asp
70                  75                  80                  85 ggc aat ctc att acg gac ttg ctg agc atc gga cgc aag acg cgg ctc     432
Gly Asn Leu Ile Thr Asp Leu Leu Ser Ile Gly Arg Lys Thr Arg Leu
                90                  95                 100 act ggg cct gat cca cca ccc ccc gct tcc gtt ggt gga ctc aat gag     480
Thr Gly Pro Asp Pro Pro Pro Pro Ala Ser Val Gly Gly Leu Asn Glu
            105                 110                 115 cat ggc acc ttc gaa ggc gac gcc agt atg acc cga ggt gac gca ttc     528
His Gly Thr Phe Glu Gly Asp Ala Ser Met Thr Arg Gly Asp Ala Phe
        120                 125                 130 ttt ggc aac aac cac gat ttc aat gag acg ctc ttc gaa cag ttg gtt     576
Phe Gly Asn Asn His Asp Phe Asn Glu Thr Leu Phe Glu Gln Leu Val
    135                 140                 145 gac tac agc aac cga ttt gga gga gga aaa tac aat ctt acc gtc gcg     624
Asp Tyr Ser Asn Arg Phe Gly Gly Gly Lys Tyr Asn Leu Thr Val Ala
150                 155                 160                 165 ggg gag ctc cgt ttc aag cgc att caa gac tcc att gcg acc aac ccc     672
```

```
Gly Glu Leu Arg Phe Lys Arg Ile Gln Asp Ser Ile Ala Thr Asn Pro
                170                 175                 180 aat ttc tcc ttt gtt gac ttt agg ttc ttt act gct tac ggc gag acc      720
Asn Phe Ser Phe Val Asp Phe Arg Phe Phe Thr Ala Tyr Gly Glu Thr
            185                 190                 195 acc ttc ccc gcg aat ctt ttt gtg gat ggg cgc agg gac gac ggc cag      768
Thr Phe Pro Ala Asn Leu Phe Val Asp Gly Arg Arg Asp Asp Gly Gln
                200                 205                 210 cta gat atg gat gct gca cgg agt ttt ttc caa ttc agc cgt atg cct      816
Leu Asp Met Asp Ala Ala Arg Ser Phe Phe Gln Phe Ser Arg Met Pro
            215                 220                 225 gac gat ttc ttc cgc gca ccc agc ccg aga agt gac aca gga gtc gag      864
Asp Asp Phe Phe Arg Ala Pro Ser Pro Arg Ser Asp Thr Gly Val Glu
230                 235                 240                 245 gta gtt gta cag gct cat cct atg cag ccc gga aaa aat gtc ggc aag      912
Val Val Val Gln Ala His Pro Met Gln Pro Gly Lys Asn Val Gly Lys
                250                 255                 260 atc aac agc tac acc gtc gac cca aca tcc tct gac ttt tcc acc ccc      960
Ile Asn Ser Tyr Thr Val Asp Pro Thr Ser Ser Asp Phe Ser Thr Pro
            265                 270                 275 tgc ttg atg tac gag aaa ttc gtc aac ata acg gtc aag tca ctc tac     1008
Cys Leu Met Tyr Glu Lys Phe Val Asn Ile Thr Val Lys Ser Leu Tyr
                280                 285                 290 ccg aat ccg acg gtg cag ctt cgc aaa gcc ctt aat acg aat ctc gat     1056
Pro Asn Pro Thr Val Gln Leu Arg Lys Ala Leu Asn Thr Asn Leu Asp
            295                 300                 305 ttc tta ttc cag gga gtc gcc gct gga tgt acc cag gtc ttc cca tac     1104
Phe Leu Phe Gln Gly Val Ala Ala Gly Cys Thr Gln Val Phe Pro Tyr
310                 315                 320                 325 ggg cga gat                                                         1113
Gly Arg Asp <210> SEQ ID NO 32
<211> LENGTH: 371
<212> TYPE: PRT
<213> ORGANISM: Artificial Sequence
<220> FEATURE:
<223> OTHER INFORMATION: Synthetic Construct

<400> SEQUENCE: 32

Met Lys Tyr Phe Pro Leu Phe Pro Thr Leu Val Tyr Ala Val Gly Val
            -40                 -35                 -30

Val Ala Phe Pro Asp Tyr Ala Ser Leu Ala Gly Leu Ser Gln Gln Glu
        -25                 -20                 -15

Leu Asp Ala Ile Ile Pro Thr Leu Glu Ala Arg Glu Pro Gly Leu Pro
    -10                  -5                  -1   1               5

Pro Gly Pro Leu Glu Asn Ser Ser Ala Lys Leu Val Asn Asp Glu Ala
                 10                  15                  20

His Pro Phe Lys Pro Leu Arg Pro Gly Asp Ile Arg Gly Pro Cys Pro
             25                  30                  35

Gly Leu Asn Thr Leu Ala Ser His Gly Tyr Leu Pro Arg Asn Gly Val
         40                  45                  50

Ala Thr Pro Ala Gln Ile Ile Asn Ala Val Gln Glu Gly Phe Asn Phe
     55                  60                  65

Asp Asn Gln Ala Ala Ile Phe Ala Thr Tyr Ala Ala His Leu Val Asp
70                  75                  80                  85

Gly Asn Leu Ile Thr Asp Leu Leu Ser Ile Gly Arg Lys Thr Arg Leu
                 90                  95                 100
```

Thr Gly Pro Asp Pro Pro Pro Ala Ser Val Gly Leu Asn Glu
        105                 110                 115

His Gly Thr Phe Glu Gly Asp Ala Ser Met Thr Arg Gly Asp Ala Phe
            120                 125                 130

Phe Gly Asn Asn His Asp Phe Asn Glu Thr Leu Phe Glu Gln Leu Val
135                 140                 145

Asp Tyr Ser Asn Arg Phe Gly Gly Lys Tyr Asn Leu Thr Val Ala
150                 155                 160                 165

Gly Glu Leu Arg Phe Lys Arg Ile Gln Asp Ser Ile Ala Thr Asn Pro
                170                 175                 180

Asn Phe Ser Phe Val Asp Phe Arg Phe Phe Thr Ala Tyr Gly Glu Thr
            185                 190                 195

Thr Phe Pro Ala Asn Leu Phe Val Asp Gly Arg Arg Asp Asp Gly Gln
        200                 205                 210

Leu Asp Met Asp Ala Ala Arg Ser Phe Phe Gln Phe Ser Arg Met Pro
215                 220                 225

Asp Asp Phe Phe Arg Ala Pro Ser Pro Arg Ser Asp Thr Gly Val Glu
230                 235                 240                 245

Val Val Val Gln Ala His Pro Met Gln Pro Gly Lys Asn Val Gly Lys
                250                 255                 260

Ile Asn Ser Tyr Thr Val Asp Pro Thr Ser Ser Asp Phe Ser Thr Pro
            265                 270                 275

Cys Leu Met Tyr Glu Lys Phe Val Asn Ile Thr Val Lys Ser Leu Tyr
        280                 285                 290

Pro Asn Pro Thr Val Gln Leu Arg Lys Ala Leu Asn Thr Asn Leu Asp
295                 300                 305

Phe Leu Phe Gln Gly Val Ala Ala Gly Cys Thr Gln Val Phe Pro Tyr
310                 315                 320                 325

Gly Arg Asp

<210> SEQ ID NO 33
<211> LENGTH: 22
<212> TYPE: DNA
<213> ORGANISM: Artificial Sequence
<220> FEATURE:
<223> OTHER INFORMATION: RMLN primer

<400> SEQUENCE: 33
cctctatact ttaacgtcaa gg                                              22

<210> SEQ ID NO 34
<211> LENGTH: 20
<212> TYPE: DNA
<213> ORGANISM: Artificial Sequence
<220> FEATURE:
<223> OTHER INFORMATION: RMLC primer

<400> SEQUENCE: 34
gggagggcgt gaatgtaagc                                                 20

<210> SEQ ID NO 35
<211> LENGTH: 42
<212> TYPE: DNA
<213> ORGANISM: Artificial Sequence
<220> FEATURE:
<223> OTHER INFORMATION: F24FOR primer

<400> SEQUENCE: 35
ctcacccatt taagccgctt cgacctggcg atattcgtgg ac                        42

<210> SEQ ID NO 36
<211> LENGTH: 42
<212> TYPE: DNA
<213> ORGANISM: Artificial Sequence
<220> FEATURE:
<223> OTHER INFORMATION: F24REV primer

<400> SEQUENCE: 36
gtccacgaat atcgccaggt cgaagcggct taaatgggtg ag 42

<210> SEQ ID NO 37
<211> LENGTH: 984
<212> TYPE: DNA
<213> ORGANISM: Artificial Sequence
<220> FEATURE:
<223> OTHER INFORMATION: SoLo variant without signal peptide
<220> FEATURE:
<221> NAME/KEY: CDS
<222> LOCATION: (1)..(984)

<400> SEQUENCE: 37

| gag | cca | gga | tta | cct | cct | ggt | cct | ctc | gag | aat | agc | tct | gca | aag | ttg | 48 |
|---|---|---|---|---|---|---|---|---|---|---|---|---|---|---|---|---|
| Glu | Pro | Gly | Leu | Pro | Pro | Gly | Pro | Leu | Glu | Asn | Ser | Ser | Ala | Lys | Leu | |
| 1 | | | | 5 | | | | | 10 | | | | | 15 | | |

| gtg | aac | gac | gag | gct | cac | cca | tgg | aag | ccg | ctt | cga | cct | ggc | gat | att | 96 |
|---|---|---|---|---|---|---|---|---|---|---|---|---|---|---|---|---|
| Val | Asn | Asp | Glu | Ala | His | Pro | Trp | Lys | Pro | Leu | Arg | Pro | Gly | Asp | Ile | |
| | | | 20 | | | | | 25 | | | | | 30 | | | |

| cgt | gga | cct | tgc | cct | ggt | ctc | aat | act | ctg | gca | tct | cac | ggg | tac | ctc | 144 |
|---|---|---|---|---|---|---|---|---|---|---|---|---|---|---|---|---|
| Arg | Gly | Pro | Cys | Pro | Gly | Leu | Asn | Thr | Leu | Ala | Ser | His | Gly | Tyr | Leu | |
| | | 35 | | | | | 40 | | | | | 45 | | | | |

| ccg | aga | aat | ggc | gtt | gca | acc | ccg | gcg | caa | ata | ata | aac | gcg | gtt | cag | 192 |
|---|---|---|---|---|---|---|---|---|---|---|---|---|---|---|---|---|
| Pro | Arg | Asn | Gly | Val | Ala | Thr | Pro | Ala | Gln | Ile | Ile | Asn | Ala | Val | Gln | |
| 50 | | | | | 55 | | | | | 60 | | | | | | |

| gaa | gga | ttc | aat | ttc | gac | aat | caa | gcc | gca | atc | ttc | gcc | aca | tat | gcg | 240 |
|---|---|---|---|---|---|---|---|---|---|---|---|---|---|---|---|---|
| Glu | Gly | Phe | Asn | Phe | Asp | Asn | Gln | Ala | Ala | Ile | Phe | Ala | Thr | Tyr | Ala | |
| 65 | | | | | 70 | | | | | 75 | | | | | 80 | |

| gcc | cac | ctt | gtg | gac | ggc | aat | ctc | att | acg | gac | ttg | ctg | agc | atc | gga | 288 |
|---|---|---|---|---|---|---|---|---|---|---|---|---|---|---|---|---|
| Ala | His | Leu | Val | Asp | Gly | Asn | Leu | Ile | Thr | Asp | Leu | Leu | Ser | Ile | Gly | |
| | | | | 85 | | | | | 90 | | | | | 95 | | |

| cgc | aag | acg | cgg | ctc | act | ggg | cct | gat | cca | cca | ccc | ccc | gct | tcc | gtt | 336 |
|---|---|---|---|---|---|---|---|---|---|---|---|---|---|---|---|---|
| Arg | Lys | Thr | Arg | Leu | Thr | Gly | Pro | Asp | Pro | Pro | Pro | Pro | Ala | Ser | Val | |
| | | | 100 | | | | | 105 | | | | | 110 | | | |

| ggt | gga | ctc | aat | gag | cat | ggc | acc | ttc | gaa | ggc | gac | gcc | agt | atg | acc | 384 |
|---|---|---|---|---|---|---|---|---|---|---|---|---|---|---|---|---|
| Gly | Gly | Leu | Asn | Glu | His | Gly | Thr | Phe | Glu | Gly | Asp | Ala | Ser | Met | Thr | |
| | | 115 | | | | | 120 | | | | | 125 | | | | |

| cga | ggt | gac | gca | ttc | ttt | ggc | aac | aac | cac | gat | ttc | aat | gag | acg | ctc | 432 |
|---|---|---|---|---|---|---|---|---|---|---|---|---|---|---|---|---|
| Arg | Gly | Asp | Ala | Phe | Phe | Gly | Asn | Asn | His | Asp | Phe | Asn | Glu | Thr | Leu | |
| 130 | | | | | 135 | | | | | 140 | | | | | | |

| ttc | gaa | cag | ttg | gtt | gac | tac | agc | aac | cga | ttt | gga | gga | gga | aaa | tac | 480 |
|---|---|---|---|---|---|---|---|---|---|---|---|---|---|---|---|---|
| Phe | Glu | Gln | Leu | Val | Asp | Tyr | Ser | Asn | Arg | Phe | Gly | Gly | Gly | Lys | Tyr | |
| 145 | | | | | 150 | | | | | 155 | | | | | 160 | |

| aat | ctt | acc | gtc | gcg | ggg | gag | ctc | cgt | ttc | aag | cgc | att | caa | gac | tcc | 528 |
|---|---|---|---|---|---|---|---|---|---|---|---|---|---|---|---|---|
| Asn | Leu | Thr | Val | Ala | Gly | Glu | Leu | Arg | Phe | Lys | Arg | Ile | Gln | Asp | Ser | |
| | | | | 165 | | | | | 170 | | | | | 175 | | |

| att | gcg | acc | aac | ccc | aat | ttc | tcc | ttt | gtt | gac | ttt | agg | ttc | tct | act | 576 |
|---|---|---|---|---|---|---|---|---|---|---|---|---|---|---|---|---|
| Ile | Ala | Thr | Asn | Pro | Asn | Phe | Ser | Phe | Val | Asp | Phe | Arg | Phe | Ser | Thr | |
| | | | 180 | | | | | 185 | | | | | 190 | | | |

| gct | tac | ggc | gag | acc | acc | ttc | ccc | gcg | aat | ctt | ttt | gtg | gat | ggg | cgc | 624 |
|---|---|---|---|---|---|---|---|---|---|---|---|---|---|---|---|---|
| Ala | Tyr | Gly | Glu | Thr | Thr | Phe | Pro | Ala | Asn | Leu | Phe | Val | Asp | Gly | Arg | |
| | | 195 | | | | | 200 | | | | | 205 | | | | |

| agg | gac | gac | ggc | cag | cta | gat | atg | gat | gct | gca | cgg | agt | ttt | ttc | caa | 672 |

```
Arg Asp Asp Gly Gln Leu Asp Met Asp Ala Ala Arg Ser Phe Phe Gln
    210                 215                 220 ttc agc cgt atg cct gac gat ttc ttc cgc gca ccc agc ccg aga agt    720
Phe Ser Arg Met Pro Asp Asp Phe Phe Arg Ala Pro Ser Pro Arg Ser
225                 230                 235                 240 gac aca gga gtc gag gta gtt gta cag gct cat cct atg cag ccc gga    768
Asp Thr Gly Val Glu Val Val Val Gln Ala His Pro Met Gln Pro Gly
                245                 250                 255 aaa aat gtc ggc aag atc aac agc tac acc gtc gac cca aca tcc tct    816
Lys Asn Val Gly Lys Ile Asn Ser Tyr Thr Val Asp Pro Thr Ser Ser
            260                 265                 270 gac ttt tcc acc ccc tgc ttg atg tac gag aaa ttc gtc aac ata acg    864
Asp Phe Ser Thr Pro Cys Leu Met Tyr Glu Lys Phe Val Asn Ile Thr
        275                 280                 285 gtc aag tca ctc tac ccg aat ccg acg gtg cag ctt cgc aaa gcc ctt    912
Val Lys Ser Leu Tyr Pro Asn Pro Thr Val Gln Leu Arg Lys Ala Leu
    290                 295                 300 aat acg aat ctc gat ttc tta ttc cag gga gtc gcc gct gga tgt acc    960
Asn Thr Asn Leu Asp Phe Leu Phe Gln Gly Val Ala Ala Gly Cys Thr
305                 310                 315                 320 cag gtc ttc cca tac ggg cga gat                                    984
Gln Val Phe Pro Tyr Gly Arg Asp
                325
```

<210> SEQ ID NO 38
<211> LENGTH: 328
<212> TYPE: PRT
<213> ORGANISM: Artificial Sequence
<220> FEATURE:
<223> OTHER INFORMATION: Synthetic Construct

<400> SEQUENCE: 38

```
Glu Pro Gly Leu Pro Pro Gly Pro Leu Glu Asn Ser Ser Ala Lys Leu
1               5                   10                  15

Val Asn Asp Glu Ala His Pro Trp Lys Pro Leu Arg Pro Gly Asp Ile
            20                  25                  30

Arg Gly Pro Cys Pro Gly Leu Asn Thr Leu Ala Ser His Gly Tyr Leu
        35                  40                  45

Pro Arg Asn Gly Val Ala Thr Pro Ala Gln Ile Ile Asn Ala Val Gln
    50                  55                  60

Glu Gly Phe Asn Phe Asp Asn Gln Ala Ala Ile Phe Ala Thr Tyr Ala
65                  70                  75                  80

Ala His Leu Val Asp Gly Asn Leu Ile Thr Asp Leu Leu Ser Ile Gly
                85                  90                  95

Arg Lys Thr Arg Leu Thr Gly Pro Asp Pro Pro Pro Ala Ser Val
            100                 105                 110

Gly Gly Leu Asn Glu His Gly Thr Phe Glu Gly Asp Ala Ser Met Thr
        115                 120                 125

Arg Gly Asp Ala Phe Phe Gly Asn Asn His Asp Phe Asn Glu Thr Leu
    130                 135                 140

Phe Glu Gln Leu Val Asp Tyr Ser Asn Arg Phe Gly Gly Lys Tyr
145                 150                 155                 160

Asn Leu Thr Val Ala Gly Glu Leu Arg Phe Lys Arg Ile Gln Asp Ser
                165                 170                 175

Ile Ala Thr Asn Pro Asn Phe Ser Phe Val Asp Phe Arg Phe Ser Thr
            180                 185                 190

Ala Tyr Gly Glu Thr Thr Phe Pro Ala Asn Leu Phe Val Asp Gly Arg
        195                 200                 205
```

```
Arg Asp Asp Gly Gln Leu Asp Met Asp Ala Ala Arg Ser Phe Phe Gln
        210                 215                 220

Phe Ser Arg Met Pro Asp Asp Phe Phe Arg Ala Pro Ser Pro Arg Ser
225                 230                 235                 240

Asp Thr Gly Val Glu Val Val Gln Ala His Pro Met Gln Pro Gly
                245                 250                 255

Lys Asn Val Gly Lys Ile Asn Ser Tyr Thr Val Asp Pro Thr Ser Ser
                260                 265                 270

Asp Phe Ser Thr Pro Cys Leu Met Tyr Glu Lys Phe Val Asn Ile Thr
            275                 280                 285

Val Lys Ser Leu Tyr Pro Asn Pro Thr Val Gln Leu Arg Lys Ala Leu
        290                 295                 300

Asn Thr Asn Leu Asp Phe Leu Phe Gln Gly Val Ala Ala Gly Cys Thr
305                 310                 315                 320

Gln Val Phe Pro Tyr Gly Arg Asp
                325

<210> SEQ ID NO 39
<211> LENGTH: 1113
<212> TYPE: DNA
<213> ORGANISM: Artificial Sequence
<220> FEATURE:
<223> OTHER INFORMATION: SoLo variant with wild signal peptide
<220> FEATURE:
<221> NAME/KEY: CDS
<222> LOCATION: (1)..(1113)
<220> FEATURE:
<221> NAME/KEY: mat_peptide
<222> LOCATION: (130)..(1113)

<400> SEQUENCE: 39 atg aaa tat ttt ccc ctg ttc cca acc ttg gtc ttc gca gcg agg gtc     48
Met Lys Tyr Phe Pro Leu Phe Pro Thr Leu Val Phe Ala Ala Arg Val
            -40                 -35                 -30 gtt gct ttt cct gcc tac gcc tca ttg gcc ggc ctc agc cag cag gaa     96
Val Ala Phe Pro Ala Tyr Ala Ser Leu Ala Gly Leu Ser Gln Gln Glu
        -25                 -20                 -15 ttg gac gct ata atc cca aca ctc gag gcc cga gag cca gga tta cct    144
Leu Asp Ala Ile Ile Pro Thr Leu Glu Ala Arg Glu Pro Gly Leu Pro
-10                  -5                  -1   1               5 cct ggt cct ctc gag aat agc tct gca aag ttg gtg aac gac gag gct    192
Pro Gly Pro Leu Glu Asn Ser Ser Ala Lys Leu Val Asn Asp Glu Ala
                10                  15                  20 cac cca tgg aag ccg ctt cga cct ggc gat att cgt gga cct tgc cct    240
His Pro Trp Lys Pro Leu Arg Pro Gly Asp Ile Arg Gly Pro Cys Pro
            25                  30                  35 ggt ctc aat act ctg gca tct cac ggg tac ctc ccg aga aat ggc gtt    288
Gly Leu Asn Thr Leu Ala Ser His Gly Tyr Leu Pro Arg Asn Gly Val
        40                  45                  50 gca acc ccg gcg caa ata ata aac gcg gtt cag gaa gga ttc aat ttc    336
Ala Thr Pro Ala Gln Ile Ile Asn Ala Val Gln Glu Gly Phe Asn Phe
    55                  60                  65 gac aat caa gcc gca atc ttc gcc aca tat gcg gcc cac ctt gtg gac    384
Asp Asn Gln Ala Ala Ile Phe Ala Thr Tyr Ala Ala His Leu Val Asp
70                  75                  80                  85 ggc aat ctc att acg gac ttg ctg agc atc gga cgc aag acg cgg ctc    432
Gly Asn Leu Ile Thr Asp Leu Leu Ser Ile Gly Arg Lys Thr Arg Leu
                90                  95                 100 act ggg cct gat cca cca ccc ccc gct tcc gtt ggt gga ctc aat gag    480
Thr Gly Pro Asp Pro Pro Pro Pro Ala Ser Val Gly Gly Leu Asn Glu
```

```
                105                 110                 115
cat ggc acc ttc gaa ggc gac gcc agt atg acc cga ggt gac gca ttc        528
His Gly Thr Phe Glu Gly Asp Ala Ser Met Thr Arg Gly Asp Ala Phe
        120                 125                 130 ttt ggc aac aac cac gat ttc aat gag acg ctc ttc gaa cag ttg gtt        576
Phe Gly Asn Asn His Asp Phe Asn Glu Thr Leu Phe Glu Gln Leu Val
135                 140                 145 gac tac agc aac cga ttt gga gga gga aaa tac aat ctt acc gtc gcg        624
Asp Tyr Ser Asn Arg Phe Gly Gly Gly Lys Tyr Asn Leu Thr Val Ala
150                 155                 160                 165 ggg gag ctc cgt ttc aag cgc att caa gac tcc att gcg acc aac ccc        672
Gly Glu Leu Arg Phe Lys Arg Ile Gln Asp Ser Ile Ala Thr Asn Pro
            170                 175                 180 aat ttc tcc ttt gtt gac ttt agg ttc tct act gct tac ggc gag acc        720
Asn Phe Ser Phe Val Asp Phe Arg Phe Ser Thr Ala Tyr Gly Glu Thr
            185                 190                 195 acc ttc ccc gcg aat ctt ttt gtg gat ggg cgc agg gac gac ggc cag        768
Thr Phe Pro Ala Asn Leu Phe Val Asp Gly Arg Arg Asp Asp Gly Gln
        200                 205                 210 cta gat atg gat gct gca cgg agt ttt ttc caa ttc agc cgt atg cct        816
Leu Asp Met Asp Ala Ala Arg Ser Phe Phe Gln Phe Ser Arg Met Pro
        215                 220                 225 gac gat ttc ttc cgc gca ccc agc ccg aga agt gac aca gga gtc gag        864
Asp Asp Phe Phe Arg Ala Pro Ser Pro Arg Ser Asp Thr Gly Val Glu
230                 235                 240                 245 gta gtt gta cag gct cat cct atg cag ccc gga aaa aat gtc ggc aag        912
Val Val Val Gln Ala His Pro Met Gln Pro Gly Lys Asn Val Gly Lys
            250                 255                 260 atc aac agc tac acc gtc gac cca aca tcc tct gac ttt tcc acc ccc        960
Ile Asn Ser Tyr Thr Val Asp Pro Thr Ser Ser Asp Phe Ser Thr Pro
            265                 270                 275 tgc ttg atg tac gag aaa ttc gtc aac ata acg gtc aag tca ctc tac       1008
Cys Leu Met Tyr Glu Lys Phe Val Asn Ile Thr Val Lys Ser Leu Tyr
            280                 285                 290 ccg aat ccg acg gtg cag ctt cgc aaa gcc ctt aat acg aat ctc gat       1056
Pro Asn Pro Thr Val Gln Leu Arg Lys Ala Leu Asn Thr Asn Leu Asp
        295                 300                 305 ttc tta ttc cag gga gtc gcc gct gga tgt acc cag gtc ttc cca tac       1104
Phe Leu Phe Gln Gly Val Ala Ala Gly Cys Thr Gln Val Phe Pro Tyr
310                 315                 320                 325 ggg cga gat                                                           1113
Gly Arg Asp <210> SEQ ID NO 40
<211> LENGTH: 371
<212> TYPE: PRT
<213> ORGANISM: Artificial Sequence
<220> FEATURE:
<223> OTHER INFORMATION: Synthetic Construct

<400> SEQUENCE: 40

Met Lys Tyr Phe Pro Leu Phe Pro Thr Leu Val Phe Ala Ala Arg Val
                -40                 -35                 -30

Val Ala Phe Pro Ala Tyr Ala Ser Leu Ala Gly Leu Ser Gln Gln Glu
        -25                 -20                 -15

Leu Asp Ala Ile Ile Pro Thr Leu Glu Ala Arg Glu Pro Gly Leu Pro
    -10                 -5                  -1  1               5

Pro Gly Pro Leu Glu Asn Ser Ser Ala Lys Leu Val Asn Asp Glu Ala
                10                  15                  20
```

His Pro Trp Lys Pro Leu Arg Pro Gly Asp Ile Arg Gly Pro Cys Pro
                25                  30                  35

Gly Leu Asn Thr Leu Ala Ser His Gly Tyr Leu Pro Arg Asn Gly Val
        40                  45                  50

Ala Thr Pro Ala Gln Ile Ile Asn Ala Val Gln Glu Gly Phe Asn Phe
    55                  60                  65

Asp Asn Gln Ala Ala Ile Phe Ala Thr Tyr Ala Ala His Leu Val Asp
70                  75                  80                  85

Gly Asn Leu Ile Thr Asp Leu Leu Ser Ile Gly Arg Lys Thr Arg Leu
                90                  95                  100

Thr Gly Pro Asp Pro Pro Pro Ala Ser Val Gly Gly Leu Asn Glu
            105                 110                 115

His Gly Thr Phe Glu Gly Asp Ala Ser Met Thr Arg Gly Asp Ala Phe
        120                 125                 130

Phe Gly Asn Asn His Asp Phe Asn Glu Thr Leu Phe Glu Gln Leu Val
    135                 140                 145

Asp Tyr Ser Asn Arg Phe Gly Gly Lys Tyr Asn Leu Thr Val Ala
150                 155                 160                 165

Gly Glu Leu Arg Phe Lys Arg Ile Gln Asp Ser Ile Ala Thr Asn Pro
                170                 175                 180

Asn Phe Ser Phe Val Asp Phe Arg Phe Ser Thr Ala Tyr Gly Glu Thr
            185                 190                 195

Thr Phe Pro Ala Asn Leu Phe Val Asp Gly Arg Arg Asp Asp Gly Gln
        200                 205                 210

Leu Asp Met Asp Ala Ala Arg Ser Phe Gln Phe Ser Arg Met Pro
215                 220                 225

Asp Asp Phe Phe Arg Ala Pro Ser Pro Arg Ser Asp Thr Gly Val Glu
230                 235                 240                 245

Val Val Val Gln Ala His Pro Met Gln Pro Gly Lys Asn Val Gly Lys
                250                 255                 260

Ile Asn Ser Tyr Thr Val Asp Pro Thr Ser Ser Asp Phe Ser Thr Pro
            265                 270                 275

Cys Leu Met Tyr Glu Lys Phe Val Asn Ile Thr Val Lys Ser Leu Tyr
        280                 285                 290

Pro Asn Pro Thr Val Gln Leu Arg Lys Ala Leu Asn Thr Asn Leu Asp
    295                 300                 305

Phe Leu Phe Gln Gly Val Ala Ala Gly Cys Thr Gln Val Phe Pro Tyr
310                 315                 320                 325

Gly Arg Asp

<210> SEQ ID NO 41
<211> LENGTH: 1113
<212> TYPE: DNA
<213> ORGANISM: Artificial Sequence
<220> FEATURE:
<223> OTHER INFORMATION: SoLo variant with modified signal peptide
<220> FEATURE:
<221> NAME/KEY: CDS
<222> LOCATION: (1)..(1113)
<220> FEATURE:
<221> NAME/KEY: mat_peptide
<222> LOCATION: (130)..(1113)

<400> SEQUENCE: 41 atg aaa tat ttt ccc ctg ttc cca acc ttg gtc tac gca gtg ggg gtc        48
Met Lys Tyr Phe Pro Leu Phe Pro Thr Leu Val Tyr Ala Val Gly Val
            -40                 -35                 -30

```
gtt gct ttt cct gac tac gcc tca ttg gcc ggc ctc agc cag cag gaa      96
Val Ala Phe Pro Asp Tyr Ala Ser Leu Ala Gly Leu Ser Gln Gln Glu
    -25             -20             -15 ttg gac gct ata atc cca aca ctc gag gcc cga gag cca gga tta cct     144
Leu Asp Ala Ile Ile Pro Thr Leu Glu Ala Arg Glu Pro Gly Leu Pro
    -10              -5              -1   1                   5 cct ggt cct ctc gag aat agc tct gca aag ttg gtg aac gac gag gct     192
Pro Gly Pro Leu Glu Asn Ser Ser Ala Lys Leu Val Asn Asp Glu Ala
                 10              15              20 cac cca tgg aag ccg ctt cga cct ggc gat att cgt gga cct tgc cct     240
His Pro Trp Lys Pro Leu Arg Pro Gly Asp Ile Arg Gly Pro Cys Pro
             25              30              35 ggt ctc aat act ctg gca tct cac ggg tac ctc ccg aga aat ggc gtt     288
Gly Leu Asn Thr Leu Ala Ser His Gly Tyr Leu Pro Arg Asn Gly Val
         40              45              50 gca acc ccg gcg caa ata ata aac gcg gtt cag gaa gga ttc aat ttc     336
Ala Thr Pro Ala Gln Ile Ile Asn Ala Val Gln Glu Gly Phe Asn Phe
     55              60              65 gac aat caa gcc gca atc ttc gcc aca tat gcg gcc cac ctt gtg gac     384
Asp Asn Gln Ala Ala Ile Phe Ala Thr Tyr Ala Ala His Leu Val Asp
70              75              80              85 ggc aat ctc att acg gac ttg ctg agc atc gga cgc aag acg cgg ctc     432
Gly Asn Leu Ile Thr Asp Leu Leu Ser Ile Gly Arg Lys Thr Arg Leu
             90              95             100 act ggg cct gat cca cca ccc ccc gct tcc gtt ggt gga ctc aat gag     480
Thr Gly Pro Asp Pro Pro Pro Pro Ala Ser Val Gly Gly Leu Asn Glu
        105             110             115 cat ggc acc ttc gaa ggc gac gcc agt atg acc cga ggt gac gca ttc     528
His Gly Thr Phe Glu Gly Asp Ala Ser Met Thr Arg Gly Asp Ala Phe
        120             125             130 ttt ggc aac aac cac gat ttc aat gag acg ctc ttc gaa cag ttg gtt     576
Phe Gly Asn Asn His Asp Phe Asn Glu Thr Leu Phe Glu Gln Leu Val
    135             140             145 gac tac agc aac cga ttt gga gga gga aaa tac aat ctt acc gtc gcg     624
Asp Tyr Ser Asn Arg Phe Gly Gly Gly Lys Tyr Asn Leu Thr Val Ala
150             155             160             165 ggg gag ctc cgt ttc aag cgc att caa gac tcc att gcg acc aac ccc     672
Gly Glu Leu Arg Phe Lys Arg Ile Gln Asp Ser Ile Ala Thr Asn Pro
            170             175             180 aat ttc tcc ttt gtt gac ttt agg ttc tct act gct tac ggc gag acc     720
Asn Phe Ser Phe Val Asp Phe Arg Phe Ser Thr Ala Tyr Gly Glu Thr
            185             190             195 acc ttc ccc gcg aat ctt ttt gtg gat ggg cgc agg gac gac ggc cag     768
Thr Phe Pro Ala Asn Leu Phe Val Asp Gly Arg Arg Asp Asp Gly Gln
        200             205             210 cta gat atg gat gct gca cgg agt ttt ttc caa ttc agc cgt atg cct     816
Leu Asp Met Asp Ala Ala Arg Ser Phe Phe Gln Phe Ser Arg Met Pro
    215             220             225 gac gat ttc ttc cgc gca ccc agc ccg aga agt gac aca gga gtc gag     864
Asp Asp Phe Phe Arg Ala Pro Ser Pro Arg Ser Asp Thr Gly Val Glu
230             235             240             245 gta gtt gta cag gct cat cct atg cag ccc gga aaa aat gtc ggc aag     912
Val Val Val Gln Ala His Pro Met Gln Pro Gly Lys Asn Val Gly Lys
            250             255             260 atc aac agc tac acc gtc gac cca aca tcc tct gac ttt tcc acc ccc     960
Ile Asn Ser Tyr Thr Val Asp Pro Thr Ser Ser Asp Phe Ser Thr Pro
            265             270             275 tgc ttg atg tac gag aaa ttc gtc aac ata acg gtc aag tca ctc tac    1008
Cys Leu Met Tyr Glu Lys Phe Val Asn Ile Thr Val Lys Ser Leu Tyr
    280             285             290
```

```
ccg aat ccg acg gtg cag ctt cgc aaa gcc ctt aat acg aat ctc gat      1056
Pro Asn Pro Thr Val Gln Leu Arg Lys Ala Leu Asn Thr Asn Leu Asp
295                 300                 305 ttc tta ttc cag gga gtc gcc gct gga tgt acc cag gtc ttc cca tac      1104
Phe Leu Phe Gln Gly Val Ala Ala Gly Cys Thr Gln Val Phe Pro Tyr
310                 315                 320                 325 ggg cga gat                                                          1113
Gly Arg Asp <210> SEQ ID NO 42
<211> LENGTH: 371
<212> TYPE: PRT
<213> ORGANISM: Artificial Sequence
<220> FEATURE:
<223> OTHER INFORMATION: Synthetic Construct

<400> SEQUENCE: 42

Met Lys Tyr Phe Pro Leu Phe Pro Thr Leu Val Tyr Ala Val Gly Val
            -40                 -35                 -30

Val Ala Phe Pro Asp Tyr Ala Ser Leu Ala Gly Leu Ser Gln Gln Glu
        -25                 -20                 -15

Leu Asp Ala Ile Ile Pro Thr Leu Glu Ala Arg Glu Pro Gly Leu Pro
    -10                  -5                 -1   1               5

Pro Gly Pro Leu Glu Asn Ser Ser Ala Lys Leu Val Asn Asp Glu Ala
                10                  15                  20

His Pro Trp Lys Pro Leu Arg Pro Gly Asp Ile Arg Gly Pro Cys Pro
            25                  30                  35

Gly Leu Asn Thr Leu Ala Ser His Gly Tyr Leu Pro Arg Asn Gly Val
            40                  45                  50

Ala Thr Pro Ala Gln Ile Ile Asn Ala Val Gln Glu Gly Phe Asn Phe
            55                  60                  65

Asp Asn Gln Ala Ala Ile Phe Ala Thr Tyr Ala Ala His Leu Val Asp
70                  75                  80                  85

Gly Asn Leu Ile Thr Asp Leu Leu Ser Ile Gly Arg Lys Thr Arg Leu
                90                  95                  100

Thr Gly Pro Asp Pro Pro Pro Ala Ser Val Gly Gly Leu Asn Glu
                105                 110                 115

His Gly Thr Phe Glu Gly Asp Ala Ser Met Thr Arg Gly Asp Ala Phe
            120                 125                 130

Phe Gly Asn Asn His Asp Phe Asn Glu Thr Leu Phe Glu Gln Leu Val
    135                 140                 145

Asp Tyr Ser Asn Arg Phe Gly Gly Lys Tyr Asn Leu Thr Val Ala
150                 155                 160                 165

Gly Glu Leu Arg Phe Lys Arg Ile Gln Asp Ser Ile Ala Thr Asn Pro
                170                 175                 180

Asn Phe Ser Phe Val Asp Phe Arg Phe Ser Thr Ala Tyr Gly Glu Thr
            185                 190                 195

Thr Phe Pro Ala Asn Leu Phe Val Asp Gly Arg Arg Asp Asp Gly Gln
            200                 205                 210

Leu Asp Met Asp Ala Ala Arg Ser Phe Gln Phe Ser Arg Met Pro
    215                 220                 225

Asp Asp Phe Phe Arg Ala Pro Ser Pro Arg Ser Asp Thr Gly Val Glu
230                 235                 240                 245

Val Val Val Gln Ala His Pro Met Gln Pro Gly Lys Asn Val Gly Lys
                250                 255                 260
```

```
Ile Asn Ser Tyr Thr Val Asp Pro Thr Ser Ser Asp Phe Ser Thr Pro
            265                 270                 275

Cys Leu Met Tyr Glu Lys Phe Val Asn Ile Thr Val Lys Ser Leu Tyr
        280                 285                 290

Pro Asn Pro Thr Val Gln Leu Arg Lys Ala Leu Asn Thr Asn Leu Asp
        295                 300                 305

Phe Leu Phe Gln Gly Val Ala Ala Gly Cys Thr Gln Val Phe Pro Tyr
310                 315                 320                 325

Gly Arg Asp
```

```
<210> SEQ ID NO 43
<211> LENGTH: 20
<212> TYPE: DNA
<213> ORGANISM: Artificial Sequence
<220> FEATURE:
<223> OTHER INFORMATION: MJaWa Fw primer

<400> SEQUENCE: 43
gcgcattcaa gactccattg                                              20

<210> SEQ ID NO 44
<211> LENGTH: 21
<212> TYPE: DNA
<213> ORGANISM: Artificial Sequence
<220> FEATURE:
<223> OTHER INFORMATION: MJaWa Rev primer

<400> SEQUENCE: 44
gatcttgccg acatttttc c                                             21

<210> SEQ ID NO 45
<211> LENGTH: 21
<212> TYPE: DNA
<213> ORGANISM: Artificial Sequence
<220> FEATURE:
<223> OTHER INFORMATION: HFJaWa Fw primer

<400> SEQUENCE: 45
caggctcatc ctatgcagcc c                                            21

<210> SEQ ID NO 46
<211> LENGTH: 24
<212> TYPE: DNA
<213> ORGANISM: Artificial Sequence
<220> FEATURE:
<223> OTHER INFORMATION: HFJaWa Rev primer

<400> SEQUENCE: 46
caaaggagaa attggggttg gtcg                                         24

<210> SEQ ID NO 47
<211> LENGTH: 61
<212> TYPE: DNA
<213> ORGANISM: Artificial Sequence
<220> FEATURE:
<223> OTHER INFORMATION: VHG R primer
<220> FEATURE:
<221> NAME/KEY: misc_feature
<222> LOCATION: (51)..(51)
<223> OTHER INFORMATION: d is a or g or t
<220> FEATURE:
<221> NAME/KEY: misc_feature
<222> LOCATION: (52)..(52)
<223> OTHER INFORMATION: b is g or c or t

<400> SEQUENCE: 47
```

```
gcaagtccgt aatgagattg ccgtccacaa ggtgggccgc atatgtggcc dbgattgcgg      60
c                                                                     61

<210> SEQ ID NO 48
<211> LENGTH: 61
<212> TYPE: DNA
<213> ORGANISM: Artificial Sequence
<220> FEATURE:
<223> OTHER INFORMATION: NDT R primer
<220> FEATURE:
<221> NAME/KEY: misc_feature
<222> LOCATION: (51)..(51)
<223> OTHER INFORMATION: h is a or c or t
<220> FEATURE:
<221> NAME/KEY: misc_feature
<222> LOCATION: (52)..(52)
<223> OTHER INFORMATION: n is a or g or c or t

<400> SEQUENCE: 48
gcaagtccgt aatgagattg ccgtccacaa ggtgggccgc atatgtggca hngattgcgg      60
c                                                                     61

<210> SEQ ID NO 49
<211> LENGTH: 61
<212> TYPE: DNA
<213> ORGANISM: Artificial Sequence
<220> FEATURE:
<223> OTHER INFORMATION: TGG R primer

<400> SEQUENCE: 49
gcaagtccgt aatgagattg ccgtccacaa ggtgggccgc atatgtggcc cagattgcgg      60
c                                                                     61

<210> SEQ ID NO 50
<211> LENGTH: 40
<212> TYPE: DNA
<213> ORGANISM: Artificial Sequence
<220> FEATURE:
<223> OTHER INFORMATION: HF F primer

<400> SEQUENCE: 50
gcggcccacc ttgtggacgg caatctcatt acggacttgc                            40

<210> SEQ ID NO 51
<211> LENGTH: 61
<212> TYPE: DNA
<213> ORGANISM: Artificial Sequence
<220> FEATURE:
<223> OTHER INFORMATION: S191 VHG R primer
<220> FEATURE:
<221> NAME/KEY: misc_feature
<222> LOCATION: (50)..(50)
<223> OTHER INFORMATION: d is a or g or t
<220> FEATURE:
<221> NAME/KEY: misc_feature
<222> LOCATION: (51)..(51)
<223> OTHER INFORMATION: b is g or c or t

<400> SEQUENCE: 51
cccatccaca aaagattcg cggggaaggt ggtctcgccg taagcagtcd bgaacctaaa      60
g                                                                     61

<210> SEQ ID NO 52
<211> LENGTH: 61
<212> TYPE: DNA
```

```
<213> ORGANISM: Artificial Sequence
<220> FEATURE:
<223> OTHER INFORMATION: NDT R primer
<220> FEATURE:
<221> NAME/KEY: misc_feature
<222> LOCATION: (50)..(50)
<223> OTHER INFORMATION: h is a or c or t
<220> FEATURE:
<221> NAME/KEY: misc_feature
<222> LOCATION: (51)..(51)
<223> OTHER INFORMATION: h is a or g or c or t

<400> SEQUENCE: 52
cccatccaca aaaagattcg cggggaaggt ggtctcgccg taagcagtah ngaacctaaa    60
g                                                                   61

<210> SEQ ID NO 53
<211> LENGTH: 61
<212> TYPE: DNA
<213> ORGANISM: Artificial Sequence
<220> FEATURE:
<223> OTHER INFORMATION: S191 TGG R primer

<400> SEQUENCE: 53
cccatccaca aaaagattcg cggggaaggt ggtctcgccg taagcagtcc agaacctaaa    60
g                                                                   61

<210> SEQ ID NO 54
<211> LENGTH: 40
<212> TYPE: DNA
<213> ORGANISM: Artificial Sequence
<220> FEATURE:
<223> OTHER INFORMATION: HF F-RMLC primer

<400> SEQUENCE: 54
cggcgagacc accttccccg cgaatctttt tgtggatggg                          40

<210> SEQ ID NO 55
<211> LENGTH: 32
<212> TYPE: DNA
<213> ORGANISM: Artificial Sequence
<220> FEATURE:
<223> OTHER INFORMATION: F69 R primer
<220> FEATURE:
<221> NAME/KEY: misc_feature
<222> LOCATION: (22)..(22)
<223> OTHER INFORMATION: m is a or c
<220> FEATURE:
<221> NAME/KEY: misc_feature
<222> LOCATION: (23)..(23)
<223> OTHER INFORMATION: n is a or g or c or t
<220> FEATURE:
<221> NAME/KEY: misc_feature
<222> LOCATION: (24)..(24)
<223> OTHER INFORMATION: n is a or g or c or t

<400> SEQUENCE: 55
gaagattgcg gcttgattgt cmnnattgaa tc                                  32

<210> SEQ ID NO 56
<211> LENGTH: 32
<212> TYPE: DNA
<213> ORGANISM: Artificial Sequence
<220> FEATURE:
<223> OTHER INFORMATION: F69 F primer
<220> FEATURE:
<221> NAME/KEY: misc_feature
<222> LOCATION: (23)..(23)
<223> OTHER INFORMATION: n is a or g or c or t
```

```
<220> FEATURE:
<221> NAME/KEY: misc_feature
<222> LOCATION: (24)..(24)
<223> OTHER INFORMATION: n is a or g or c or t
<220> FEATURE:
<221> NAME/KEY: misc_feature
<222> LOCATION: (25)..(25)
<223> OTHER INFORMATION: k is g or t

<400> SEQUENCE: 56
cgcggttcag gaaggattca atnnkgacaa tc                                          32

<210> SEQ ID NO 57
<211> LENGTH: 31
<212> TYPE: DNA
<213> ORGANISM: Artificial Sequence
<220> FEATURE:
<223> OTHER INFORMATION: F121 R primer
<220> FEATURE:
<221> NAME/KEY: misc_feature
<222> LOCATION: (19)..(19)
<223> OTHER INFORMATION: m is a or c
<220> FEATURE:
<221> NAME/KEY: misc_feature
<222> LOCATION: (20)..(20)
<223> OTHER INFORMATION: n is a or g or c or t
<220> FEATURE:
<221> NAME/KEY: misc_feature
<222> LOCATION: (21)..(21)
<223> OTHER INFORMATION: n is a or g or c or t

<400> SEQUENCE: 57
catactggcg tcgccttcmn nggtgccatg c                                           31

<210> SEQ ID NO 58
<211> LENGTH: 31
<212> TYPE: DNA
<213> ORGANISM: Artificial Sequence
<220> FEATURE:
<223> OTHER INFORMATION: F121 F primer
<220> FEATURE:
<221> NAME/KEY: misc_feature
<222> LOCATION: (22)..(22)
<223> OTHER INFORMATION: n is a or g or c or t
<220> FEATURE:
<221> NAME/KEY: misc_feature
<222> LOCATION: (23)..(23)
<223> OTHER INFORMATION: n is a or g or c or t
<220> FEATURE:
<221> NAME/KEY: misc_feature
<222> LOCATION: (24)..(24)
<223> OTHER INFORMATION: k is g or t

<400> SEQUENCE: 58
ggactcaatg agcatggcac cnnkgaaggc g                                           31

<210> SEQ ID NO 59
<211> LENGTH: 32
<212> TYPE: DNA
<213> ORGANISM: Artificial Sequence
<220> FEATURE:
<223> OTHER INFORMATION: F199 R primer
<220> FEATURE:
<221> NAME/KEY: misc_feature
<222> LOCATION: (20)..(20)
<223> OTHER INFORMATION: m is a or c
<220> FEATURE:
<221> NAME/KEY: misc_feature
<222> LOCATION: (21)..(21)
<223> OTHER INFORMATION: n is a or g or c or t
<220> FEATURE:
<221> NAME/KEY: misc_feature
<222> LOCATION: (22)..(22)
```

<223> OTHER INFORMATION: n is a or g or c or t

<400> SEQUENCE: 59
ccacaaaaag attcgcgggm nnggtggtct cg        32

<210> SEQ ID NO 60
<211> LENGTH: 32
<212> TYPE: DNA
<213> ORGANISM: Artificial Sequence
<220> FEATURE:
<223> OTHER INFORMATION: F199 F primer
<220> FEATURE:
<221> NAME/KEY: misc_feature
<222> LOCATION: (24)..(24)
<223> OTHER INFORMATION: n is a or g or c or t
<220> FEATURE:
<221> NAME/KEY: misc_feature
<222> LOCATION: (25)..(25)
<223> OTHER INFORMATION: n is a or g or c or t
<220> FEATURE:
<221> NAME/KEY: misc_feature
<222> LOCATION: (26)..(26)
<223> OTHER INFORMATION: k is g or t

<400> SEQUENCE: 60
ctactgctta cggcgagacc accnnkcccg cg        32

<210> SEQ ID NO 61
<211> LENGTH: 987
<212> TYPE: DNA
<213> ORGANISM: Artificial Sequence
<220> FEATURE:
<223> OTHER INFORMATION: Wt-SoLo variant without signal peptide
<220> FEATURE:
<221> NAME/KEY: CDS
<222> LOCATION: (1)..(987)

<400> SEQUENCE: 61

| gag | cca | gga | tta | cct | cct | ggt | cct | ctc | gag | aat | agc | tct | gca | aag | ttg | 48 |
|---|---|---|---|---|---|---|---|---|---|---|---|---|---|---|---|---|
| Glu | Pro | Gly | Leu | Pro | Pro | Gly | Pro | Leu | Glu | Asn | Ser | Ser | Ala | Lys | Leu | |
| 1 | | | | 5 | | | | | 10 | | | | | 15 | | |

| gtg | aac | gac | gag | gct | cac | cca | tgg | aag | ccg | ctt | cga | cct | ggc | gat | att | 96 |
|---|---|---|---|---|---|---|---|---|---|---|---|---|---|---|---|---|
| Val | Asn | Asp | Glu | Ala | His | Pro | Trp | Lys | Pro | Leu | Arg | Pro | Gly | Asp | Ile | |
| | | | 20 | | | | | 25 | | | | | 30 | | | |

| cgt | gga | cct | tgc | cct | ggt | ctc | aat | act | ctg | gca | tct | cac | ggg | tac | ctc | 144 |
|---|---|---|---|---|---|---|---|---|---|---|---|---|---|---|---|---|
| Arg | Gly | Pro | Cys | Pro | Gly | Leu | Asn | Thr | Leu | Ala | Ser | His | Gly | Tyr | Leu | |
| | | 35 | | | | | 40 | | | | | 45 | | | | |

| ccg | aga | aat | ggc | gtt | gca | acc | ccg | gtg | caa | ata | ata | aac | gcg | gtt | cag | 192 |
|---|---|---|---|---|---|---|---|---|---|---|---|---|---|---|---|---|
| Pro | Arg | Asn | Gly | Val | Ala | Thr | Pro | Val | Gln | Ile | Ile | Asn | Ala | Val | Gln | |
| 50 | | | | | 55 | | | | | 60 | | | | | | |

| gaa | gga | ctc | aat | ttc | gac | aat | caa | gcc | gca | gtc | ttc | gcc | aca | tat | gcg | 240 |
|---|---|---|---|---|---|---|---|---|---|---|---|---|---|---|---|---|
| Glu | Gly | Leu | Asn | Phe | Asp | Asn | Gln | Ala | Ala | Val | Phe | Ala | Thr | Tyr | Ala | |
| 65 | | | | 70 | | | | | 75 | | | | | 80 | | |

| gcc | cac | ctt | gtg | gac | ggc | aat | ctc | att | acg | gac | ttg | ctg | agc | atc | gga | 288 |
|---|---|---|---|---|---|---|---|---|---|---|---|---|---|---|---|---|
| Ala | His | Leu | Val | Asp | Gly | Asn | Leu | Ile | Thr | Asp | Leu | Leu | Ser | Ile | Gly | |
| | | | | 85 | | | | | 90 | | | | | 95 | | |

| cgc | aag | acg | cgg | ctc | act | ggg | cct | gat | cca | cca | ccc | ccc | gct | tcc | gtt | 336 |
|---|---|---|---|---|---|---|---|---|---|---|---|---|---|---|---|---|
| Arg | Lys | Thr | Arg | Leu | Thr | Gly | Pro | Asp | Pro | Pro | Pro | Pro | Ala | Ser | Val | |
| | | | 100 | | | | | 105 | | | | | 110 | | | |

| ggt | gga | ctc | aat | gag | cat | ggc | acc | ttc | gaa | ggc | gac | gcc | agt | atg | acc | 384 |
|---|---|---|---|---|---|---|---|---|---|---|---|---|---|---|---|---|
| Gly | Gly | Leu | Asn | Glu | His | Gly | Thr | Phe | Glu | Gly | Asp | Ala | Ser | Met | Thr | |
| | | | | 115 | | | | | 120 | | | | | 125 | | |

| cga | ggt | gac | gca | ttc | ttt | ggc | aac | aac | cac | gat | ttc | aat | gag | acg | ctc | 432 |
|---|---|---|---|---|---|---|---|---|---|---|---|---|---|---|---|---|
| Arg | Gly | Asp | Ala | Phe | Phe | Gly | Asn | Asn | His | Asp | Phe | Asn | Glu | Thr | Leu | |
| 130 | | | | | 135 | | | | | 140 | | | | | | |

```
ttc gaa cag ttg gtt gac tac agc aac cga ttt gga gga gga aaa tac    480
Phe Glu Gln Leu Val Asp Tyr Ser Asn Arg Phe Gly Gly Gly Lys Tyr
145                 150                 155                 160 aat ctt acc gtc gcg ggg gag ctc cgt ttc aag cgc att caa gac tcc    528
Asn Leu Thr Val Ala Gly Glu Leu Arg Phe Lys Arg Ile Gln Asp Ser
                165                 170                 175 att gcg acc aac ccc aat ttc tcc ttt gtt gac ttt agg ttc tct act    576
Ile Ala Thr Asn Pro Asn Phe Ser Phe Val Asp Phe Arg Phe Ser Thr
            180                 185                 190 gct tac ggc gag acc acc ttc ccc gcg aat ctt ttt gtg gat ggg cgc    624
Ala Tyr Gly Glu Thr Thr Phe Pro Ala Asn Leu Phe Val Asp Gly Arg
        195                 200                 205 agg gac gac ggc cag cta gat atg gat gct gca cgg agt ttt ttc caa    672
Arg Asp Asp Gly Gln Leu Asp Met Asp Ala Ala Arg Ser Phe Phe Gln
    210                 215                 220 ttc agc cgt atg cct gac gat ttc ttc cgc gca ccc agc ccg aga agt    720
Phe Ser Arg Met Pro Asp Asp Phe Phe Arg Ala Pro Ser Pro Arg Ser
225                 230                 235                 240 ggc aca gga gtc gag gta gtt ata cag gct cat cct atg cag ccc gga    768
Gly Thr Gly Val Glu Val Val Ile Gln Ala His Pro Met Gln Pro Gly
                245                 250                 255 aga aat gtc ggc aag atc aac agc tac acc gtc gac cca aca tcc tct    816
Arg Asn Val Gly Lys Ile Asn Ser Tyr Thr Val Asp Pro Thr Ser Ser
            260                 265                 270 gac ttt tcc acc ccc tgc ttg atg tac gag aaa ttc gtc aac ata acg    864
Asp Phe Ser Thr Pro Cys Leu Met Tyr Glu Lys Phe Val Asn Ile Thr
        275                 280                 285 gtc aag tca ctc tac ccg aat ccg acg gtg cag ctt cgc aaa gcc ctt    912
Val Lys Ser Leu Tyr Pro Asn Pro Thr Val Gln Leu Arg Lys Ala Leu
    290                 295                 300 aat acg aat ctc gat ttc ttc ttc cag gga gtc gcc gct gga tgt acc    960
Asn Thr Asn Leu Asp Phe Phe Phe Gln Gly Val Ala Ala Gly Cys Thr
305                 310                 315                 320 cag gtc ttc cca tac ggg cga gat tga                                987
Gln Val Phe Pro Tyr Gly Arg Asp
                325

<210> SEQ ID NO 62
<211> LENGTH: 328
<212> TYPE: PRT
<213> ORGANISM: Artificial Sequence
<220> FEATURE:
<223> OTHER INFORMATION: Synthetic Construct

<400> SEQUENCE: 62

Glu Pro Gly Leu Pro Pro Gly Pro Leu Glu Asn Ser Ser Ala Lys Leu
1               5                   10                  15

Val Asn Asp Glu Ala His Pro Trp Lys Pro Leu Arg Gly Asp Ile
            20                  25                  30

Arg Gly Pro Cys Pro Gly Leu Asn Thr Leu Ala Ser His Gly Tyr Leu
        35                  40                  45

Pro Arg Asn Gly Val Ala Thr Pro Val Gln Ile Ile Asn Ala Val Gln
    50                  55                  60

Glu Gly Leu Asn Phe Asp Asn Gln Ala Ala Val Phe Ala Thr Tyr Ala
65                  70                  75                  80

Ala His Leu Val Asp Gly Asn Leu Ile Thr Asp Leu Leu Ser Ile Gly
            85                  90                  95

Arg Lys Thr Arg Leu Thr Gly Pro Asp Pro Pro Pro Ala Ser Val
        100                 105                 110
```

```
Gly Gly Leu Asn Glu His Gly Thr Phe Glu Gly Asp Ala Ser Met Thr
            115                 120                 125

Arg Gly Asp Ala Phe Phe Gly Asn Asn His Asp Phe Asn Glu Thr Leu
130                 135                 140

Phe Glu Gln Leu Val Asp Tyr Ser Asn Arg Phe Gly Gly Lys Tyr
145                 150                 155                 160

Asn Leu Thr Val Ala Gly Glu Leu Arg Phe Lys Arg Ile Gln Asp Ser
                165                 170                 175

Ile Ala Thr Asn Pro Asn Phe Ser Phe Val Asp Phe Arg Phe Ser Thr
            180                 185                 190

Ala Tyr Gly Glu Thr Thr Phe Pro Ala Asn Leu Phe Val Asp Gly Arg
        195                 200                 205

Arg Asp Asp Gly Gln Leu Asp Met Asp Ala Ala Arg Ser Phe Phe Gln
210                 215                 220

Phe Ser Arg Met Pro Asp Asp Phe Arg Ala Pro Ser Pro Arg Ser
225                 230                 235                 240

Gly Thr Gly Val Glu Val Val Ile Gln Ala His Pro Met Gln Pro Gly
                245                 250                 255

Arg Asn Val Gly Lys Ile Asn Ser Tyr Thr Val Asp Pro Thr Ser Ser
            260                 265                 270

Asp Phe Ser Thr Pro Cys Leu Met Tyr Glu Lys Phe Val Asn Ile Thr
        275                 280                 285

Val Lys Ser Leu Tyr Pro Asn Pro Thr Val Gln Leu Arg Lys Ala Leu
290                 295                 300

Asn Thr Asn Leu Asp Phe Phe Phe Gln Gly Val Ala Ala Gly Cys Thr
305                 310                 315                 320

Gln Val Phe Pro Tyr Gly Arg Asp
                325
```

<210> SEQ ID NO 63
<211> LENGTH: 1116
<212> TYPE: DNA
<213> ORGANISM: Artificial Sequence
<220> FEATURE:
<223> OTHER INFORMATION: Wt-SoLo variant with wild signal peptide
<220> FEATURE:
<221> NAME/KEY: CDS
<222> LOCATION: (1)..(1113)
<220> FEATURE:
<221> NAME/KEY: mat_peptide
<222> LOCATION: (130)..(1116)

<400> SEQUENCE: 63

```
atg aaa tat ttt ccc ctg ttc cca acc ttg gtc tac gca gtg ggg gtc      48
Met Lys Tyr Phe Pro Leu Phe Pro Thr Leu Val Tyr Ala Val Gly Val
            -40                 -35                 -30 gtt gct ttt cct gac tac gcc tca ttg gcc ggc ctc agc cag cag gaa      96
Val Ala Phe Pro Asp Tyr Ala Ser Leu Ala Gly Leu Ser Gln Gln Glu
        -25                 -20                 -15 ttg gac gct ata atc cca aca ctc gag gcc cga gag cca gga tta cct     144
Leu Asp Ala Ile Ile Pro Thr Leu Glu Ala Arg Glu Pro Gly Leu Pro
    -10                 -5                  -1  1               5 cct ggt cct ctc gag aat agc tct gca aag ttg gtg aac gac gag gct     192
Pro Gly Pro Leu Glu Asn Ser Ser Ala Lys Leu Val Asn Asp Glu Ala
                10                  15                  20 cac cca tgg aag ccg ctt cga cct ggc gat att cgt gga cct tgc cct     240
His Pro Trp Lys Pro Leu Arg Pro Gly Asp Ile Arg Gly Pro Cys Pro
            25                  30                  35 ggt ctc aat act ctg gca tct cac ggg tac ctc ccg aga aat ggc gtt     288
Gly Leu Asn Thr Leu Ala Ser His Gly Tyr Leu Pro Arg Asn Gly Val
```

```
Gly Leu Asn Thr Leu Ala Ser His Gly Tyr Leu Pro Arg Asn Gly Val
             40                  45                  50 gca acc ccg gtg caa ata ata aac gcg gtt cag gaa gga ctc aat ttc      336
Ala Thr Pro Val Gln Ile Ile Asn Ala Val Gln Glu Gly Leu Asn Phe
 55                  60                  65 gac aat caa gcc gca gtc ttc gcc aca tat gcg gcc cac ctt gtg gac      384
Asp Asn Gln Ala Ala Val Phe Ala Thr Tyr Ala Ala His Leu Val Asp
 70                  75                  80                  85 ggc aat ctc att acg gac ttg ctg agc atc gga cgc aag acg cgg ctc      432
Gly Asn Leu Ile Thr Asp Leu Leu Ser Ile Gly Arg Lys Thr Arg Leu
                 90                  95                 100 act ggg cct gat cca cca ccc ccc gct tcc gtt ggt gga ctc aat gag      480
Thr Gly Pro Asp Pro Pro Pro Pro Ala Ser Val Gly Gly Leu Asn Glu
                105                 110                 115 cat ggc acc ttc gaa ggc gac gcc agt atg acc cga ggt gac gca ttc      528
His Gly Thr Phe Glu Gly Asp Ala Ser Met Thr Arg Gly Asp Ala Phe
                120                 125                 130 ttt ggc aac aac cac gat ttc aat gag acg ctc ttc gaa cag ttg gtt      576
Phe Gly Asn Asn His Asp Phe Asn Glu Thr Leu Phe Glu Gln Leu Val
135                 140                 145 gac tac agc aac cga ttt gga gga gga aaa tac aat ctt acc gtc gcg      624
Asp Tyr Ser Asn Arg Phe Gly Gly Gly Lys Tyr Asn Leu Thr Val Ala
150                 155                 160                 165 ggg gag ctc cgt ttc aag cgc att caa gac tcc att gcg acc aac ccc      672
Gly Glu Leu Arg Phe Lys Arg Ile Gln Asp Ser Ile Ala Thr Asn Pro
                170                 175                 180 aat ttc tcc ttt gtt gac ttt agg ttc tct act gct tac ggc gag acc      720
Asn Phe Ser Phe Val Asp Phe Arg Phe Ser Thr Ala Tyr Gly Glu Thr
                185                 190                 195 acc ttc ccc gcg aat ctt ttt gtg gat ggg cgc agg gac gac ggc cag      768
Thr Phe Pro Ala Asn Leu Phe Val Asp Gly Arg Arg Asp Asp Gly Gln
                200                 205                 210 cta gat atg gat gct gca cgg agt ttt ttc caa ttc agc cgt atg cct      816
Leu Asp Met Asp Ala Ala Arg Ser Phe Phe Gln Phe Ser Arg Met Pro
215                 220                 225 gac gat ttc ttc cgc gca ccc agc ccg aga agt ggc aca gga gtc gag      864
Asp Asp Phe Phe Arg Ala Pro Ser Pro Arg Ser Gly Thr Gly Val Glu
230                 235                 240                 245 gta gtt ata cag gct cat cct atg cag ccc gga aga aat gtc ggc aag      912
Val Val Ile Gln Ala His Pro Met Gln Pro Gly Arg Asn Val Gly Lys
                250                 255                 260 atc aac agc tac acc gtc gac cca aca tcc tct gac ttt tcc acc ccc      960
Ile Asn Ser Tyr Thr Val Asp Pro Thr Ser Ser Asp Phe Ser Thr Pro
                265                 270                 275 tgc ttg atg tac gag aaa ttc gtc aac ata acg gtc aag tca ctc tac     1008
Cys Leu Met Tyr Glu Lys Phe Val Asn Ile Thr Val Lys Ser Leu Tyr
                280                 285                 290 ccg aat ccg acg gtg cag ctt cgc aaa gcc ctt aat acg aat ctc gat     1056
Pro Asn Pro Thr Val Gln Leu Arg Lys Ala Leu Asn Thr Asn Leu Asp
295                 300                 305 ttc ttc ttc cag gga gtc gcc gct gga tgt acc cag gtc ttc cca tac     1104
Phe Phe Phe Gln Gly Val Ala Ala Gly Cys Thr Gln Val Phe Pro Tyr
310                 315                 320                 325 ggg cga gat tga                                                     1116
Gly Arg Asp <210> SEQ ID NO 64
<211> LENGTH: 371
<212> TYPE: PRT
<213> ORGANISM: Artificial Sequence
```

<220> FEATURE:
<223> OTHER INFORMATION: Synthetic Construct

<400> SEQUENCE: 64

```
Met Lys Tyr Phe Pro Leu Phe Pro Thr Leu Val Tyr Ala Val Gly Val
            -40                 -35                 -30

Val Ala Phe Pro Asp Tyr Ala Ser Leu Ala Gly Leu Ser Gln Gln Glu
        -25                 -20                 -15

Leu Asp Ala Ile Ile Pro Thr Leu Glu Ala Arg Glu Pro Gly Leu Pro
    -10                  -5                  -1   1               5

Pro Gly Pro Leu Glu Asn Ser Ser Ala Lys Leu Val Asn Asp Glu Ala
                 10                  15                  20

His Pro Trp Lys Pro Leu Arg Pro Gly Asp Ile Arg Gly Pro Cys Pro
             25                  30                  35

Gly Leu Asn Thr Leu Ala Ser His Gly Tyr Leu Pro Arg Asn Gly Val
         40                  45                  50

Ala Thr Pro Val Gln Ile Ile Asn Ala Val Gln Glu Gly Leu Asn Phe
     55                  60                  65

Asp Asn Gln Ala Ala Val Phe Ala Thr Tyr Ala Ala His Leu Val Asp
70                   75                  80                  85

Gly Asn Leu Ile Thr Asp Leu Leu Ser Ile Gly Arg Lys Thr Arg Leu
                 90                  95                 100

Thr Gly Pro Asp Pro Pro Pro Ala Ser Val Gly Gly Leu Asn Glu
                105                 110                 115

His Gly Thr Phe Glu Gly Asp Ala Ser Met Thr Arg Gly Asp Ala Phe
             120                 125                 130

Phe Gly Asn Asn His Asp Phe Asn Glu Thr Leu Phe Glu Gln Leu Val
    135                 140                 145

Asp Tyr Ser Asn Arg Phe Gly Gly Lys Tyr Asn Leu Thr Val Ala
150                 155                 160                 165

Gly Glu Leu Arg Phe Lys Arg Ile Gln Asp Ser Ile Ala Thr Asn Pro
                170                 175                 180

Asn Phe Ser Phe Val Asp Phe Arg Phe Ser Thr Ala Tyr Gly Glu Thr
            185                 190                 195

Thr Phe Pro Ala Asn Leu Phe Val Asp Gly Arg Arg Asp Asp Gly Gln
        200                 205                 210

Leu Asp Met Asp Ala Ala Arg Ser Phe Gln Phe Ser Arg Met Pro
    215                 220                 225

Asp Asp Phe Phe Arg Ala Pro Ser Pro Arg Ser Gly Thr Gly Val Glu
230                 235                 240                 245

Val Val Ile Gln Ala His Pro Met Gln Pro Gly Arg Asn Val Gly Lys
                250                 255                 260

Ile Asn Ser Tyr Thr Val Asp Pro Ser Ser Asp Phe Ser Thr Pro
            265                 270                 275

Cys Leu Met Tyr Glu Lys Phe Val Asn Ile Thr Val Lys Ser Leu Tyr
        280                 285                 290

Pro Asn Pro Thr Val Gln Leu Arg Lys Ala Leu Asn Thr Asn Leu Asp
    295                 300                 305

Phe Phe Phe Gln Gly Val Ala Ala Gly Cys Thr Gln Val Phe Pro Tyr
310                 315                 320                 325

Gly Arg Asp
```

<210> SEQ ID NO 65
<211> LENGTH: 1116

```
<212> TYPE: DNA
<213> ORGANISM: Artificial Sequence
<220> FEATURE:
<223> OTHER INFORMATION: Wt-SoLo variant with modified signal peptide
<220> FEATURE:
<221> NAME/KEY: CDS
<222> LOCATION: (1)..(1113)
<220> FEATURE:
<221> NAME/KEY: mat_peptide
<222> LOCATION: (130)..(1116)

<400> SEQUENCE: 65
```

| | | | | | | | | | | | | | | | | |
|---|---|---|---|---|---|---|---|---|---|---|---|---|---|---|---|---|
| atg | aaa | tat | ttt | ccc | ctg | ttc | cca | acc | ttg | gtc | tac | gca | gtg | ggg | gtc | 48 |
| Met | Lys | Tyr | Phe | Pro | Leu | Phe | Pro | Thr | Leu | Val | Tyr | Ala | Val | Gly | Val | |
| | | | -40 | | | | -35 | | | | | -30 | | | | |
| gtt | gct | ttt | cct | gac | tac | gcc | tca | ttg | gcc | ggc | ctc | agc | cag | cag | gaa | 96 |
| Val | Ala | Phe | Pro | Asp | Tyr | Ala | Ser | Leu | Ala | Gly | Leu | Ser | Gln | Gln | Glu | |
| | | | -25 | | | | -20 | | | | -15 | | | | | |
| ttg | gac | gct | ata | atc | cca | aca | ctc | gag | gcc | cga | gag | cca | gga | tta | cct | 144 |
| Leu | Asp | Ala | Ile | Ile | Pro | Thr | Leu | Glu | Ala | Arg | Glu | Pro | Gly | Leu | Pro | |
| | -10 | | | | -5 | | | | -1 | 1 | | | | 5 | | |
| cct | ggt | cct | ctc | gag | aat | agc | tct | gca | aag | ttg | gtg | aac | gac | gag | gct | 192 |
| Pro | Gly | Pro | Leu | Glu | Asn | Ser | Ser | Ala | Lys | Leu | Val | Asn | Asp | Glu | Ala | |
| | | | | 10 | | | | 15 | | | | 20 | | | | |
| cac | cca | tgg | aag | ccg | ctt | cga | cct | ggc | gat | att | cgt | gga | cct | tgc | cct | 240 |
| His | Pro | Trp | Lys | Pro | Leu | Arg | Pro | Gly | Asp | Ile | Arg | Gly | Pro | Cys | Pro | |
| | | 25 | | | | 30 | | | | 35 | | | | | | |
| ggt | ctc | aat | act | ctg | gca | tct | cac | ggg | tac | ctc | ccg | aga | aat | ggc | gtt | 288 |
| Gly | Leu | Asn | Thr | Leu | Ala | Ser | His | Gly | Tyr | Leu | Pro | Arg | Asn | Gly | Val | |
| | | 40 | | | | 45 | | | | 50 | | | | | | |
| gca | acc | ccg | gtg | caa | ata | ata | aac | gcg | gtt | cag | gaa | gga | ctc | aat | ttc | 336 |
| Ala | Thr | Pro | Val | Gln | Ile | Ile | Asn | Ala | Val | Gln | Glu | Gly | Leu | Asn | Phe | |
| | 55 | | | | 60 | | | | 65 | | | | | | | |
| gac | aat | caa | gcc | gca | gtc | ttc | gcc | aca | tat | gcg | gcc | cac | ctt | gtg | gac | 384 |
| Asp | Asn | Gln | Ala | Ala | Val | Phe | Ala | Thr | Tyr | Ala | Ala | His | Leu | Val | Asp | |
| 70 | | | | 75 | | | | 80 | | | | 85 | | | | |
| ggc | aat | ctc | att | acg | gac | ttg | ctg | agc | atc | gga | cgc | aag | acg | cgg | ctc | 432 |
| Gly | Asn | Leu | Ile | Thr | Asp | Leu | Leu | Ser | Ile | Gly | Arg | Lys | Thr | Arg | Leu | |
| | | | 90 | | | | 95 | | | | 100 | | | | | |
| act | ggg | cct | gat | cca | cca | ccc | ccc | gct | tcc | gtt | ggt | gga | ctc | aat | gag | 480 |
| Thr | Gly | Pro | Asp | Pro | Pro | Pro | Pro | Ala | Ser | Val | Gly | Gly | Leu | Asn | Glu | |
| | | | 105 | | | | 110 | | | | 115 | | | | | |
| cat | ggc | acc | ttc | gaa | ggc | gac | gcc | agt | atg | acc | cga | ggt | gac | gca | ttc | 528 |
| His | Gly | Thr | Phe | Glu | Gly | Asp | Ala | Ser | Met | Thr | Arg | Gly | Asp | Ala | Phe | |
| | | 120 | | | | 125 | | | | 130 | | | | | | |
| ttt | ggc | aac | aac | cac | gat | ttc | aat | gag | acg | ctc | ttc | gaa | cag | ttg | gtt | 576 |
| Phe | Gly | Asn | Asn | His | Asp | Phe | Asn | Glu | Thr | Leu | Phe | Glu | Gln | Leu | Val | |
| | 135 | | | | 140 | | | | 145 | | | | | | | |
| gac | tac | agc | aac | cga | ttt | gga | gga | gga | aaa | tac | aat | ctt | acc | gtc | gcg | 624 |
| Asp | Tyr | Ser | Asn | Arg | Phe | Gly | Gly | Gly | Lys | Tyr | Asn | Leu | Thr | Val | Ala | |
| 150 | | | | 155 | | | | 160 | | | | 165 | | | | |
| ggg | gag | ctc | cgt | ttc | aag | cgc | att | caa | gac | tcc | att | gcg | acc | aac | ccc | 672 |
| Gly | Glu | Leu | Arg | Phe | Lys | Arg | Ile | Gln | Asp | Ser | Ile | Ala | Thr | Asn | Pro | |
| | | | 170 | | | | 175 | | | | 180 | | | | | |
| aat | ttc | tcc | ttt | gtt | gac | ttt | agg | ttc | tct | act | gct | tac | ggc | gag | acc | 720 |
| Asn | Phe | Ser | Phe | Val | Asp | Phe | Arg | Phe | Ser | Thr | Ala | Tyr | Gly | Glu | Thr | |
| | | 185 | | | | 190 | | | | 195 | | | | | | |
| acc | ttc | ccc | gcg | aat | ctt | ttt | gtg | gat | ggg | cgc | agg | gac | gac | ggc | cag | 768 |
| Thr | Phe | Pro | Ala | Asn | Leu | Phe | Val | Asp | Gly | Arg | Arg | Asp | Asp | Gly | Gln | |
| | 200 | | | | 205 | | | | 210 | | | | | | | |
| cta | gat | atg | gat | gct | gca | cgg | agt | ttt | ttc | caa | ttc | agc | cgt | atg | cct | 816 |
| Leu | Asp | Met | Asp | Ala | Ala | Arg | Ser | Phe | Phe | Gln | Phe | Ser | Arg | Met | Pro | |

```
              215                 220                 225
gac gat ttc ttc cgc gca ccc agc ccg aga agt ggc aca gga gtc gag        864
Asp Asp Phe Phe Arg Ala Pro Ser Pro Arg Ser Gly Thr Gly Val Glu
230                 235                 240                 245 gta gtt ata cag gct cat cct atg cag ccc gga aga aat gtc ggc aag        912
Val Val Ile Gln Ala His Pro Met Gln Pro Gly Arg Asn Val Gly Lys
                250                 255                 260 atc aac agc tac acc gtc gac cca aca tcc tct gac ttt tcc acc ccc        960
Ile Asn Ser Tyr Thr Val Asp Pro Thr Ser Ser Asp Phe Ser Thr Pro
                265                 270                 275 tgc ttg atg tac gag aaa ttc gtc aac ata acg gtc aag tca ctc tac       1008
Cys Leu Met Tyr Glu Lys Phe Val Asn Ile Thr Val Lys Ser Leu Tyr
                280                 285                 290 ccg aat ccg acg gtg cag ctt cgc aaa gcc ctt aat acg aat ctc gat       1056
Pro Asn Pro Thr Val Gln Leu Arg Lys Ala Leu Asn Thr Asn Leu Asp
295                 300                 305 ttc ttc ttc cag gga gtc gcc gct gga tgt acc cag gtc ttc cca tac       1104
Phe Phe Phe Gln Gly Val Ala Ala Gly Cys Thr Gln Val Phe Pro Tyr
310                 315                 320                 325 ggg cga gat tga                                                       1116
Gly Arg Asp <210> SEQ ID NO 66
<211> LENGTH: 371
<212> TYPE: PRT
<213> ORGANISM: Artificial Sequence
<220> FEATURE:
<223> OTHER INFORMATION: Synthetic Construct

<400> SEQUENCE: 66

Met Lys Tyr Phe Pro Leu Phe Pro Thr Leu Val Tyr Ala Val Gly Val
                -40                 -35                 -30

Val Ala Phe Pro Asp Tyr Ala Ser Leu Ala Gly Leu Ser Gln Gln Glu
            -25                 -20                 -15

Leu Asp Ala Ile Ile Pro Thr Leu Glu Ala Arg Glu Pro Gly Leu Pro
        -10                  -5                  -1   1               5

Pro Gly Pro Leu Glu Asn Ser Ser Ala Lys Leu Val Asn Asp Glu Ala
                 10                  15                  20

His Pro Trp Lys Pro Leu Arg Pro Gly Asp Ile Arg Gly Pro Cys Pro
             25                  30                  35

Gly Leu Asn Thr Leu Ala Ser His Gly Tyr Leu Pro Arg Asn Gly Val
         40                  45                  50

Ala Thr Pro Val Gln Ile Ile Asn Ala Val Gln Glu Gly Leu Asn Phe
     55                  60                  65

Asp Asn Gln Ala Ala Val Phe Ala Thr Tyr Ala Ala His Leu Val Asp
70                  75                  80                  85

Gly Asn Leu Ile Thr Asp Leu Leu Ser Ile Gly Arg Lys Thr Arg Leu
                 90                  95                 100

Thr Gly Pro Asp Pro Pro Pro Ala Ser Val Gly Gly Leu Asn Glu
             105                 110                 115

His Gly Thr Phe Glu Gly Asp Ala Ser Met Thr Arg Gly Asp Ala Phe
         120                 125                 130

Phe Gly Asn Asn His Asp Phe Asn Glu Thr Leu Phe Glu Gln Leu Val
     135                 140                 145

Asp Tyr Ser Asn Arg Phe Gly Gly Gly Lys Tyr Asn Leu Thr Val Ala
150                 155                 160                 165

Gly Glu Leu Arg Phe Lys Arg Ile Gln Asp Ser Ile Ala Thr Asn Pro
```

-continued

```
                170               175               180
Asn Phe Ser Phe Val Asp Phe Arg Phe Ser Thr Ala Tyr Gly Glu Thr
            185               190               195

Thr Phe Pro Ala Asn Leu Phe Val Asp Gly Arg Arg Asp Asp Gly Gln
            200               205               210

Leu Asp Met Asp Ala Ala Arg Ser Phe Phe Gln Phe Ser Arg Met Pro
            215               220               225

Asp Asp Phe Phe Arg Ala Pro Ser Pro Arg Ser Gly Thr Gly Val Glu
230               235               240               245

Val Val Ile Gln Ala His Pro Met Gln Pro Gly Arg Asn Val Gly Lys
            250               255               260

Ile Asn Ser Tyr Thr Val Asp Pro Thr Ser Ser Asp Phe Ser Thr Pro
            265               270               275

Cys Leu Met Tyr Glu Lys Phe Val Asn Ile Thr Val Lys Ser Leu Tyr
            280               285               290

Pro Asn Pro Thr Val Gln Leu Arg Lys Ala Leu Asn Thr Asn Leu Asp
            295               300               305

Phe Phe Phe Gln Gly Val Ala Ala Gly Cys Thr Gln Val Phe Pro Tyr
310               315               320               325

Gly Arg Asp
```

POLYNUCLEOTIDE, HOST CELL AND A METHOD TO RECOMBINANTLY PRODUCE THE PROTEIN ENCODED BY SAID POLYNUCLEOTIDE HAVING PEROXYGENATIVE ACTIVITY

CROSS-REFERENCE TO RELATED APPLICATIONS

The present patent application is a national phase application of International Application No. PCT/ES2016/070809, filed Nov. 14, 2016, which claims priority to Spanish Application No. P201531641, filed Nov. 13, 2015, the disclosures of which are incorporated herein by reference.

INCORPORATION BY REFERENCE

An electronic copy of the Sequence Listing entitled "Sequence Listing.txt" and having a file size of 178,000 bytes, the ASCII text file named SequenceListing2.txt, created on May 23, 2018, having a file size of 178,000 byes, and the ASCII text file named SequenceListing3.txt, created on Aug. 15, 2018, having a file size of 178,000 bytes, are incorporated herein by reference. The Sequence Listings consist of [SEQ ID NOs: 1-66].

TECHNICAL FIELD OF THE ART

The present invention belongs to the field of molecular biology, recombinant DNA technology and biotechnology. Specifically, it relates to a peroxygenase enzyme with enhanced functional expression in an active, soluble and stable form, showing improved peroxygenase activity and reduced peroxidase activity with respect to the native enzyme or wild-type, and which has been obtained through a process of directed molecular evolution. Said enzyme may be used in chemical processes, including industrial transformations such as the selective oxyfunctionalisation of carbon-hydrogen bonds of various organic compounds, preferably those hydroxylation processes that transform naphthalene into 1-naphthol and/or propranolol into 5'-hydroxypropranolol.

STATE OF THE ART

The methods of organic synthesis, preferably processes aimed at selective oxyfunctionalisation of carbon-hydrogen bonds of various organic compounds and, more specifically, those compounds that by hydroxylation processes give rise to other products with characteristics more suitable for different uses such as, for example, synthesis of agrochemical products, herbicides, insecticides, pharmaceuticals, cosmetics and dye precursors, are currently carried out using chemical catalysts, such as sulfonic acid and platinum compounds, which are highly polluting products, with low turnover numbers and reduced regioselectivity, in addition to high energy consumption (high temperatures and pressures), high production costs and large release of waste.

In the search for a more environmentally friendly alternative and, thus, prevent the aforementioned drawbacks of the use of chemical catalysts in this type of reactions, microorganisms such as *Cunninghamella, Bacillus cereus* ATCC14579, the green algae *Chlorella* and various fungi and enzymes which transform, by means of hydroxylation procedures, for example naphthalene into 1-naphthol, have been used.

In this regard, enzymes with monooxygenase activity which conduct selective oxyfunctionalisation of aromatic rings may offer a more ecological alternative to conventional chemical processes.

For example, in the case of the aromatic hydrocarbon 1-naphthol, naphthalene-based synthesis is carried out with enzymes that show monooxygenase activity. Specifically, P450 monooxygenases are enzymes that show such activity and which have been subjected to engineering for different purposes over the years, from the selective hydroxylation of alkanes—including terminal hydroxylation- to the unnatural cyclopropanation of olefins by means of carbon transfer. Said P450 monooxygenase enzymes transform naphthalene into 1-naphthol either by means of the peroxide shunt pathway or by means of its NAD(P)H-dependent natural activity (H. J. Zhanglin, F. H. Arnold, *Nature* 1999. 399, 670-673; P. C. Cirino, F. H. Arnold, Angew. *Chem. Int. Ed.* 2003. 42, 3299-3301; P. Meinhold, et al. *Adv. Synth. Catal.* 2006. 348, 763-772; P. S. Coelho, et al. *Science* 2013. 339, 307-310). More recently, the evolution of the toluene ortho-monooxygenase enzyme (TOM) and its involvement in the process of a cell biocatalytic system has also been described (K. A. Canada, et al. *J. Bacteriol.* 2002. 184, 344-349; L. Rui, et al. *Appl. Environ. Microbiol.* 2004. 70, 3246-3252; J. Garikipati, et al. *Appl. Environ. Microbiol.* 2009. 75, 6545-6552). In all these cases, the low enzyme stability of the aforementioned enzymes, along with the high requirements in terms of high-cost redox cofactors (NADPH) and associated reducing domains (flavins), have prevented the industrial use thereof in the synthesis of the aromatic hydrocarbon 1-naphthol from naphthalene.

Furthermore, Human Drug Metabolites (HDMs) are the result of the metabolism of pharmaceutical compounds, mainly by hepatic P450 monooxygenase enzymes. For the pharmaceutical industry, the toxicity evaluation, effectiveness and activity of these metabolites is key, but to date the chemical synthesis thereof produces very low yields besides being very complicated. The most important HDMs include, namely, those derived from hydrocarbon propranolol, such as 5'-hydroxypropranolol. Propranolol is a beta-blocker drug commonly used for the treatment of hypertension, migraine prophylaxis in children and attenuation of physical manifestations of anxiety. Heretofore, known enzymatic alternatives for obtaining propranolol derivatives are P450 monooxygenase enzymes or unspecific fungal peroxygenases such as *Agrocybe aegerita* (AaeUPO) and *Coprinellus radians* (CraUPO). Specifically, P450 monooxygenases require cellular environments and/or expensive redox cofactors (NADPH), in addition to associated reducing domains (flavins), and show low operational stabilities and low regioselectivity. Furthermore, the specific fungal peroxygenases described require antioxidants such as ascorbic acid to prevent the subsequent oxidation of the product of interest.

One of the enzymes studied for the synthesis of the aforementioned compounds, 1-naphthol and 5'-hydroxypropranolol, was the enzyme UPO (Unspecific PerOxygenase, E.C. 1.11.2.1), secreted by the basidiomycete fungus *Agrocybe aegerita*, and known as the first "true" natural aromatic peroxygenase. The enzyme AaeUPO has properties resembling those of P450 monooxygenase enzymes as regards the selective oxyfunctionalisation of carbon-hydrogen bonds of various organic compounds. AaeUPO is an extracellular, highly active and stable enzyme, besides not requiring cofactors or auxiliary redox flavoproteins, i.e. it is self-sufficient. With minimal requirements, just catalytic concentrations of $H_2O_2$ (acting as an enzyme co-oxidant—primary electron acceptor—and oxygen source), AaeUPO is capable of carrying out a wide variety of highly complex transformations in organic synthesis, such as for example the hydroxylation of aromatic and aliphatic compounds, olefin epoxidation, N- and S-oxidation of heterocyclic compounds or breakage of ether linkages, among many others. Furthermore, it has natural mono(per)oxygenase activity, such as P450 monooxygenase enzyme, and peroxidase on phenolic substrates (M. Kluge, et al. *Appl. Microbiol. Biotechnol.* 2009. 81, 1071-1076). The coexistence of both activities, peroxygenase and peroxidase, in the same enzyme is a problem when the objective is to use this enzyme in an industrial process, since the products of hydroxylation of AaeUPO always appear with different amounts of oxidation products derived from the former. This is especially true in the case of aromatic hydroxylations wherein the product(s) released by the peroxygenase activity may in turn again be substrates for the peroxidase activity of the UPO, promoting the formation of quinones involving non-enzymatic polymerisation which affects the overall efficiency of the process.

Therefore, in the state of the art there is a need for enzymes showing improved monooxygenase activity, to the detriment of its peroxidase activity, together with high enzyme stability, high regioselectivity and which are self-sufficient, i.e. they do not require the presence of cofactors to carry out their monooxygenase activity. It is also important to note that said enzymes require robust expression systems that provide high levels of active enzyme. Therefore, these enzymes, due to the aforementioned characteristics, are suitable for use in methods of organic synthesis, preferably in processes of oxyfunctionalisation, oxidation or selective hydroxylation of hydrocarbons in general, both aromatic and aliphatic linear, branched and cyclic, preferably the method of hydroxylation of cyclic aromatic compounds, both single cyclic or condensed compounds, more preferably the method of hydroxylation for the synthesis of 1-naphthol and/or synthesis of 5'-hydroxypropranolol, where said processes are carried out in a single step under mild conditions, such as ambient temperature, atmospheric pressure and in an aqueous solution, with low organic co-solvent content, to reduce energy consumption, as well as the harmful effects of chemical synthesis.

DESCRIPTION OF THE INVENTION

The present invention describes the directed evolution of the unspecific peroxygenase UPO (E.C. 1.11.2.1) of *A. aegerita* (AaeUPO of SEQ ID NO: 1), to obtain variants or mutants showing a functional expression in a soluble, active and highly stable form in a eukaryote heterologous host, preferably *Saccharomyces cerevisiae* or *Pichia pastoris*, besides showing an improved peroxygenase activity and reduced peroxidase activity relative to the wild-type UPO enzyme of *A. aegerita* (SEQ ID NO: 2) expressed in *S. cerevisiae*. Said variants or mutants, due to the aforementioned characteristics, are suitable for use in methods of organic synthesis, preferably in processes of oxyfunctionalisation, oxidation or selective hydroxylation of hydrocarbons in general, both aromatic and aliphatic linear, branched and cyclic, preferably the method of hydroxylation of cyclic aromatic compounds, both single cyclic or condensed compounds, more preferably the method of hydroxylation for the synthesis of 1-naphthol and/or synthesis of 5'-hydroxypropranolol wherein these processes are carried out in a single step, without requiring the presence of cofactors, under mild conditions such as ambient temperature, atmospheric pressure and in an aqueous solution, with low organic co-solvent content, to reduce energy consumption, as well as the adverse consequences of the chemical synthesis.

The peroxygenase UPO1 of *A. aegerita* (AaeUPO of SEQ ID NO: 1) was subjected to several cycles of laboratory-directed evolution combined with semi-rational approaches (i.e. rational semi-rational and random design methods were used) for the different variants described herein. On the one hand, the peroxygenase UPO1 of *A. aegerita* (AaeUPO of SEQ ID NO: 1) was subjected to five cycles of directed evolution, giving rise to the mutant, hereinafter and throughout the present invention PaDa-I, SEQ ID NO: 14 and which is encoded by the nucleotide sequence SEQ ID NO: 13. Said PaDa-I mutant comprises the L67F, I248V, F311L, V75I and V57A mutations with respect to wild AaeUPO1 of SEQ ID NO: 2, encoded by the sequence SEQ ID NO: 1. Similarly, the nucleotide sequence that encodes the native signal peptide of AaeUPO1 (SEQ ID NO: 25) was also subjected to directed evolution cycles and gave rise to a modified or evolved signal peptide of SEQ ID NO: 27, as described in P. Molina-Espeja et al. *Appl. Environ. Microbiol.* 2014. 80, 3496-3507. In this manner, the PaDa-I mutant that comprised the evolved signal peptide (SEQ ID NO: 27) was obtained, whose nucleotide sequence is SEQ ID NO: 17, which encodes the PaDa-I peptide of SEQ ID NO: 18. Said PaDa-I mutant, as demonstrated by the inventors (P. Molina-Espeja, et al. *Appl. Environ. Microbiol.* 2014. 80, 3496-507) has high functional expression, enhanced catalytic constants, high thermostability and greater resistance to the presence of organic co-solvents with respect to the wild-type UPO expressed in *S. cerevisiae*. Enzyme substrate promiscuity was preserved performing a dual assay in High-Throughput Screening (HTS) format to explore both oxidative activities and those relating to oxygen transfer from mutant libraries, besides incorporating an assay to avoid the loss of kinetic thermostability.

Two new cycles of laboratory-directed evolution were carried out based on the previously described PaDa-I mutant, which gave rise to the JaWa variant of SEQ ID NO: 23, with two added mutations in the protein sequence SEQ ID NO: 24: G241D y R257K, regarding the sequence of the PaDa-I mutant. In this manner, the JaWa mutant of the nucleotide sequence SEQ ID NO: 23 or SEQ ID NO: 19 is obtained, which encode the peptides of SEQ ID NO: 24 or SEQ ID NO: 20, depending on whether or not they have the evolved or modified signal peptide of SEQ ID NO: 28 encoded for the nucleotide sequence of SEQ ID NO: 27. On the other, these two new mutations, G241D and R257K, were also incorporated to the sequence of the native peroxygenase AaeUPO1 (SEQ ID NO: 1) by means of directed mutagenesis, giving rise to a variant we will call wt-JaWa of SEQ ID NO: 8 or SEQ ID NO: 12, respectively encoded by the nucleotide sequences SEQ ID NO: 7 or SEQ ID NO: 11, depending on whether or not the evolved signal peptide of SEQ ID NO: 28 encoded for the nucleotide sequence of SEQ ID NO: 27.

Based on the JaWa mutant SEQ ID NO: 23 encoded for the nucleotide sequence SEQ ID NO: 24, previously described, another three new laboratory-directed evolution cycles were carried out which gave rise to the SoLo variant of SEQ ID NO: 41, with an added mutation in the protein sequence SEQ ID NO: 42: F191S, with respect to the sequence of the JaWa mutant. In this manner, the SoLo mutant of the nucleotide sequence SEQ ID NO: 41 or SEQ ID NO: 37 is obtained, which encode the peptides of SEQ ID NO: 42 or SEQ ID NO: 38, depending on whether or not they have the evolved or modified signal peptide of SEQ ID NO: 28, encoded by the nucleotide sequence of SEQ ID NO: 27. Furthermore, this new mutation, F191S, was also incorporated to the sequence of the native peroxygenase AaeUPO1 (SEQ ID NO: 1) by means of directed mutagenesis, giving rise to a variant we will call wt-SoLo of SEQ ID NO: 62 or SEQ ID NO: 66, respectively encoded by the nucleotide sequences SEQ ID NO: 61 or SEQ ID NO: 65, depending on whether or not they have the evolved signal peptide of SEQ ID NO: 28 encoded for the nucleotide sequence of SEQ ID NO: 27.

Thus, the variants described herein, preferably the variants JaWa and SoLo, have all the characteristics and advantages previously mentioned for the PaDa-I mutant, but also show a greater increase in thermostability (values of $T_{50}$=59.7° C., an increase in thermostability of 2° C., with respect to the variant PaDa-I), greater stability against the presence of co-solvents and kinetic values against naphthalene of $k_{cat}/K_m$ of around 1.56 fold higher than those described for the PaDa-I variant when said mutants are expressed in a heterologous organism, preferably in yeasts, for the case of the variant JaWa and around 1.47 fold higher in $k_{cat}$ for the case of the variant SoLo. Therefore, the main advantages of the variants with improved peroxygenase activity and reduced peroxidase activity, with respect to wild AaeUPO, or to other variants of the state of the art, such as for example the variant PaDa-I, are as follows:

i) they show a high production rate,
ii) they show high activity,
iii) they show high stability,
iv) they show an increase in TTN of 2.5 fold (TTN of approximately 50,000) in the case of the synthesis of 1-naphthol and of three fold in the absence of antioxidants (45,000 for the SoLo mutant against 15,000 of the JaWa mutant) or of 15 fold (3,000 in the case of wild AaeUPO) for the synthesis of 5'-hydroxypropranolol,
v) shows an increase in $k_{cat}$ for 1-naphthol of up to 1.5 fold and an increase in $k_{cat}$ for 5'-hydroxypropranolol of up to 3.6 fold,
vi) shows enhanced catalytic efficiency for naphthalene up to values of $6.2 \times 10^5$ $s^{-1}M^{-1}$; and for 5'-hydroxypropranolol of $3.1 \times 10^6$ $s^{-1}$ $M^{-1}$, two orders of magnitude higher than those of any enzyme described,
vii) show a reduction of approximately 1.5 fold in the ratio 1.4-naphthoquinone:1-naphthol, and up to 50% less oxidation with respect to 5'-hydroxypropranolol,
viii) They have a regioselectivity against 1-naphthol of approximately 97% and of approximately 99% against 5'-hydroxypropranolol.

Therefore, the present invention provides new peroxygenases showing all the aforementioned advantages over native or wild-type peroxygenase, such as the functional expression in a heterologous organism, preferably, *S. cerevisiae* or *P. pastoris*, as well as with respect to other variants or mutants currently known in the state of the art, such as the PaDa-I variant. Additionally, the variants described herein have greater selectivity and the highest total turnover numbers (TTN) for methods of organic synthesis, preferably in processes of oxyfunctionalisation or selective oxidation of hydrocarbons in general, both aromatic and aliphatic linear, branched and cyclic, preferably the method of hydroxylation of cyclic aromatic compounds, both single cyclic or condensed compounds, more preferably the method of hydroxylation for the synthesis of 1-naphthol and/or synthesis of 5'-hydroxypropranolol, known to date for this enzyme superfamily. Heterologously secreted in an active, soluble and very stable form, these variants carry out selective aromatic oxygenations in the absence of cofactors NAD(P)H and reductase domains. Its self-sufficient mono(per)oxygenase activity, together with its reduced peroxidase activity, make these UPO variants a valuable biocatalyst for the future of applications in the field of organic synthesis.

Thus, the present invention relates to the amino acid sequences of said peroxygenase variants, and the nucleotide sequences that encode said peroxygenase variants. Below is a list of the polynucleotides and polypeptides described herein:

SEQ ID NO: 1—Nucleotide sequence of the gene that encodes AaeUPO1 without signal peptide.
SEQ ID NO: 2—Polypeptide sequence of AaeUPO1 without signal peptide.
SEQ ID NO: 3—Nucleotide sequence of the gene that encodes AaeUPO1 with wild-type signal peptide.
SEQ ID NO: 4—Polypeptide sequence of AaeUPO1 with wild-type signal peptide.
SEQ ID NO: 5—Nucleotide sequence of the gene that encodes AaeUPO1 with modified signal peptide.
SEQ ID NO: 6—Polypeptide sequence AaeUPO1 with modified signal peptide.
SEQ ID NO: 7—Nucleotide sequence that encodes the wt-JaWa variant without signal peptide.
SEQ ID NO: 8—Polypeptide sequence of the wt-JaWa variant without signal peptide.
SEQ ID NO: 9—Nucleotide sequence that encodes the wt-JaWa variant with wild-type signal peptide.
SEQ ID NO: 10—Polypeptide sequence of the wt-JaWa variant with wild-type signal peptide.
SEQ ID NO: 11—Nucleotide sequence that encodes the wt-JaWa variant with modified signal peptide.
SEQ ID NO: 12—Polypeptide sequence of the wt-JaWa variant with modified signal peptide.
SEQ ID NO: 13—Nucleotide sequence that encodes the PaDa-I variant without signal peptide.
SEQ ID NO: 14—Polypeptide sequence of the PaDa-I variant without signal peptide.
SEQ ID NO: 15—Nucleotide sequence that encodes the PaDa-I variant with wild-type signal peptide.
SEQ ID NO: 16—Polypeptide sequence of the PaDa-I variant with wild-type signal peptide.
SEQ ID NO: 17—Nucleotide sequence that encodes the PaDa-I variant with modified signal peptide.
SEQ ID NO: 18—Polypeptide sequence of the PaDa-I variant with modified signal peptide.
SEQ ID NO: 19—Nucleotide sequence that encodes the JaWa variant without signal peptide.
SEQ ID NO: 20—Polypeptide sequence of the JaWa variant without signal peptide.
SEQ ID NO: 21—Nucleotide sequence that encodes the JaWa variant with wild-type signal peptide.
SEQ ID NO: 22—Polypeptide sequence of the JaWa variant with wild-type signal peptide.
SEQ ID NO: 23—Nucleotide sequence that encodes the JaWa variant with modified peptide.
SEQ ID NO: 24—Polypeptide sequence of the JaWa variant with modified signal peptide.
SEQ ID NO: 25—Nucleotide sequence that encodes the native signal peptide of AaeUPO1.
SEQ ID NO: 26—Polypeptide sequence of the native signal peptide of AaeU P01
SEQ ID NO: 27—Nucleotide sequence that encodes the modified signal peptide comprising mutations F[12]Y, A[14]V, R[15]G and A[21]D with respect to the nucleotide sequence that encodes the native signal peptide of AaeUPO1 of SEQ ID NO: 26.

SEQ ID NO: 28—Polypeptide sequence of the modified signal peptide comprising the mutations F[12]Y, A[14]V, R[15]G and A[21]D with respect to the polypeptide sequence of SEQ ID NO: 26.

SEQ ID NO: 29—Nucleotide sequence that encodes the W24F variant obtained from the PaDa-I mutant of SEQ ID NO: 17.

SEQ ID NO: 30—Polypeptide sequence that encodes the W24F variant obtained from the PaDa-I mutant of SEQ ID NO: 18.

SEQ ID NO: 31—Nucleotide sequence that encodes the W24F variant obtained from the JaWa mutant of SEQ ID NO: 23.

SEQ ID NO: 32—Polypeptide sequence that encodes the W24F variant obtained from the JaWa mutant of SEQ ID NO: 24.

SEQ ID NO: 37—Nucleotide sequence that encodes the SoLo variant without signal peptide.

SEQ ID NO: 38—Polypeptide sequence of the SoLo without signal peptide.

SEQ ID NO: 39—Nucleotide sequence that encodes the SoLo variant with wild-type signal peptide.

SEQ ID NO: 40—Polypeptide sequence of the SoLo variant with wild-type signal peptide.

SEQ ID NO: 41—Nucleotide sequence that encodes the SoLo variant with modified signal peptide.

SEQ ID NO: 42—Polypeptide sequence of the SoLo variant with modified signal peptide.

SEQ ID NO: 61—Nucleotide sequence that encodes the wt-SoLo variant without signal peptide.

SEQ ID NO: 62—Polypeptide sequence of the wt-SoLo variant without signal peptide.

SEQ ID NO: 63—Nucleotide sequence that encodes the wt-SoLo variant with wild-type signal peptide.

SEQ ID NO: 64—Polypeptide sequence of the wt-SoLo variant with wild-type signal peptide.

SEQ ID NO: 65—Nucleotide sequence that encodes the wt-SoLo variant with modified signal peptide.

SEQ ID NO: 66—Polypeptide sequence of the wt-SoLo variant with modified signal peptide.

The authors of the present invention have used a methodological combination based on directed evolution and mutagenesis and have obtained peroxygenase variants or mutants that resolve the need for a biocatalyst with high activity and thermostability, a high functional production rate, in addition to showing enhanced peroxygenase activity and reduced peroxidase activity, with respect to the wild-type UPO enzyme or even with respect to other UPO variants such as the PaDa-I variant.

The peroxygenases of the present invention, preferably the so-called JaWa and SoLo variants, are highly stable against temperature (values of $T_{50}$=59.7° C./59.5° C., an increase in thermostability of 2° C. with respect to the PaDa-I variant, being $T_{50}$ the temperature at which the enzyme maintains 50% of its initial activity after 10 minutes of incubation) and against the presence of co-solvents. Said peroxygenases have kinetic values with respect to naphthalene of $k_{cat}/K_m$ of around 1.56 fold higher than those described for the PaDa-I variant and around 46 fold higher than that described for wild AaeUPO with respect to propranolol, expressed in a heterologous organism, preferably yeasts, due to which its evolutionary design has given rise to:

i) Functional heterologous expression in yeast (0.2 g/L),
ii) increase in catalytic constants and efficiencies,
iii) increased stability against various factors (temperature, co-solvents).

Therefore, the main advantages of the variants with enhanced peroxygenase activity and reduced peroxidase activity, with respect to the wild UPO, or to other variants of the state of the art, such as for example the PaDa-I variant, as mentioned earlier, are as follows:

i) it shows a high production rate,
ii) it shows high activity,
iii) it shows high stability,
iv) it shows an increase in TTN of up to 2.5 fold (TTN of approximately 50,000), for the case of synthesis of 1-naphthol, and for the synthesis of 5'-hydroxypropranolol of three fold in the absence of antioxidants (45,000 for the SoLo mutant against 15,000 of the JaWa mutant) or 15 fold (3,000 in the case of wild AaeUPO),
v) it shows an increase in $k_{cat}$ for 1-naphthol of up to 1.5 times and an increase in $k_{cat}$ for 5'-hydroxypropranolol of up to 3.6 fold,
vi) it shows enhanced catalytic efficiency for naphthalene up to values of $6.2\times10^5$ $s^{-1}M^{-1}$; and for 5'-hydroxypropranolol of $3'1\times10^6$ $s^{-1}$ $M^{-1}$, two orders of magnitude higher than those of any enzyme described,
vii) it shows a reduction of approximately 1.5 fold in the ratio 1.4-naphthoquinone:1-naphthol and up to 50% less oxidation on 5'-hydroxypropranolol,
viii) it shows regioselectivity against 1-naphthol of approximately 97% and of approximately 99% against 5'-hydroxypropranolol.

For the purposes of the present invention, the term "peroxygenase" relates to the unspecific peroxygenase enzyme in accordance with EC 1.11.2.1, which catalyses the insertion of an oxygen atom from $H_2O_2$ or other peroxide which acts as a source of oxygen, in a wide variety of substrates. For the purposes of the present invention, peroxygenase is preferably unspecific peroxygenase (UPO) secreted by the basidiomycete fungus *A. aegerita*, whose nucleotide sequence is SEQ ID NO: 3 or SEQ ID NO: 1 that encodes a protein whose amino acid sequence is SEQ ID NO: 4 or SEQ ID NO: 2, depending on whether or not it comprises a signal peptide, respectively.

The terms "oxygen donors", "oxidising agent" and "oxidant" relate to a substance, molecule or compound that donates oxygen to a substrate in an oxidation reaction.

Typically, the oxygen donor is reduced (it accepts electrons). By way of example, non-limiting oxygen donors include molecular oxygen or dioxygen ($O_2$) and peroxides, including alkyl peroxides such as t-butyl, cumene hydroperoxide, paracetic acid and, more preferably, hydrogen peroxide ($H_2O_2$). A "peroxide" is any compound other than molecular oxygen ($O_2$) which has two oxygen atoms bonded to each other.

For the purposes of the present invention, the term "mutant" or "variant", used indistinctly throughout the present invention and relating to the UPO peroxygenases of the invention obtained by means of the methods described herein and which have at least two mutations, preferably at least three mutations, more preferably at least four mutations, more preferably at least five mutations, more preferably at least six mutations, more preferably at least seven mutations, more preferably at least eight mutations, more preferably at least nine mutations, more preferably at least ten mutations, more preferably at least eleven mutations and more preferably at least twelve mutations, resulting from greater peroxygenase activity and lower peroxidase activity, in addition to all the aforementioned advantages, than that showed by the corresponding native or wild-type UPO enzyme or any other UPO variant, preferably the PaDa-I variant, expressed in a heterologous host, preferably in yeasts of the genus *Saccharomyces* sp. and *Pichia* sp. and more preferably in the *S. cerevisiae* and *P. pastoris* species.

For the purposes of the present invention, the term "cofactor" relates to any substance that is necessary or beneficial to the activity of an enzyme. "Coenzyme" means a cofactor that interacts directly with and serves to promote a reaction catalysed by an enzyme. Many coenzymes also serve as carriers. For example, NAD$^+$ and NADP$^+$ carry hydrogen atoms from one enzyme to another (in the form of NADH and NADPH, respectively). An "auxiliary protein" means any protein substance necessary or beneficial to the activity of an enzyme.

In a first aspect, the present invention relates to a polynucleotide that encodes a polypeptide with peroxygenase activity, hereinafter polynucleotide of the invention, characterised in that the amino acid sequence of the polypeptide encoding show an identity of at least 70% with SEQ ID NO: 2 (AaeUPO1), and comprising at least two amino acid alterations in the positions homologous to positions 241 and 257 of the sequence, which replace the amino acids: original glycine (G) by ascorbic acid (D) in position 241 (G241D) and original arginine (R) by lysine (K) in position 257 (R257K).

In a preferred embodiment of the nucleotide of the invention, it is characterised in that the amino acid sequence of the polypeptide encoding showing an identity of at least 70% with SEQ ID NO: 2 (AaeUPO1), and further comprises an amino acid alteration in the homologous position to position 191 of the sequence SEQ ID NO: 2, which replaces the original amino acid phenylalanine (F) by serine (S) (F191S).

In another preferred embodiment of the polynucleotide of the invention, it is characterised in that the amino acid sequence of the polypeptide encoding showing an identity of at least 70% with SEQ ID NO: 2 (AaeUPO1), and comprises the amino acid alterations in the homologous positions 241, 257 and 191 of said sequence, which replace the amino acids: original glycine (G) by aspartic acid (D) in position 241 (G241D), original arginine (R) by lysine (K) in position 257 (R257K) and original phenylalanine (F) by serine (S) (F191S).

With the information supplied in the present invention, a person skilled in the art is capable of identifying nucleotide sequences homologous to those described in the present invention and that encode peroxygenase with identical characteristics to those described for the peroxygenase of the invention. Therefore, the polynucleotide of the invention is the coding sequence of an AaeUPO1 peroxygenase variant with the described enhanced activity, whose nucleotide sequence corresponds to:
a) nucleic acid molecules of the isolated polynucleotide sequence or in its complementary strand,
b) nucleic acid molecules whose complementary strand is capable of hybridising in astringent conditions with a polynucleotide sequence of (a), or
c) nucleic acid molecules, whose sequence differs from (a) and/or (b) due to the degeneration of the genetic code.

The term "astringent conditions" or "astringent hybridisation conditions" makes reference to conditions in which a hybridisation probe with its target sequence has a higher level than that of the other sequences (i.e. at least two fold higher than the base). The astringent conditions depend on the nature of the sequence and may vary according to the circumstances. Fully homologous target sequences can be identified by controlling astringency and washing conditions. Alternatively, astringency conditions may be adjusted to allow certain non-homologous pairings which may be detected at lower homology levels. A probe generally has less than 1,000 nucleotides in length and optionally less than 500 nucleotides. An average person skilled in the art has a deep understanding of nucleic acid hybridisation techniques.

The polynucleotides that encode the polypeptides of amino acid sequences described in the invention correspond to variants obtained by means of directed evolution of AaeUPO1 peroxygenase (E.C. 1.11.2.1). Said protein, AaeUPO1, corresponds to the nucleotide or polynucleotide sequence of SEQ ID NO: 3 or SEQ ID NO: 1, that are the coding sequences of the polypeptide with the amino acid sequence SEQ ID NO: 4 or SEQ ID NO: 2, depending on whether or not it comprises the signal peptide, respectively.

The term "polynucleotide", as used in the description, relates to polymeric forms of nucleotides of any length, both ribonucleotides and deoxyribonucleotides.

The term "identity" or "percentage of identity" between two sequences (nucleic acids or proteins) is understood to be the designation of a percentage of nucleotides or identical amino acid residues between the two compared sequences, obtained after the best alignment, being said percentage purely statistic and wherein the differences between the two sequences are distributed randomly and along the entire length. The term "best alignment" or "optimum alignment" is understood to be the designation of the alignment whereby the percentage of identity determined as described below is the highest. Comparisons between two nucleotide or amino acid sequences are traditionally performed: comparing these sequences once optimally aligned, performing said comparison by segment or by "comparison window" to identify and compare local regions of similarity regions. The optimum alignment of these sequences for comparison can be performed, in particular, with the help of one of the following algorithm: the local homology algorithm, Smith and Waterman (1981); the local homology algorithm, Neddleman and Wunsch (1970); the similarity search method, Pearson and Lipman (1988); the computer programs that use these algorithms (GAP, BESTFIT, BLASTP, BLASTN, BLASTX, TBLASTX, FASTA and TFASTA in the Wisconsin Genetics software package (Genetics Computer Group, 575 Science Dr., Madison, Wis.), or the Internet servers in particular of the National Centre for Biotechnology (NCBI), EMBL and the Ensembl project. In order to obtain optimum alignment, the BLAST program is preferably used, with the BLOSUM 62 matrix. The PAM or PAM250 matrices may also be used, in addition to an identity matrix for the nucleotide sequences.

In a preferred aspect of the invention, the polynucleotide and polypeptide sequences described herein comprise at least approximately 60%, at least approximately 65%, at least approximately 70%, at least approximately 75%, at least approximately 80%, at least approximately 85%, at least approximately 88% of identity, at least approximately 89%, at least approximately 90%, at least approximately 91%, at least approximately 92%, at least approximately 93%, at least approximately 94%, at least approximately 95%, at least approximately 96%, at least approximately 97%, at least approximately 98%, at least approximately 99% or 100% of identity against a reference sequence, when compared and aligned for a maximum correspondence against a comparison window or designated region as measured using the aforementioned algorithms.

The term "homology" or "percentage of homology" (percentage of homology, identity+similarity) is determined using homology comparison software, such as BLASP, TBLASTN or tBLASTX, of the National Centre of Biotechnology Information (NCBI), using the specific parameters. For the purposes of the present invention, the term "homology" relates to the identity of two or more nucleic acid sequences or to the identity of two or more amino acid sequences. Homologous sequences include "paralogous" and "orthologous". The term "paralogous" relates to gene duplications within the genome of a species, giving rise to paralogous genes. The term "orthologous" relates to homologous genes in different organisms due to the ancestral relationship.

In a preferred aspect, the polynucleotides that encode the polypeptide of the present invention show an enhancement of at least 20%, for example, at least 40%, at least 50%, at least 60%, at least 70%, at least 80%, at least 90%, at least 91%, at least 92%, at least 93%, at least 94%, at least 95%, at least 96%, at least 97%, at least 98%, at least 99% or at least 100% in the peroxygenase activity of the polynucleotide that encodes the mature polypeptide of SEQ ID NO: 4, SEQ ID NO: 2, SEQ ID NO: 14 or SEQ ID NO: 18.

In a preferred aspect, the polynucleotides that encode the polypeptide of the present invention show a reduction of at least 20%, for example, at least 40%, at least 50%, at least 60%, at least 70%, at least 80%, at least 90%, at least 91%, at least 92%, at least 93%, at least 94%, at least 95%, at least 96%, at least 97%, at least 98%, at least 99% or at least 100% in the peroxydase activity of the polynucleotide that encodes the mature polypeptide of SEQ ID NO: 4, SEQ ID NO: 2, SEQ ID NO: 14 or SEQ ID NO: 18.

The term "allelic variation" means any of two or more alternative forms of a gene that occupies the same chromosome locus. Allelic variation occurs naturally through mutation and can lead to polymorphism within populations. Gene mutations may be silent (without changes in the encoded polypeptide) or may encode polypeptides with altered amino acid sequences. An allelic variant of a polypeptide is a polypeptide encoded by an allelic variant of a gene.

The term "encodes", as used in the description, makes reference to the correlation existing between the nucleotide triplets or codons in a DNA sequence and the amino acids that form the peptides, the amino acid sequences or the proteins. Where it states that a nucleotide sequence encodes a peptide, it means that when said nucleotide sequence is transcribed to messenger RNA (mRNA) and this mRNA is translated, said peptide will be generated.

For the purposes of the present invention, the term "encoding sequence" or sequence "that encodes" a polypeptide, protein or enzyme is a nucleotide sequence which, when expressed, gives rise to the production of this polypeptide, protein o enzyme, i.e. the nucleotide sequence encodes an amino acid sequence for that polypeptide, protein or enzyme. A coding sequence is "under the control" of sequences that control cell transcription and translation when the RNA polymerase transcribes the mRNA-coding sequence, which is subsequently transcribed and translated into the protein encoded by the coding sequence. Preferably, the coding sequence is a double-stranded DNA sequence which is transcribed and translated into a polypeptide in a cell in vitro or in vivo when placed under the control of appropriate regulating sequences. The boundaries of the coding sequence are determined by a start codon at the 5' (amino) terminus and a translation stop codon at the 3' (carboxyl) terminus. A coding sequence can include, but is not limited to, prokaryotic, DNA, cDNA and synthetic DNA sequences or a recombinant nucleotide sequence. If the coding sequence is intended for expression in a eukaryotic cell, a transcription termination sequence and polyadenylation signal will be generally located 3' to the coding sequence.

The term "cDNA" is defined herein as a DNA molecule that can be prepared for reverse transcription using a mature, full-length mRNA molecule obtained from a eukaryotic cell. cDNA lacks sequences of introns that are normally present in the corresponding genomic DNA. The transcription of primary (initial) RNA is a mRNA precursor which is processed through a series of steps before appearing as mature, full-length mRNA. These steps include the elimination of intronic sequences through a process called linking. Therefore, cDNA derived from mRNA lacks any intronic sequence.

The term "gene" relates to a DNA sequence that encodes or corresponds to a particular amino acid sequence comprising all or part of one or more proteins or enzymes, and may or may not include regulatory DNA sequences, such as promoter sequences, which determine for example the conditions in which the gene is expressed. Some genes, which are not structured genes, may be transcribed from DNA to RNA, but are not translated into an amino acid sequence. Other genes can function as structural gene regulators or as DNA transcription regulators. A gene that encodes a protein of the invention for use in an expression system, if the DNA is genomic or cDNA, can be isolated from any source, particularly using fungal cDNA or a genomic library. Methods for obtaining genes are well known in the art, for example, Sambrook et al. (supra).

Thus, in a preferred object of the invention, the polynucleotide that encodes a polypeptide with improved peroxygenase activity and reduced peroxidase activity, as described in the present invention, said encoded polypeptide comprises the amino acid replacements: glycine (G) in position 241 and arginine (R) in position 257, of SEQ ID NO: 2, by the amino acids: aspartic acid (D) and lysine (K), respectively, giving rise to the G241D and R257K mutations in said sequence. In a preferred embodiment of the invention, the polynucleotide described herein further comprises, in addition to the G241D and R257K mutations, an additional amino acid alteration in the homologous position to position 191 of said SEQ ID NO: 2 which replaces the original amino acid phenylalanine (F) by serine (S), giving rise to the mutation F191S.

In another particular embodiment of the nucleotide of the invention, it can further comprise the two aforementioned mutations, common to all the UPO mutants obtained in the present invention, or alternatively the three previously described mutations, at least one of the following mutations, whether isolated or in combinations thereof:

a) replacement of the original amino acid leucine (L) by the amino acid phenylalanine (F) in the homologous position to position 67 of SEQ ID NO: 2 (L67F),
b) replacement of the original amino acid isoleucine (I) by the amino acid valine (V) in the homologous position to position 248 of SEQ ID NO: 2 (I248V),
c) replacement of the original amino acid phenylalanine (F) by the amino acid leucine (L) in the homologous position to position 311 of SEQ ID NO: 2 (F311L),
d) replacement of the original amino acid valine (V) by the amino acid isoleucine (I) in the homologous position to position 75 of SEQ ID NO: 2 (V75I), and
e) replacement of the original amino acid valine (V) by the amino acid alanine (A) in the homologous position to 57 of SEQ ID NO: 2 (V57A).

In another particular embodiment of the invention that encodes a polypeptide with improved peroxygenase activity and reduced peroxidase activity, with respect to a wild-type UPO enzyme of SEQ ID NO: 2, or with respect to a variant with UPO activity such as, for example, the PaDa-I variant of SEQ ID NO: 14, as described herein, said encoded polypeptide is characterised in that it can further comprise the nucleotide sequence that encodes the signal peptide of SEQ ID NO: 26.

In another particular embodiment of the nucleotide of the invention, which encodes a polypeptide with improved peroxygenase activity and reduced peroxidase activity, as described herein, said polypeptide is characterised in that the polynucleotide sequence encoding the signal peptide of SEQ ID NO: 26, has further at least one of the following additional mutation or any of its combinations:

a) replacement of the amino acid phenylalanine (F) by the amino acid tyrosine (Y) in the homologous position to position 12 of SEQ ID NO: 26 (F[12]Y),
b) replacement of the amino acid alanine (A) by the amino acid valine (V) in the homologous position to position 14 of SEQ ID NO: 26 (A[14]V),
c) replacement of the amino acid arginine (R) by the amino acid glycine (G) in the homologous position to position 15 of SEQ ID NO: 26 (R[15]G), and
d) replacement of the amino acid alanine (A) by the amino acid aspartic (D) in the homologous position to position 21 of SEQ ID NO: 26 (A[21]D).

All these mutations and combinations thereof give rise to peroxygenase mutants or variants having a wide spectrum of biotechnological applications, specifically with high functional expression, high monooxygenase activity to the detriment of the peroxidase activity, high thermostability and greater resistance to the presence of organic co-solvents, maintenance of regioselectivity against 1-naphthol, reduction in the ratio 1.4-naphthoquinone:1-naphthol, enhanced catalytic efficiency for naphthalene; additionally, it improves regioselectivity against 5'-hydroxypropranolol up to 99%, reduces the oxidation of 5'-hydroxypropanol up to 50% and enhances catalytic efficiency for propranolol by two orders of magnitude for different applications, with respect to the wild-type UPO or respect to other UPO variants, such as the PaDa-I variant.

In a preferred embodiment of the invention, the polynucleotide of the invention that encodes a polypeptide with improved peroxygenase activity and reduced peroxidase activity, as described herein, said encoded polypeptide shows the amino acidic alterations G241D and R257K, with respect to SEQ ID NO: 2. In a particular embodiment of the invention, the polynucleotide of the invention corresponds to SEQ ID NO: 9 that encodes the variant of SEQ ID NO: 10, or with SEQ ID NO: 7 that encodes the variant of SEQ ID NO: 8 (UPO wt-JaWa UPO variants, with and without signal peptide, respectively).

In another preferred embodiment of the invention, the polynucleotide of the invention that encodes a polypeptide with improved peroxygenase activity and reduced peroxidase activity, as described herein, said encoded polypeptide has the amino acidic alterations G241D, R257K and additionally F191S, with respect to SEQ ID NO: 2. In a particular embodiment of the invention, the polynucleotide of the invention corresponds to SEQ ID NO: 63 that encodes the variant of SEQ ID NO: 64, or with SEQ ID NO: 61 that encodes the variant of SEQ ID NO: 62 (UPO wt-SoLo variants, with and without signal peptide, respectively).

In another preferred embodiment of the invention, the polynucleotide of the invention that encodes a polypeptide with improved peroxygenase activity and reduced peroxidase activity, as described herein, said encoded polypeptide shows the amino acid alterations G241D and R257K, with respect to SEQ ID NO: 2, or the amino acid alterations G241D, R257K and F191S, with respect to SEQ ID NO: 2, and further comprise the amino acid alterations F[12]Y, A[14]V, R[15]G and A[21]D, in the signal peptide of SEQ ID NO: 26. In a particular embodiment of the invention, the polynucleotide of the invention is selected from the list consisting of: SEQ ID NO: 11 that encodes the variant of SEQ ID NO: 12 (UPO mutant wt-JaWa variant with modified signal peptide) and SEQ ID NO: 65 that encodes the variant of SEQ ID NO: 66 (UPO mutant wt-SoLo with modified signal peptide).

Thus, in another preferred embodiment of the invention, the polynucleotide of the invention that encodes a polypeptide with improved peroxygenase activity and reduced peroxidase activity, as described herein, said encoded polypeptide shows the amino acid alterations G241D, R257K, L67F, I248V, F311L, V57A and V75I, with respect to SEQ ID NO: 2. In another preferred embodiment of the invention, the polynucleotide of the invention that encodes a polypeptide with improved peroxygenase activity and reduced peroxidase activity, as described herein, said encoded polypeptide shows the amino acid alterations G241D, R257K, F191S, L67F, I248V, F311L, V57A and V75I, with respect to SEQ ID NO: 2. In a particular embodiment of the invention, the polynucleotide of the invention corresponds to SEQ ID NO: 21 that encodes the variant of SEQ ID NO: 22, or with SEQ ID NO: 19 that encodes the variant of SEQ ID NO: 20 (JaWa variants, with and without signal peptide, respectively). In a particular embodiment of the invention, the polynucleotide of the invention corresponds to SEQ ID NO: 39 that encodes the variant of SEQ ID NO: 40, or with SEQ ID NO: 37 that encodes the variant of SEQ ID NO: 38 (SoLo variants, with and without signal peptide, respectively).

In another preferred embodiment of the invention, the polynucleotide of the invention that encodes a polypeptide with improved peroxygenase activity and reduced peroxidase activity, as described herein, said encoded polypeptide shows the amino acid alterations G241D, R257K, L67F, I248V, F311L, V57A and V75I, with respect to SEQ ID NO: 2, and further comprises the amino acid alterations F[12]Y, A[14]V, R[15]G and A[21]D in the signal peptide of SEQ ID NO: 26. In another preferred embodiment of the invention, the polynucleotide of the invention that encodes a polypeptide with peroxygenase activity, as described herein, said encoded polypeptide shows the amino acid alterations G241D, R257K, F191S, L67F, I248V, F311L, V57A and V75I, with respect to SEQ ID NO: 2, and further comprises the amino acid alterations F[12]Y, A[14]V, R[15]G and A[21]D in the signal peptide of SEQ ID NO: 26.

In a particular embodiment of the invention, the polynucleotide of the invention corresponds to SEQ ID NO: 23 that encodes the variant of SEQ ID NO: 24 (JaWa variant with modified signal peptide). In another particular embodiment of the invention, the polynucleotide of the invention corresponds to SEQ ID NO: 41 that encodes the variant of SEQ ID NO: 42 (SoLo variant with modified signal peptide).

Since the peroxygenases secreted by ligninolytic basidiomycetes fungi may be considered to be related in terms of their evolution, it is to be expected that the global identity of the genes will be 50% or higher and, more specifically, at the level of the amino acid sequence corresponding to SEQ ID NO: 4 or SEQ ID NO: 2 (peroxygenase AaeUPO1, with and without signal peptide, respectively), or of the amino acid sequence corresponding to SEQ ID NO: 18 or SEQ ID NO: 14 (peroxygenase PaDa-I, with and without modified signal peptide, respectively), is 70% or higher. The correspondence between the amino acid sequence of the artificial peroxygenase(s) that are the objects of the invention and the sequence of other peroxygenases can be determined by means of method known in the art. For example, they can be determined by direct comparison of the amino acid sequence information of the putative peroxygenase and the amino acid sequence corresponding to SEQ ID NO: 24 or SEQ ID NO: 20 of this specification (JaWa peroxygenase variant, with and without modified signal peptide, respectively) or to SEQ ID NO: 42 or SEQ ID NO: 38 (SoLo peroxygenase variant, with and without modified signal peptide, respectively).

With the information provided in the present invention, a person skilled in the art is capable of combining the previously described mutation to generate new peroxygenase variants with improved peroxygenase activity and reduced peroxidase activity, in addition to the other functional characteristics mentioned herein.

Another of the objects described herein relates to a polynucleotide sequence that encodes a polypeptide with peroxygenase activity, characterised in that the amino acid sequence of the polypeptide it encodes shows an identity of at least of 70% with SEQ ID NO: 14 (PaDa-I), and in that it comprises at least two amino acid alterations in the homologous positions to positions 241 and 257 of said sequence, replacing the amino acids: original glycine (G) by aspartic acid (D) in position 241 (G241D) and original arginine (R) by lysine (K) in position 257 (R257K). In a preferred embodiment, the polynucleotide sequence that encodes a polypeptide as described herein further comprises an additional amino acid alteration in the homologous position to position 191 of said sequence SEQ ID NO: 14, replacing the original amino acid phenylalanine (F) by serine (S) in position 191 (F191S).

Alternatively, another of the objects described in the present invention relate to a polynucleotide sequence that encodes a polypeptide with peroxygenase activity, characterised in that the amino acid sequence of the polypeptide shows an identity of at least 70% with SEQ ID NO: 14 (PaDa-I), and which comprises the amino acids alanine (A), phenylalanine (F), isoleucine (I), valine (V) and leucine (L) in positions 57, 67, 75, 248 and 31, respectively, with respect to SEQ ID NO: 14, characterised in that it further comprises two amino acid alterations in the homologous positions to positions 241 and 257 of said sequence, replacing the amino acids: original glycine (G) by aspartic acid (D) in position 241 (G241D) and original arginine (R) by lysine (K) in position 257 (R257K) and optionally, it may further comprise an additional amino acid alteration in position 191 of said sequence SEQ ID NO: 14, which replace the original amino acid phenylalanine (F) by serine (S) (F191S).

In a particular embodiment of the polynucleotide of the invention that encodes a polypeptide with improved peroxygenase activity and reduced peroxidase activity, with respect to a variant with UPO activity of SEQ ID NO: 14, as described herein, said encoded polypeptide is characterised in that it can further comprise the nucleotide sequence that encode the signal peptide of SEQ ID NO: 26.

In another particular embodiment of the nucleotide of the invention, which encodes a polypeptide with improved peroxygenase activity and reduced peroxidase activity, as described herein, said polypeptide is characterised in that the polynucleotide sequence that encodes the signal peptide of SEQ ID NO: 26, has further at least one of the following additional mutation or any of its combinations:

a) replacement of the amino acid phenylalanine (F) by the amino acid tyrosine (Y) in the homologous position to position 12 of SEQ ID NO: 26 (F[12]Y), b) replacement of the amino acid alanine (A) by the amino acid valine (V) in the homologous position to position 14 of SEQ ID NO: 26 (A[14]V), c) replacement of the amino acid arginine (R) by the amino acid glycine (G) in the homologous position to position 15 of SEQ ID NO: 26 (R[15]G), and d) replacement of the amino acid alanine (A) by the amino acid aspartic (D) in the homologous position to position 21 of SEQ ID NO: 26 (A[21]D).

All these mutations give rise to mutants or variants of the peroxygenases with a wide spectrum of biotechnological applications, specifically with high functional expression, high monooxygenase activity and low peroxidase activity, high thermostability, greater resistance to the presence of organic co-solvents, maintenance of regioselectivity against 1-naphthol, decrease in the ratio 1.4-naphthoquinone:1-naphthol, enhanced catalytic efficiency for naphthalene, decreasing oxidation by up to 50% on 5'-hydroxypropranolol, enhancement of catalytic efficiency by two orders of magnitude, for different applications, with respect to the PaDa-I variant of SEQ ID NO: 18.

In a preferred embodiment of the invention, the polynucleotide of the invention that encodes a polypeptide with improved peroxygenase activity and reduced peroxidase activity, as described herein, said encoded polypeptide shows the amino acid alterations G241D and R257K, with respect to SEQ ID NO: 14. In another preferred embodiment of the invention, the polynucleotide of the invention that encodes a polypeptide with the characteristics and advantages mentioned herein, said encoded polypeptide shows the amino acid alterations G241D, R257K and F191S, with respect to SEQ ID NO: 14. In a particular embodiment of the invention, the polynucleotide of the invention corresponds to SEQ ID NO: 21 that encodes the variant of SEQ ID NO: 22, or with SEQ ID NO: 19 that encodes the variant of SEQ ID NO: 20 (UPO JaWa variant, with and without signal peptide, respectively). In a particular embodiment of the invention, the polynucleotide of the invention corresponds to SEQ ID NO: 39 that encodes the variant of SEQ ID NO: 40, or with SEQ ID NO: 37 that encodes the variant of SEQ ID NO: 38 (SoLo UPO variant, with and without signal peptide, respectively).

In another preferred embodiment of the invention, the polynucleotide of the invention that encodes a polypeptide with improved peroxygenase activity and reduced peroxidase activity, as described herein, said encoded polypeptide shows the amino acid alterations G241D and R257K, with respect to SEQ ID NO: 14, and further comprises the amino acid alterations F[12]Y, A[14]V, R[15]G and A[21]D, in the signal peptide of SEQ ID NO: 26. In a particular embodiment of the invention, the polynucleotide of the invention corresponds to SEQ ID NO: 23 that encodes the variant of SEQ ID NO: 24 (UPO JaWa variant with modified signal peptide).

In another preferred embodiment of the invention, the polynucleotide of the invention that encodes a polypeptide with improved peroxygenase activity and reduced peroxidase activity, as described herein, said encoded polypeptide shows the amino acid alterations G241D, R257K and F191S, with respect to SEQ ID NO: 14, and further comprises the amino acid alterations F[12]Y, A[14]V, R[15]G and A[21]D, in the signal peptide of SEQ ID NO: 26. In a particular embodiment of the invention, the polynucleotide of the invention corresponds to SEQ ID NO: 41 that encodes the variant of SEQ ID NO: 42 (UPO SoLo variant with modified signal peptide).

As mentioned earlier, with the information supplied in the present invention, a person skilled in the art is capable of combining the previously described mutations to generate new peroxygenase variants with improved peroxygenase activity and reduced peroxidase activity, in addition to the other functional characteristics mentioned herein.

Another object described in the present invention relates to the amino acid sequence encoded by the polynucleotide of the invention, hereinafter polypeptide of the invention, characterised in that it shows a sequence identity of at least 70% with SEQ ID NO: 2 (AaeUPO1, without signal peptide) and because it comprises at least two amino acid alterations, preferably replacements, in the homologous positions to positions 241 and 257 of said sequence, which replace the amino acids: original glycine (G) by aspartic acid (D) in position 241 (G241D) and original arginine (R) by lysine (K) in position 257 (R257K).

In a preferred embodiment, the polypeptide of the invention further comprises an additional amino acid alteration, preferably a replacement, in the homologous position to position 191 of SEQ ID NO: 2, which replace the original amino acid phenylalanine (F) by serine (S) in position 191 (F191S).

The term "peptide", "polypeptide" or "protein", as used in the description, relates to a polymeric form of amino acids of any length.

Thus, in a preferred aspect of the invention, the replacements of the amino acids: glycine (G) in position 241 and arginine (R) in position 257 of SEQ ID NO: 2, by the amino acids aspartic acid (D) and lysine (K), respectively, gives rise to the G241D and R257K mutations, respectively, obtaining the wt-JaWa variant of SEQ ID NO: 8.

In another preferred aspect of the invention, the replacement of the amino acid phenylalanine (F) in position 191 of SEQ ID NO: 2, by the amino acid serine (S), gives rise to the F191S mutation, obtaining the wt-SoLo variant of SEQ ID NO: 62.

The polypeptide of the invention can also show additional mutations to those mentioned earlier that improve its activity and stability, both thermal and in the presence of different co-solvents and their functional expression in heterologous organisms. Additionally, the variants with improved peroxygenase activity and reduced peroxidase activity, show an increase in TTN of approximately 2.5 fold, an increase in $k_{cat}$ for 1-naphthol of up to 1.5 fold, enhanced catalytic efficiency for naphthalene of up to $6.2 \times 10^5$ $s^{-1}$ $M^{-1}$, a decrease of approximately 1.5 fold in the ratio 1.4-naphthoquinone:1-naphthol, and regioselectivity against 1-naphthol of approximately 97%, in addition to an increase in TTN for the synthesis of 5'-hydroxypropranolol of 3 fold in the absence of antioxidants (45,000 for the SoLo mutant against 15,000 of the JaWa mutant) or of 15 fold (3,000 in the case of wild AaeUPO), an increase in $k_{cat}$ for 5'-hydroxypropranolol of up to 3.6 fold, enhanced catalytic efficiency for 5'-hydroxypropranolol of up to $3.1 \times 10^6$ $s^{-1}$ $M^{-1}$, two orders of magnitude higher than those of any enzyme described and show 50% less oxidation on 5'-hydroxypropranolol. These mutations described earlier in this invention can show various combinations jointly with the mutation described earlier, as is known to a person skilled in the art.

In a preferred aspect, the polypeptides of the present invention show an improvement of at least 20%, for example, at least 40%, at least 50%, at least 60%, at least 70%, at least 80%, at least 90%, at least 91%, at least 92%, at least 93%, at least 94%, at least 95%, at least 96%, at least 97%, at least 98%, at least 99% or at least 100% in the peroxygenase activity with respect to the peroxygenase activity of the mature polypeptide of SEQ ID NO: 4, SEQ ID NO: 2, SEQ ID NO: 14 or SEQ ID NO: 18.

In a preferred aspect, the polypeptides of the present invention show a reduction of at least 20%, for example, at least 40%, at least 50%, at least 60%, at least 70%, at least 80%, at least 90%, at least 91%, at least 92%, at least 93%, at least 94%, at least 95%, at least 96%, at least 97%, at least 98%, at least 99% or at least 100% in the peroxydase activity with respect to the peroxygenase activity of the mature polypeptide of SEQ ID NO: 4, SEQ ID NO: 2, SEQ ID NO: 14 or SEQ ID NO: 18.

In a particular embodiment of the polypeptide of the invention, it may comprise, in addition to the two aforementioned mutations, common to all the UPO mutants obtained and described in the present invention, an additional mutation comprising the replacement of the original amino acid phenylalanine (F) by the amino acid serine (S) in the homologous position to position 191 of SEQ ID NO: 2 (F191S).

In a particular embodiment of the polypeptide of the invention, it can comprise, in addition to the aforementioned mutations, whether isolated or in combinations thereof:

a) replacement of the original amino acid leucine (L) by the amino acid phenylalanine (F) in the homologous position to position 2 of SEQ ID NO: 2 (L67F), b) replacement of the original amino acid isoleucine (I) by the amino acid valine (V) in the homologous position to position 248 of SEQ ID NO: 2 (I248V), c) replacement of the original amino acid phenylalanine (F) by the amino acid leucine (L) in the homologous position to position 311 of SEQ ID NO: 2 (F311L), d) replacement of the original amino acid valine (V) by the amino acid isoleucine (I) in the homologous position to position 75 of SEQ ID NO: 2 (V75I), and e) replacement of the original amino acid valine (V) by the amino acid alanine (A) in the homologous position to 57 of SEQ ID NO: 2 (V57A).

In another preferred embodiment of the polypeptide of the invention, it is characterised in that can further comprise the sequence that encodes the signal peptide of SEQ ID NO: 26.

In another preferred embodiment of the polypeptide of the invention, it is characterised in that it also has at least one of the following additional mutations or any of its combinations in the nucleotide sequence that encodes the signal peptide of SEQ ID NO: 26:

a) replacement of the amino acid phenylalanine (F) by the amino acid tyrosine (Y) in the homologous position to position 12 of SEQ ID NO: 26 (F[12]Y)

b) replacement of the amino acid alanine (A) by the amino acid valine (V) in the homologous position to position 14 of SEQ ID NO: 26 (A[14]V), c) replacement of the amino acid arginine (R) by the amino acid glycine (G) in the homologous position to position 15 of SEQ ID NO: 26 (R[15]G), and d) replacement of the amino acid alanine (A) by the amino acid aspartic (D) in the homologous position to position 21 of SEQ ID NO: 26 (A[21]D).

All these mutations give rise to mutants or variants of the peroxygenases with a wide spectrum of biotechnological applications, specifically with high functional expression, high monooxygenase activity and low peroxidase activity, high thermostability, greater resistance to the presence of organic co-solvents, greater regioselectivity and an increase in TTN, for different applications, with respect to the wild-type UPO, or with respect to other UPO mutants such as, for example, the PaDa-I mutant.

Thus, in a preferred embodiment of the invention, the polypeptide has amino acid alterations G241D and R257K with respect to SEQ ID NO: 2. In a particular embodiment of the invention, the polypeptide of the invention corresponds to the peptide of SEQ ID NO: 10 or of SEQ ID NO: 8 (wt-JaWa variant, with and without signal peptide, respectively).

Thus, in a preferred embodiment of the invention, the polypeptide shows the amino acid alteration F191S with respect to SEQ ID NO: 2. In a particular embodiment of the invention, the polypeptide of the invention corresponds to the peptide of SEQ ID NO: 64 or of SEQ ID NO: 62 (wt-SoLo variant, with and without signal peptide, respectively).

In another preferred embodiment of the invention, the polypeptide show the amino acids alterations G241D and R257K with respect to SEQ ID NO: 2, and further comprises the amino acid alterations F[12]Y, A[14]V, R[15]G and A[21]D, in the signal peptide of SEQ ID NO: 26. In a particular embodiment of the invention, the polypeptide of the invention corresponds to the peptide of SEQ ID NO: 12 (wt-JaWa variant, with modified signal peptide). In another preferred embodiment of the invention, the polypeptide shows the amino acid alteration F191S with respect to SEQ ID NO: 2, and further comprises the amino acid alterations F[12]Y, A[14]V, R[15]G and A[21]D, in the signal peptide of SEQ ID NO: 26. In a particular embodiment of the invention, the polypeptide of the invention corresponds to the peptide of SEQ ID NO: 66 (wt-SoLo variant, with modified signal peptide).

Thus, in another preferred embodiment of the invention, the polypeptide of the invention has the amino alterations G241D, R257K, L67F, I248V, F311L, V57A and V75I, with respect to SEQ ID NO: 2. In a particular embodiment of the invention, the polypeptide of the invention corresponds to the peptide of SEQ ID NO: 22 or of SEQ ID NO: 20 (JaWa variant, with and without signal peptide, respectively).

Thus, in another preferred embodiment of the invention, the polypeptide of the invention has the amino acid alterations G241D, R257K, F191S, L67F, I248V, F311L, V57A and V75I, with respect to SEQ ID NO: 2. In a particular embodiment of the invention, the polypeptide of the invention corresponds to the peptide of SEQ ID NO: 40 or of SEQ ID NO: 38 (SoLo variant, with and without signal peptide, respectively).

In another preferred embodiment of the invention, the polypeptide shows the amino acid alterations G241D, R257K, L67F, I248V, F311L, V57A and V75I, with respect to SEQ ID NO: 2, and further comprises the amino acid alterations F[12]Y, A[14]V, R[15]G and A[21]D, in the signal peptide of SEQ ID NO: 26. In a particular embodiment of the invention, the polypeptide of the invention corresponds to the peptide of SEQ ID NO: 24 (JaWa variant, with modified signal peptide).

In another preferred embodiment of the invention, the polypeptide shows the amino acid alterations G241D, R257K, F191S, L67F, I248V, F311L, V57A and V75I, with respect to SEQ ID NO: 2, and further comprises the amino acid alterations F[12]Y, A[14]V, R[15]G and A[21]D, in the signal peptide of SEQ ID NO: 26. In a particular embodiment of the invention, the polypeptide of the invention corresponds to the peptide of SEQ ID NO: 42 (SoLo variant, with modified signal peptide).

With the information provided in the present invention, a person skilled in the art is capable of combining the previously described mutations to generate new peroxygenase variants with improved peroxygenase activity and reduced peroxidase activity and greater stability, in addition to comprising the functional characteristics mentioned throughout this specification.

Another object described in the present invention relates to the amino acid sequence that encodes the polynucleotide of the invention, characterised in that its sequence show an identity of at least 70% with SEQ ID NO: 14 (PaDa-I, without signal peptide), and in that it comprises at least two amino acid alterations, preferably replacements, in the homologous positions to positions 241 and 257 of said sequence, replacing the amino acids: original glycine (G) by aspartic acid (D) in position 241 (G241D) and original arginine (R) by lysine (K) in position 257 (R257K). In a preferred embodiment, the amino acid sequence encoded by the polynucleotide of the invention further comprises an additional amino acid alteration, preferably a replacement, in the homologous position to position 191 of said sequence SEQ ID NO: 14, replacing the original amino acid phenylalanine (F) by serine (S) in position 191 (F191S).

Alternatively, the present invention also relates to the amino acid sequence coded by the polynucleotide of the invention, characterised in that it shows a sequence identity of at least 70% with SEQ ID NO: 14 (PaDa-I), and which comprises the amino acids alanine (A), phenylalanine (F), isoleucine (I), valine (V) and leucine (L) in positions 57, 67, 75, 248 and 311, respectively, with respect to SEQ ID NO: 14, characterised in that it further comprises two amino acid alterations in homologous positions to positions 241 and 257 of said sequence, replacing the amino acids: original glycine (G) by aspartic acid (D) in position 241 (G241D) and original arginine (R) by lysine (K) in position 257 (R257K). Also alternatively, the amino acid sequence coded by the polynucleotide of the invention, characterised in that it shows a sequence identity of at least 70% with SEQ ID NO: 14 (PaDa-I), and which comprises the amino acids alanine (A), phenylalanine (F), isoleucine (I), valine (V) and leucine (L) in positions 57, 67, 75, 248 and 311, respectively, with respect to SEQ ID NO: 14, characterised in that it further comprises at least three amino acid alterations in homologous positions in positions 241, 257 and 191 of said sequence, replacing the amino acids: original glycine (G) by aspartic acid (D) in position 241 (G241D), original arginine (R) by lysine (K) in position 257 (R257K) and original phenylalanine (F) by serine (S) (F191S).

Thus, in a preferred aspect of the invention, the replacements of the amino acids: glycine (G) in position 241 and arginine (R) in position 257 of SEQ ID NO: 14, by the amino acids aspartic acid (D) and lysine (K), respectively, gives rise to the G241 D and R257K mutations, respectively, obtaining the JaWa variant of SEQ ID NO: 20.

In another preferred aspect of the invention, the replacements of the amino acids: glycine (G) in position 241, arginine (R) in position 257 and phenylalanine (F) in position 191 of SEQ ID NO: 14, by the amino acids aspartic acids (D), lysine (K) and serine (S), respectively, gives rise to the G241D, R257K and F191S mutations, respectively, obtaining the SoLo variant of SEQ ID NO: 38.

In another preferred embodiment of the polypeptide of the invention, it is characterised in that it can further comprises the sequence that encodes the signal peptide of SEQ ID NO: 26.

In another preferred embodiment of the polypeptide of the invention, it is characterised in that has further at least one of the following additional mutations or any of its combinations in the nucleotide sequence that encodes the signal peptide of SEQ ID NO: 26:

a) replacement of the amino acid phenylalanine (F) by the amino acid tyrosine (Y) in the homologous position to position 12 of SEQ ID NO: 26 (F[12]Y),
b) replacement of the amino acid alanine (A) by the amino acid valine (V) in the homologous position to position 14 of SEQ ID NO: 26 (A[14]V),
c) replacement of the amino acid arginine (R) by the amino acid glycine (G) in the homologous position to position 15 of SEQ ID NO: 26 (R[15]G), and
d) replacement of the amino acid alanine (A) by the amino acid aspartic (D) in the homologous position to position 21 of SEQ ID NO: 26 (A[21]D).

As mentioned earlier, all these mutations give rise to peroxygenase mutants or variants with a wide spectrum of biotechnological applications, specifically with high functional expression, high monooxygenase activity and low peroxidase activity, high thermostability, greater resistance to the presence of organic co-solvents, greater regioselectivity and increase in TTN, for different applications, with respect to the PaDa-I variant.

Thus, in a preferred embodiment of the invention, the polypeptide shows the amino acid alterations G241D and R257K with respect to SEQ ID NO: 14. In a particular embodiment of the invention, the polypeptide of the invention corresponds to the peptide of SEQ ID NO: 22 or SEQ ID NO: 20 (JaWa variant, with and without signal peptide, respectively).

In another preferred embodiment of the invention, the polypeptide shows the amino acid alterations G241D, R257K and F191S with respect to SEQ ID NO: 14. In a particular embodiment of the invention, the polypeptide of the invention corresponds to the peptide of SEQ ID NO: 40 or SEQ ID NO: 38 (SoLo variant, with and without signal peptide, respectively).

In another preferred embodiment of the invention, the polypeptide show the amino acids alterations G241D and R257K with respect to SEQ ID NO: 14, also alternatively shows the alteration F191S and further comprises the amino acid alterations F[12]Y, A[14]V, R[15]G and A[21]D, in the signal peptide of SEQ ID NO: 26. In a particular embodiment of the invention, the polypeptide of the invention corresponds to the peptide of SEQ ID NO: 24 or with the peptide of SEQ ID NO: 42 (JaWa or SoLo variants, with modified signal peptide, respectively).

Another object described in the present invention relates to the use of the polypeptide of the invention in methods of organic synthesis, preferably in processes of oxyfunctionalisation or selective oxidation of hydrocarbon in general, both aromatic and linear aliphatic, branched and cyclic (alkanes such as propane, 2,3-dimethylbutane or cyclohexane, fatty acids such as lauric acid), linear, branched and cyclic unsaturated hydrocarbonated chains (olefins such as propene, 2-methyl-2-butene or limonene), more preferably in the production of 1-naphthol for applications in the textile industry (dyes), agrochemicals (herbicides, pesticides) or in bioremediation, more preferably in the production of HDMs and even more preferably in the production of 5'-hydroxypropranolol. Also for cosmetic and/or food applications, synthesis of metabolites for drugs or pharmaceutical compositions, other bioremediation processes, preferably, transformation of recalcitrant PAHs (polycyclic aromatic hydrocarbons) into less-polluting derivatives, biosensor design, preferably, immunoassays for detection by means of chemoluminescence and in the manufacture of bioelectronic devices containing immobilised enzymes. Additionally, the polypeptides described in the present invention can transform any compound that is a substrate of AaeUPO, such a for example: O— and N— can dealkylate compounds such as tetrahydrofurane or lidocaine, respectively; heterocyclic compounds showing sulphur or nitrogen atoms in their structure, wherein said compounds may be S- or N-oxygenated, as in the case of dibenzothiophene or pyridine, respectively.

The polynucleotide of the invention can be found isolated as such or forming part of gene constructions or vectors which allow the propagation of said polynucleotides in suitable host cells. Such gene expression vectors include control sequences such as, for example, translation (such as start and stop codes) and transcription (for example, promoter-operator regions, binding sites) control elements. The vectors according to the invention may include bacterial plasmids and viral vectors, and other vectors in accordance with the well-known and documented methods in the state of the art, and can be expressed in a variety of different expression systems, also well known and documented. A variety of techniques that can be used to introduce such vectors in prokaryotic or eukaryotic cells (host cells) for expression thereof are also known. Suitable transformation or transfection techniques are well known to the person skilled in the art and are described in the state of the art. Therefore, in another aspect, the invention relates to a vector, hereinafter vector of the invention, that comprises the polynucleotide of the invention as described earlier.

The term "nucleic acid construction" as used herein relates to a nucleic acid molecule—single or double-stranded—which is isolated from a naturally occurring gene or which is modified to contain nucleic acid segments in such a manner that it would not do otherwise should it occur naturally or that is synthetic. The term "nucleic acid construction" is synonymous of the term "expression cassette" when the nucleic acid construct contains the control sequence required for the expression of an encoding sequence of the present invention.

The terms "vector" or "expression vector" relate to the vehicle whereby a DNA or RNA sequence (for example, a heterologous gene) can be introduced in a host cell, for the purpose of transforming the host and promoting the expression (for example, transcription and translation) of the sequence introduced. The vectors typically comprise the DNA of a transmissible agent, wherein the foreign DNA encodes a protein inserted using restriction enzyme technology. A common type of vector is a "plasmid", which is generally a double-stranded DNA molecule, which can easily accept additional DNA (foreign) and that can be easily introduced in a suitable host cell. A large number of vectors, including plasmidic and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or PrEP plasmids (Invitrogen, San Diego, Calif.), pMAL plasmids (New England Biolabs, Beverly, Mass.), pGAPZaA, pcWori+, pET-26b (+), pXTD14, pYEX-S1, pMAL and pET22-b (+), or the plasmid used in the present invention, pJRoC30, donated by Dr. Frances Arnold, of the Californian Institute of Technology (CALTECH, USA). Recombinant clonation vectors often include one or more replication systems for cloning or expression, one or more markers for selection in the host, for example, resistance to antibiotics, and one or more expression cassettes. Suitable vectors for insertion of said polynucleotide are vectors derived from expression vectors in prokaryotes such as, by way of example, pUC18, pUC19, Bluescript and its derivatives, mp18, mp19, pBR322, pMB9, ColE1, pCR1, RP4, phages and "launch" vectors, such as pSA3 and pAT28; expression vectors in yeasts such as the 2 micron plasmid of *S. cerevisiae*, integration plasmids, YEP vectors, centromere and similar plasmids; expression vectors in insect cells such as pAC series vectors and pVL series expression vectors; expression vectors in plant cells such as piBi, pEarleyGate, PAVA, pCAMBIA, PGSA, PGWB, PMDC, PMY, pore and similar series, and other expression vectors in eukaryotic cells, including baculovirus suitable for transfection of insect cells using any commercially available baculovirus system. Other vectors can be used as desired by a person skilled in the art. Routine experimentation in biotechnology can be used to determine the most suitable vectors for use with the invention, if different to that described in the Examples. In general, the choice of the vector depends on the size of the polynucleotide and of the host cell to be used in the methods of this invention.

The term "control sequences" is defined herein to include all the necessary components for the expression of the polypeptide coding sequences of the present invention. Each control sequence may be native or foreign to the nucleotide sequence that encodes the native or foreign polypeptide therebetween. Such control sequences include, but are not limited to, a leader, polyadenylation sequence, pro-peptide sequence, promoter, signal peptide sequence and transcription terminator. The control sequences include, at least, a promoter and translation and transcription stop signals.

The control sequences may have links in order to introduce specific restriction sites that facilitate the linkage of the control sequences with the coding region of the nucleotide sequence that encodes a polypeptide.

A "promoter sequence" is a DNA regulatory region capable of binding to the RNA polymerase in a cell and initiating the transcription of a gene (direction 3') downstream from the coding sequence. For the purpose of defining this invention, the promoter sequence is limited at its 3' terminus by the transcription start site and extends upstream (5' direction) to include the minimum number of necessary bases or elements to begin the transcription at detectable levels above the base.

The expression "operationally linked" relates to a juxtaposition wherein the components thus described have a relationship that allows them to function intentionally. A control sequence "operationally linked" to a coding sequence is linked in such a manner that the expression of the coding sequence is achieved under conditions compatible with the control sequences.

In a preferred embodiment, the genetic construction of the invention further comprises a polynucleotide that encodes a signal peptide enhanced by directed evolution which favours the functional expression of the polypeptide of the invention.

The term "signal peptide", as used in the description, relates to a peptide which is located at the amino end of a polypeptide or protein, and whose function is to direct the localisation of the protein at different compartments of the cell (nucleus, mitochondria, chloroplast, endoplasmic reticulum (ER), Golgi apparatus (GA), etc.) or to the extracellular space, in the case that the protein is secreted.

The signal peptide of the factor α is a polypeptide with 83 amino acids. The first 19 amino acids constitute the pre-leader that directs the polypeptide being created towards the ER. After entering the ER, the pre-leader is cleaved by a peptidase, giving rise to a pro-protein. At this point, the N-glycosylations of three asparagine residues facilitate the transit of the pro-protein of the ER to the GA. In the GA, the pro-leader can act as a chaperone until it is processed by the proteases KEX1, KEX2 and STE13 (M. A. Romanos, et al., 1992. *Yeast* 8, 423-488; J. R. Shuster, 1991. *Curr. Opin. Biotechnol.* 2, 685-690). Additionally, the pro-leader seems to be involved in an indicated vacuolar process, which is detrimental to heterologous secretion (J. A. Rakestraw, et al. *Biotechnol. Bioeng.* 2009. 103, 1192-1201).

Preferably, the signal peptide is that of the AaeUPO1 of the nucleotide sequence SEQ ID NO: 25 which encodes the amino acid sequence SEQ ID NO: 26. In a more preferred embodiment, the signal peptide comprises at least one of the following mutations or any combination thereof:

a) the replacement of the original phenylalanine (F) amino acid by the tyrosine (Y) amino acid in the homologous position to position 12 of SEQ ID NO: 26 (F[12]Y),
   b) the replacement of the original alanine (A) amino acid by the valine (V) amino acid in the homologous position to position 14 of SEQ ID NO: 26 (A[14]V),
   c) the replacement of the original arginine (R) amino acid by the glycine (G) amino acid in the homologous position to position 15 of SEQ ID NO: 26 (R[15]G), and
   d) the replacement of the original alanine (A) amino acid by the aspartic acid (D) amino acid in the homologous position to position 21 of SEQ ID NO: 26 (A[21]D).

In another even more preferred embodiment, the signal peptide of the invention corresponds to the peptide sequence SEQ ID NO: 28, encoded by the nucleotide sequence SEQ ID NO: 27. Said signal peptide favours the functional expression of the polypeptide of the invention.

Another object described in the present invention relates to a host cell characterised in that it comprises the nucleotide of the invention and is capable of producing the polypeptide of the invention as described throughout the present document.

As used in the present specification, a "host cell" includes any culturable cell that can be modified through the introduction of DNA not contained naturally in the cell, hereinafter host cell of the invention. Preferably, a host cell is that in which the nucleotide of the invention can be expressed, giving rise to a stable, post-translationally modified polypeptide located in the appropriate subcellular compartment. The choice of an appropriate host cell can also be influenced by the choice of the detection signal.

For example, the use of constructions with reporter genes (for example, lacZ, luciferase, thymidine kinase or GFP) can provide a selectable signal by activating or inhibiting the transcription of the gene of interest in response to a transcription-regulating protein. The phenotype of the host cell must be considered in order to achieve an optimal selection or screening.

A host cell of the present invention includes prokaryotic and eukaryotic cells. Prokaryotes include gram-negative organisms (for example, *Escherichia coli*) or gram-positive organisms (for example, bacteria of the genus *Bacillus* sp.). Prokaryotic cells are used, preferably, to propagate the transcription-control sequence of the vector that contains the polynucleotide(s) of the invention, which will make it possible to obtain a larger number of copies of the vector containing the polynucleotide(s) that is/are the object of the invention. The appropriate prokaryotic host cells for transforming this vector include, for example, *E. coli, Bacillus subtilis, Salmonella typhimurium* and other species within the genera *Pseudomonas, Streptomyces* and *Staphylococcus*. Eukaryotic cells include, inter alia, yeast cells, plant cells, fungus cells, insect cells, mammal cells and parasite organism cells (for example, *Trypanosomas*). As used herein, the term yeast does not include only yeast in the strictly taxonomic sense, i.e. unicellular organisms, but also multicellular fungi similar to yeasts or filamentous fungi. Examples of species include *Kluyveromyces lactis, Schizosaccharomyces pombe* and *Ustilago maydis*, with *S. cerevisiae* and *P. pastoris* as preferred organisms. Other yeasts that can be used in the production of the polyamino acid sequence(s) of the present invention are *Neurospora crassa, Aspergillus niger, A. nidulans, A. sojae, A. oryzae, Candida tropicalis* and *Hansenula polymorpha*. Mammal host cell culture systems include established cell lines such as COS cells, L cells, 3T3 cells, Chinese hamster ovarian cells (CHO), embryonic stem cells, with BHK, HeK or HeLa cells such as preferred cells. Eukaryotic cells are, preferably, used for the expression of the recombinant gene through the application of the transcription regulation sequence or the expression vector of the present invention.

Brewer's yeast *S. cerevisiae* is a unicellular fungus that belongs to the Superkingdom Eukarya (Metazoa/Fungi group), Kingdom Fungi, Subkingdom Dikarya, Phylum Ascomycota, Subphylum Saccharomycotina, Class Saccharomycetes, Order Saccharomycetales, Family Saccharomycetaceae and Genus *Saccharomyces*.

The methylotrophic yeast *P. pastoris* belongs to the Superkingdom Eukarya, (Metazoa/Fungi group), Kingdom Fungi, Subkingdom Dikarya, Phylum Ascomycota, Subphylum Saccharomycotina, Class Saccharomycetes, Order Saccharomycetales, Family Saccharomycetaceae and Genus *Komagataella*.

Another aspect described in the present invention relates to the method for obtaining the polypeptide of the invention, which comprises the following steps:
  a) Introducing the vector of the invention, as described earlier, in an appropriate host cell (host cell of the invention),
  b) culturing the host cell of the invention in an appropriate medium, and
  c) purifying the polypeptide of the invention with improved peroxygenase activity and reduced peroxidase activity, with respect to the same activities of a wild-type AaeUPO enzyme or of a variant with UPO activity such as, for example, the PaDa-I variant.

The terms "purify", "isolate", "isolation" or "purification" of the polypeptides or enzymes described in the present invention relate to the separation of the peptides of the invention and, alternatively, to their concentration, as of the culture medium of the cell of the invention. The methods for separating and purifying polypeptides are well known in the art, without limitation, differential solubility, chromatography, electrophoresis or isoelectrofocus techniques. For some purposes, it is preferable to produce the polypeptide in a recombinant system wherein the protein contains an additional sequence ticket that facilitates the purification, such as, but not limited to, polyhistidine. Chromatography techniques can be based on the molecular weight, load or affinity of the protein and can be performed in a column, on paper or in a plate. Protein separation can be performed, for example, using Fast Protein Liquid Chromatography (FPLC), in an automated system that significantly reduces purification time and enhances purification performance.

Another aspect of the invention relates to a host cell culture of the invention.

A host cell culture relates to the process of maintaining and growing the host cells. Cell cultures require controlled conditions: temperature, pH, gas percentages (oxygen and carbon dioxide), in addition to the presence of appropriate nutrients to allow cellular viability and division. Cell cultures can be developed in solid substrates such as agar, or in liquid medium, which makes it possible to culture large amounts of cells in suspension.

Another object of the invention relates to the use of the host cell of the invention, or of the host cell culture of the invention, to obtain the polypeptide of the invention. Preferably, the host cell of the invention is a yeast, more preferably of the genera *Saccharomyces* sp. or *Pichia* sp and, even more preferably, the species are *Saccharomyces cerevisiae* or *Pichia pastoris*.

Peroxygenases, as in the case of the polypeptides of the invention, are known for their large number of applications such as, for example, their use in organic synthesis, preferably in processes of oxyfunctionalisation, oxidation or selective hydroxylation of hydrocarbons in general, both aromatic and aliphatic, linear, branched and cyclic, preferably the method of hydroxylation of cyclic aromatic compounds, both simple or condensed cyclic compounds, more preferably a method of hydroxylation for the synthesis of 1-naphthol and/or synthesis of 5'-hydroxypropranolol, limonene derivatives for cosmetic and/or nutritional applications, synthesis of drug metabolites or pharmaceutical compositions, synthesis of 1-naphthol for dyes, herbicides or pesticides, bioremediation (transformation of recalcitrant PAHs) and biosensor design (chemoluminescence detection immunoassays). Thus, the polypeptide of the invention and the host cell of the invention may have any of the currently known uses for these enzymes in the state of the art.

Another aspect of the invention relates to the use of the polynucleotide of the invention, or of the vectors, or genetic constructions of the invention, or of the host cell of the invention, for obtaining enzymes with improved peroxygenase activity and reduced peroxidase activity, which show a high production rate, high regioselectivity, preferably against 1-naphthol and/or against propranolol, and high thermostability with respect to the wild-type or native AaeUPO1 peroxygenase expressed in the yeast, or with respect to UPO variants such as, for example, the PaDa-I variant.

Thus, another object of the invention relates to the use of the polypeptide of the invention in the manufacture of diagnosis/prognosis kits for biomedical purposes for detecting metabolites and measuring their concentration in, for example, blood, saliva, tear and/or urine samples.

Another particular object of the invention relates to the use of the polypeptide of the invention in the manufacture of electronic devices containing immobilised enzymes for, for example, biomedical diagnosis by detecting metabolites and measuring their concentration in vivo through, by way of example, wireless nanodevices that work on different physiological fluids (blood, saliva, tears and/or urine).

Diagnosis kits for biomedical purposes and electronic devices containing immobilised enzymes, specifically the polypeptides described in the present invention, also form part of the invention.

Thus, another object described in the present invention relates to a kit or to an electronic device comprising at least one polypeptide as described in the present invention.

Another object described in the present invention relates to methods of organic synthesis, preferably in processes of oxyfunctionalisation, oxidation or selective hydroxylation of hydrocarbons in general, both aromatic and aliphatic, linear, branched and cyclic, preferably the method of hydroxylation of cyclic aromatic compounds, of both simple or condensed cyclic compounds, more preferably the method of hydroxylation for the synthesis of 1-naphthol and/or synthesis of 5'-hydroxypropranolol, through the use of variants, of the host cell, of the kit, or of the device of the invention.

Throughout the description and the claims, the word "comprises" and its variants are not intended to exclude other technical characteristics, additives, components or steps. For the persons skilled in the art, other objects, advantages and characteristics of the invention will be inferred partly from the description and partly from the practice of the invention. The following examples and drawings are provided by way of example of the invention and are not intended to limit the present invention.

EXAMPLES

Figure 1:
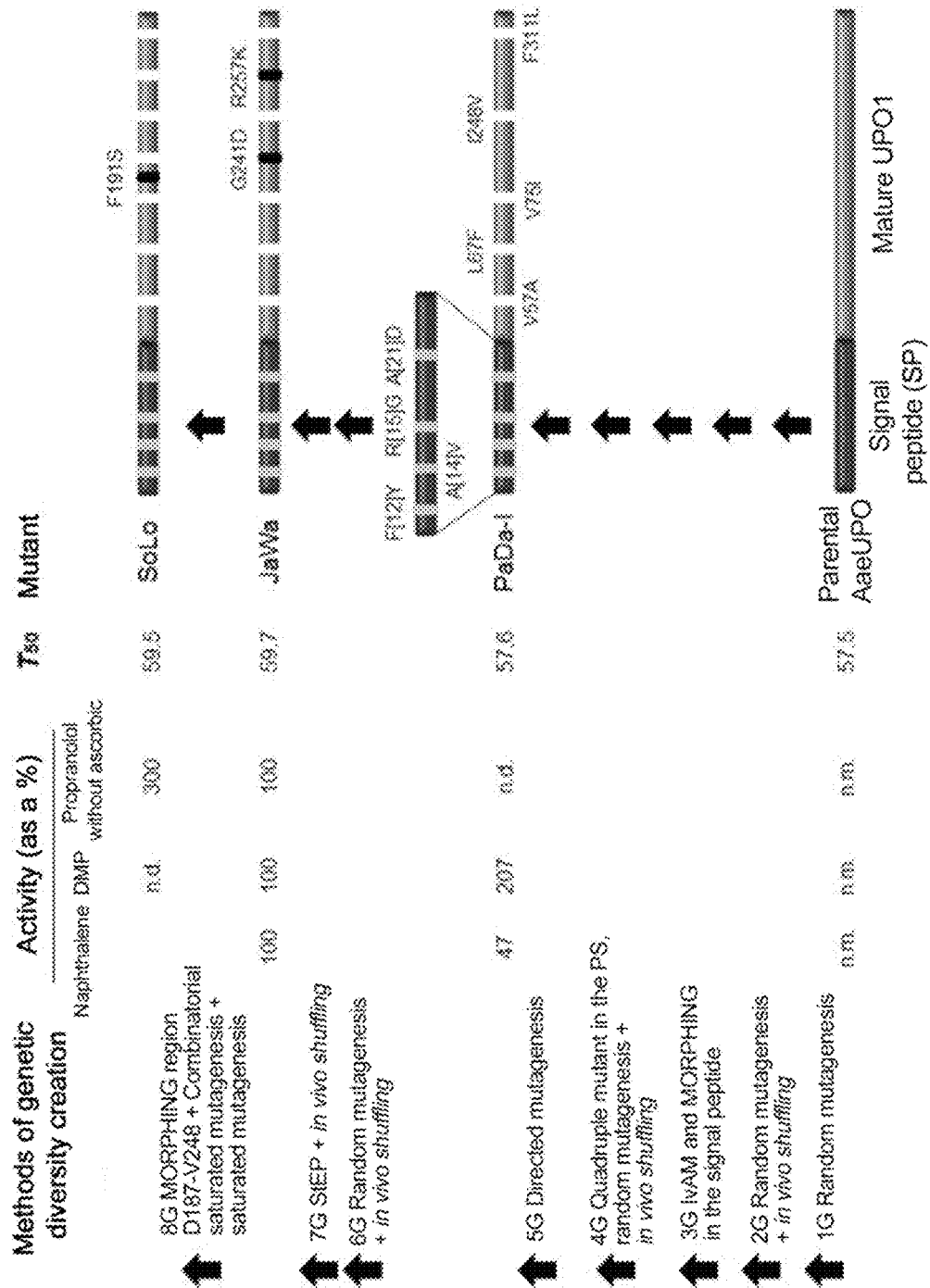
FIG. 1 Directed evolution of AaeUPO1. From cycles 1 to 5, the enzyme was improved in terms of functional expression and activity (the accumulated mutations are detailed as light grey rectangles). Starting from the parental AaeUPO, it was subjected to five directed evolution cycles until obtaining the PaDa-I mutant, which was subjected to two more cycles of directed evolution, in this case to improve the production capacity of 1-naphthol (the new mutations appear as black rectangles), and three further cycle grouped together in a single generation to improve the production of 5'-hydroxypropranolol. The activities (as a %) stem from measurements using microcultures of *S. cerevisiae* in 96-well microplates of the second re-screening. Thermostability ($T_{50}$) was determined using flask culture supernatants: n.m. not measurable, n.d. not determined.

Following are examples of the invention by means of assays carried out by the inventors, which evidence the effectiveness of the product of the invention. The following examples serve to illustrate the invention and must not be considered to limit the scope thereof.

Example 1. Obtainment and Characterisation of the Variants of the Present Invention Materials and Methods
Reagents and Enzymes ABTS (2,2'-azino-bis(3-ethylbenzothiazolin-6-sulfonic) acid), DMP (2,6-dimetoxiphenol), benzyl alcohol, 1-naphthol, 2-naphthol, 1,4-naphthoquinone, Fast Red (Fast Red TR Salt hemi(zinc chloride) salt), Taq DNA polymerase and the *Saccharomyces cerevisiae* transformation kit were obtained from Sigma-Aldrich (Saint Louis, Mo., USO). NBD (5-nitro-1,3-benzodioxole) was acquired from TCI America (Portland, Oreg., USA), while the naphthalene is from Acros Organics (Geel, Belgium).

The cDNA of upo1 (C1A-2 clone) of *A. aegerita* was provided by Dr. Martin Hofrichter (M. J. Pecyna, et al. *Appl. Microbiol. Biotechnol.* 2009, 84, 885-897).

The competent *Escherichia coli* XL2-Blue cells and the Genemorph II Random Mutagenesis (Mutazyme II) kit were obtained from Agilent Technologies (Santa Clara, Calif., USA) and the iProof high-fidelity DNA polymerase was acquired from Bio-Rad (Hercules, Calif., USA). The BamHI and XhoI restriction enzymes were obtained from New England Biolabs (Ipswich, Mass., USA) and the protease-deficient strain of *S. cerevisiae* BJ5465 from LGCPromochem (Barcelona, Spain). The Zymoprep Yeast Plasmid Miniprep and Zymoclean Gel DNA Recovery kits are marketed by Zymo Research (Orange, Calif., USA). The NucleoSpin Plasmid kit is from Macherey-Nagel (Düren, Germany) and the oligonucleotides used were synthesised by Isogen Life Science (Barcelona, Spain). All the chemical compounds are of the highest purity available in the market.

Directed Evolution

The PaDa-I mutant (SEQ ID NO: 18) comprising the mutated signal peptide of SEQ ID NO: 28, was obtained as described in P. Molina-Espeja, et al. *Appl. Environ. Microbiol.* 2014. 80, 3496.-3507. After each evolution cycle, the PCR products were loaded in a semi-preparative agarose gel and were purified using the Zymoclean Gel DNA Recovery kit. The DNA fragments recovered were cloned in the pJRoC30 plasmid under the control of the GAL1 promoter linearised with BamHI and XhoI (wherewith the parental or predecessor gene is also eliminated). The linearised plasmid was loaded in a low-melting-point preparatory agarose gel and was purified using the Zymoclean Gel DNA Recovery kit.

First Generation (1G)

In order to obtain the variants described in the present invention, an error-prone PCR was performed in a final volume of 50 µL. This reaction contained 3% dimethyl sulfoxide (DMSO), 0.37 µM of RMLN (SEQ ID NO: 33 5'-cctctatactttaacgtcaagg-3'), 0.37 µM of RMLC (SEQ ID NO: 34 5'-gggagggcgtgaatgtaagc-3'), 0.8 mM deoxynucleotide triphosphate (dNTPs, 0.2 mM each), 0.05 U/µL of Mutazyme II (Genemorph II kit, Stratagene) and 2.822 ng of template (pJRoC30 plasmid (from the California Institute of Technology (CALTECH, USA), which comprises the nucleotide sequence of the PaDa-I mutant of SEQ ID NO:17, 300 ng of the target DNA). This mutagenic PCR was performed in a gradient thermocyclator (Mycycler, Bio-Rad, USA), determining the following parameters: 95° C. 2 min (1 cycle); 94° C. 45 s, 53° C. 45 s and 74° C. 3 min (28 cycles); and 74° C. 10 min (1 cycle). 200 ng of the PCR product were mixed with 100 g of the linearised plasmid and competent *S. cerevisiae* cells were transformed so as to produce in vivo DNA shuffling and cloning (using the yeast transformation kit for such purpose). The volume resulting from the transformation was plated in (solid) minimal plates (for SC drop-out plates, said (solid) minimum consists of 100 mL of 6.7% yeast nitrogen base, 100 mL of 19.2 g/L uracil-free amino acid supplement, 100 mL of 20% glucose, 20 g of bacto agar, 700 mL of distilled water and 1 mL of 25 g/L chloramphenicol) were incubated for three days at 30° C. The individual colonies that were formed were selected and subjected to a dual colorimetric High-Throughput Screening (HTS) assay, to efficiently explore mutant libraries without altering enzyme stability thereof, in addition to various re-screenings, as described below.

Second Generation (2G)

Mutagenic StEP (Staggered Extension Process) was performed using the best mutants obtained in the first generation (H. Zhao, et al. *Nat Biotechnol.* 1998. 16, 258-261; E. Garcia-Ruiz, et al. *Biochem. J.* 2012. 441, 487-498) combined with in vivo shuffling. The conditions of the StEP PCR were: 3% DMSO, 90 nM RMLN (SEQ ID NO: 33 5'-cctctatactttaacgtcaagg-3'), 90 nM RMLC (SEQ ID NO: 34 5'-gggagggcgtgaatgtaagc-3'), 0.3 mM dNTPs (0.075 mM each), 0.05 U/µL Taq DNA polymerase and 16 ng of the templates (pJRoC30 with the four best mutants of the first generation). The PCRs were performed in a gradient thermocyclator using the following parameters: 95° C. 5 min (1 cycle); 94° C. 30 s, 55° C. 20 s (90 cycles). 200 ng of the PCR products were mixed with 100 ng of the linearised plasmid and transformed into competent S. cerevisiae cells). The rest of the procedure was followed as explained previously to obtain the first generation. In this evolution cycle a new variant, JaWa, was obtained, wherein the two new mutations took place: G241D and R257K, with respect to any of the enzymes AaeUPO1 or PaDa-I.

W24F Variants

Two individual high-fidelity PCRs were performed for each PaDa-I variant (PaDa-I of SEQ ID NO: 18, encoded by SEQ ID NO: 17) and JaWa (SEQ ID NO: 24, encoded by SEQ ID NO: 23), using the nucleotide sequences that encode both as a template and thereby introducing the change required in their sequence. Starting the numbering of the upo1 gene of SEQ ID NO: 1 from the start of the mature protein of SEQ ID NO: 2, the two nucleotide changes made were G71T and G72T (change in codon: TGG-W— to TTT-F). Two primers were designed for these PCRs, wherein the aforementioned changes were included. Said primers were the F24FOR primer of sequence SEQ ID NO: 35 (F24FOR: 5'-ctcacccatttaagccgcttcgacctgg cgatat-tcgtggac-3') and the F24REV primer of sequence SEQ ID NO: 36 (5'-gtccacgaatatcgccaggtcgaagcggcttaaatggg tgag-3'). The changes made to said primer to perform the mutagenesis appear underlined in the nucleotide sequence thereof.

The conditions of these PCRs were: (i) in a final volume of 50 µL, 3% DMSO, 0.5 µM RMLN (SEQ ID NO: 33), 0.5 µM F24REV of SEQ ID NO: 36, 1 mM dNTPs (0.25 mM each), 0.02 U/µL of iProof high-fidelity DNA polymerase and 10 ng of the templates; or (ii) in a final volume of 50 µL, 3% DMSO, 0.5 µM F24FOR of SEQ ID NO: 35, 0.5 µM RMLC of SEQ ID NO: 34, 1 mM dNTPs (0.25 of each), 0.02 U/µL of iProof high-fidelity DNA polymerase and 10 ng of the templates. The following parameters were used: (i) 98° C. 30 s (1 cycle), 98° C. 10 s, 47° C. 25 s, 72° C. 15 s (28 cycles) and 72° C. 10 min (1 cycle); or (ii) 98° C. 30 s (1 cycle), 98° C. 10 s, 58° C. 25 s, 72° C. 45 s (35 cycles) and 72° C. 10 min (1 cycle). 200 ng of the two PCR products corresponding to their respective template were mixed with 100 g of the linearised plasmid and were transformed into S. cerevisiae in order to perform the in vivo assembly of the genes and cloning using the In Vivo Overlap Extension (IVOE) technique (M. Alcalde. Methods Mol. Biol. 2010. 634, 3, -14).

Preparation of the Mutant Libraries

Individual colonies corresponding to clones were selected and inoculated in 96 sterile wells (Greiner Bio-One GmbH, Germany), hereinafter mother plates, with 200 µL/minimal medium for expression per well (100 mL of 6.7% yeast nitrogen base, 100 mL of 19.2 g/L, 67 mL of 1M pH 6.0 potassium phosphate buffer, 111 mL of 20% galactose, 22 mL of 0.1 M MgSO$_4$, 31.6 mL of absolute ethanol, 1 mL of 25 g/L chloramphenicol and ddH$_2$O up to 1,000 mL). Column 6 of each column was inoculated with the corresponding parental and well H1 with untransformed S. cerevisiae. The plates were sealed to avoid evaporation and were incubated at 30° C., 220 RPM and 80% of relative humidity (in a Minitron, INFORS, Switzerland) for five days.

Dual Colorimetric High-Throughput Screening (HTS)

The mother plates were centrifuged (Eppendorf 5810R centrifuge, Germany) for 10 minutes at 3,500 RPM and 4° C. 20 µL of supernatant were transferred from these mother plates to two replica daughter plates with the help of a Freedom EVO liquid handling robot (Tecan, Switzerland). 180 µL of reaction mixture were added with 2,6-dimethoxy-phenol (DMP) or naphthalene to the daughter plates using a pipetting robot (Multidrop Combi Reagent Dispenser, Thermo Scientific, USA).

The DMP reaction mixture was composed of 100 mM pH 7.0 potassium phosphate buffer, 3 mM DMP and 1 mM H$_2$O$_2$. Simultaneously, this same screening assay was carried out but adding 10% acetonitrile to the reaction mixture in order to determine changes in the activity caused by the appearance of resistance to this organic co-solvent (present in the naphthalene screening reaction mixture, necessary so it remains dissolved). The reaction mixture with naphthalene contained 100 mM pH 7.0 potassium phosphate buffer, 0.5 mM naphthalene, 10% acetonitrile and 1 mM H$_2$O$_2$. The plates were briefly agitated and initial absorbance was measured at 469 nm and 510 nm, respectively, using a plate reader for such purpose (SPECTRAMax Plus 384, Molecular Devices, USA). After a reaction time of 10 minutes, 20 µL of Fast Red (Fast Red TR Salt hemi(zinc chloride) salt) were added to each naphthalene screening well (so that its final concentration in each well was 0.5 mM). The plates were kept at room temperature until they turned orange (DMP) or red (naphthol-Fast Red), at which time the absorbance was newly measured. The values were normalised against the parental of each plate. In order to rule out false positives, two re-screenings were carried out, in addition to a third re-screening wherein kinetic stability was determined ($T_{50}$) (P. Molina-Espeja, et al. Appl. Environ. Microbiol. 2014. 80, 3496-3507). The Fast Red compound was specifically coupled to the 1-naphthol to form an azo-type red dye that can be measured at 510 nm ($\varepsilon_{510}$=4,700 M$^{-1}$ cm$^{-1}$), wavelength at which the interference in the measurement produced by the culture medium is minimal.

First Re-Screening

The best screening clones were selected (~50 clones), of which 5 µL aliquots were taken and transferred to sterile plates containing of 200 µL minimal medium for expression per well. Columns 1 and 12 plus rows A and H were not inoculated, for the purpose of avoiding evaporation and, thus, the appearance of false positives. They were incubated for 5 days at 30° C. and 220 RPM. The parental was treated in the same manner (row D, wells 7-11). The plates were treated following the same protocol as the previously described screening.

Second Re-Screening

An aliquot with the ~10 best clones of the first re-screening was inoculated in 3 mL of YPD culture medium (10 g of yeast extract, 20 g of peptone, 100 mL of 20% glucose, 1 mL of 25 g/L chloramphenicol and ddH$_2$O up to 1,000 mL) at 30° C. and 220 RPM for 16 hours. The plasmids of those cultures were extracted using the Zymo-prep Yeast Plasmid Miniprep kit. Due to the impurity and low concentration of the DNA extracted, the plasmids were transformed into supercompetent E. coli XL2-Blue cells and plated in LB-amp plates (Luria-Bertani medium is composed of 5 g of yeast extract, 10 g of peptone, 10 g of NaCl, 100 mg of ampicillin and ddH$_2$O up to 1,000 mL). An individual colony was selected from each clone, inoculated in 5 mL of LB and grown for 16 hours at 37° C. and at 250 RPM. The plasmids were extracted using the NucleoSpin Plasmid kit and transformed into competent S. cerevisiae cells (as well as with the parental). Five individual colonies of each clone were selected and inoculated to undergo the same previously described screening protocol.

Third Re-Screening. Thermostability Assay

An individual *S. cerevisiae* colony was selected with the corresponding clone (grown in a SC drop-out minimal medium plate: 100 mL of 6.7% yeast nitrogen base, 100 mL of 19.2 g/L uracil-free amino acid supplement, 100 mL of 20% glucose, 1 mL of 25 g/L chloramphenicol and ddH$_2$O up to 1,000 mL) was inoculated in 2 mL of selective minimal medium (as in the SC plate medium, but with 20 g of bacto agar and rafinose instead of galactose) and was incubated for 48 hour at 30° C. and 220 RPM. An aliquot of this culture was taken such that, upon inoculating it in 5 mL of new minimal medium, optical density at 600 nm would have a value of 0.25 (optical density, OD$_{600}$=0.25). This starter was incubated until completing two full growth cycles (between 6 and 8 hours), at which time 1 mL of cells were taken to inoculate 9 mL of expression medium in a 100 mL flask (OD$_{600}$=0.1). This culture of each clone was incubated for 72 hours at 25° C. and 220 RPM (at peak UPO activity; OD$_{600}$=25-30), the cells were separated by centrifugation (10 minutes at 4,500 RPM and 4° C.) and supernatant was filtered (using a glass and nitrocellulose filter with a pore size of 0.45 μm). Appropriate dilutions of the supernatants were prepared so that aliquots of 20 μL would give rise to a linear response in kinetic mode. 50 μL of supernatant were used for each point in a temperature gradient created by means of thermocyclator, from 30 to 80° C. After incubating for 10 minutes, the aliquots were cooled in ice for 10 minute and tempered at room temperature for 5 minutes. Lastly, these supernatants were subjected to the colorimetric assay using ABTS (100 mM pH 4.0 sodium phosphate/citrate buffer, 0.3 mM ABTS and 2 mM H$_2$O$_2$). The thermostability values were calculated in accordance with the ratio between the residual activities incubated at different temperatures and the value of initial activity at room temperature. The value of T$_{50}$ was determined as the value of the temperature at which the protein loses 50% of it initial activity after incubating for 10 minutes.

Production of UPO Recombinant Variants in *S. cerevisiae*

An independent *S. cerevisiae* colony that comprised the corresponding variant of the invention was selected from a SC drop-out minimal medium plate and inoculated in 20 mL of liquid SC minimal medium, cultures which were incubated at 48 h at 30° C. and 220 RPM. An aliquot of this culture was taken so that, upon inoculating it in 100 mL of new minimal medium, OD$_{600}$ would have a value of 0.25. This starter was incubated until completing two full growth cycles (between 6 and 8 hours), at which time 100 mL of cells were taken to inoculate 900 mL of minimal medium for expression in a 2,000 mL flask (OD$_{600}$=0.1). This culture of each clone was incubated for 72 hours at 25° C. at at 220 RPM (at peak UPO activity; OD$_{600}$=25-30), the cells were separated by centrifugation (10 minutes at 4,500 RPM and 4° C.) and the supernatant was filtered (with glass and nitrocellulose filter with a pore size of 0.45 μm).

Purification of Recombinant AaeUPO1 Variants

The purification of the recombinant AaeUPO variants described in the present invention was carried out by means of ion-exchange chromatography (ÄKTA purifier, GE Healthcare). The raw extract was firstly treated by fractional precipitation with ammonium sulphate (55%, first cut) and, after eliminating the pellet, the supernatant was newly subjected to precipitation with ammonium sulphate (85%, second cut). The final pellet was re-suspended in the 10 mM pH 4.3 sodium phosphate/citrate buffer (buffer A) and the sample was filtered and loaded on a strong cation-exchange column (HiTrap SP FF, GE Healthcare), pre-balanced with buffer A. The proteins were eluded by means of a linear gradient of 0 to 25% of buffer A with 1 M of NaCl in 55 mL and of 25 to 100% of buffer A with 1 M NaCl in 5 mL, at a flow rate of 1 mL/min. The fractions with UPO activity were recovered, concentrated and dialysed in 10 mM pH 6.5 Bis Tris buffer (buffer B) and loaded on a high-resolution anion-exchange column (Biosuite Q, Waters), pre-balanced with buffer B. The proteins were eluded by means of a linear gradient of 0 to 15% of buffer B with 1 M of NaCl in 40 mL y de 15 a 100% de buffer B with 1 M NaCl in 5 mL, at a flow rate of 1 mL/min. The fractions with UPO activity were recovered, concentrated and dialysed in 50 mM pH 7.0 potassium phosphate buffer and stored at 4° C. Reinheitszahl [Rz] [A$_{418}$/A$_{280}$] values of ~2 were obtained. The fractions of the different purification steps were analysed in a 12% SDS/PAGE acrylamide gel, dyed with Coomassie blue. The concentrations of the raw extracts of these steps were determined by means of Bradford reagent and BSA as standard.

Kinetic Constants Values

The kinetic constants of the variants of the invention for ABTS were estimated in 100 mM pH 4.0 sodium phosphate/citrate buffer and 2 mM H$_2$O$_2$; and for the rest of the substrates, in 100 mM pH 7.0 potassium phosphate buffer, 2 mM H$_2$O$_2$ (DMP) or 1 mM H$_2$O$_2$ (NBD and naphthalene, in 20% of acetonitrile—final concentration). For H$_2$O$_2$, benzyl alcohol was used as substrate at the corresponding saturation conditions. The reactions were performed in triplicate and the oxidations of the substrates were followed by spectrophotometric changes (ABTS: $\varepsilon_{418}$=36,000 M$^{-1}$ cm$^{-1}$; DMP: $\varepsilon_{469}$=27,500 M$^{-1}$ cm$^{-1}$; NBD: $\varepsilon_{425}$=9,700 M$^{-1}$ cm$^{-1}$, naphthalene: $\varepsilon_{303}$=2,010 M$^{-1}$ cm$^{-1}$, and benzyl alcohol: $\varepsilon_{280}$=1,400 M$^{-1}$ cm$^{-1}$). The kinetics for naphthalene were performed following the protocol described in M. G. Kluge, et al. *Appl. Microbiol. Biotechnol.* 2007. 75, 1473-1478. In order to calculate the values of K$_m$ and k$_{cat}$, values of V$_{max}$ were represented at substrate concentrations and the hyperbole function was adjusted (using SigmaPlot 10.0, wherein the parameter a is equal to k$_{cat}$ and the parameter b, to K$_m$).

HPLC Analysis

The reactions were analysed by means of chromatography in reverse phase (HPLC). The equipment is composed by a tertiary pump (Varian-Agilent Technologies, USA) coupled to an autosampler (Merck Millipore, MA, USA); an ACE C18 PFP column was used for separation (pentafluorophenyl, 15 cm×4.6 cm) at 45° C. and detection was performed using a photodiode detector (PDA) (Varian-Agilent Technologies, USA). The mobile phase selected was 70% methanol and 30% ddH$_2$O (in both cases with 0.1% of acetic acid) at a flow rate of 0.8 mL/min. The reaction was quantified at 268 nm (based on standard HPLCs). For the 15 minute reaction, the mixture contained 6.6 nM of pure enzyme, 1 mM naphthalene, 20% acetonitrile and 1 mM H$_2$O$_2$ in 100 mM pH 7.0 potassium phosphate buffer (1 mL of final volume). The reaction started with the addition of H$_2$O$_2$ and stopped with 20 μL of 37% HCl. For long reaction times, the conditions used were those described earlier but without stopping the reaction with HCl. A sample of 10 μL was injected and analysed at different reaction times (from 1 to 270 minutes).

For the kinetic values of the 1-naphthol, the reaction was performed using 40 nM of pure enzyme, 1 mM 1-naphthol, 20% acetonitrile and 1 mM H$_2$O$_2$ in 100 mM pH 7.0 potassium phosphate buffer (0.2 mL of final volume).

The standard deviations were less than 5% in all cases.

Analysis Using MALDI-TOF-MS and Determination of the Isoelectric Point

The analyses were performed using an Autoflex III MALDI-TOF-TOF unit with smartbeam laser (Bruker Daltonics). The samples were evaluated in positive mode. The method was calibrated using BSA with standard, thereby covering a range of 15,000 to 70,000 Da. In order to determine the isoelectric point of the UPO variants, 8 µg of pure enzyme were subjected to two-dimensional electrophoresis. These experiments were carried out at the Proteomic and Genomic Service of the Biological Research Centre (CIB-CSIC, Spain).

Analysis by Liquid Chromatography/Mass Spectrometry (LC/MS)

These analyses were performed using a mass spectrometer with a Q-TOF hybrid analyser (QSTAR, ABSciex, MA, USA). Electrospray (ESI) was used as an ionisation source and, as ionising phase, methanol. In this case, the entrance system was direct injection in a HPLC 1100 (Agilent Technologies, USA). The resolution of the assay corresponds to 9,000 FWHM (Full Width at Half Maximum), accuracy, 5-10 ppm and was performed in negative mode.

Results

Taking the PaDa-I mutant enzyme of SEQ ID NO: 18 encoded by SEQ ID NO: 17 as parental to carry out the directed evolution experiments, UPO mutant libraries were built by means of random mutagenesis and recombination by StEP and in vivo DNA shuffling with the objective of obtaining a mutant enzyme or variant that shows less peroxidase activity on the 1-naphthol, while boosting peroxygenase activity on the naphthalene, also taking into account that said variant must be expressed robustly in heterologous organisms and secreted in an active, soluble and very stable form. To this end, each variant obtained in the mutant libraries was subjected to ad hoc double screening for the purpose of obtaining the variants with the aforementioned capabilities, greater peroxygenase activity against naphthalene and less peroxidase activity against 1-naphthol.

After subjecting the PaDa-I mutant (SEQ ID NO: 17) to two cycles of directed evolution (~4,000 clones analysed), a double mutant was identified which was called JaWa and which comprises the nucleotide sequence SEQ ID NO: 23, that encodes the variant of SEQ ID NO: 24. Said JaWa mutant (SEQ ID NO: 24) comprises the G241D and R257K mutations with respect to the PaDa-I mutant of SEQ ID NO: 18, with a peroxygenase activity on microplate that doubled that of its parental and a peroxidase activity that was reduced to half (FIG. 1).

Both variants, PaDa-I and JaWa, were produced, purified at homogeneity (Reinheitszahl [Rz] [$A_{418}/A_{280}$] value ~2) and biochemically characterised. No changes were detected with regard to general spectral characteristics, processing of the N-terminus, molecular mass or degree of glycosylation (Table 1).

TABLE 1

Biochemical characteristics of wild-type AaeUPO (SEQ ID NO: 4) and of the PaDa-I (SEQ ID NO: 18) y JaWa (SEQ ID NO: 24) variants.

| Spectroscopic and biochemical characteristics | Wild-type UPO | PaDa-I | JaWa |
|---|---|---|---|
| Pm (Da)[1] | 46,000 | 52,000 | 52,000 |
| Pm (Da)[2] | n.d. | 51,100 | 51,100 |
| Pm (Da)[3] | 35,942 | 35,914 | 35,944 |
| Degree of glycosylation (%) | 22 | 30 | 30 |
| Thermal stability, $T_{50}$ (° C.)[4] | n.d. | 57.6 | 59.7 |
| pI | 4.9-5.7 | 5.5 | 5.3 |
| Optimum pH for ABTS | 4.0 | 4.0 | 4.0 |
| Optimum pH for DMP | 7.0 | 6.0 | 6.0 |
| Optimum pH for naphthalene | 6.5 | 6.0 | 6.0 |
| Rz, ($A_{418}/A_{280}$) | 2.4 | 1.8 | 2.3 |
| Soret region (nm) | 420 | 418 | 418 |
| CT1 (nm) | 572 | 570 | 570 |
| CT2 (nm) | 540 | 537 | 537 |

[1]Estimated by SDS-PAGE;
[2]estimated using MALDI-TOF;
[3]estimated according to the amino acid composition.
[4]Estimated in culture supernatants. n.d. not determined.

Figure 2:
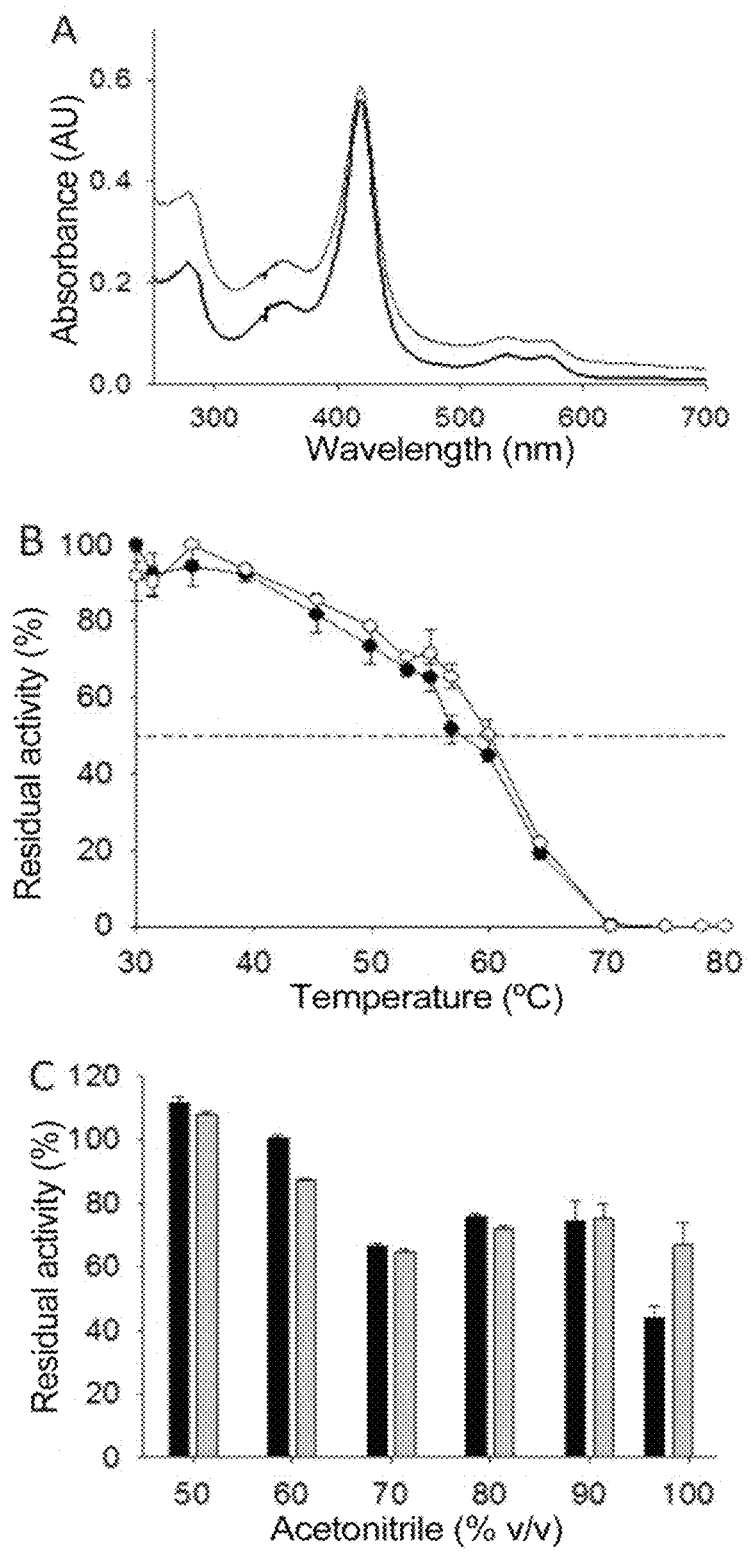
FIG. 2 Biochemical characteristics of the variants of the invention. A) Spectroscopic characteristics of the PaDa-I (thin line) and JaWa (thick line) mutants at rest. AU, arbitrary units. B) Thermostability analysis ($T_{50}$) of the PaDa-I (black circles) and JaWa (white circles) mutants. The experiments were carried out using culture supernatants and each point represents the average value and standard deviation of three individual experiments. C) Stability of the PaDa-I (black bars) and JaWa (grey bars) mutants at high acetonitrile concentrations. The stabilities were determined after 5 hours of incubation of the enzyme in increasing concentrations of the co-solvent (from 50% to 100%) at 20° C. in 10 mM pH 7.0 potassium phosphate buffer. After that time, aliquots were taken and analysed using ABTS substrate (100 mM pH 4.0 sodium phosphate/citrate buffer, 2 mM $H_2O_2$ and 0.3 mM ABTS). The error bars indicate standard deviations.

As can be observed in Table 1 and in FIG. 2, the JaWa mutant enzyme of SEQ ID NO: 24 showed greater kinetic thermostability than the PaDa-I variant of SEQ ID NO: 18 (2° C. higher $T_{50}$-temperature at which the enzyme retains 50% of its activity after 10 minutes of incubation-), in addition to higher stability in the presence of acetonitrile, necessary for the bioavailability of the naphthalene (the solubility of the naphthalene in water is 31.7 mg/L) (FIG. 2).

The naphthalene transformation reaction performed by the JaWa (SEQ ID NO: 24) and PaDa-I (SEQ ID NO: 18) mutants and that was analysed by means of HPLC-PDA has evidenced that the oxygenation of the naphthalene by AaeUPO occurs through an unstable intermediary compound, 1,2-naphthalene oxide (epoxide). It undergoes quick hydrolysis to naphthol (1- and 2-naphthol) when the pH is acid (M. Kluge, et al. *Appl. Microbiol. Biotechnol.* 2009. 81, 1071-1076). Therefore, the distribution of the resulting products after 15 minutes of reaction was firstly measured (stopped with HCl). Both the PaDa-I (SEQ ID NO: 18) and JaWa (SEQ ID NO: 24) variants demonstrated similar regioselectivity (92% 1-naphthol, 8% 2-naphthol), but the JaWa variant showed a significant increase in the production of 1-naphthol (156% more than PaDa-I) without detectable traces of 1,4-naphthoquinone, its oxidation product (FIG. 3A).

Figure 3:
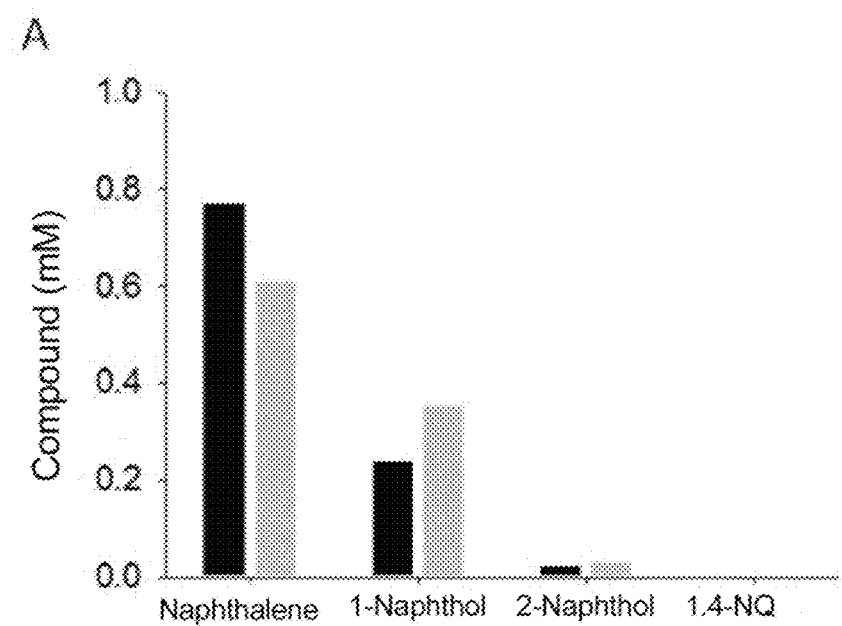
FIG. 3 Transformation of naphthalene by means of the variants described in the invention. A) Products formed after 15 minutes of reaction stopped with 20 μL of HCl 37% (PaDa-I, black bars; JaWa, grey bars). The reactions were carried out at room temperature using 6.6 nM of pure enzyme, 100 mM pH 7.0 of potassium phosphate buffer, 1 mM naphthalene, 20% acetonitrile and 1 mM $H_2O_2$ (1 mL of final volume). As can be observed in the figure, the products obtained were mainly naphthalene, 1-naphthol and 2-naphthol. B) Chromatograms of the naphthalene transformation reaction after 270 minutes (1: naphthalene; 2: 1-naphthol; 3: 2-naphthol and 4: 1.4-naphthoquinone (1.4-NQ)). C) and D) Monitoring of the reaction for 270 minutes (without adding HCl) for the PaDa-I (C) and JaWa (D) mutants. Black circles: naphthalene; white circles: 1.2-naphthalene oxide; white squares: 1-naphthol and black squares: 2-naphthol. Total turnover numbers (TTN, expressed as μmoles of product/μmoles of enzyme) were calculated using the production value of 1-naphthol after 270 minutes.
Figure 3:
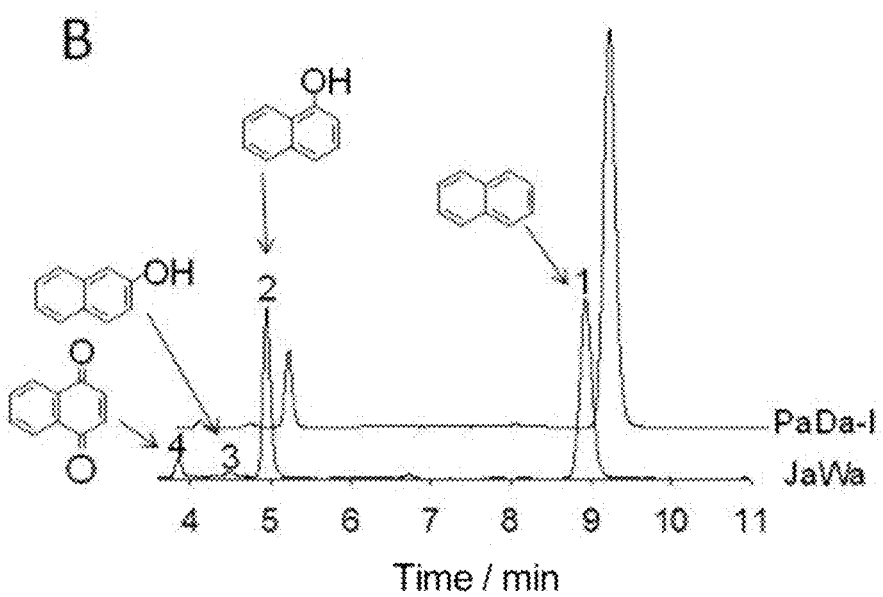
Figure 3:
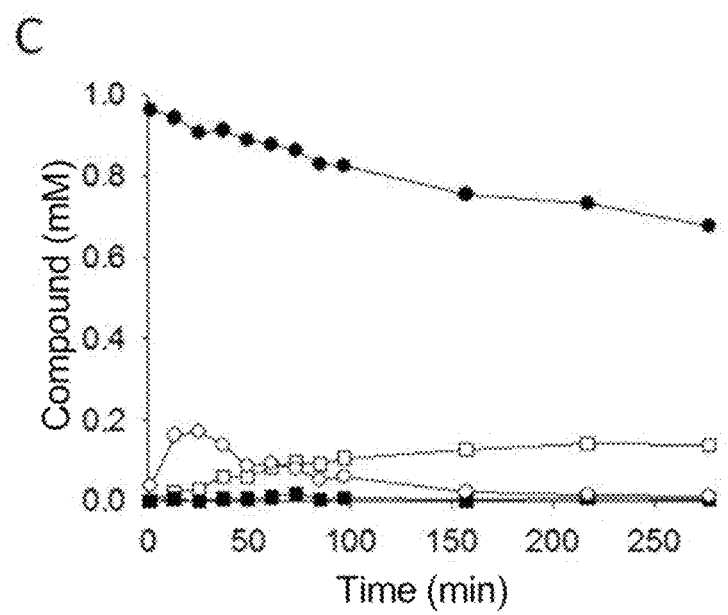
Figure 3:
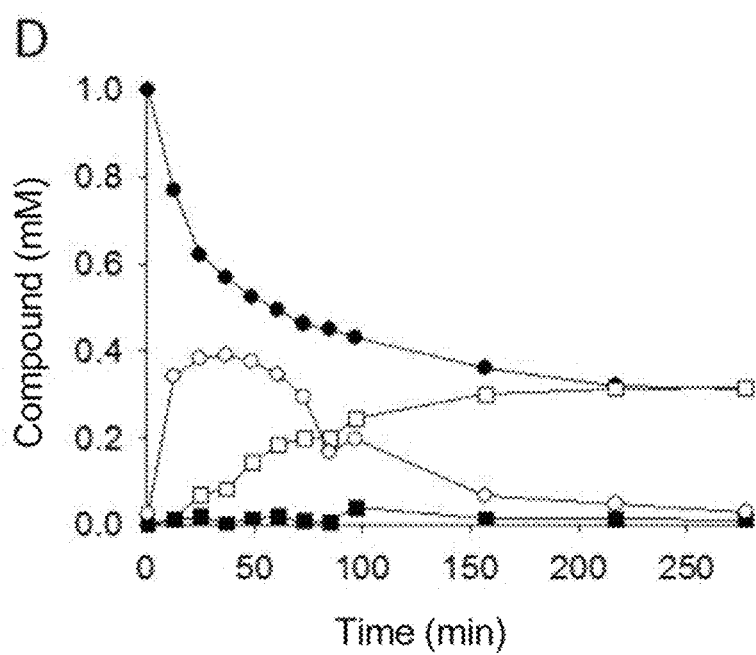

When the long reaction times were monitored (270 minutes at pH 7.0 without stopping the reaction), a similar behaviour was observed, which indicates that the transformation of the 1,2-naphthalene oxide to naphtholes also occurs at neutral pH, although it is true that, at lower speed, traces of 1,4-naphthoquinone were also detected (FIG. 3B, C, D).

While with both variants, PaDa-I and JaWa, the formation of the epoxide intermediary reached its maximum at ~40 minutes (due to the oxidative damage caused by the $H_2O_2$ in all the peroxidases), regioselectivity increased to 97% of 1-naphthol. This result corresponds to the loss of selectivity observed in acid conditions given by a greater reactivity of the epoxide.

The composition of the resulting products did not vary for any of the PaDa-I (SEQ ID NO: 18) and JaWa (SEQ ID NO: 24) variants, as observed in the mass spectrometry analysis performed, but the differences between the two mutants in terms of production performance were very significant, reaching values of 0.14 and 0.32 mM of 1-naphthol for PaDa-I and JaWa, respectively. The JaWa variant obtained total turnover numbers (TTN) of nearly 50,000 against the 20,000 of PaDa-I.

Additionally, the kinetic values of the two variants were determined using substrates of both peroxygenase and peroxidase activity (Table 2), as described in the section on materials and methods. Briefly, the kinetic constants for the ABTS were measured in 100 mM pH 4.0 sodium phosphate/citrate buffer and 2 mM $H_2O_2$, while 100 mM pH 7.0 potassium phosphate and 2 mM $H_2O_2$ (DMP) or 1 mM (naphthalene or NBD, in 20% acetonitrile—final concentration) was used for the other buffers. For the $H_2O_2$, benzyl alcohol was used as substrate to the corresponding saturation conditions.

TABLE 2

Kinetic parameters for PaDa-I (SEQ ID NO: 18) and JaWa (SEQ ID NO: 24) variants.

| Substrate | Kinetic constants | PaDa-I | JaWa |
|---|---|---|---|
| ABTS | $K_m$ (μM) | 48.0 ± 4.5 | 181 ± 22 |
| | $k_{cat}$ (s$^{-1}$) | 395 ± 13 | 125 ± 5 |
| | $k_{cat}/K_m$ (s$^{-1}$ M$^{-1}$) | 8.2 × 10$^6$ ± 6 × 10$^5$ | 6.9 × 10$^5$ ± 6.3 × 10$^4$ |
| DMP | $K_m$ (μM) | 126 ± 14 | 866 ± 108 |
| | $k_{cat}$ (s$^{-1}$) | 68 ± 2 | 142 ± 8 |
| | $k_{cat}/K_m$ (s$^{-1}$ M$^{-1}$) | 5.4 × 10$^5$ ± 4.8 × 10$^4$ | 1.6 × 10$^5$ ± 1.2 × 10$^4$ |
| Naphthalene | $K_m$ (μM) | 578 ± 106 | 127 ± 27 |
| | $k_{cat}$ (s$^{-1}$) | 229 ± 17 | 78 ± 3 |
| | $k_{cat}/K_m$ (s$^{-1}$ M$^{-1}$) | 4 × 10$^5$ ± 4 × 10$^4$ | 6.2 × 10$^5$ ± 1.1 × 10$^5$ |
| NBD | $K_m$ (μM) | 483 ± 95 | 769 ± 80 |
| | $k_{cat}$ (s$^{-1}$) | 338 ± 22 | 154 ± 8 |
| | $k_{cat}/K_m$ (s$^{-1}$ M$^{-1}$) | 7 × 10$^5$ ± 9.9 × 10$^4$ | 2.0 × 0$^5$ ± 1.2 × 10$^4$ |
| $H_2O_2$ | $K_m$ (μM) | 486 ± 55 | 1,250 ± 300 |
| | $k_{cat}$ (s$^{-1}$) | 238 ± 8 | 447 ± 40 |
| | $k_{cat}/K_m$ (s$^{-1}$ M$^{-1}$) | 5.0 × 10$^5$ ± 4.2 × 10$^4$ | 3.6 × 10$^5$ ± 5.9 × 10$^4$ |

As can be observed in Table 2, the $k_{cat}/K_m$ value (catalytic efficiency) for naphthalene was 1.5 times higher for the JaWa variant (SEQ ID NO: 24) with respect to the PaDa-I variant (SEQ ID NO: 18). Also, the peroxidase activity of the JaWa variant (SEQ ID NO: 24) was reduced (with a significant decrease in catalytic efficiencies of 3 to 11 times for the substrates of peroxidase activity DMP and ABTS, respectively). The $k_{cat}/K_m$ value for $H_2O_2$ with benzyl alcohol as substrate was also affected. In the results obtained with NBD, another oxygen transfer substrate such as naphthalene, the trend is similar, i.e. $k_{cat}$ decreases in the JaWa variant while the affinity to the $K_m$ substrate improves, despite the fact that this entails higher $k_{cat}/K_m$ for the PaDa-I variant. The fact that the catalytic efficiency of the JaWa variant for NBD has not improved is significant, since it is not a substrate used in the screenings of this part of the evolution. However, the fact that the tendency of the catalytic constant and affinity to the substrate is similar in two monooxygenase substrates indicates that there is an enzyme action mechanism acting in some way to favour the formation of 1-naphtol while reducing peroxidase activity.

Figure 4:
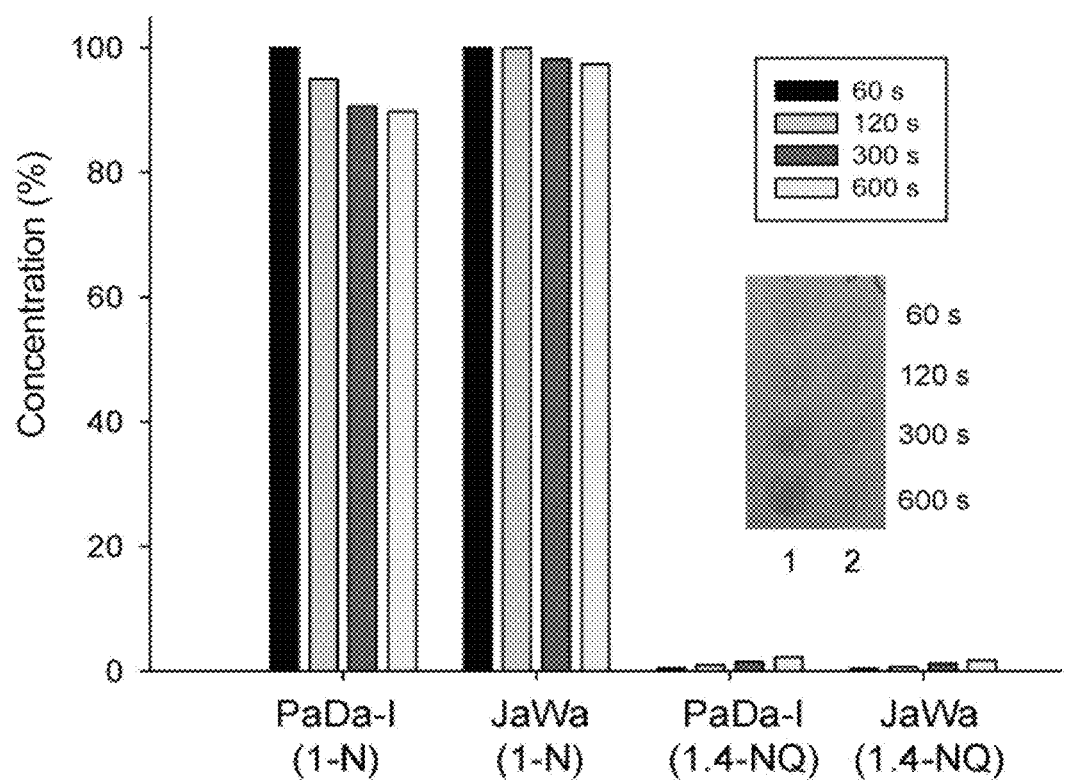
FIG. 4 Conversion of naphthalene at 1-naphthol by means of the PaDa-I and JaWa variants. The reactions were performed at room temperature and their composition was as follows: 40 nM of pure enzyme, 100 mM pH 7.0 potassium phosphate buffer, 1 mM naphthalene, 20% acetonitrile and 1 mM $H_2O_2$ (1 mL of final volume). 1-N: 1-naphthol; 1,4-NQ: 1-4-naphthoquinone. Each reaction was performed in triplicate and were stopped with HCl (pH<1) at different times (between 60 and 600 s). Inset: polymeric colorimetric products derived from 1.4-naphthoquinone, 1: PaDa-I and 2: JaWa.

To confirm the decrease in peroxidase activity with respect to the hydroxylation of the naphthalene, the values of the catalytic constant were measured by using HPLC (μmol product μmol enzyme$^{-1}$ min$^{-1}$) for the conversion of 1-naphthol into 1,4-naphthoquinone. Although the catalytic constant of the PaDa-I variant (SEQ ID NO: 18) for 1-naphthol was already low (200 min$^{-1}$), with the JaWa variant (SEQ ID NO: 24) this value decreased to 92 min$^{-1}$, in addition to a reduction of ~1.5 times in the ratio 1,4-naphthoquinone:1-naphthol (FIG. 4). This effect can also be observed at first glance, since the polymeric products produced in the reaction with the PaDa-I variants (SEQ ID NO: 18) (due to non-enzymatic quinone regrouping processes) are coloured (FIG. 4). There are hypotheses in literature on the possibility that UPO is similar to CPO in the existence of different sites with peroxidase activity in its structure. To suppress these alternative peroxidation pathways, the structure of the AaeUPO1 crystal was closely examined and a variant was built by mean of directed mutagenesis in Trp24 (FIG. 5A), a highly oxidable residue, found on the protein surface, using the PaDa-I (SEQ ID NO: 18) and JaWa (SEQ ID NO: 24) variants as templates, as described in the section on materials and methods.

Figure 5:
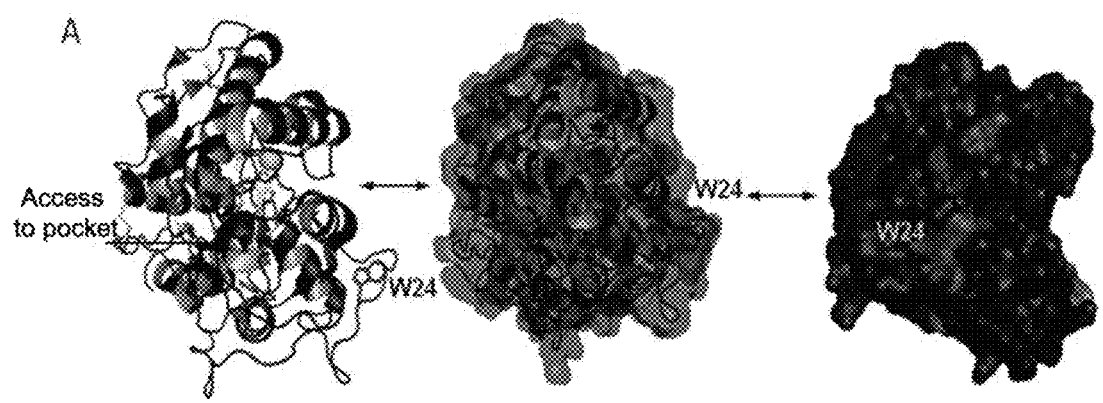
FIG. 5 W24F variants obtained by means of directed mutagenesis. A) Model built on the crystal structure of the AaeUPO1 enzyme (PDB access number: 2YOR), comprising the mutations of the JaWa variant as well as the W24F modification with respect to wild AaeUPO1. The model is shown without a surface, with a transparent surface and with an opaque surface, showing position W24. B) Activity of the W24F variants using different substrates with respect to their respective parentals, relativised to the PaDa-I activity. The experiments were carried out using 100 mL flask culture supernatants. The buffer used was 100 mM pH 7.0 potassium phosphate buffer, except for the ABTS, in which case 100 mM pH 4.0 sodium phosphate/citrate was used. The components of the mixture were: 0.5 mM naphthalene, 1 mM NBD, 3 mM DMP and 0.3 mM ABTS. In all cases, 1 mM $H_2O_2$ and 15% acetonitrile were added to the mixtures. For the activity with naphthalene, the Fast Red method was applied (after 10 minutes of reaction, Fast Red was added—final concentration 0.5 mM—and when the red colour appeared and became stabilised, final absorbance was measured). The molar extinction coefficients are: naphthalene+Fast Red, $\varepsilon_{510}=4,700$ $M^{-1}$ $cm^{-1}$; NBD, $\varepsilon_{425}=9,700$ $M^{-1}$ $cm^{-1}$; DMP, $\varepsilon_{469}=27,500$ $M^{-1}$ $cm^{-1}$ and ABTS, $\varepsilon_{418}=36,000$ $M^{-1}$ $cm^{-1}$.
Figure 5:
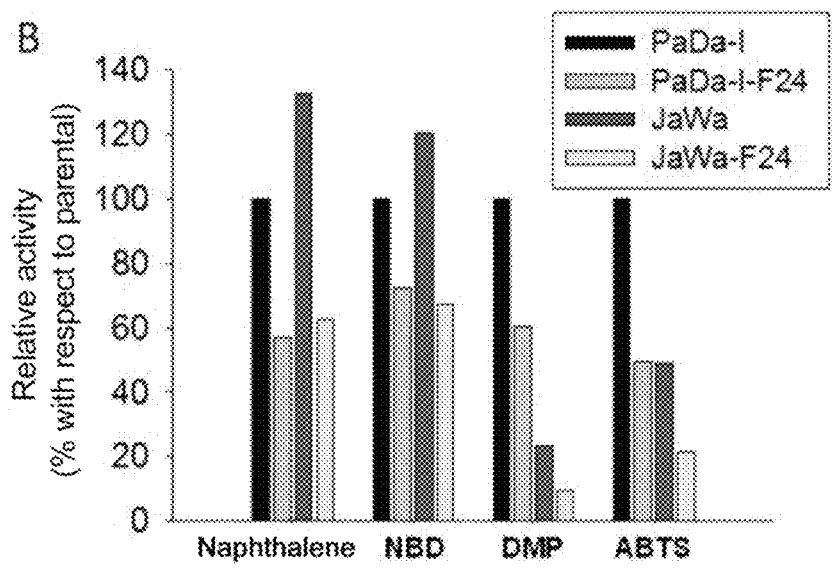

Next, the activities of the PaDa-I-W24F (SEQ ID NO: 30) and JaWa-W24F (SEQ ID NO: 32) variants were determined. The W24F mutation reduced 60% of the peroxidase activity in both variants and with all the tested substrates, but caused a decrease in the peroxygenase activity, with a reduction of 50% in the activity on the naphthalene and NBD (FIG. 5B). This indicates that the Trp24 residue probably also affects the peroxygenase activity of the UPO.

Example 2. Mutational Analysis of the Variants of the Invention

Figure 6:
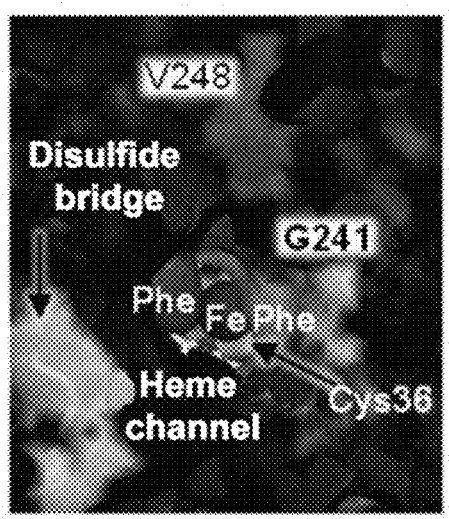
FIG. 6 Mutations in the UPO variants described in the invention. Model built on the structure of the AaeUPO1 crystal (PDB access number: 2YOR). A) PaDa-I; B) JaWa. The V248 mutant stems from the previous evolution pathway. The phenylalanine (Phe) residues are responsible for the accommodation of the substrates in the catalytic pocket, the Cys36 residue is the axial heme ligand; R189 is a component of the acid-base pair involved in the catalysis, and heme $Fe^{3+}$ is represented as a sphere.
Figure 6:
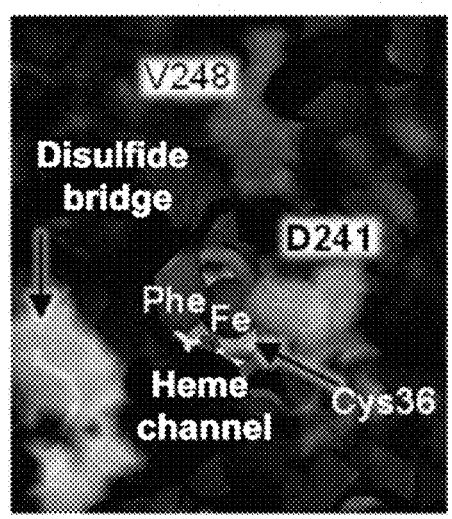
Figure 6:
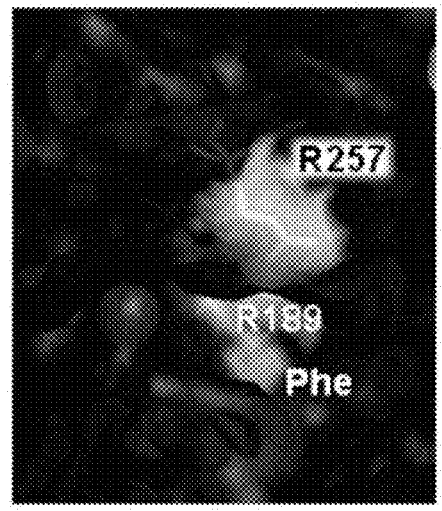
Figure 6:
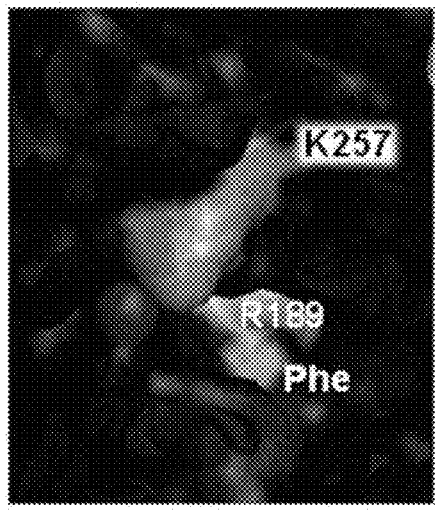
Figure 7:
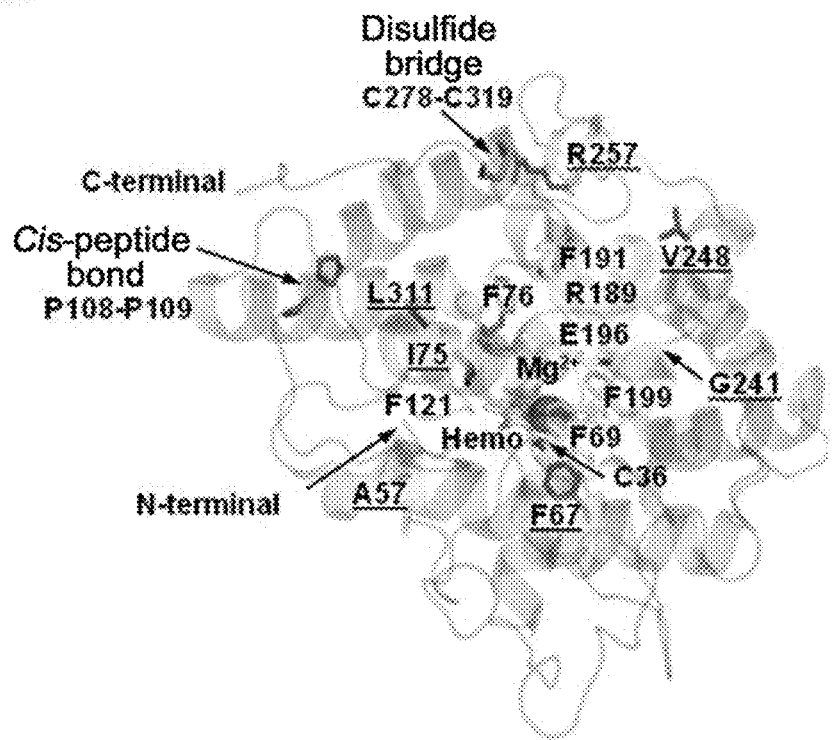
FIG. 7 Protein model of A) PaDa-I and B) JaWa. The protein model for PaDa-I (A) was built on the structure of the AaeUPO1 crystal (PDB access number: 2YOR) and the software PyMOL Molecular Graphics System, Version 1.3 Schrödinger, LLC. The new mutations of the PaDa-I mutant with respect to the native UPO are shown underlined, while the residues with a zig-zag underline are those which have been changed in JaWa (B). The image shows the five Phe that participate in the accommodation of the substrate: Phe 69, Phe 76, Phe 121, Phe 191 and Phe 199; the two catalytic residues are R189 and E196.
Figure 7:
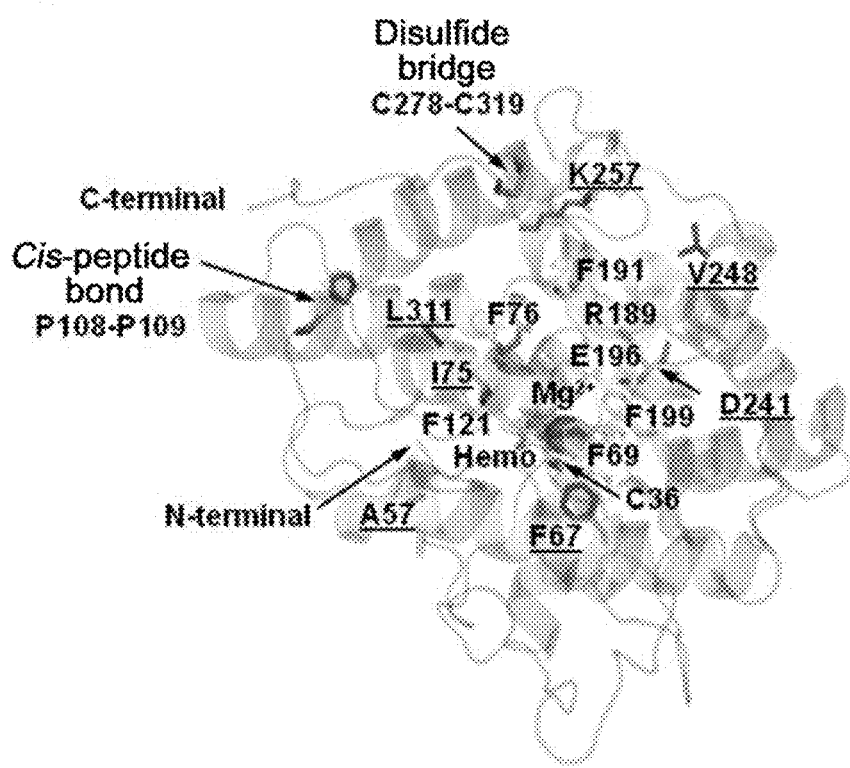
Figure 8:
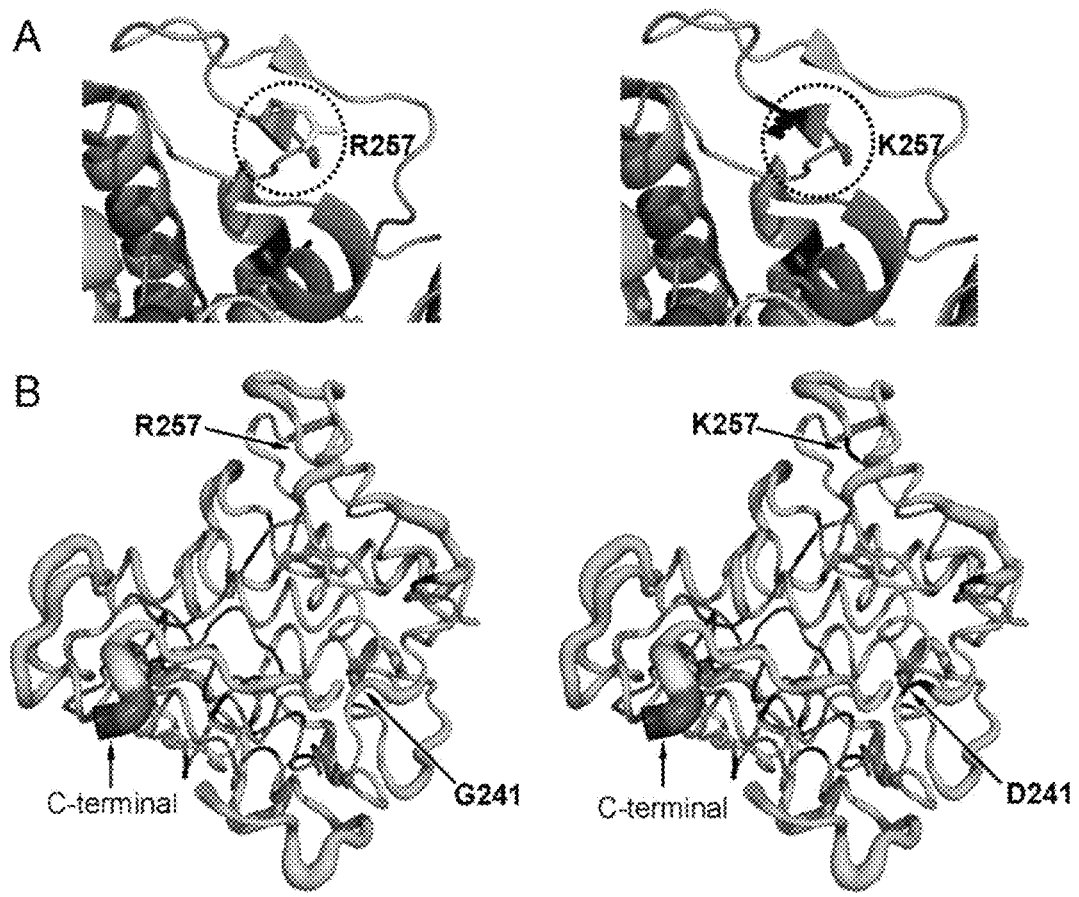
FIG. 8 B factors for the evolved UPOs of the present invention. Representation of the B factors (obtained using PyMOL Molecular Graphics System, Version 1.3 Schrödinger, LLC.) of the PaDa-I variant (left) and the JaWa variant (right). Said B factors make reference to the rigidity/flexibility of a protein region or of an amino acid. A) Detail of the mutation in position 257, located on the surface: darker shades indicated greater rigidity. B) Representation in "putty" mode of the complete structure of the PaDa-I and JaWa variants. The greater the thickness of the lines, the greater the flexibility.

The mutations of the JaWa variant were mapped (SEQ ID NO: 24) onto the structure of the wild AaeUPO1 (SEQ ID NO: 4), which shows a very characteristic catalytic pocket wherein linkage with the substrate takes place, dominated by a Phe triad (Phe69-Phe121-Phe199) involved in the correct orientation of the aromatic compounds (FIG. 6 and FIG. 7). The G241D mutation is at the entrance to the heme channel. The dramatic change of a Gly, apolar and small, for an Asp, loaded and larger, seems to narrow the cavity, which can affect the accommodation of the naphthalene in the catalytic pocket. This theory is not consistent with the fact that the affinity to naphthalene was improved in the JaWa variant, with a decrease in its $K_m$ of 3 times (Table 2). On the contrary, the introduction of a negative charge in the heme-thiolate domain (in which there is a Glu196-Arg189 acid-base pair involved in the formation of the Compound I-porphyrin with a radical cation and oxo-Fe IV=O—) may negatively affect the $k_{cat}$ value, depending on the chemical nature of the bound substrate. The R257K mutation is located on the surface of the protein, far from catalysis-relevant regions, but is at the start of a "pathway" towards the catalytic R189 residue. It is a known fact that some peroxidases show various surface-exposed entrances for electron-mediated substrate oxidation through a long-range electron transfer pathway towards the heme domain, as also described in the present work for W24F variants. In this regard, the R257K replacement may be affecting any of these circuits with a possible beneficial lateral effect on thermostability through localised remodelling in the secondary structure (the two mutations, G241D and R257K, vary the estimation of factor B (FIG. 8)). B factor makes reference to the rigidity/flexibility of a protein or amino acid region present in a protein or peptide.

These results evidence that the UPO variants described herein show greater selectivity and the highest TTN known for the production of 1-naphthol for this enzyme superfamily to date. Additionally, as demonstrated, said variants are heterologously secreted in an active, soluble and very stable form, being capable of carrying out selective aromatic oxygenations in the absence of NAD(P)H cofactors and reductase domains. Their self-sufficient mono(per)oxygenase activity make this UPO variant a valuable biocatalyst for application in the field of organic synthesis.

Example 3. Obtainment and Characterisation of Variants of the Invention for the Synthesis of Human Drug Metabolites (HDMs)

The most important HDMs include, namely, derivatives of propranolol, a beta-blocker drug commonly used for the treatment of hypertension, migraine prophylaxis in children and attenuation of physical manifestations of anxiety. This example shows how the UPO variants of the invention are capable of forming 5'-hydroxypropranolol from propranolol oxygenation, without inorganic pollutants, at room temperature, atmospheric pressure and in the absence of organic solvents, in a single step, with catalytic concentrations of $H_2O_2$ and without requiring the addition of antioxidants such as ascorbic acid to the reaction.

In addition to the variants described in Example 1, a new variant was built based on the JaWa variant, which even showed an improvement in the production of 5'-hydroxypropranolol with respect to said JaWa mutant. Following is a description of the obtainment of a new variant called SoLo comprising SEQ ID NO: 42 and which is encoded by the nucleotide sequence SEQ ID NO: 41.

Materials and Methods

Reagents and Enzymes

ABTS (2,2'-azino-bis(3-ethylbenzothiazolin-6-sulfonic acid)), L-ascorbic acid, 4-aminoantipyrine, benzyl alcohol, Taq DNA polymerase and the *Saccharomyces cerevisiae* transformation kit were obtained from Sigma-Aldrich (Saint Louis, Mo., USA). NBD (5-nitro-1,3-benzodioxole) was acquired from TCI America (Portland, Oreg., USA), while the naphthalene, propranolol and potassium persulfate are from Acros Organics (Geel, Belgium). 5-hydroxypropranolol was acquired from Santa Cruz Biotechnology (Santa Cruz, Calif., USA).

The competent *Escherichia coli* XL2-Blue cells and Pfu ultra DNA polymerase were obtained from Agilent Technologies (Santa Clara, Calif., USA) and iProof high-fidelity DNA polymerase was acquired from Bio-Rad (Hercules, Calif., USA). The BamHI and XhoI restriction enzymes were obtained from New England Biolabs (Ipswich, Mass., USA) and the protease-deficient strain of *S. cerevisiae* BJ5465 from LGCPromochem (Barcelona, Spain). The Zymoprep Yeast Plasmid Miniprep and Zymoclean Gel DNA Recovery kits are marketed by Zymo Research (Orange, Calif., USA). The NucleoSpin Plasmid kit is from Macherey-Nagel (Düren, Germany) and the oligonucleotides used were synthesised by Metabion (Bayern, Germany). All the chemical compounds are of the highest purity available in the market.

Directed Evolution

Based on the JaWa mutant comprising SEQ ID NO: 24, which is encoded by the nucleotide sequence SEQ ID NO: 23, after each evolution cycle, the PCR products were loaded on a semi-preparative agarose gel and purified using the Zymoclean Gel DNA Recovery kit. The recovered DNA fragments were cloned in the pJRoC30 plasmid under the control of the GAL1 promoter linearised with BamHI and XhoI (also eliminating the parental gel or predecessor). The linearised plasmid was loaded in a low-melting-point preparatory agarose gel and was purified using the Zymoclean Gel DNA Recovery kit.

First Generation (1G)

To obtain the SoLo mutant (SEQ ID NO: 42, encoded by SEQ ID NO: 41), docking studies were performed on the JaWa mutant (SEQ ID NO: 24, encoded by SEQ ID NO: 23) using the Molecular Operating Environment program (MOE, Chemical Computing Group Inc.) and propranolol as a substrate. Based on these, a region of the protein was selected to be subjected to random mutagenesis using the MORPHING technique (Mutagenic Organized Recombination Process by Homologous in vivo Grouping) (D. González-Perez et al., *PLoS ONE* 2014. 9:e90919). To obtain the different variants additional to those described earlier, two error-prone PCRs were performed in a specific zone of the nucleotide sequence (SEQ ID NO: 23) that encodes that JaWa mutant (SEQ ID NO: 24), specifically in the coding zone from the D187-V248 region of the JaWa mutant of SEQ ID NO: 24 in a final volume of 50 µL. These reactions contained 3% of dimethyl sulfoxide (DMSO), 90 nM MJaWa Fw (SEQ ID NO: 43; 5'-gcgcattcaagactccattg-3'), 90 nM MJaWa Rev (SEQ ID NO: 44; 5'-gatcttgccgacattttttcc-3'), 0.3 mM deoxynucleotide triphosphates (dNTPs, 0.075 mM of each), 0.1 mM or 0.2 mM $MnCl_2$, 1.5 mM $MgCl_2$, 0.05 U/µL Taq DNA polymerase and 1 ng/µl of the template (pJRoC30 plasmid from the California Institute of Technology (CALTECH, USA), comprising the nucleotide sequence of the JaWa mutant of SEQ ID NO: 23). This mutagenic PCR was performed in a gradient thermocyclator (Mycycler, Bio-Rad, EEUU), determining the following parameters: 94° C. 2 min (1 cycle); 94° C. 45 s, 48° C. 30 s and 72° C. 90 s (28 cycles); and 72° C. 10 min (1 cycle). Furthermore high-fidelity PCRs were performed in the fragments that must remain non-mutagenic in a final volume of 50 µL. These reactions contained 3% of dimethyl sulfoxide (DMSO), 0.5 µM HFJaWa Fw (SEQ ID NO: 45; 5'-caggctcatcctatgcagccc-3') and 0.5 µM RMLC (SEQ ID NO: 34; 5'-gggagggcgtgaatgtaagc-3') or 0.5 µM HFJaWa Rev (SEQ ID NO: 46; 5'-caaaggagaaattggggttggtcg-3') and 0.5 µM RMLN (SEQ ID NO: 33; 5'-cctctatactttaacgtcaagg-3') for the other high-fidelity fragment, 1 mM dNTPs (0.25 mM of each), 0.05 U/µL PfuUltra DNA polymerase and 2 ng/µL of template. These reactions were performed in the same gradient thermocyclator, determining the following paramenters: 95° C. 2 min (1 cycle); 95° C. 45 s, 48° C. 30 s and 72° C. 90 s (28 cycles); and 72° C. 10 min (1 cycle). 200 ng of PCR products were mixed with 100 ng of the linearised plasmid and competent *S. cerevisiae* cells were transformed such as to produce in vivo shuffling of the DNA and cloning (using the yeast transformation kit for such purpose). The volume resulting from the transformation was plated in minimal solid medium plates (for SC drop-out plates, said minimal solid medium consists of 100 mL of 6.7% yeast nitrogen base, 100 mL of 19.2 g/L uracil-free amino acid supplement, 100 mL of 20% glucose, 20 g bacto agar, 700 mL of distilled water and 1 mL of 25 g/L chloramphenicol) and were incubated for 3 days at 30° C. The individual colonies that were formed were selected and subjected to the dual colorimetric High-Throughput Screening (HTS) assay to efficiently explore mutant libraries without altering the enzyme stability thereof, in addition to various re-screenings, as described below. In this evolution cycle, a new variant was obtained called SoLo, which comprises the nucleotide sequence SEQ ID NO: 41, that encodes the variant of SEQ ID NO: 42, wherein a new mutation took place: F191S, with respect to the JaWa variant (SEQ ID NO: 24).

Second Generation (2G)

Since the mutation that appeared in the SoLo variant (SEQ ID NO: 42) is found in one of the two phenylalanines that delimit the entrance to the heme channel, combinatorial saturation mutagenesis (CSM) was performed using the 22c-trick method, as described in S. Kille, et al. *ACS Synth. Biol.* 2013. 2.83-92, in positions S191 and F76.

To this end, three PCRs were performed in a final volume of 50 μL. All contained 3% of DMSO, 0.3 mM dNTPs (0.075 mM each), 0.05 U/μL PfuUltra DNA polymerase and 2 ng/μL of template, but each with different primers. PCR 1 with 0.25 μM of RMLN (SEQ ID NO: 33), 0.25 μM of F76 VHG R (SEQ ID NO: 47;
5'-gcaagtccgtaatgagattgccgtccacaaggtgggccgcatatgtg
gccdbgattgcggc-3), 0.25 μM of F76 NDT R (SEQ ID NO: 48;
5'-gcaagtccgtaatgagattgccgtccacaaggtgggccgcatatgt
ggcahngattgcggc-3' and 0.25 μM of F76 TGG R (SEQ ID NO: 49;
5'-gcaagtccgtaatgagattgccgtccacaaggtgggccgcatatgtg
gcccagattgcggc-3').

PCR 2 con 0.25 μM of HF F (SEQ ID NO: 50;
5'-gcggcccaccttgtggacggcaatctcattacggacttgc-3'

0.25 μM of S191 VHG R (SEQ ID NO: 51;
5'-cccatccacaaaaagattcgcggggaaggtggtctcgccgtaagca
gtcdbgaacctaaag-3'

0.25 μM of S191 NDT R (SEQ ID NO: 52;
5'-cccatccacaaaaagattcgcggggaaggtggtctcgccgtaagca
gtahngaacctaaag-3')

y 0.25 μM of S191 TGG R (SEQ ID NO: 53;
5'-cccatccacaaaaagattcgcggggaaggtggtctcgccgtaagca
gtccagaacctaaag-3').

PCR 3 con 0.25 μM de HF F-RMLC (SEQ ID NO: 54;
5'-cggcgaciaccaccttccccgcgaatcttttgtggatggg-3')

and 0.25 μM of RMLC (SEQ ID NO: 34). The underlined regions are those in which in vivo DNA assembly occurs and the region in italics is the changed codon (where N=A/T/C/G; D=no C; V=no T; H=no G; and B=no A). These reactions were performed in the gradient thermocyclator, determining the following parameters: 95° C. 2 min (1 cycle); 95° C. 45 s, 48° C. 45 s and 72° C. 60 s (28 cycles); and 72° C. 10 min (1 cycle). 200 ng of each of the PCR products were mixed with 100 ng of the linearised plasmid and transformed into competent *S. cerevisiae* cells. The rest of the procedure was followed as explained previously to obtain the first generation. No improved variant was obtained with respect to the SoLo mutant.

Third Generation (3G)

There is a phenylalanine triad in the catalytic pocket of AaeUPO, PaDa-I and JaWa (F69-F121-F199). Due to the complex catalytic pocket and to the fact that these phenylalanines are in charge correctly orienting the aromatic substrates, it was decided to carry out mutagenesis on these residues with NNK degenerated codons (N=A/T/C/G; D; K=T/G, M=A/C) independently, i.e. creating three different libraries.

Library F69: two PCRs were performed in a final volume of 50 μL. The first contained 3% of DMSO, 0.2 mM dNTPs (0.05 mM of each), 0.5 μM RMLN (SEQ ID NO: 33), 0.5 μM F69 R (SEQ ID NO: 55; 5'-gaagattgcggcttgattgtcmnnattgaatc-3'), 0.02 U/μL iProof DNA polymerase and 2 ng/μL of template (SoLo comprising SEQ ID NO: 41). And the second contained 3% of DMSO, 0.2 mM dNTPs (0.05 mM of each), 0.5 μM RMLC (SEQ ID NO: 34), 0.5 μM F69 F (SEQ ID NO: 56; 5'-cgcggttcaggaaggattcaatnnkgacaatc-3'), 0.02 U/μL iProof DNA polymerase and 2 ng/μL of template (SoLo comprising SEQ ID NO: 41).

F121 library: two PCRs were performed in a final volume of 50 μL. The first contained 3% of DMSO, 0.2 mM dNTPs (0.05 mM of each), 0.5 μM RMLN (SEQ ID NO: 33), 0.5 μM F121 R (SEQ ID NO: 57; 5'-catactggcgtcgccttcmnnggtgccatgc-3'), 0.02 U/μL iProof DNA polymerase and 2 ng/μL of template (SoLo comprising SEQ ID NO: 41). And the second contained 3% of DMSO, 0.2 mM dNTPs (0.05 mM of each), 0.5 μM RMLC (SEQ ID NO: 34), 0.5 μM F121 F (SEQ ID NO: 58; 5'-ggactcaatgagcatggcaccnnkgaaggcg-3'), 0.02 U/μL iProof DNA polymerase and 2 ng/μL of template (SoLo comprising SEQ ID NO: 41).

F199 library: two PCRs were performed in a final volume of 50 μL. The first contained 3% of DMSO, 0.2 mM dNTPs (0.05 mM of each), 0.5 μM RMLN (SEQ ID NO: 33), 0.5 μM F199 R (SEQ ID NO: 59; 5'-ccacaaaaagattcgcgggmnnggtggtctcg-3'), 0.02 U/μL iProof DNA polymerase and 2 ng/μL of template (SoLo comprising SEQ ID NO: 41). And the second contained 3% of DMSO, 0.2 mM dNTPs (0.05 mM of each), 0.5 μM RMLC (SEQ ID NO: 34), 0.5 μM F199 F (SEQ ID NO: 60; 5'-ctactgcttacggcgagaccaccnnkcccgcg-3'), 0.02 U/μL iProof DNA polymerase and 2 ng/μL of template (SoLo comprising SEQ ID NO: 41).

These reactions were performed in the gradient thermocyclator, determining the following parameters: 98° C. 30 s (1 cycle); 98° C. 10 s, 48° C. 30 s and 72° C. 30 s (28 cycles); and 72° C. 10 min (1 cycle). 200 ng of each of the PCR products were mixed with 100 ng of the linearised plasmid (each library separately) and transformed into competent *S. cerevisiae* cells. The rest of the method was followed as explained earlier to obtain the first and second generation. Neither was any variant better than SoLo found (SEQ ID NO: 42), due to which this mutant was selected, together with the JaWa mutant (SEQ ID NO: 24) and the parental AaeUPO1, to analyse the synthesis of HDMs, taking 5'-hydroxypropranolol with each by way of example.

Preparation of the Mutant Libraries

Individual colonies corresponding to clones were selected and inoculated in sterile 96-well plates (Greiner Bio-One GmbH, Germany), hereinafter mother plates, with 200 μL/minimal medium for expression per well (100 mL of 6.7% yeast nitrogen base, 100 mL of 19.2 g/L uracil-free amino acid supplement, 67 mL of 1 M pH 6.0 potassium phosphate buffer, 111 mL of 20% galactose, 22 mL of 0.1 M MgSO$_4$, 31.6 mL of absolute ethanol, 1 mL of 25 g/L chloramphenicol and ddH$_2$O up to 1,000 mL). Column 6 of each column was inoculated with the corresponding parental and well H1 with *S. cerevisiae* transformed with the pJRoC30-MtL plasmid (laccase without functional expression). The plates were sealed to avoid evaporation and were incubated at 30° C., 220 RPM and 80% of relative humidity (in a Minitron, INFORS, Switzerland) for five days.

Dual Colorimetric High-Throughput Screening (HTS)

The mother plates were centrifuged (Eppendorf 5810R centrifuge, Germany) for 10 minutes at 3,500 RPM and 4° C. 20 μL of supernatant of these mother plates were transferred to two replica daughter plates with the help of a Freedom EVO liquid-handling robot (Tecan, Switzerland). 50 μL of reaction mixture with propranolol were added to the daughter plates using a pipetting robot (Multidrop Combi Reagent Dispenser, Thermo Scientific, USA).

The reaction mixture with propranolol was composed of 50 mM pH 7.0 potassium phosphate buffer, 5 mM propranolol and 2 mM $H_2O_2$ to detect the peroxygenase activity of the enzyme on the substrate and its subsequent peroxidase activity on the product. This same screening assay was simultaneously carried out but adding ascorbic acid (4 mM) to the reaction mixture in order to exclusively detect the peroxygenase activity of the enzyme on propranolol and avoid the subsequent peroxidase activity. Without ascorbic, the plates were incubated for 30 minutes and with ascorbic for 60 minutes. Subsequently, by means of the 4 aminoantipyrine (4-AAP, C. R. Otey and J. M. Joern, *Methods Mol. Biol.* 2003. 230, 141-8) the amount of product formed per well was revealed. The plates were briefly agitated and absorbance measured at 530 nm, using a plate reader for such purpose (SPECTRAMax Plus 384, Molecular Devices, USA). The values were normalised against the parental of each plate. To rule out false positives, re-screenings were carried out, in addition to a third re-screening wherein kinetic stability was determined ($T_{50}$) (P. Molina-Espeja, et al. *Appl. Environ. Microbiol.* 2014. 80, 3496-3507).

Second Re-Screening

An aliquot with the ~10 best screening clones was inoculated in 3 mL of YPD culture medium (10 g of yeast extract, 20 g of peptone, 100 mL of 20% glucose, 1 mL of 25 g/L chloramphenicol and ddH2O up to 1,000 mL) at 30° C. and 220 RPM for 24 hours. The plasmids of those cultures were extracted using the Zymoprep Yeast Plasmid Miniprep kit. Due to the impurity and low concentration of the DNA extracted, the plasmids were transformed into supercompetent *E. coli* XL2-Blue cells and plated in LB-amp plates (Luria-Bertani medium is composed of 5 g of yeast extract, 10 g of peptone, 10 g of NaCl, 100 mg of ampicillin and ddH2O up to 1,000 mL). An individual colony was selected from each clone, inoculated in 5 mL of LB and grown for 16 hours at 37° C. and at 250 RPM. The plasmids were extracted using the NucleoSpin Plasmid kit and transformed into competent *S. cerevisiae* cells (as in the parental, which in the first generation is JaWa and in the second and third is SoLo). Five individual colonies of each clone were selected and inoculated to undergo the same previously described screening protocol.

Third Re-Screening. Thermostability Assay

An individual *S. cerevisiae* colony was selected with the corresponding clone (grown on a SC drop-out minimal medium plate: 100 mL of 6.7% yeast nitrogen base, 100 mL of 19.2 g/L uracil-free amino acid supplement, 100 mL of 20% glucose, 1 mL of 25 g/L chloramphenicol and ddH$_2$O up to 1,000 mL), was inoculated in 3 mL of selective minimal medium (like the SC plate medium, but with 20 g of bacto agar and rafinose instead of galactose) and incubated for 48 hours at 30° C. and 220 RPM. An aliquot of this culture was taken such that, upon inoculating it in 5 mL of new minimal medium, optical density at 600 nm would have a value of 0.25 (optical density, $OD_{600}$=0.25). This starter was incubated until completing two full growth cycles (between 6 and 8 hours), at which time 1 mL of cells were taken to inoculate 9 mL of expression medium in a 100 mL flask ($OD_{600}$=0.1). This culture of each clone was incubated for 72 hours at 25° C. and 220 RPM (at peak UPO activity; $OD_{600}$=25-30), the cells were separated by centrifugation (10 minutes at 4,500 RPM and 4° C.) and the supernatant was filtered (using a glass and nitrocellulose filter with a pore size of 0.45 μm). Appropriate supernatant dilutions were prepared so that aliquots of 20 μL would give rise to a linear response in kinetic mode. 50 μL of supernatant were used for each point at a temperature gradient created using a thermocyclator, from 30 to 80° C. After incubating for 10 minutes, the aliquots were cooled in ice for 10 minutes and tempered at room temperature for 5 minutes. Lastly, these supernatants were subjected to the colorimetric assay using ABTS (100 mM pH 4.0 sodium phosphate/citrate buffer, 0.3 mM ABTS and 2 mM $H_2O_2$). The thermostability values were calculated in accordance with the ratio between the residual activities incubated at different temperatures and the value of initial activity at room temperature. The value of $T_{50}$ was determined as as the temperature value at which the protein loses 50% of its initial activity after incubating for 30 minutes.

Production of UPO Recombinant Variants in *S. cerevisiae*

An independent *S. cerevisiae* colony that comprised the corresponding variant of the invention, on the one hand JaWa and on the other SoLo, was selected from a SC drop-out minimal medium plate and inoculated in 20 mL of liquid SC minimal medium, cultures that were incubated for 48 hours at 30° C. and 220 RPM. An aliquot of this culture was taken so that, upon inoculating it in 100 mL of new minimal medium, $OD_{600}$ would have a value of 0.25. This starter was incubated until completing two full growth cycles (between 6 and 8 hours), at which time 100 mL of cells were taken to inoculate 900 mL of minimal medium for expression in a 2,000 mL flask ($OD_{600}$=0.1). This culture of each clone was incubated for 72 hours at 25° C. and at 220 RPM (at peak UPO activity; $OD_{600}$=25-30), the cells were separated by centrifugation (10 minutes at 4,500 RPM and 4° C.) and the supernatant was filtered (using a glass and nitrocellulose filter with a pore size of 0.45 μm).

Purification of Recombinant AaeUPO1 Variants

The purification of the variants described in the present invention, JaWa and SoLo, was carried out using cation-exchange chromatography followed by anion-exchange chromatography (ÄKTA purifier, GE Healthcare). The raw extract was concentrated and dialysed in 20 mM pH 3.3 sodium phosphate/citrate buffer (buffer A) by means of tangential ultrafiltration (Pellicon; Millipore, Temecula, Calif., USA) through a membrane with a pore size of 10 kDa (Millipore) using a peristaltic pump (Masterflex Easy Load; Cole-Parmer, Vernon Hills, Ill.). The sample was filtered and loaded on a strong cation-exchange column (HiTrap SP FF, GE Healthcare), pre-balanced with buffer A. The proteins were eluded by means of a linear gradient of 0 to 40% of buffer A with 1M NaCl in 60 mL and from 40 to 100% of buffer A with 1 M NaCl in 5 mL, at a flow rate of 1 mL/min. The fractions with UPO activity were recovered, concentrated and dialysed in 20 mM pH 7.8 Tris-HCl buffer (buffer B) and loaded on a high-resolution anion-exchange column (Biosuite Q, Waters), pre-balanced with buffer B. The proteins were eluded by means of a linear gradient of 0 to 20% of buffer B with 1 M NaCl in 40 mL and from 20 to 100% of buffer B with 1 M NaCl in 5 mL, at a flow rate of 1 mL/min. The fractions with UPO activity were recovered, concentrated and dialysed in 10 mM pH 7.0 potassium phosphate buffer and stored at 4° C. Reinheitszahl [Rz] [$A_{418}/A_{280}$] values of ~2 were obtained. The fractions of the different purification steps were analysed in a 12% SDS/PAGE acrylamide gel, dyed with Coomassie blue. The concentrations of the raw extracts of these steps were determined by means of Bradford reagent and BSA as standard.

Kinetic Constants Values

The kinetic constants of the variants of the invention, AaeUPO, PaDa-I, JaWa and SoLo, for ABTS were estimated in 100 mM pH 4.0 sodium phosphate/citrate buffer and 2 mM $H_2O_2$; and for the other substrates, in 100 mM pH 7.0 potassium phosphate buffer and 2 mM $H_2O_2$ (propranolol). For $H_2O_2$, benzyl alcohol was used as substrate at the corresponding saturation conditions. The reactions were performed in triplicate and the oxidations of the substrates were followed by spectrophotometric changes (ABTS: $\varepsilon_{418}$=36,000 $M^{-1}$ $cm^{-1}$; Propranolol: $\varepsilon_{325}$: 1,996 $M^{-1}$ $cm^{-1}$, and benzyl alcohol: $\varepsilon_{280}$=1,400 $M^{-1}$ $cm^{-1}$). The kinetics for propranolol were performed calculating $\varepsilon_{325}$ experimentally at pH 7.0. In order to calculate the values of $K_m$ and $k_{cat}$, values of $V_{max}$ were represented at substrate concentrations and the hyperbole function was adjusted (using SigmaPlot 10.0, wherein the parameter a is equal to $k_{cat}$ and the parameter b, to $K_m$).

HPLC Analysis

The reactions were analysed by means of chromatography in reverse phase (HPLC). The equipment was composed of a tertiary pump (Varian-Agilent Technologies, USA) coupled to an autosampler (Merck Millipore, MA, USA); for the separation, a Zorbax Eclipse plus C18 column (15 cm×4.6 cm) at 40° C. was used and the detection was performed using a photodiode detector (PDA) (Varian, Agilent Technologies, USA). The mobile phase selected was a gradient from 10% methanol and 90% dd$H_2O$ (in both cases with 0.1% of acetic acid) up to 90% methanol and 10% dd$H_2O$ at a flow rate of 0.8 mL/min. The reaction was quantified at 280 nm (based on HPLC standards). For the 15 minute reaction, the mixture contained 0.03 µM of pure enzyme, 4 mM propranolol and 2 mM $H_2O_2$ in 50 mM pH 7.0 potassium phosphate buffer (0.5 mL of final volume). The reaction was started with the addition of $H_2O_2$ and was stopped with 20 µL of 37% HCl. In order to determine the turnover rates of the variants with 5'-hydroxypropranolol (product of interest), the mixture contained 0.03 µM of pure enzyme, 0.4 mM 5'-hydroxypropranolol and 2 mM $H_2O_2$ in 50 mM pH 7.0 potassium phosphate buffer (0.3 mL of final volume). In order to calculate the total turnover number (TTN) of the assayed variants, the assay was carried out using 0.03 µM of pure enzyme, 5 mM propranolol and 2 mM $H_2O_2$ in 50 mM pH 7.0 potassium phosphate buffer and in the same manner, but also adding 4 mM ascorbic acid. In both cases, 2 mM $H_2O_2$ was added every 10 minutes, monitoring the reaction in each addition point taking different aliquots. The standard deviations were less than 5% in all cases.

Analysis by Liquid Chromatography/Mass Spectrometry (LC/MS)

These analyses were performed using a mass spectrometer with a Q-TOF hybrid analyser (QSTAR, ABSciex, MA, USA). Electrospray (ESI) was used as an ionisation source and, as ionising phase, methanol. In this case, the entrance system was direct injection in a HPLC 1100 (Agilent Technologies, USA). The resolution of the assay corresponds to 9,000 FWHM (Full Width at Half Maximum), accuracy at 5-10 ppm and it was performed in positive mode.

Results

Figure 9:
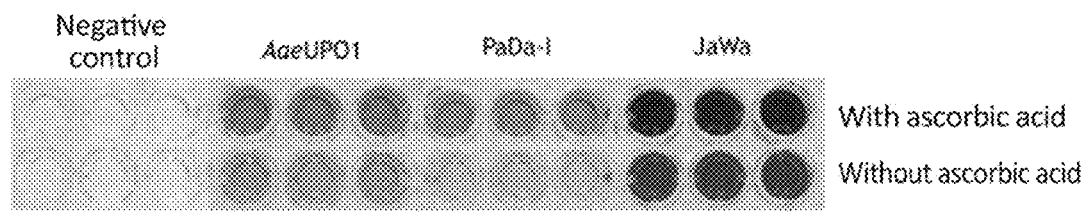
FIG. 9 Assay of 4-AAP (4-aminoantipyrine) with different pure UPO variants (AaeUPO1, PaDa-1 and JaWa). The reactions were performed at room temperature and their composition was as follows: 0.2 μM of each pure UPO variant, 50 mM pH 7.0 potassium phosphate buffer, 5 mM propranolol, 2 mM $H_2O_2$ (0.05 mL of final volume) and, in the case of reactions with ascorbic acid, it was added to a concentration of 4 mM. Each reaction was performed in triplicate.
Figure 10:
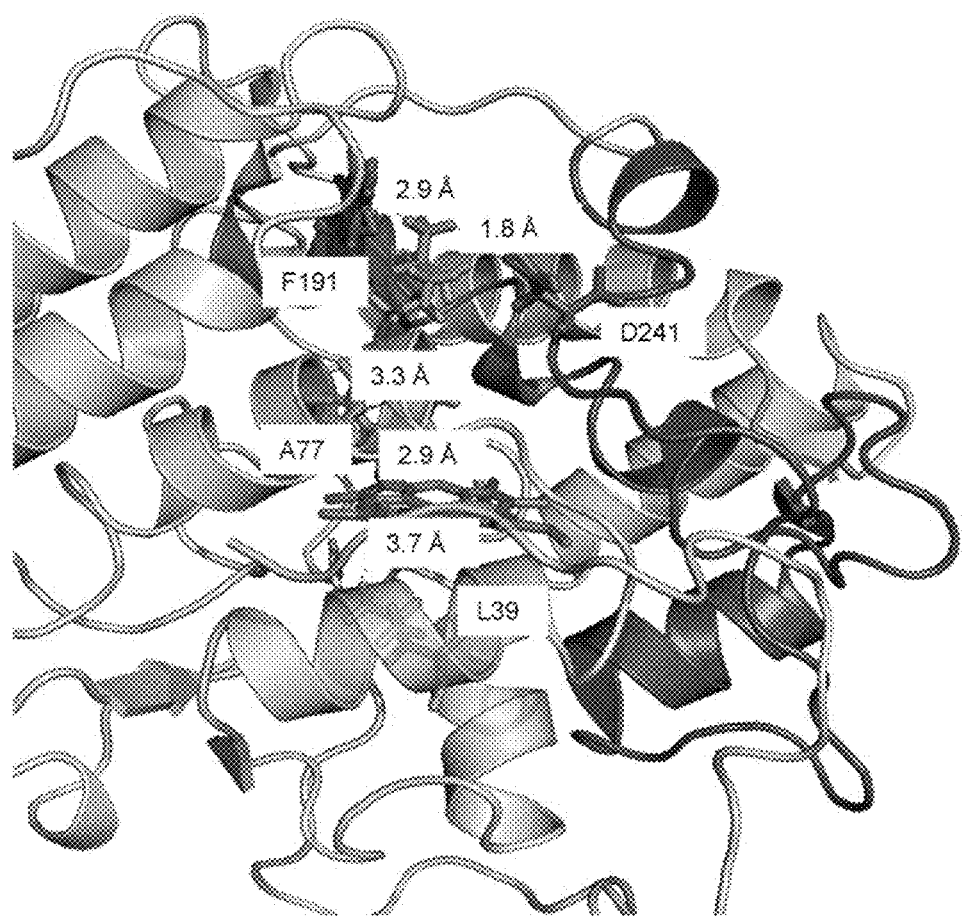
FIG. 10 Molecular docking with JaWa and propranolol. Amino acids that interact with propranolol are indicated, with the distances therefrom. The zone selected for MORPHING experiments due to its proximity to the protein-substrate contact points is indicated in dark grey.
Figure 11:
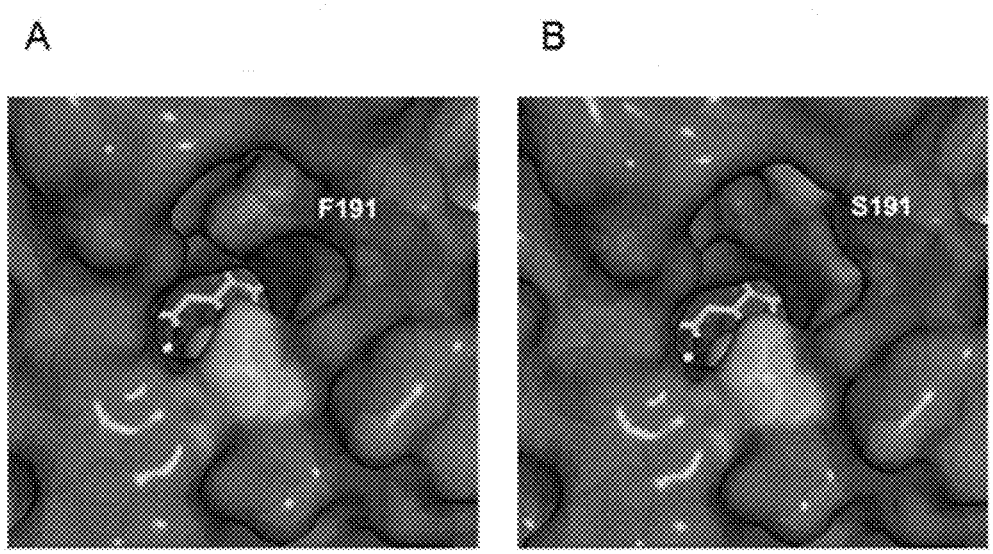
FIG. 11 Mutations in SoLo variants with respect to the JaWa variant described in the invention. Model built on the structure of the PaDa-I crystal. A) JaWa; B) SoLo.

The activity of the different UPO variants was evaluated by means of the 4-AAP assay to determine the most appropriate starting point for determining the capacity of said variants for HDM synthesis (FIG. 9). As can be observed in the figure, the variant with the greatest activity against propranolol and best ratio among its activity with and without ascorbic was JaWa (SEQ ID NO: 24, encoded by SEQ ID NO: 23), due to which it was the mutant selected for the docking assays (FIG. 10). Based on these results, wherein it was observed that the substrate interacted with a series of residues of the catalytic pocket and of the heme access channel, a region of the JaWa mutant that was in direct contact with the substrate was selected (residues D187-V248 of SEQ ID NO: 24). The objective is to obtain a mutant enzyme or variant that shows less peroxidase activity on 5'-hydroxypropranolol (which is the product of the reaction with propranolol) while improving peroxygenase activity on propranolol, also taking into account that said variant must be expressed robustly in heterologous organisms and secreted in an active, soluble and very stable form. To this end, each variant obtained in the mutant libraries was subjected to double screening designed ad hoc for the purpose of obtaining the variants with the aforementioned capabilities, greater peroxygenase activity on propranolol (measured in the presence of ascorbic acid) and less peroxidase activity against 5'-hydroxypropranolol (in the absence of ascorbic acid). Two libraries with different mutagenic rates (concentration of $MnCl_2$) were analysed, identifying a single mutant in both libraries and repeatedly to that called SoLo and which comprises the nucleotide sequence SEQ ID NO: 41 that encodes the variant of SEQ ID NO: 42. Said SoLo mutant (SEQ ID NO: 42) has the F191S mutation (FIG. 11) with respect to the JaWa mutant of SEQ ID NO: 24, with a peroxygenase activity on microplate 30% higher than its parental (JaWa) and decrease in peroxidase activity of more than two fold.

Two further cycles of evolution (2G and 3G) were performed using the SoLo variant (SEQ ID NO: 41) as parental, wherein no enhanced variant was detected.

Both variants, JaWa (SEQ ID NO: 24) and SoLo (SEQ ID NO: 42), were produced, purified at homogeneity (Reinheitszahl [Rz] [$A_{418}/A_{280}$] value ~2) and biochemically characterised.

Figure 12:
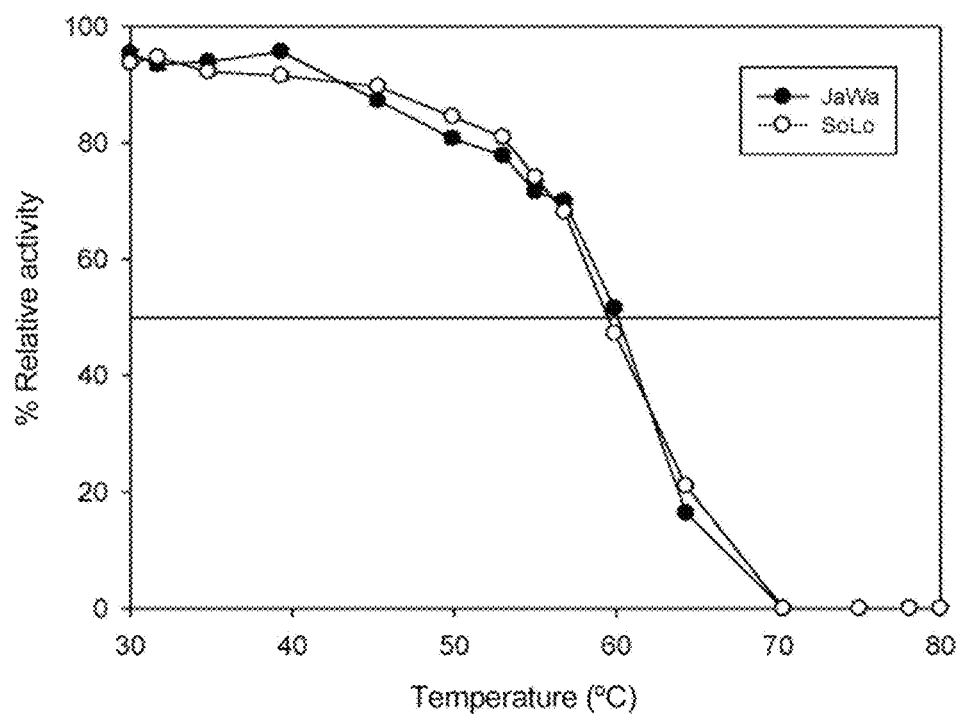
FIG. 12 Thermostability analysis ($T_{50}$) of the JaWa (black circles) and SoLo (white circles) mutants. The experiments were carried out using culture supernatants and each point represents the average value and standard deviation of three individual experiments.

As can be observed in FIG. 12, the SoLo variant of SEQ ID NO: 42 showed very similar kinetic thermostability to that of the JaWa mutant (SEQ ID NO: 24).

Figure 13:
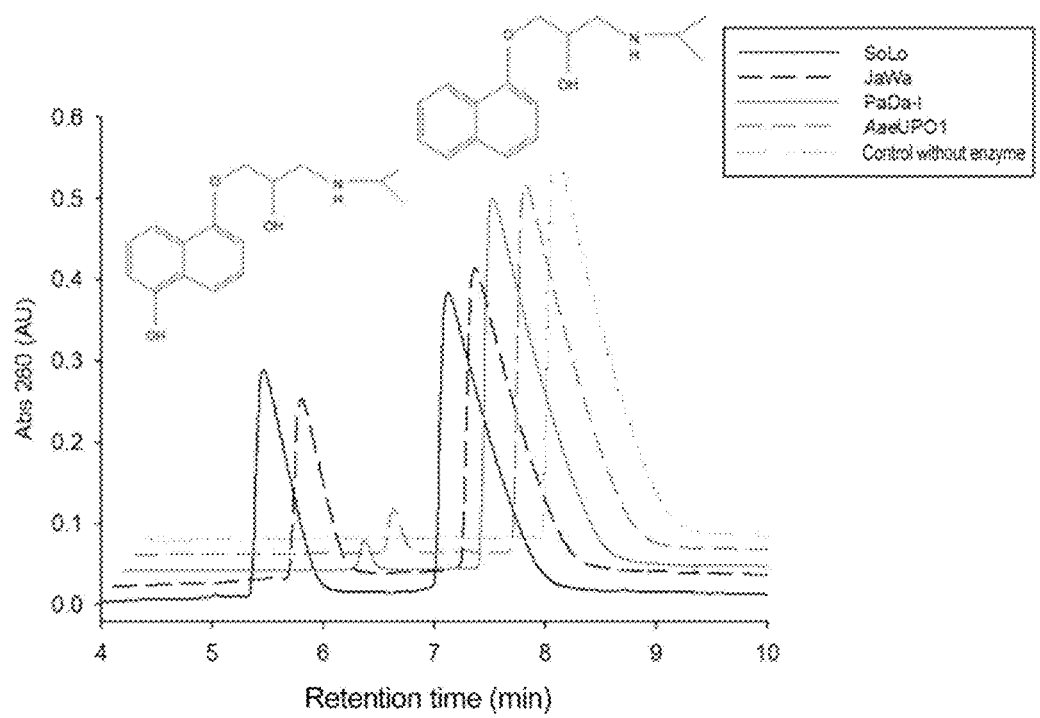
FIG. 13 Chromatogram showing the enzyme reactions. The reactions were performed at room temperature and their composition was as follows: 0.03 µM of each pure UPO variant, 50 mM pH 7.0 of potassium phosphate buffer, 4 mM propranolol, 2 mM $H_2O_2$ (0.5 mL of final volume).

The propranolol transformation reaction performed by the wild AaeUPO enzyme (SEQ ID NO: 2), and the PaDa-I (SEQ ID NO: 18), JaWa (SEQ ID NO: 24) and SoLo (SEQ ID NO: 42) variants in the absence of ascorbic acid and was analysed using HPLC-PDA is included in FIG. 13. It can be observed that both JaWa and SoLo are those that produce the largest amount of 5'-hydroxypropranolol, in addition to having 99% of regioselectivity, since traces of neither 4'-hydroxypropranolol nor N-desisopropyl propranolol (DYP) were detected.

The kinetic value of AaeUPO, JaWa and SoLo for propranolol, and for ABTS and $H_2O_2$ (Table 3) were determined.

TABLE 3

Kinetic parameters for the variants of the invention and for wild AaeUPO.

| Substrate | Kinetic constants | AaeUPO1 | PaDa-I | JaWa | SoLo |
|---|---|---|---|---|---|
| ABTS | $K_m$ (μM) | 25-0 ± 2.5 | 48.8 ± 4.5 | 181 ± 22 | 568 ± 91 |
| | $K_{cat}$ (s$^{-1}$) | 221 ± 6 | 395 ± 13 | 125 ± 5 | 365 ± 23 |
| | $K_{cat}/K_m$ (s$^{-1}$M$^{-1}$) | $8.8 \times 10^6 \pm 6.9 \times 10^5$ | $8.2 \times 10^6 \pm 6.0 \times 10^5$ | $6.9 \times 10^5 \pm 6.3 \times 10^4$ | $6.4 \times 10^5 \pm 6.7 \times 10^4$ |
| Propranolol | $K_m$ (μM) | 2,239 ± 333 | 2,268 ± 220 | 244 ± 92 | 391 ± 97 |
| | $K_{cat}$ (s$^{-1}$) | 150 ± 12 | 212 ± 11 | 765 ± 76 | 497 ± 35 |
| | $K_{cat}/K_m$ (s$^{-1}$M$^{-1}$) | $6.7 \times 10^4 \pm 4.8 \times 10^3$ | $9.3 \times 10^4 \pm 4.3 \times 10^3$ | $3.1 \times 10^6 \pm 0.9 \times 10^5$ | $1.3 \times 10^6 \pm 0.2 \times 10^5$ |
| Naphthalene | $K_m$ (μM) | 156 ± 20 | 578 ± 106 | 127 ± 27 | 789 ± 96 |
| | $K_{cat}$ (s$^{-1}$) | 92 ± 3 | 229 ± 17 | 78 ± 3 | 337 ± 20 |
| | $K_{cat}/K_m$ (s$^{-1}$M$^{-1}$) | $5.9 \times 10^5 \pm 5.9 \times 10^4$ | $4.0 \times 10^5 \pm 4.0 \times 10^4$ | $6.2 \times 10^5 \pm 1.1 \times 10^4$ | $4.3 \times 10^5 \pm 2.8 \times 10^4$ |
| $H_2O_2$ | $K_m$ (μM) | 1,370 ± 162 | 486 ± 55 | 1,250 ± 153 | 1,430 ± 153 |
| | $K_{cat}$ (s$^{-1}$) | 290 ± 15 | 238 ± 8 | 446 ± 23 | 446.23. |
| | $K_{cat}/K_m$ (s$^{-1}$M$^{-1}$) | $2.1 \times 10^5 \pm 1.5 \times 10^4$ | $5.0 \times 10^5 \pm 4.2 \times 10^4$ | $3.1 \times 10^5 \pm 1.8 \times 10^4$ | $3.1 \times 10^5 \pm 1.8 \times 10^4$ |

As can be observed in Table 3, both the JaWa (SEQ ID NO: 24) and SoLo (SEQ ID NO: 42) variants increased the $k_{cat}/K_m$ (catalytic efficiency) values for propranolol by two orders of magnitude. It can also be observed that the JaWa (SEQ ID NO: 24) and SoLo (SEQ ID NO: 42) variants show a reduction in peroxidase activity, measured with ABTS, of one order of magnitude in catalytic efficiency, being the affinity to the substrate, in the case of the SoLo variant, three fold worse with respect to its parental. The values for $H_2O_2$ with benzyl alcohol were not affected. As in the case of the propranolol between JaWa and SoLo, JaWa has kinetic constants similar to AaeUPO with the naphthalene as substrate, differentiating itself in the total turnover values, which are higher for JaWa.

Figure 14:
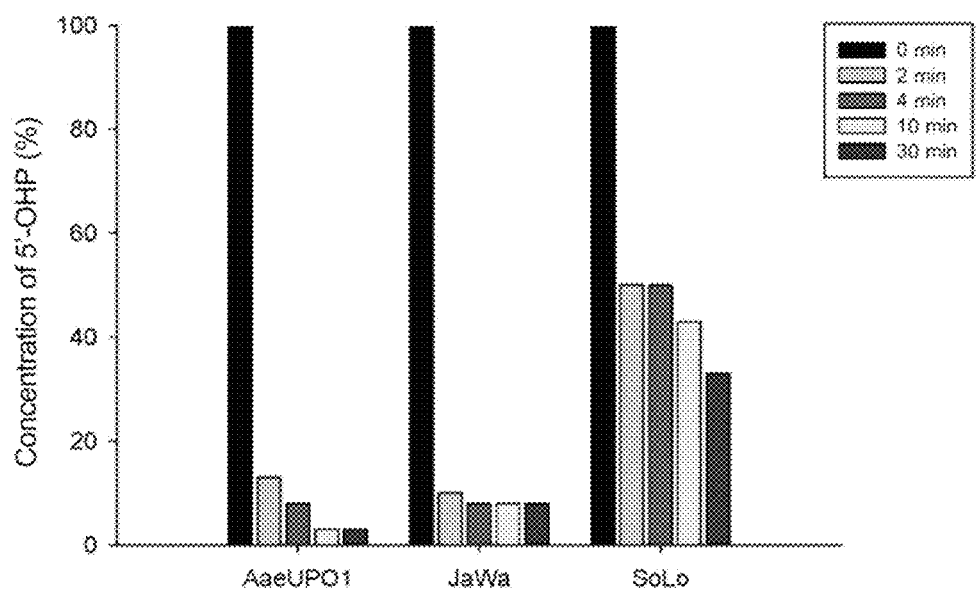
FIG. 14 Turnover rates of AaeUPO, JaWa and SoLo. The reaction mixture contained 0.03 µM of each pure UPO variant, 0.4 mM 5'-hydroxypropranolol, and 2 mM $H_2O_2$ in 50 mM pH 7.0 potassium phosphate buffer (0.3 mL of final volume). The disappearance of the product 5'-hydroxypropranolol can be observed due to the formation of its corresponding quinone by means of the peroxidase activity of the enzyme.

Since the kinetics with propranolol of the JaWa and SoLo variants are very similar, the turnover rates were calculated with 5'-hydroxypropranolol as a substrate in the absence of ascorbic acid, in order to evaluate the peroxidase activity of each variant against its propranolol reaction product. In FIG. 14 it can be observed that JaWa and AaeUPO oxidise practically the entire product, but SoLo is capable of maintaining approximately 50% thereof without oxidising. It follows that the SoLo variant (SEQ ID NO: 42), has significantly reduced its peroxidase activity on its own product, allowing higher performances in the production of this propranolol metabolite.

Figure 15:
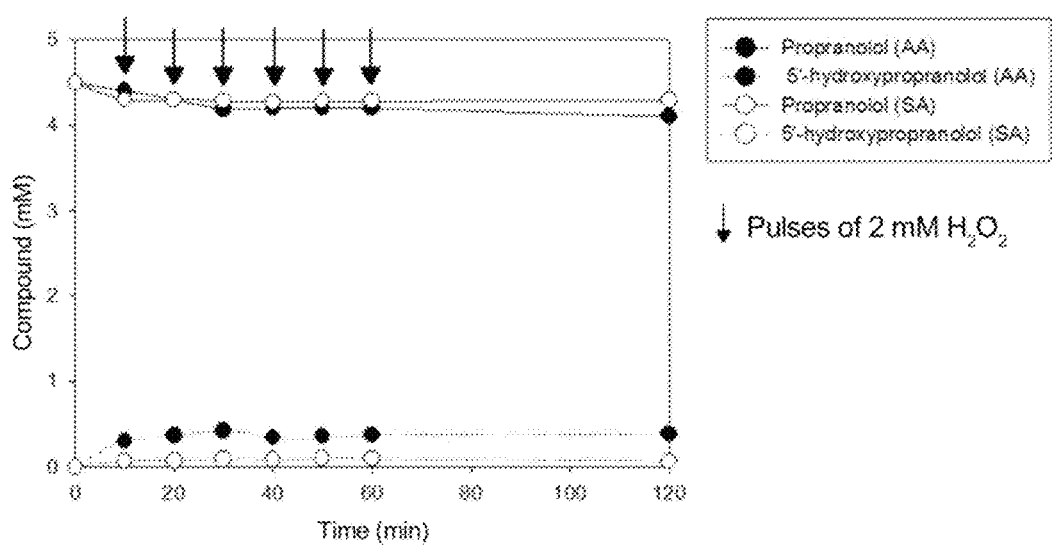
FIG. 15 Calculation of the total turnover number (TTN) of AaeUPO and SoLo. The assay was carried out using 0.03 µM of each pure enzyme, 4 mM propranolol and 2 mM $H_2O_2$ in 50 mM pH 7.0 potassium phosphate buffer and in the same manner, but also with 4 mM ascorbic acid. In both cases, 2 mM $H_2O_2$ was added every 10 minutes, monitoring the reaction in each addition point taking different aliquots.
Figure 15:
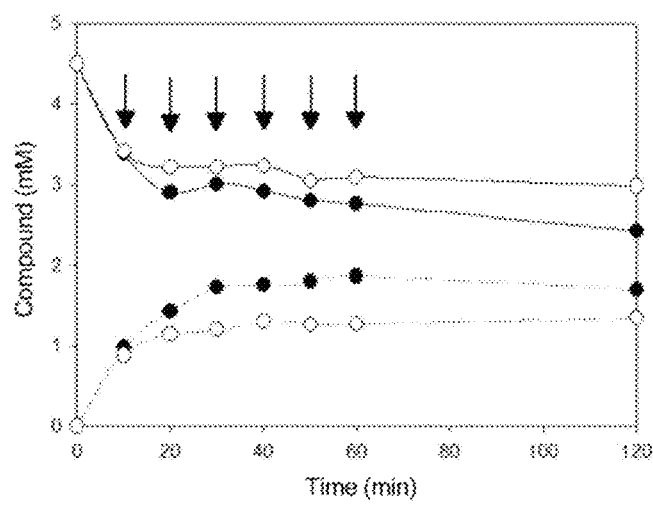

When the reaction was monitored for long reaction times with the addition of 2 mM $H_2O_2$, the total turnover numbers (TTNs) were determined, obtaining a value of 45,000 for SoLo, 15,000 for JaWa and 3,000 for AaeUPO in the absence of ascorbic acid; and in the presence of ascorbic acid, 62,000 for SoLo, 48,000 for JaWa and 14,000 for AaeUPO (Table 4). This implies that, even by adding ascorbic acid to the reaction, the independent use of this antioxidant in the reaction medium is possible, simplifying the process. (FIG. 15).

TABLE 4

Determination of the total turnover numbers (TTNs) for the variants of the invention and for wild AaeUPO.

| | TTNs | |
|---|---|---|
| | With ascorbic acid | Without ascorbic acid |
| AaeUPO | 14,000 | 3,000 |
| JaWa | 48,000 | 15,000 |
| SoLo | 62,000 | 45,000 |

The invention claimed is:

1. A polynucleotide that encodes a polypeptide with peroxygenase activity, wherein the polypeptide comprises an amino acid sequence at least 95% identical to SEQ ID NO: 2 (AaeUPO1), and comprises at least two amino acid substitutions at positions corresponding to positions 241 and 257 of the polypeptide of SEQ ID NO: 2, wherein the amino acid at position corresponding to position 241 of the polypeptide of SEQ ID NO: 2 is replaced with aspartic acid and the amino acid at position 257 of the polypeptide of SEQ ID NO: 2 is replaced with lysine.

2. The polynucleotide of claim 1, wherein the polypeptide with peroxygenase activity further comprises an amino acid substitution at the position corresponding to position 191 of the polypeptide of SEQ ID NO: 2, wherein the amino acid at the position corresponding to position 191 of the polypeptide of SEQ ID NO: 2 is replaced with serine.

3. The polynucleotide of claim 1, wherein the polypeptide with peroxygenase activity further comprises one or more substitutions selected from the group consisting of:
   a) the amino acid at the position corresponding to position 67 of the polypeptide of SEQ ID NO: 2 is replaced with phenylalanine,
   b) the amino acid at the position corresponding to position 248 of the polypeptide of SEQ ID NO: 2 is replaced with valine,
   c) the amino acid at the position corresponding to position 311 of the polypeptide of SEQ ID NO: 2 is replaced with leucine,
   d) the amino acid at the position corresponding to position 75 of the polypeptide of SEQ ID NO: 2 is replaced with isoleucine, and
   e) the amino acid at the position corresponding to position 57 of the polypeptide of SEQ ID NO: 2 is replaced with alanine.

4. The polynucleotide of claim 1, further comprising a nucleotide sequence encoding the signal peptide of SEQ ID NO: 26.

5. The polynucleotide of claim 1, further comprising a nucleotide sequence encoding a variant of the signal peptide of SEQ ID NO: 26, wherein said variant comprises one or more substitutions selected from the group consisting of:
   a) the replacement of the amino acid at the position corresponding to position 12 of the signal peptide of SEQ ID NO: 26 with tyrosine,
   b) the replacement of the amino acid at the position corresponding to position 14 of the signal peptide of SEQ ID NO: 26 with valine,
   c) the replacement of the amino acid at the position corresponding to position 15 of the signal peptide of SEQ ID NO: 26 with glycine, and
   d) the replacement of the amino acid at the position corresponding to position 21 of the signal peptide of SEQ ID NO: 26 with aspartic acid.

6. The polynucleotide of claim 1, wherein said polynucleotide comprises a nucleotide sequence selected from the group consisting of SEQ ID NO: 11, SEQ ID NO: 9, SEQ ID NO: 7, SEQ ID NO: 23, SEQ ID NO: 21, SEQ ID NO: 19, SEQ ID NO: 41, SEQ ID NO: 39 and SEQ ID NO: 37.

7. A method for obtaining a polypeptide with peroxygenase activity comprising the steps of:
   i. introducing a vector with a polynucleotide that encodes a polypeptide with peroxygenase activity, wherein the polypeptide comprises an amino acid sequence at least 95% identical to SEQ ID NO: 2 (AaeUPO1), and comprises at least two amino acid substitutions at positions corresponding to positions 241 and 257 of the polypeptide of SEQ ID NO: 2, wherein the amino acid at position corresponding to position 241 of the polypeptide of SEQ ID NO: 2 is replaced with aspartic acid and the amino acid at position 257 of the polypeptide of SEQ ID NO: 2 is replaced with lysine, in a suitable host cell,
   ii. culturing the host cell in a suitable medium, and
   iii. purifying the synthesized polypeptide.

8. A host cell comprising the polynucleotide according to claim 1.

9. The host cell; according to claim 8, wherein the host cell is a yeast or fungus cell.

10. The host cell, according to claim 8, wherein the host cell is a yeast cell that belongs to the genus *Saccharomyces* sp or *Pichia* sp, or the host cell is a fungus cell that belongs to the genus *Aspergillus* sp.

* * * * *